(12) United States Patent
Choi

(10) Patent No.: US 9,518,100 B2
(45) Date of Patent: Dec. 13, 2016

(54) **METHODS FOR INCREASING N-GLYCAN OCCUPANCY AND REDUCING PRODUCTION OF HYBRID N-GLYCANS IN *PICHIA PASTORIS* STRAINS LACKING ALG3 EXPRESSION**

(71) Applicant: Merck Sharp & Dohme Corp., Rahway, NJ (US)

(72) Inventor: Byung-Kwon Choi, Norwich, VT (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/764,993

(22) PCT Filed: Feb. 7, 2014

(86) PCT No.: PCT/US2014/015186
§ 371 (c)(1),
(2) Date: Jul. 31, 2015

(87) PCT Pub. No.: WO2014/126787
PCT Pub. Date: Aug. 21, 2014

(65) Prior Publication Data
US 2015/0376249 A1    Dec. 31, 2015

Related U.S. Application Data

(60) Provisional application No. 61/764,198, filed on Feb. 13, 2013.

(51) Int. Cl.
| | | |
|---|---|---|
| C12N 1/15 | (2006.01) | |
| C07K 14/44 | (2006.01) | |
| C07K 14/39 | (2006.01) | |
| C12P 21/00 | (2006.01) | |
| C12N 9/10 | (2006.01) | |
| C07K 14/62 | (2006.01) | |
| C07K 16/28 | (2006.01) | |
| A61K 38/00 | (2006.01) | |

(52) U.S. Cl.
CPC .............. *C07K 14/44* (2013.01); *C07K 14/39* (2013.01); *C07K 14/62* (2013.01); *C07K 16/2863* (2013.01); *C12N 9/1051* (2013.01); *C12P 21/005* (2013.01); *A61K 38/00* (2013.01); *C07K 2317/14* (2013.01); *C07K 2317/41* (2013.01); *Y02P 20/52* (2015.11)

(58) Field of Classification Search
None
See application file for complete search history.

(56) References Cited

FOREIGN PATENT DOCUMENTS

| WO | WO2011106389 | 9/2011 |
|---|---|---|
| WO | WO2011134643 | 11/2011 |

OTHER PUBLICATIONS

International Search Report, Search Report PCT/US2014/015186—Mailing date: Apr. 25, 2014.
Szathmary et al., Protein is Essential for Degradation of Misfolded Glycoproteins and May Function as Lectin in ERAD, Molecular Cell, 2005, pp. 765-777, 19.
Zachariae et al., Glucose repression of lactose/galactose metabolism inKluyv/eromyces lactis is determined by the concentration ofthe transcriptional activator LA1 9 (KiGAL4), Nucleic Acids Res., 1993, pp. 69-77, 21.

*Primary Examiner* — Jim Ketter
(74) *Attorney, Agent, or Firm* — John David Reilly; Gloria Fuentes

(57) ABSTRACT

Methods are disclosed for increasing the yield and N-glycosylation site occupancy of paucimannose or complex N-glycans of recombinant glycoproteins produced in a recombinant host cell lacking dolichyl-P-Man:Man$_5$GlcNAc$_2$-PP-dolichyl alpha-1,3 mannosyltransferase (Alg3p) activity. In particular, the present invention provides recombinant host cells for producing recombinant glycoproteins that comprise a disruption of the expression of an OS-9 family gene in the host cell and which overexpress one or more *Trypanosoma brucei* STT3 proteins.

9 Claims, 17 Drawing Sheets

*MW with Na adduct (K adduct)
MW: hexose: 180 (162 loss of H₂O), GlcNAc:221 (203 loss of H₂O), Sialic acid: 309 (291 loss of H₂O), Phosphate: 80

US 9,518,100 B2

METHODS FOR INCREASING N-GLYCAN OCCUPANCY AND REDUCING PRODUCTION OF HYBRID N-GLYCANS IN PICHIA PASTORIS STRAINS LACKING ALG3 EXPRESSION

CROSS REFERENCE TO RELATED APPLICATIONS

This application is the National Stage of International Application No. PCT/US2014/015186 filed on Feb. 7, 2014, which claims the benefit under 35 U.S.C. 119(e) of U.S. Provisional Application No. 61/764,198, filed Feb. 13, 2013, both of which are incorporated herein in their entirety.

REFERENCE TO SEQUENCE LISTING SUBMITTED ELECTRONICALLY

The sequence listing of the present application is submitted electronically via EFS-Web as an ASCII formatted sequence listing with a file name "23434 US PCT SEQ LIST.txt", creation date of 24 Jun. 2015, and a size of 105 KB. This sequence listing submitted via EFS-Web is part of the specification and is herein incorporated by reference in its entirety.

BACKGROUND OF THE INVENTION (1) Field of the Invention

The present invention relates to methods for increasing the yield and N-glycosylation site occupancy of paucimannose or complex N-glycans of recombinant glycoproteins produced in a recombinant host cell lacking dolichyl-P-Man:Man$_5$GlcNAc$_2$-PP-dolichyl alpha-1,3 mannosyltransferase (Alg3p) activity. In particular, the present invention provides recombinant host cells that comprise a disruption of the expression of an OS-9 family gene in the host cell and which overexpress one or more *Trypanosoma brucei* STT3 proteins.

(2) Description of Related Art

The ability to produce recombinant human proteins has led to major advances in human health care and remains an active area of drug discovery. Many therapeutic proteins require the posttranslational addition of glycans to specific asparagine residues (N-glycosylation) of the protein to ensure proper structure-function activity and subsequent stability in human serum. For therapeutic use in humans, glycoproteins require human-like N-glycosylation. Mammalian cell lines (e.g., Chinese hamster ovary (CHO) cells, human retinal cells) that can mimic human-like glycoprotein processing have several drawbacks including low protein titers, long fermentation times, heterogeneous products, and continued viral containment. It is therefore desirable to use an expression system that not only produces high protein titers with short fermentation times, but can also produce human-like glycoproteins.

Fungal hosts such as *Saccharomyces cerevisiae* or methylotrophic yeast such as *Pichia pastoris* have distinct advantages for therapeutic protein expression, for example, they do not secrete high amounts of endogenous proteins, strong inducible promoters for producing heterologous proteins are available, they can be grown in defined chemical media and without the use of animal sera, and they can produce high titers of recombinant proteins (Cregg et al., FEMS Microbiol. Rev. 24: 45-66 (2000)). However, glycosylated proteins expressed in yeast generally contain additional mannose sugars resulting in "high mannose" glycans. Because these high mannose N-glycans can result in adverse responses when administered to certain individuals, yeast have not generally been used to produce therapeutic glycoproteins intended for human use. However, methods for genetically engineering yeast to produce human-like N-glycans are described in U.S. Pat. Nos. 7,029,872 and 7,449,308 along with methods described in U.S. Published Application Nos. 20040230042, 20040171826, 20050170452, 20050208617, 20050208617, and 20060286637. These methods have been used to construct recombinant yeast that can produce therapeutic glycoproteins that have predominantly human-like complex or hybrid N-glycans thereon instead of yeast type N-glycans.

It has been found that while the genetically engineered yeast can produce glycoproteins that have mammalian- or human-like N-glycans, the occupancy of N-glycan attachment sites on glycoproteins varies widely and is generally lower than the occupancy of these same sites in glycoproteins produced in mammalian cells. This has been observed for various recombinant antibodies produced in *Pichia pastoris*. However, variability of occupancy of N-glycan attachment sites has also been observed in mammalian cells as well. For example, Gawlitzek et al., Identification of cell culture conditions to control N-glycosylation site-occupancy of recombinant glycoproteins expressed in CHO cells, Biotechnol. Bioengin. 103: 1164-1175 (2009), disclosed that N-glycosylation site occupancy can vary for particular sites for particular glycoproteins produced in CHO cells and that modifications in growth conditions can be made to control occupancy at these sites. International Published Application No. WO 2006107990 discloses a method for improving protein N-glycosylation of eukaryotic cells using the dolichol-linked oligosaccharide synthesis pathway. Control of N-glycosylation site occupancy has been reviewed by Jones et al., Biochim. Biophys. Acta. 1726: 121-137 (2005).

However, there still remains a need for methods for increasing N-glycosylation site occupancy of therapeutic proteins produced in recombinant host cells having particular genetic backgrounds.

BRIEF SUMMARY OF THE INVENTION

The present invention provides methods for increasing the yield and N-glycosylation site occupancy of paucimannose or complex N-glycans of recombinant glycoproteins produced in a recombinant host cell does not display dolichyl-P-Man:Man$_5$GlcNAc$_2$-PP-dolichyl alpha-1,3 mannosyltransferase (Alg3p) activity. In particular, the present invention provides recombinant host cells that do not display Alg3p and OS-9 family protein activity in the host cell and which overexpress one or more *Trypanosoma brucei* STT3 proteins. The *Trypanosoma brucei* STT3s include the STT3A, STT3B, and STT3C proteins. These recombinant host cells may then be used for producing the recombinant glycoproteins having predominantly paucimannose or complex N-glycans. In general, recombinant host cells that express various *Trypanosoma brucei* STT3 proteins have been found to be capable of producing glycoproteins that have a greater amount of N-glycosylation site occupancy than recombinant host cells that do not express the particular oligosaccharyltransferase. In recombinant host cells genetically engineered to produce predominantly paucimannose N-glycans or complex N-glycans, the mole percent of hybrid N-glycans in a composition of glycoproteins produced by the recombinant host cells will be reduced compared to the amount that would be present in host cells that express the OS-9 family gene.

Therefore, the present invention provides a host cell that does not display dolichyl-P-Man:Man$_5$GlcNAc$_2$-PP-dolichyl alpha-1,3 mannosyltransferase (alg3p) activity and does not display osteosarcoma 9 (OS-9) protein activity comprising a nucleic acid molecule encoding a *Trypanosoma brucei* STT3 protein integrated into the genome of the host cell.

In particular aspects of the above, the host cell is a yeast or filamentous fungus. In a further aspect, the host cell is *Pichia pastoris*. In particular aspects of the above, the OS-9 protein activity is Yos9p activity. In particular aspects of the above, the host cell further does not display Att1p activity. In particular aspects of the above, the host cell further includes a nucleic acid molecule encoding a heterologous protein. In particular aspects of the above, the host cell is genetically engineered to produce glycoproteins comprising one or more mammalian- or human-like N-glycans.

The present invention further provides a method for producing a heterologous glycoprotein, comprising (a) providing a host cell that does not display dolichyl-P-Man:Man$_5$GlcNAc$_2$-PP-dolichyl alpha-1,3 mannosyltransferase (Alg3p) activity, does not display osteosarcoma 9 (OS-9) protein activity, and having integrated into the genome of the host cell a nucleic acid molecule encoding a *Trypanosoma brucei* STT3 protein and a nucleic acid molecule encoding the heterologous glycoprotein; and (b) culturing the host cell under conditions for expressing the heterologous glycoprotein to produce the heterologous glycoprotein.

In particular aspects of the above, the host cell is a yeast or filamentous fungus. In a further aspect, the host cell is *Pichia pastoris*. In particular aspects of the above, the OS-9 protein activity is Yos9p activity. In particular aspects of the above, the host cell further does not display Att1p activity. In particular aspects of the above, the host cell is genetically engineered to produce glycoproteins comprising one or more mammalian- or human-like N-glycans.

The present invention further provides for the use of a host cell that does not display dolichyl-P-Man:Man$_5$GlcNAc$_2$-PP-dolichyl alpha-1,3 mannosyltransferase (Alg3p) activity and does not display osteosarcoma 9 (OS-9) protein activity; and having integrated into the genome of the host cell a first nucleic acid molecule encoding a *Trypanosoma brucei* STT3 protein and a second nucleic acid molecule encoding the heterologous glycoprotein; for the manufacture of a medicament for treating a disease.

In particular aspects of the above, the host cell is a yeast or filamentous fungus. In particular aspects of the above, the OS-9 protein activity is Yos9p activity. In a further aspect, the host cell is *Pichia pastoris*. In particular aspects of the above, the host cell further does not display Att1p activity. In particular aspects of the above, the host cell is genetically engineered to produce glycoproteins comprising one or more mammalian- or human-like N-glycans.

In another embodiment, provided is a method for producing a heterologous glycoprotein in a recombinant host cell, comprising providing a recombinant host cell that includes a disruption or deletion in the expression of the endogenous dolichyl-P-Man:Man$_5$GlcNAc$_2$-PP-dolichyl alpha-1,3 mannosyltransferase (ALG3) gene, a disruption or deletion in the expression of the endogenous osteosarcoma 9 (OS-9) family gene or homolog thereof, and integrated into the genome of the host cell a nucleic acid molecule encoding a *Trypanosoma brucei* STT3 protein and a nucleic acid molecule encoding the heterologous glycoprotein, and wherein the endogenous host cell genes encoding the proteins comprising the endogenous OTase complex are expressed; and culturing the host cell under conditions for expressing the heterologous glycoprotein to produce the heterologous glycoprotein.

In a further aspect of the above, provided is a method for producing a heterologous glycoprotein with mammalian- or human-like complex or hybrid N-glycans in a host cell, comprising providing a recombinant host cell that includes a disruption or deletion in the expression of the endogenous dolichyl-P-Man:Man$_5$GlcNAc$_2$-PP-dolichyl alpha-1,3 mannosyltransferase (ALG3) gene, a disruption or deletion in the expression of the endogenous osteosarcoma 9 (OS-9) family gene or homolog thereof, a nucleic acid molecule encoding a *Trypanosoma brucei* STT3 protein integrated into the genome of the host cell, and a nucleic acid molecule encoding the heterologous glycoprotein integrated into the genome of the host cell; and culturing the host cell under conditions for expressing the heterologous glycoprotein to produce the heterologous glycoprotein.

In further aspects of the above method, the host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum,* and *Neurospora crassa*. In other aspects, the host cell is an insect, plant or mammalian host cell.

In a further aspect of the above, provided is a method for producing a heterologous glycoprotein in a lower eukaryote host cell, comprising providing a recombinant lower eukaryote host cell that includes a disruption or deletion in the expression of the endogenous dolichyl-P-Man:Man$_5$GlcNAc$_2$-PP-dolichyl alpha-1,3 mannosyltransferase (ALG3) gene, a disruption or deletion in the expression of the endogenous osteosarcoma 9 (OS-9) family gene or homolog thereof, a nucleic acid molecule encoding a *Trypanosoma brucei* STT3 protein integrated into the genome of the host cell, and a nucleic acid molecule encoding the heterologous glycoprotein integrated into the genome of the host cell, and wherein the endogenous host cell genes encoding the proteins comprising the endogenous OTase complex are expressed; and culturing the host cell under conditions for expressing the heterologous glycoprotein to produce the heterologous glycoprotein.

In further aspects of the above method, the lower eukaryote host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum,* and *Neurospora crassa*.

In a further aspect of the above, provided is a method for producing a heterologous glycoprotein in a recombinant yeast host cell, comprising providing a recombinant yeast host cell that includes a disruption or deletion in the expression of the endogenous dolichyl-P-Man:Man$_5$GlcNAc$_2$-PPdolichyl alpha-1,3 mannosyltransferase (ALG3) gene, a disruption or deletion in the expression of the endogenous YOS9 gene or homolog thereof, a nucleic acid molecule encoding a *Trypanosoma brucei* STT3 protein integrated into the genome of the host cell, and a nucleic acid molecule encoding the heterologous glycoprotein integrated into the genome of the host cell; and culturing the host cell under conditions for expressing the heterologous glycoprotein to produce the heterologous glycoprotein.

In the above methods, the recombinant yeast host cell either produces the glycoprotein with a yeast N-glycan pattern or the yeast has been genetically engineered to produce glycoproteins with a yeast pattern but which lack hypermannosylation but which produce high mannose N-glycans. For example, the yeast can be genetically engineered to lack α1,6-mannosyltransferase activity, e.g., Och1p activity. In further aspects, the yeast is genetically engineered to produce glycoproteins that have mammalian or human-like N-glycans.

In further embodiments, the host cell further includes at least one nucleic acid molecule encoding a second heterologous single-subunit oligosaccharyltransferase in addition to the *Trypanosoma brucei* STT3 protein. In particular aspects, the second single-subunit oligosaccharyltransferase is capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. In particular aspects, the second single-subunit oligosaccharyltransferase is the *Leishmania* sp. STT3A protein, STT3B protein, STT3C protein, STT3D protein, or combinations thereof. In particular aspects, the second single-subunit oligosaccharyltransferase is the *Leishmania major* STT3A protein, STT3B protein, STT3D protein, or combinations thereof. In particular aspects, the second single-subunit oligosaccharyltransferase is the *Leishmania major* STT3D protein. In further aspects, the for example second single-subunit oligosaccharyltransferase is the *Leishmania major* STT3D protein, which is capable of functionally suppressing (or rescuing or complementing) the lethal phenotype of at least one essential protein of the *Saccharomyces cerevisae* OTase complex. In further aspects, the endogenous host cell genes encoding the proteins comprising the endogenous oligosaccharyltransferase (OTase) complex are expressed.

In further aspects of the above method, the yeast host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia* sp., *Saccharomyces cerevisiae, Saccharomyces* sp., *Hansenula polymorpha, Kluyveromyces* sp., *Kluyveromyces lactis,* and *Candida albicans.*

In a further aspect of the above, provided is a method for producing a heterologous glycoprotein in a recombinant yeast host cell, comprising providing a recombinant host cell that includes a disruption or deletion in the expression of the endogenous dolichyl-P-Man:Man$_5$GlcNAc$_2$-PP-dolichyl alpha-1,3 mannosyltransferase (ALG3) gene, a disruption or deletion in the expression of the endogenous YOS9 gene or homolog thereof, a nucleic acid molecule encoding a *Trypanosoma brucei* STT3 protein integrated into the genome of the host cell, and a nucleic acid molecule encoding the heterologous glycoprotein, and wherein the endogenous host cell genes encoding the proteins comprising the endogenous OTase complex are expressed; and culturing the host cell under conditions for expressing the heterologous glycoprotein to produce the heterologous glycoprotein.

In the above methods, the recombinant yeast host cell either produces the glycoprotein with a yeast N-glycan pattern or the yeast has been genetically engineered to produce glycoproteins with a yeast pattern that includes high mannose N-glycans but which lack hypermannosylation. For example, the yeast can be genetically engineered to lack α1,6-mannosyltransferase activity, e.g., Och1p activity. In further aspects, the yeast is genetically engineered to produce glycoproteins that have mammalian or human-like N-glycans.

In further embodiments, the host cell further includes at least one nucleic acid molecule encoding a heterologous single-subunit oligosaccharyltransferase. In particular aspects, the single-subunit oligosaccharyltransferase is capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. In particular aspects, the single-subunit oligosaccharyltransferase is the *Leishmania* sp. STT3A protein, STT3B protein, STT3C protein, STT3D protein, or combinations thereof. In particular aspects, the single-subunit oligosaccharyltransferase is the *Leishmania major* STT3A protein, STT3B protein, STT3D protein, or combinations thereof. In particular aspects, the single-subunit oligosaccharyltransferase is the *Leishmania major* STT3D protein. In further aspects, the for example single-subunit oligosaccharyltransferase is the *Leishmania major* STT3D protein, which is capable of functionally suppressing (or rescuing or complementing) the lethal phenotype of at least one essential protein of the *Saccharomyces cerevisae* OTase complex. In further aspects, the endogenous host cell genes encoding the proteins comprising the endogenous oligosaccharyltransferase (OTase) complex are expressed.

In further aspects of the above method, the yeast host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia* sp., *Saccharomyces cerevisiae, Saccharomyces* sp., *Hansenula polymorpha, Kluyveromyces* sp., *Kluyveromyces lactis,* and *Candida albicans.*

In a further aspect of the above, provided is a method for producing a heterologous glycoprotein in a filamentous fungus host cell, comprising providing a recombinant filamentous host cell that includes a disruption or deletion in the expression of the endogenous dolichyl-P-Man:Man$_5$GlcNAc$_2$-PP-dolichyl alpha-1,3 mannosyltransferase (ALG3) gene, a disruption or deletion in the expression of the endogenous YOS9 gene or homolog thereof, a nucleic acid molecule encoding a *Trypanosoma brucei* STT3 protein integrated into the genome of the host cell and a nucleic acid molecule encoding the heterologous glycoprotein, and wherein the endogenous host cell genes encoding the proteins comprising the endogenous OTase complex are expressed; and culturing the host cell under conditions for expressing the heterologous glycoprotein to produce the heterologous glycoprotein. The filamentous fungus host cell produces the glycoprotein in which the N-glycans have a filamentous fungus pattern or it is genetically engineered to produce glycoproteins that have mammalian or human-like N-glycans.

In further embodiments, the host cell further includes at least one nucleic acid molecule encoding a heterologous single-subunit oligosaccharyltransferase. In particular aspects, the single-subunit oligosaccharyltransferase is capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. In particular aspects, the single-subunit oligosaccharyltransferase is the *Leishmania* sp. STT3A protein, STT3B protein, STT3C protein, STT3D protein, or combinations thereof. In particular aspects, the single-subunit oligosaccharyltransferase is the *Leishmania major* STT3A protein, STT3B protein, STT3D protein, or combinations thereof. In particular aspects, the single-subunit oligosaccharyltransferase is the *Leishmania major* STT3D protein. In further aspects, the for example single-subunit oligosaccharyltransferase is the *Leishmania major* STT3D protein, which is capable of functionally suppressing (or rescuing or complementing) the lethal phenotype of at least one essential protein of the *Saccharomyces cerevisae* OTase complex. In further aspects, the endogenous host cell genes encoding the proteins comprising the endogenous oligosaccharyltransferase (OTase) complex are expressed.

In further aspects of the above, the filamentous fungus host cell is selected from the group consisting of *Aspergillus nidulans, Aspergillus niger, Aspergillus oryzae, Trichoderma reesei, Chrysosporium lucknowense, Fusarium sp., Fusarium gramineum, Fusarium venenatum,* and *Neurospora crassa.*

In particular embodiments of any one of the above methods, the *Trypanosoma brucei* STT3 protein is the *Trypanosoma brucei* STT3B protein. In another embodiment of the above method, the *Trypanosoma brucei* STT3 protein is the *Trypanosoma brucei* STT3C protein and the host cell further includes a nucleic acid that encodes and expresses therefrom a *Leishmania major* STT3D protein.

In particular aspects of the above methods, the host cell has a disruption of the expression of the Outer Chain (OCH1) gene or homologue thereof, the Acquired Thermo-Tolerance 1 (ATT1) gene or homologue thereof, or both. Disruption of expression includes but is not limited to deletion or disruption of the OCH1 gene or ORF encoding the Och1p and/or deletion or disruption of the ATT1 gene or ORF encoding the Att1p.

In further embodiments of any one of the above methods, the host cell is genetically engineered to produce glycoproteins comprising one or more N-glycans shown in FIG. 1. In further aspects of any one of the above methods, the host cell is genetically engineered to produce glycoproteins comprising one or more mammalian- or human-like complex N-glycans shown selected from G0, G1, G2, A1, or A2. In further embodiments, the host cell is genetically engineered to produce glycoproteins comprising one or more mammalian- or human-like complex N-glycans that have bisected N-glycans or have multiantennary N-glycans. In other embodiments, the host cell is genetically engineered to produce glycoproteins comprising one or more mammalian- or human-like hybrid N-glycans selected from GlcNAcMan$_3$GlcNAc$_2$; GalGlcNAcMan$_3$GlcNAc$_2$; and NANAGalGlcNAcMan$_3$GlcNAc$_2$. In further embodiments, the N-glycan structure consists of the paucimannose (G-2) structure Man$_3$GlcNAc$_2$ or the Man$_5$GlcNAc$_2$ (GS 1.3) structure.

In particular embodiments of any one of the above methods, the heterologous protein or glycoprotein may a therapeutic protein or glycoprotein. Examples of therapeutic proteins and glycoproteins, include but are not limited to, erythropoietin (EPO); cytokines such as interferon α, interferon β, interferon γ, and interferon ω; and granulocyte-colony stimulating factor (GCSF); granulocyte macrophage-colony stimulating factor (GM-CSF); coagulation factors such as factor VIII, factor IX, and human protein C; antithrombin III; thrombin; soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4-Ig; transmembrane activator and calcium modulator and cyclophilin ligand; glucagon like protein 1; or IL-2 receptor agonist. In further aspects, the heterologous glycoprotein is a protein that is not normally N-glycosylated but which has been modified to comprise one or more N-glycosylation sites. For example, the glycoprotein may be insulin in which an N-glycosylation site has been introduced into the insulin amino acid sequence.

In further embodiments of any one of the above methods, the heterologous protein is an antibody, examples of which, include but are not limited to, an anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, or anti-CD20 antibody.

In particular aspects of any one of the above methods, the host cell includes one or more nucleic acid molecules encoding one or more catalytic domains of a glycosidase, mannosidase, or glycosyltransferase activity derived from a member of the group consisting of UDP-GlcNAc transferase (GnT) I, GnT II, GnT III, GnT IV, GnT V, GnT VI, UDP-galactosyltransferase (GalT), fucosyltransferase, and sialyltransferase. In particular embodiments, the mannosidase is selected from the group consisting of *C. elegans* mannosidase IA, *C. elegans* mannosidase IB, *D. melanogaster* mannosidase IA, *H. sapiens* mannosidase IB, *P. citrinum* mannosidase I, mouse mannosidase IA, mouse mannosidase IB, *A. nidulans* mannosidase IA, *A. nidulans* mannosidase IB, *A. nidulans* mannosidase IC, mouse mannosidase II, *C. elegans* mannosidase II, *H. sapiens* mannosidase II, and mannosidase III.

In certain aspects of any one of the above methods, at least one catalytic domain is localized by forming a fusion protein comprising the catalytic domain and a cellular targeting signal peptide. The fusion protein can be encoded by at least one genetic construct formed by the in-frame ligation of a DNA fragment encoding a cellular targeting signal peptide with a DNA fragment encoding a catalytic domain having enzymatic activity. Examples of targeting signal peptides include, but are not limited to, membrane-bound proteins of the ER or Golgi, retrieval signals, Type II membrane proteins, Type I membrane proteins, membrane spanning nucleotide sugar transporters, mannosidases, sialyltransferases, glucosidases, mannosyltransferases, and phosphomannosyltransferases.

In particular aspects of any one of the above methods, the host cell further includes one or more nucleic acid molecules encode one or more enzymes selected from the group consisting of UDP-GlcNAc transporter, UDP-galactose transporter, GDP-fucose transporter, CMP-sialic acid transporter, and nucleotide diphosphatases.

In further aspects of any one of the above methods, the host cell includes one or more nucleic acid molecules encoding an α1,2-mannosidase activity, a UDP-GlcNAc transferase (GnT) I activity, a mannosidase II activity, and a GnT II activity.

In further still aspects of any one of the above methods, the host cell includes one or more nucleic acid molecules encoding an α1,2-mannosidase activity, a UDP-GlcNAc transferase (GnT) I activity, a mannosidase II activity, a GnT II activity, and a UDP-galactosyltransferase (GalT) activity.

In further still aspects of any one of the above methods, the host cell is deficient in the activity of one or more enzymes selected from the group consisting of mannosyltransferases and phosphomannosyltransferases. In further still aspects, the host cell does not express an enzyme selected from the group consisting of 1,6 mannosyltransferase, 1,3 mannosyltransferase, and 1,2 mannosyltransferase.

In a particular aspect of any one of the above methods, the host cell is an och1 mutant of *Pichia pastoris.*

In a particular aspect of the host cells, the host cell includes a one or more nucleic acid molecules encoding an α1,2-mannosidase activity and a heterologous glycoprotein and the host cell lacks or does not display with respect to an N-glycan on a glycoprotein detectable phosphomannosyltransferase activity, initiating α1,6-mannosyltransferase activity, and β1,2-mannosyltransferase activity. In a further aspect, the host cell includes one or more nucleic acid molecules encoding an α1,2-mannosidase activity and an endomannosidase activity.

Further provided is a host cell, comprising (a) a disruption or deletion in the expression of the endogenous dolichyl-P-Man:$Man_5GlcNAc_2$-PP-dolichyl alpha-1,3 mannosyltransferase (ALG3) gene, (b) a disruption or deletion in the expression of the endogenous osteosarcoma 9 (OS-9) family gene or homolog thereof, and (c) a nucleic acid molecule encoding a *Trypanosoma brucei* STT3 protein integrated into the genome of the host cell. In further embodiments, the host cell includes a second nucleic acid molecule encoding a heterologous glycoprotein.

Further provided is a lower eukaryotic host cell, comprising (a) a disruption or deletion in the expression of the endogenous dolichyl-P-Man:$Man_5GlcNAc_2$-PP-dolichyl alpha-1,3 mannosyltransferase (ALG3) gene, (b) a disruption or deletion in the expression of the endogenous osteosarcoma 9 (OS-9) family gene or homolog thereof; and (c) a nucleic acid molecule encoding a *Trypanosoma brucei* STT3 protein integrated into the genome of the host cell. In further embodiments, the host cell includes a second nucleic acid molecule encoding a heterologous glycoprotein.

Further provided is a yeast host cell, comprising (a) a disruption or deletion in the expression of the endogenous dolichyl-P-Man:$Man_5GlcNAc_2$-PP-dolichyl alpha-1,3 mannosyltransferase (ALG3) gene, (b) a disruption or deletion in the expression of the endogenous osteosarcoma 9 (OS-9) family gene or homolog thereof, and (c) a nucleic acid molecule encoding a *Trypanosoma brucei* STT3 protein integrated into the genome of the host cell. In further embodiments, the host cell includes a second nucleic acid molecule encoding a heterologous glycoprotein.

Further provided is a yeast host cell, comprising (a) a disruption or deletion in the expression of the endogenous dolichyl-P-Man:$Man_5GlcNAc_2$-PP-dolichyl alpha-1,3 mannosyltransferase (ALG3) gene, (b) a disruption or deletion in the expression of the YOS9 gene, and (c) a nucleic acid molecule encoding a *Trypanosoma brucei* STT3 protein integrated into the genome of the host cell. In further embodiments, the host cell includes a second nucleic acid molecule encoding a heterologous glycoprotein.

Further provided is a *Pichia pastoris* host cell, comprising (a) a disruption or deletion in the expression of the endogenous dolichyl-P-Man:$Man_5GlcNAc_2$-PP-dolichyl alpha-1,3 mannosyltransferase (ALG3) gene, (b) a disruption or deletion in the expression of the YOS9 gene, and (c) a nucleic acid molecule encoding a *Trypanosoma brucei* STT3 protein integrated into the genome of the host cell. In further embodiments, the host cell includes a second nucleic acid molecule encoding a heterologous glycoprotein.

Further provided is a filamentous fungus host cell comprising (a) a disruption or deletion in the expression of the endogenous dolichyl-P-Man:$Man_5GlcNAc_2$-PP-dolichyl alpha-1,3 mannosyltransferase (ALG3) gene, (b) a disruption or deletion in the expression of the endogenous osteosarcoma 9 (OS-9) family gene or homolog thereof, and (c) a nucleic acid molecule encoding a *Trypanosoma brucei* STT3 protein integrated into the genome of the host cell. In further embodiments, the host cell includes a second nucleic acid molecule encoding a heterologous glycoprotein.

In further embodiments, the host cell further includes at least one nucleic acid molecule encoding a heterologous single-subunit oligosaccharyltransferase, and a nucleic acid molecule encoding the heterologous glycoprotein. In particular aspects, the single-subunit oligosaccharyltransferase is capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. In particular aspects, the single-subunit oligosaccharyltransferase is the *Leishmania* sp. STT3A protein, STT3B protein, STT3C protein, STT3D protein, or combinations thereof. In particular aspects, the single-subunit oligosaccharyltransferase is the *Leishmania major* STT3A protein, STT3B protein, STT3D protein, or combinations thereof. In particular aspects, the single-subunit oligosaccharyltransferase is the *Leishmania major* STT3D protein. In further aspects, the for example single-subunit oligosaccharyltransferase is the *Leishmania major* STT3D protein, which is capable of functionally suppressing (or rescuing or complementing) the lethal phenotype of at least one essential protein of the *Saccharomyces cerevisae* OTase complex. In further aspects, the endogenous host cell genes encoding the proteins comprising the endogenous oligosaccharyltransferase (OTase) complex are expressed.

In particular embodiments of any one of the above host cells, the *Trypanosoma brucei* STT3 protein is the *Trypanosoma brucei* STT3B protein. In another embodiment of the above host cells, the *Trypanosoma brucei* STT3 protein is the *Trypanosoma brucei* STT3C protein and the host cell further includes a nucleic acid that encodes and expresses the *Leishmania major* STT3D protein.

Further provided is a host cell, comprising (a) a disruption or deletion in the expression of the endogenous dolichyl-P-Man:Man$_5$GlcNAc$_2$-PP-dolichyl alpha-1,3 mannosyltransferase (ALG3) gene, and (b) a disruption or deletion in the expression of the endogenous osteosarcoma 9 (OS-9) family gene or homolog thereof; and (c) a first nucleic acid molecule encoding a *Trypanosoma brucei* STT3 protein integrated into the genome of the host cell; and the endogenous host cell genes encoding the proteins comprising the endogenous oligosaccharyltransferase (OTase) complex are expressed. In further embodiments, the host cell includes a second nucleic acid molecule encoding a heterologous glycoprotein.

Further provided is a lower eukaryotic host cell, comprising (a) a disruption or deletion in the expression of the endogenous dolichyl-P-Man:Man$_5$GlcNAc$_2$-PP-dolichyl alpha-1,3 mannosyltransferase (ALG3) gene, and (b) a disruption or deletion in the expression of the endogenous osteosarcoma 9 (OS-9) family gene or homolog thereof; and (c) a first nucleic acid molecule encoding a *Trypanosoma brucei* STT3 protein integrated into the genome of the host cell; and the endogenous host cell genes encoding the proteins comprising the endogenous oligosaccharyltransferase (OTase) complex are expressed. In further embodiments, the host cell includes a second nucleic acid molecule encoding a heterologous glycoprotein.

Further provided is a yeast host cell, comprising (a) a disruption or deletion in the expression of the endogenous dolichyl-P-Man:Man$_5$GlcNAc$_2$-PP-dolichyl alpha-1,3 mannosyltransferase (ALG3) gene, and (b) a disruption or deletion in the expression of the endogenous osteosarcoma 9 (OS-9) family gene YOS9 or homolog thereof; and (c) a first nucleic acid molecule encoding a *Trypanosoma brucei* STT3 protein integrated into the genome of the host cell; and the endogenous host cell genes encoding the proteins comprising the endogenous oligosaccharyltransferase (OTase) complex are expressed. In further embodiments, the host cell includes a second nucleic acid molecule encoding a heterologous glycoprotein.

Further provided is a *Pichia pastoris* host cell, comprising (a) a disruption or deletion in the expression of the endogenous dolichyl-P-Man:Man$_5$GlcNAc$_2$-PP-dolichyl alpha-1,3 mannosyltransferase (ALG3) gene, and (b) a disruption or deletion in the expression of the endogenous osteosarcoma 9 (OS-9) family gene YOS9 or homolog thereof; and (c) a first nucleic acid molecule encoding a *Trypanosoma brucei* STT3 protein integrated into the genome of the host cell; and the endogenous host cell genes encoding the proteins comprising the endogenous oligosaccharyltransferase (OTase) complex are expressed. In further embodiments, the host cell includes a second nucleic acid molecule encoding a heterologous glycoprotein.

Further provided is a filamentous fungus host cell comprising (a) a disruption or deletion in the expression of the endogenous dolichyl-P-Man:Man$_5$GlcNAc$_2$-PP-dolichyl alpha-1,3 mannosyltransferase (ALG3) gene, (b) a disruption or deletion in the expression of the endogenous osteosarcoma 9 (OS-9) family gene or homolog thereof; and (c) a first nucleic acid molecule encoding a *Trypanosoma brucei* STT3 protein integrated into the genome of the host cell; and the endogenous host cell genes encoding the proteins comprising the endogenous oligosaccharyltransferase (OTase) complex are expressed. In further embodiments, the host cell includes a second nucleic acid molecule encoding a heterologous glycoprotein.

In particular aspects, the host cell further includes a third nucleic acid molecule, which encodes a single-subunit oligosaccharyltransferase capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. In particular aspects, the single-subunit oligosaccharyltransferase encoded by the third nucleic acid molecule is the *Leishmania* sp. STT3A protein, STT3B protein, STT3C protein, STT3D protein, or combinations thereof. In particular aspects, the single-subunit oligosaccharyltransferase is the *Leishmania major* STT3A protein, STT3B protein, STT3D protein, or combinations thereof. In particular aspects, the single-subunit oligosaccharyltransferase is the *Leishmania major* STT3D protein. In further aspects, the for example single-subunit oligosaccharyltransferase is the *Leishmania major* STT3D protein, which is capable of functionally suppressing (or rescuing or complementing) the lethal phenotype of at least one essential protein of the *Saccharomyces cerevisae* OTase complex. In further aspects, the endogenous host cell genes encoding the proteins comprising the endogenous oligosaccharyltransferase (OTase) complex are expressed.

In particular embodiments of any one of the above host cells, the *Trypanosoma brucei* STT3 protein is the *Trypanosoma brucei* STT3B protein. In another embodiment of the above host cells, the *Trypanosoma brucei* STT3 protein is the *Trypanosoma brucei* STT3C protein and the host cell further includes a nucleic acid that encodes and expresses the *Leishmania major* STT3D protein.

In further embodiments, the host cell further expresses an endomannosidase activity (e.g., a full-length endomannosidase or a chimeric endomannosidase comprising an endomannosidase catalytic domain fused to a cellular targeting signal peptide not normally associated with the catalytic domain and selected to target the endomannosidase activity to the ER or Golgi apparatus of the host cell. See for example, U.S. Pat. No. 7,332,299) and/or glucosidase II activity (a full-length glucosidase II or a chimeric glucosidase II comprising a glucosidase II catalytic domain fused to a cellular targeting signal peptide not normally associated with the catalytic domain and selected to target the glucosidase II activity to the ER or Golgi apparatus of the host cell. See for example, U.S. Pat. No. 6,803,225).

In particular aspects, the host cell further includes a deletion or disruption of the ALG6 (α1,3-glucosylatransferase) gene (alg6Δ), which has been shown to increase N-glycan occupancy of glycoproteins in alg3Δ host cells (See for example, De Pourcq et al., PloSOne 2012; 7(6): e39976. Epub 2012 Jun. 29, which discloses genetically engineering *Yarrowia lipolytica* to produce glycoproteins that have Man$_5$GlcNAc$_2$ (GS 1.3) or paucimannose N-glycan structures). The nucleic acid sequence encoding the *Pichia pastoris* ALG6 is disclosed in EMBL database, accession number CCCA38426. In further aspects, the host cell further includes a deletion or disruption of the OCH1 gene (och1Δ).

In particular aspects of any one of the above host cell, the host cell has a disruption or deletion of the expression of the Outer Chain (OCH1) gene and/or homologue thereof, the Acquired Thermo-Tolerance 1 (ATT1) gene or homologue thereof, or both. Disruption of expression includes but is not limited to deletion or disruption of the OCH1 gene or ORF encoding the Och1p and/or deletion or disruption of the ATT1 gene or ORF encoding the Att1p.

In further embodiments of any one of the above, the host cell is genetically engineered to produce glycoproteins comprising one or more N-glycans shown in FIG. 1. In further aspects of any one of the above methods, the host cell is genetically engineered to produce glycoproteins comprising one or more mammalian- or human-like complex N-glycans shown selected from G0, G1, G2, A1, or A2. In further embodiments, the host cell is genetically engineered to produce glycoproteins comprising one or more human-like complex N-glycans that bisected N-glycans or have multi-antennary N-glycans. In other embodiments, the host cell is genetically engineered to produce glycoproteins comprising one or more mammalian- or human-like hybrid N-glycans selected from GlcNAcMan$_3$GlcNAc$_2$; GalGlcNAcMan$_3$GlcNAc$_2$; and NANAGalGlcNAcMan$_3$GlcNAc$_2$. In further embodiments, the N-glycan structure consists of the paucimannose (G-2) structure Man$_3$GlcNAc$_2$ or the Man$_5$GlcNAc$_2$ (GS 1.3) structure.

In particular embodiments of any one of the above host cells, the heterologous protein or glycoprotein may be a therapeutic protein or glycoprotein (e.g., a protein or glycoprotein that may be administered to a human or animal patient). In further aspects, the therapeutic protein or glycoprotein may be for example, selected from the group consisting of erythropoietin (EPO); cytokines such as interferon α, interferon β, interferon γ, and interferon ω; and granulocyte-colony stimulating factor (GCSF); granulocyte macrophage-colony stimulating factor (GM-CSF); coagulation factors such as factor VIII, factor IX, and human protein C; antithrombin III; thrombin; soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4-Ig; transmembrane activator and calcium modulator and cyclophilin ligand; glucagon like protein 1; and IL-2 receptor agonist. In further aspects, the glycoprotein is a normally non-N-glycosylated protein that has been modified to comprise at least one N-linked glycosylation site. For example, insulin modified to comprise at least one N-linked glycosylation site.

In further embodiments of any one of the above host cells, the heterologous protein is an antibody, examples of which, include but are not limited to, an anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD1 is antibody, anti-EGF receptor antibody, or anti-CD20 antibody.

In particular aspects of the above host cells, the host cell includes one or more nucleic acid molecules encoding one or more catalytic domains of a glycosidase, mannosidase, or glycosyltransferase activity derived from a member of the group consisting of UDP-GlcNAc transferase (GnT) I, GnT II, GnT III, GnT IV, GnT V, GnT VI, UDP-galactosyltransferase (GalT), fucosyltransferase, and sialyltransferase. In particular embodiments, the mannosidase is selected from the group consisting of C. elegans mannosidase IA, C. elegans mannosidase IB, D. melanogaster mannosidase IA, H. sapiens mannosidase IB, P. citrinum mannosidase I, mouse mannosidase IA, mouse mannosidase IB, A. nidulans mannosidase IA, A. nidulans mannosidase IB, A. nidulans mannosidase IC, mouse mannosidase II, C. elegans mannosidase II, H. sapiens mannosidase II, and mannosidase III.

In certain aspects of any one of the above host cells, at least one catalytic domain is localized by forming a fusion protein comprising the catalytic domain and a cellular targeting signal peptide. The fusion protein can be encoded by at least one genetic construct formed by the in-frame ligation of a DNA fragment encoding a cellular targeting signal peptide with a DNA fragment encoding a catalytic domain having enzymatic activity. Examples of targeting signal peptides include, but are not limited to, those to membrane-bound proteins of the ER or Golgi, retrieval signals such as HDEL or KDEL, Type II membrane proteins, Type I membrane proteins, membrane spanning nucleotide sugar transporters, mannosidases, sialyltransferases, glucosidases, mannosyltransferases, and phosphomannosyltransferases.

In particular aspects of any one of the above host cells, the host cell further includes one or more nucleic acid molecules encoding one or more enzymes selected from the group consisting of UDP-GlcNAc transporter, UDP-galactose transporter, GDP-fucose transporter, CMP-sialic acid transporter, and nucleotide diphosphatases.

In further aspects of any one of the above host cells, the host cell includes one or more nucleic acid molecules encoding an α1,2-mannosidase activity, a UDP-GlcNAc transferase (GnT) I activity, a mannosidase II activity, and a GnT II activity.

In further still aspects of any one of the above host cells, the host cell includes one or more nucleic acid molecules encoding an α1,2-mannosidase activity, a UDP-GlcNAc transferase (GnT) I activity, a mannosidase II activity, a GnT II activity, and a UDP-galactosyltransferase (GalT) activity.

In a particular aspect of the host cells, the host cell includes a one or more nucleic acid molecules encoding an α1,2-mannosidase activity and a heterologous glycoprotein and the host cell lacks or does not display with respect to an N-glycan on a glycoprotein detectable phosphomannosyltransferase activity, initiating α1,6-mannosyltransferase activity, and β1,2-mannosyltransferase activity. In a further aspect, the host cell includes one or more nucleic acid molecules encoding an α1,2-mannosidase activity and an endomannosidase activity.

In further aspects of any one of the above host cells, the host cell is selected from the group consisting of Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Neurospora crassa, plant cells, insect cells, and mammalian cells.

In further still aspects of any one of the above host cells, the host cell is deficient in or does not display detectable activity of one or more enzymes selected from the group consisting of mannosyltransferases and phosphomannosyltransferases. In further still aspects, the host cell does not express an enzyme selected from the group consisting of 1,6 mannosyltransferase, 1,3 mannosyltransferase, and 1,2 mannosyltransferase.

In a particular aspect of any one of the above host cells, the host cell is *Pichia pastoris*. In a further aspect, the host cell is an och1 mutant of *Pichia pastoris*. In particular aspects of any one of the above, the host cell is an att1 mutant of *Pichia pastoris*. In particular aspects of any one of the above, the host cell is an att1 and och1 mutant of *Pichia pastoris*.

In a particular aspect of any one of the above host cells, the host cell is *Pichia pastoris* and lacks expression of the OCH1 gene, the ATT1 gene, or both the OCH1 and ATT1 genes.

In a particular aspect of any one of the above host cells, the host cell is *Pichia pastoris* and has a deletion or disruption of the OCH1 gene, the ATT1 gene, or both the OCH1 and ATT1 genes.

In a particular aspect of any one of the above host cells, the host cell is *Pichia pastoris* and lacks activity of the OCH1 gene, the ATT1 gene, or both the OCH1 and ATT1 genes.

The methods and host cells herein can be used to produce glycoprotein compositions in which at least 70%, 75%, 80%, 85%, 90%, 95%, 98%, or 99% of the N-glycosylation sites of the glycoproteins in the composition are occupied.

Further, the methods and host cells herein can be used to produce glycoprotein compositions in which at least 70%, 75%, 80%, 85%, 90%, 95%, 98%, or 99% of the N-glycosylation sites of the glycoproteins in the composition are occupied and which in further aspects have mammalian- or human-like N-glycans that lack fucose.

Further, the methods and yeast or filamentous fungus host cells are genetically engineered to produce mammalian-like or human-like N-glycans can be used to produce glycoprotein compositions in which at least 70%, 75%, 80%, 85%, 90%, 95%, 98%, or 99% of the N-glycosylation sites of the glycoproteins in the composition are occupied and which in further aspects have mammalian- or human-like N-glycans that lack fucose.

In some aspects, the yeast or filamentous host cells genetically engineered to produce fucosylated mammalian- or human-like N-glycans can be used to produce glycoprotein compositions in which at least 70%, 75%, 80%, 85%, 90%, 95%, 98%, or 99% of the N-glycosylation sites of the glycoproteins in the composition are occupied and which in further aspects have mammalian- or human-like N-glycans that have fucose.

The methods and host cells herein can be used to produce antibody compositions in which at least 70%, 75%, 80%, 85%, 90%, 95%, 98%, or 99% antibody molecules in the compositions have both N-glycosylation sites occupied.

Further, the methods and host cells herein can be used to produce antibody compositions in which at least 70%, 75%, 80%, 85%, 90%, 95%, 98%, or 99% antibody molecules in the compositions have both N-glycosylation sites occupied and the N-glycans lack fucose.

Further, the methods and yeast or filamentous fungus host cells herein can be used to produce antibody compositions in which at least 70%, 75%, 80%, 85%, 90%, 95%, 98%, or 99% antibody molecules in the compositions have both N-glycosylation sites occupied and the N-glycans lack fucose.

Further, the methods and yeast or filamentous fungus host cells genetically engineered to produce mammalian-like or human-like N-glycans can be used to produce antibody compositions in which at least 70%, 75%, 80%, 85%, 90%, 95%, 98%, or 99% antibody molecules in the compositions have both N-glycosylation sites occupied and the antibodies have mammalian- or human-like N-glycans that lack fucose.

In some aspects, the yeast or filamentous host cells genetically engineered to produce fucosylated mammalian- or human-like N-glycans can be used to produce antibody compositions in which at least 70%, 75%, 80%, 85%, 90%, 95%, 98% or 99% antibody molecules in the compositions have both N-glycosylation sites occupied and the antibodies have mammalian- or human-like N-glycans with fucose.

In particular embodiments, the antibodies comprise an antibody selected from the group consisting of anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, and anti-CD20 antibody.

Further provided are compositions comprising one ore more glycoproteins produced by the host cells and methods described herein.

In particular embodiments, the glycoprotein compositions provided herein comprise glycoproteins having fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the glycoprotein compositions provided herein comprise glycoproteins having at least one hybrid N-glycan selected from the group consisting of $GlcNAcMan_3GlcNAc_2$; $GalGlcNAcMan_3GlcNAc_2$; $NANAGalGlcNAcMan_3GlcNAc_2$; $GlcNAcMan_5GlcNAc_2$; $GalGlcNAcMan_5GlcNAc_2$; and $NANAGalGlcNAcMan_5GlcNAc_2$. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the glycoprotein compositions provided herein comprise glycoproteins having at least one complex N-glycan selected from the group consisting of $GlcNAc_2Man_3GlcNAc_2$; $GalGlcNAc_2Man_3GlcNAc_2$; $Gal_2GlcNAc_2Man_3GlcNAc_2$; $NANAGal_2GlcNAc_2Man_3GlcNAc_2$; and $NANA_2Gal_2GlcNAc_2Man_3GlcNAc_2$. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition.

In particular embodiments, the N-glycan is fusosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of $GlcNAcMan_5GlcNAc_2(Fuc)$, $GlcNAcMan_3GlcNAc_2(Fuc)$, $GlcNAc_2Man_3GlcNAc_2(Fuc)$, $GalGlcNAc_2Man_3GlcNAc_2(Fuc)$, $Gal_2GlcNAc_2Man_3GlcNAc_2(Fuc)$, NANAGal$_2$GlcNAc$_2$Man$_3$GlcNAc$_2$(Fuc), and NANA$_2$Gal$_2$GlcNAc$_2$Man$_3$GlcNAc$_2$(Fuc); in an α1,3-linkage or α1,4-linkage fucose to produce a glycoform selected from the group consisting of GlcNAc(Fuc)Man$_5$GlcNAc$_2$, GlcNAc(Fuc)Man$_3$GlcNAc$_2$, GlcNAc$_2$(Fuc$_{1-2}$)Man$_3$GlcNAc$_2$, GalGlcNAc$_2$(Fuc$_{1-2}$)Man$_3$GlcNAc$_2$, Gal$_2$GlcNAc$_2$(Fuc1-2)Man3GlcNAc2, NANAGal2GlcNAc2(Fuc$_{1-2}$)Man$_3$GlcNAc$_2$, and NANA$_2$Gal2GlcNAc$_2$(Fuc$_{1-2}$)Man$_3$GlcNAc$_2$; or in an α1,2-linkage fucose to produce a glycoform selected from the group consisting of Gal(Fuc)GlcNAc$_2$Man$_3$GlcNAc$_2$, Gal$_2$(Fuc$_{1-2}$)GlcNAc$_2$Man$_3$GlcNAc$_2$, NANAGal$_2$(Fuc$_{1-2}$)GlcNAc$_2$Man$_3$GlcNAc$_2$, and NANA$_2$Gal$_2$(Fuc$_{1-2}$)GlcNAc$_2$Man$_3$GlcNAc$_2$.

In further aspects of the above, the complex N-glycans further include fucosylated and non-fucosylated bisected and multiantennary species.

In further aspects, the glycoproteins comprise high mannose N-glycans, including but not limited to, Man$_5$GlcNAc$_2$, or N-glycans that consist of the Man$_3$GlcNAc$_2$ N-glycan structure.

The present invention provides for the use of a host cell comprising (a) a disruption or deletion in the expression of the endogenous dolichyl-P-Man:Man$_5$GlcNAc$_2$-PP-dolichyl alpha-1,3 mannosyltransferase (ALG3) gene; (b) a disruption or deletion in the expression of the endogenous osteosarcoma 9 (OS-9) family gene or homolog; and (c) a nucleic acid molecule encoding a *Trypanosoma brucei* STT3 protein integrated into the genome of the host cell for the manufacture of a medicament for treating a disease. In particular embodiments, the *Trypanosoma brucei* STT3 protein is the *Trypanosoma brucei* STT3B protein. In another embodiment, the *Trypanosoma brucei* STT3 protein is the *Trypanosoma brucei* STT3C protein and the host cell further includes a nucleic acid that encodes and expresses the *Leishmania major* STT3D protein.

The present invention provides for the use of any one of the foregoing host cells for the manufacture of a medicament for treating a disease.

DEFINITIONS

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetylneuraminic acid (NANA)). The processing of the sugar groups occurs co-translationally in the lumen of the ER and continues post-translationally in the Golgi apparatus for N-linked glycoproteins.

N-glycans have a common pentasaccharide core of Man$_3$GlcNAc$_2$ ("Man" refers to mannose; "Glc" refers to glucose; and "NAc" refers to N-acetyl; GlcNAc refers to N-acetylglucosamine) Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the Man$_3$GlcNAc$_2$ ("Man3") core structure which is also referred to as the "triammnose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal mannose of the 1,3 mannose arm of the trimannose core and zero or more mannoses on the 1,6 mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as Man$_3$GlcNAc$_2$ or paucimannose; the term "G-1" refers to an N-glycan structure that can be characterized as GlcNAcMan$_3$GlcNAc$_2$; the term "G0" refers to an N-glycan structure that can be characterized as GlcNAc$_2$Man$_3$GlcNAc$_2$; the term "G1" refers to an N-glycan structure that can be characterized as GalGlcNAc$_2$Man$_3$GlcNAc$_2$; the term "G2" refers to an N-glycan structure that can be characterized as Gal$_2$GlcNAc$_2$Man$_3$GlcNAc$_2$; the term "A1" refers to an N-glycan structure that can be characterized as NANAGal$_2$GlcNAc$_2$Man$_3$GlcNAc$_2$; and, the term "A2" refers to an N-glycan structure that can be characterized as NANA$_2$Gal$_2$GlcNAc$_2$Man$_3$GlcNAc$_2$. Unless otherwise indicated, the terms G-2", "G-1", "G0", "G1", "G2", "A1", and "A2" refer to N-glycan species that lack fucose attached to the GlcNAc residue at the reducing end of the N-glycan. When the term includes an "F", the "F" indicates that the N-glycan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas GlcNAc$_{(2-4)}$Man$_3$GlcNAc$_2$, Gal$_{(1-4)}$GlcNAc$_{(2-4)}$Man$_3$GlcNAc$_2$, or NANA$_{(1-4)}$Gal$_{(1-4)}$GlcNAc$_{(2-4)}$Man$_3$GlcNAc$_2$. The term "1-4" refers to 1, 2, 3, or 4 residues.

With respect to bisected N-glycans, the term "bisected N-glycan" refers to N-glycans in which a GlcNAc residue is linked to the mannose residue at the reducing end of the N-glycan. A bisected N-glycan can be characterized by the formula GlcNAc$_3$Man$_3$GlcNAc$_2$ wherein each mannose residue is linked at its non-reducing end to a GlcNAc residue. In contrast, when a multiantennary N-glycan is characterized as GlcNAc$_3$Man$_3$GlcNAc$_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

Abbreviations used herein are of common usage in the art, see, e.g., abbreviations of sugars, above. Other common abbreviations include "PNGase", or "glycanase" or "glucosidase" which all refer to peptide N-glycosidase F (EC 3.2.2.18).

As used herein, the term "glycoprotein" refers to any protein having one or more N-glycans attached thereto. Thus, the term refers both to proteins that are generally recognized in the art as a glycoprotein and to proteins which have been genetically engineered to contain one or more N-linked glycosylation sites, for example insulin modified to comprise one or more N-linked glycosylation sites.

As used herein, the term "heterologous glycoprotein" or "recombinant heterologous glycoprotein" refers to a glycoprotein that is not endogenous to or not normally present in the host cell. The "heterologous glycoprotein" or "recombinant heterologous glycoprotein" is expressed from a nucleic acid molecule that has been introduced into the host cell using recombinant DNA methodologies. In further aspects, the "heterologous glycoprotein" or "recombinant heterologous glycoprotein" is a therapeutic glycoprotein used for the treatment or amelioration of a disease in humans or animals.

As used herein, a "humanized glycoprotein" or a "humanlike glycoprotein" refers alternatively to a protein having attached thereto N-glycans having fewer than four mannose residues, and synthetic glycoprotein intermediates (which are also useful and can be manipulated further in vitro or in vivo) having at least five mannose residues. Preferably, glycoproteins produced according to the invention contain at least 30 mole %, preferably at least 40 mole % and more preferably 50, 60, 70, 80, 90, or even 100 mole % of the $Man_5GlcNAc_2$ intermediate, at least transiently. This may be achieved, e.g., by engineering a host cell of the invention to express a "better", i.e., a more efficient glycosylation enzyme. For example, a mannosidase is selected such that it will have optimal activity under the conditions present at the site in the host cell where proteins are glycosylated and is introduced into the host cell preferably by targeting the enzyme to a host cell organelle where activity is desired.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. Preferred host cells are yeasts and fungi.

When referring to "mole percent" of a glycan present in a preparation of a glycoprotein, the term means the molar percent of a particular glycan present in the pool of N-linked oligosaccharides released when the protein preparation is treated with PNGase and then quantified by a method that is not affected by glycoform composition, (for instance, labeling a PNGase released glycan pool with a fluorescent tag such as 2-aminobenzamide and then separating by high performance liquid chromatography or capillary electrophoresis and then quantifying glycans by fluorescence intensity). For example, 50 mole percent $GlcNAc_2Man_3GlcNAc_2Gal_2NANA_2$ means that 50 percent of the released glycans are $GlcNAc_2Man_3GlcNAc_2Gal_2NANA_2$ and the remaining 50 percent are comprised of other N-linked oligosaccharides. In embodiments, the mole percent of a particular glycan in a preparation of glycoprotein will be between 20% and 100%, preferably above 25%, 30%, 35%, 40% or 45%, more preferably above 50%, 55%, 60%, 65% or 70% and most preferably above 75%, 80% 85%, 90% or 95%.

The term "operably linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "transfect", transfection", "transfecting" and the like refer to the introduction of a heterologous nucleic acid into eukaryote cells, both higher and lower eukaryote cells. Historically, the term "transformation" has been used to describe the introduction of a nucleic acid into a yeast or fungal cell; however, herein the term "transfection" is used to refer to the introduction of a nucleic acid into any eukaryote cell, including yeast and fungal cells.

The term "eukaryotic" refers to a nucleated cell or organism, and includes insect cells, plant cells, mammalian cells, animal cells and lower eukaryotic cells.

The term "lower eukaryotic cells" includes yeast and filamentous fungi. Yeast and filamentous fungi include, but are not limited to *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa. Pichia* sp., any *Saccharomyces* sp., *Hansenula polymorpha*, any *Kluyveromyces* sp., *Candida albicans*, any

*Aspergillus* sp., *Trichoderma reesei*, *Chrysosporium lucknowense*, any *Fusarium* sp. and *Neurospora crassa*.

As used herein, the terms "antibody," "immunoglobulin," "immunoglobulins" and "immunoglobulin molecule" are used interchangeably. Each immunoglobulin molecule has a unique structure that allows it to bind its specific antigen, but all immunoglobulins have the same overall structure as described herein. The basic immunoglobulin structural unit is known to comprise a tetramer of subunits. Each tetramer has two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Light chains are classified as either kappa or lambda. Heavy chains are classified as gamma, mu, alpha, delta, or epsilon, and define the antibody's isotype as IgG, IgM, IgA, IgD, and IgE, respectively.

The light and heavy chains are subdivided into variable regions and constant regions (See generally, Fundamental Immunology (Paul, W., ed., 2nd ed. Raven Press, N. Y., 1989), Ch. 7. The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. The terms include naturally occurring forms, as well as fragments and derivatives. Included within the scope of the term are classes of immunoglobulins (Igs), namely, IgG, IgA, IgE, IgM, and IgD. Also included within the scope of the terms are the subtypes of IgGs, namely, IgG1, IgG2, IgG3, and IgG4. The term is used in the broadest sense and includes single monoclonal antibodies (including agonist and antagonist antibodies) as well as antibody compositions which will bind to multiple epitopes or antigens. The terms specifically cover monoclonal antibodies (including full length monoclonal antibodies), polyclonal antibodies, multispecific antibodies (for example, bispecific antibodies), and antibody fragments so long as they contain or are modified to contain at least the portion of the CH2 domain of the heavy chain immunoglobulin constant region which comprises an N-linked glycosylation site of the CH2 domain, or a variant thereof. Included within the terms are molecules comprising only the Fc region, such as immunoadhesions (U.S. Published Patent Application No. 2004/0136986; the disclosure of which is incorporated herein by reference), Fc fusions, and antibody-like molecules.

The term "Fc fragment" refers to the 'fragment crystallized' C-terminal region of the antibody containing the CH2 and CH3 domains. The term "Fab fragment" refers to the 'fragment antigen binding' region of the antibody containing the VH, CH1, VL and CL domains.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, monoclonal antibodies are advantageous in that they can be produced, for example, by hybridoma culture, uncontaminated by other immunoglobulins. The term "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) Nature, 256:495, or may be made by recombinant DNA methods (See, for example, U.S. Pat. No. 4,816,567; the disclosure of which is incorporated herein by reference).

The term "fragments" within the scope of the terms "antibody" or "immunoglobulin" include those produced by digestion with various proteases, those produced by chemical cleavage and/or chemical dissociation and those produced recombinantly, so long as the fragment remains capable of specific binding to a target molecule. Among such fragments are Fc, Fab, Fab', Fv, F(ab')2, and single chain Fv (scFv) fragments. Hereinafter, the term "immunoglobulin" also includes the term "fragments" as well.

Immunoglobulins further include immunoglobulins or fragments that have been modified in sequence but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (See, for example, Intracellular Antibodies: Research and Disease Applications, (Marasco, ed., Springer-Verlag New York, Inc., 1998).

The term "catalytic antibody" refers to immunoglobulin molecules that are capable of catalyzing a biochemical reaction. Catalytic antibodies are well known in the art and have been described in U.S. Pat. Nos. 7,205,136; 4,888,281; 5,037,750 to Schochetman et al., U.S. Pat. Nos. 5,733,757; 5,985,626; and 6,368,839 to Barbas, III et al. (the disclosures of which are all incorporated herein by reference).

The interaction of antibodies and antibody-antigen complexes with cells of the immune system and the variety of responses, including antibody-dependent cell-mediated cytotoxicity (ADCC) and complement-dependent cytotoxicity (CDC), clearance of immunocomplexes (phagocytosis), antibody production by B cells and IgG serum half-life are defined respectively in the following: Daeron et al., Annu. Rev. Immunol. 15: 203-234 (1997); Ward and Ghetie, Therapeutic Immunol. 2:77-94 (1995); Cox and Greenberg, Semin. Immunol. 13: 339-345 (2001); Heyman, Immunol. Lett. 88:157-161 (2003); and Ravetch, Curr. Opin. Immunol. 9: 121-125 (1997).

As used herein, the term "consisting essentially of" will be understood to imply the inclusion of a stated integer or group of integers; while excluding modifications or other integers which would materially affect or alter the stated integer. With respect to species of N-glycans, the term "consisting essentially of" a stated N-glycan will be understood to include the N-glycan whether or not that N-glycan is fucosylated at the N-acetylglucosamine (GlcNAc) which is directly linked to the asparagine residue of the glycoprotein.

As used herein, the term "predominantly" or variations such as "the predominant" or "which is predominant" will be understood to mean the glycan species that has the highest mole percent (%) of total neutral N-glycans after the glycoprotein has been treated with PNGase and released glycans analyzed by mass spectroscopy, for example, MALDI-TOF MS or HPLC. In other words, the phrase "predominantly" is defined as an individual entity, such as a specific glycoform, is present in greater mole percent than any other individual entity. For example, if a composition consists of species A at 40 mole percent, species B at 35 mole percent and species C at 25 mole percent, the composition comprises predominantly species A, and species B would be the next most predominant species. Some host cells may produce compositions comprising neutral N-glycans and charged N-glycans such as mannosylphosphate. Therefore, a composition of glycoproteins can include a plurality of charged and uncharged or neutral N-glycans. In the present invention, it is within the context of the total plurality of neutral N-glycans in the composition in which the predominant N-glycan determined. Thus, as used herein, "predominant N-glycan" means that of the total plurality of neutral N-glycans in the composition, the predominant N-glycan is of a particular structure.

As used herein, the term "essentially free of" a particular sugar residue, such as fucose, or galactose and the like, is used to indicate that the glycoprotein composition is substantially devoid of N-glycans which contain such residues. Expressed in terms of purity, essentially free means that the amount of N-glycan structures containing such sugar residues does not exceed 10%, and preferably is below 5%, more preferably below 1%, most preferably below 0.5%, wherein the percentages are by weight or by mole percent. Thus, substantially all of the N-glycan structures in a glycoprotein composition according to the present invention are free of, for example, fucose, or galactose, or both.

As used herein, a glycoprotein composition "lacks" or "is lacking" a particular sugar residue, such as fucose or galactose, when no detectable amount of such sugar residue is present on the N-glycan structures at any time. For example, in preferred embodiments of the present invention, the glycoprotein compositions are produced by lower eukaryotic organisms, as defined above, including yeast (for example, *Pichia* sp.; *Saccharomyces* sp.; *Kluyveromyces* sp.; *Aspergillus* sp.), and will "lack fucose," because the cells of these organisms do not have the enzymes needed to produce fucosylated N-glycan structures. Thus, the term "essentially free of fucose" encompasses the term "lacking fucose." However, a composition may be "essentially free of fucose" even if the composition at one time contained fucosylated N-glycan structures or contains limited, but detectable amounts of fucosylated N-glycan structures as described above.

Figure 11:
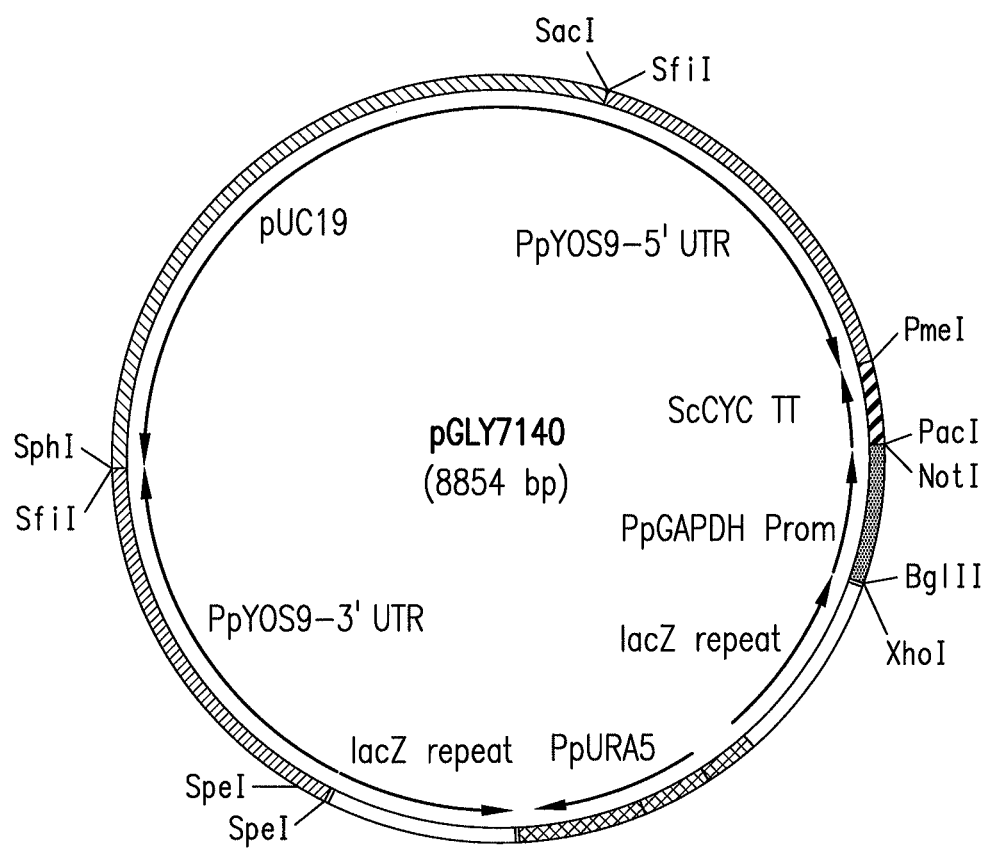

FIG. 11 shows a map of plasmid pGLY7140. The plasmid is a knock-out vector that targets the YOS9 locus comprising the *P. pastoris* URA5 gene or transcription unit (PpURA5) flanked by lacZ repeats (lacZ repeat) for selection flanked on one side with the 5' nucleotide sequence of the *P. pastoris* YOS9 gene (PpYOS9-5') and on the other side with the 3' nucleotide sequence of the *P. pastoris* YOS9 gene (PpYOS9-3').

Figure 12:
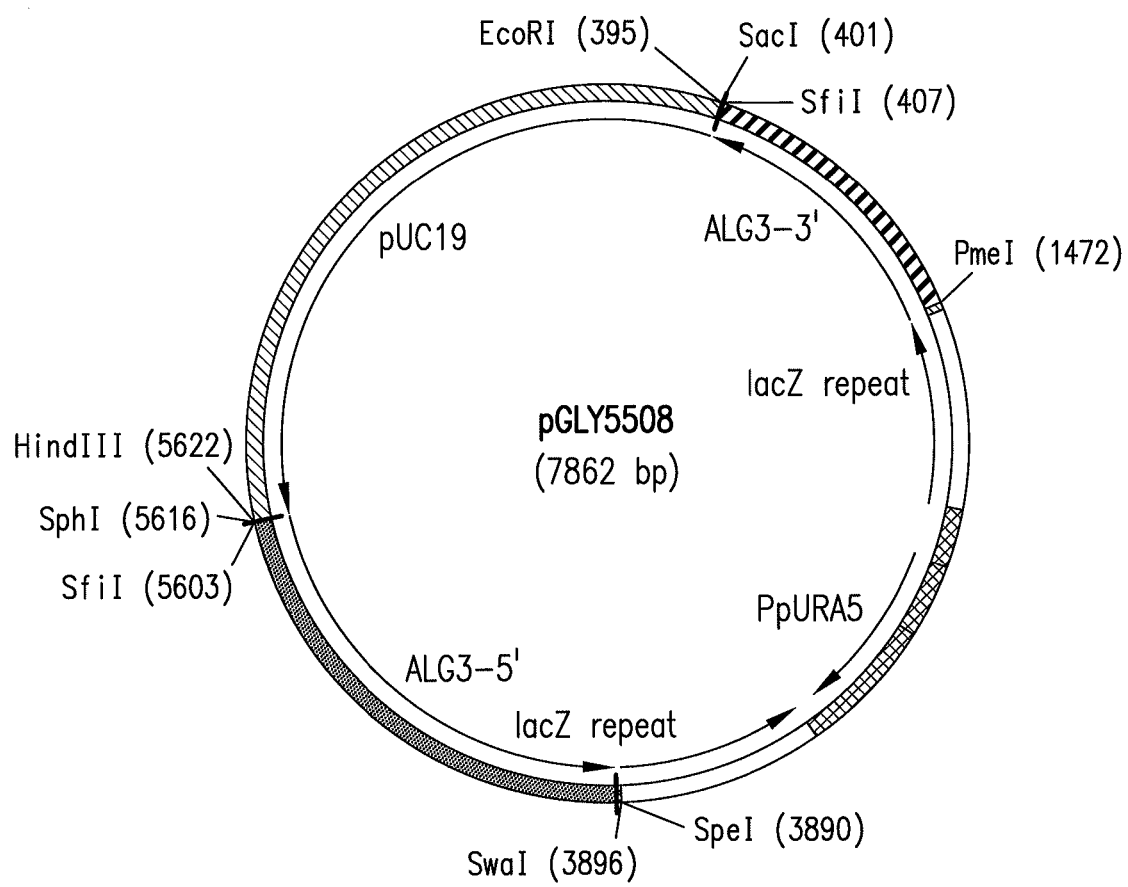

FIG. 12 shows a map of plasmid pGLY5508. The plasmid is a knock-out vector that targets the ALG3 locus comprising the *P. pastoris* URA5 gene or transcription unit (PpURA5) flanked by lacZ repeats (lacZ repeat) for selection flanked on one side with the 5' nucleotide sequence of the *P. pastoris* ALG3 gene (PpALG3-5') and on the other side with the 3' nucleotide sequence of the *P. pastoris* ALG3 gene (PpALG3-3').

Figure 13:
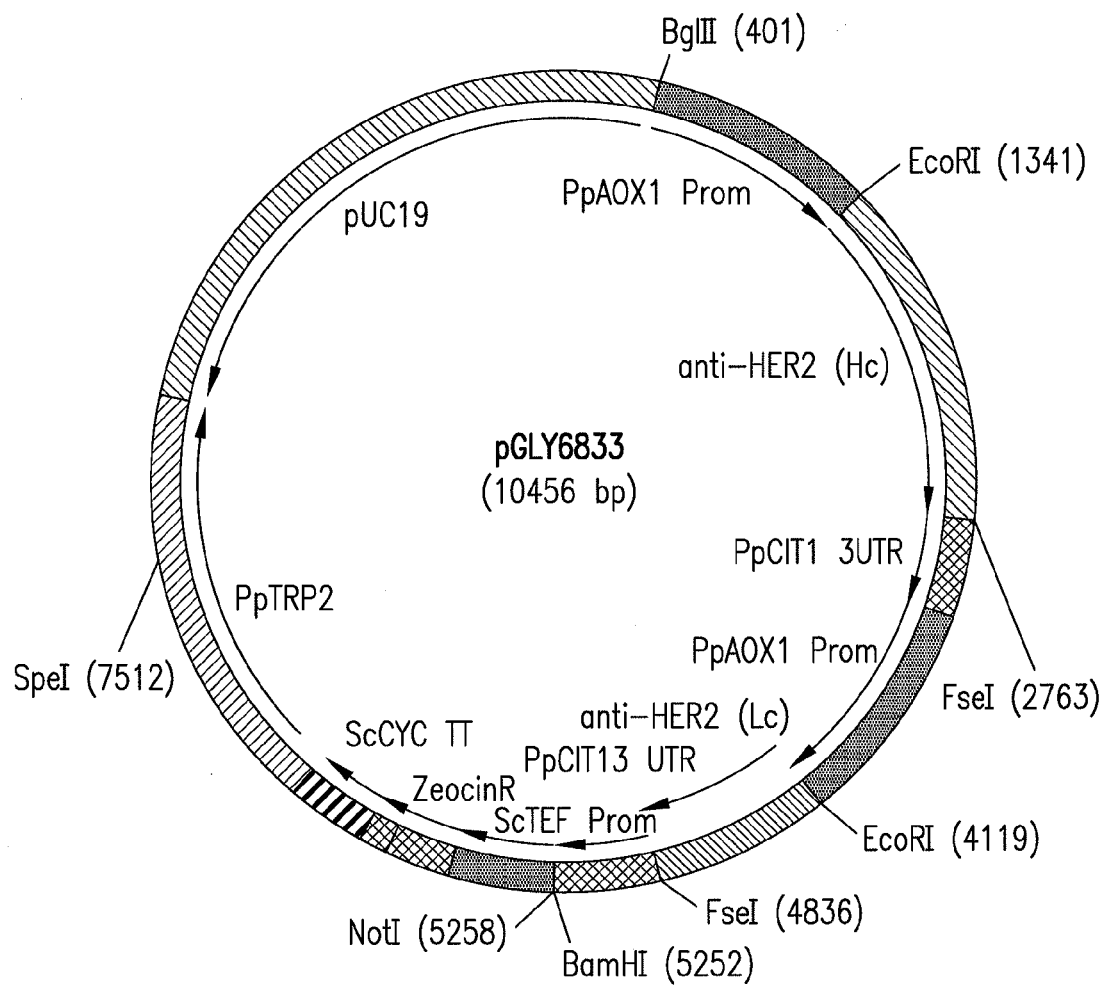

FIG. 13 shows a map of pGLY6833 encoding the light and heavy chains of an anti-Her2 antibody. The plasmid is a roll-in vector that targets the TRP2 locus. The ORFs encoding the light and heavy chains are under the control of a *P. pastoris* AOX1 promoter and the *P. pastoris* CIT1 transcription termination sequence. Selection of transformants uses zeocin resistance encoded by the zeocin resistance protein (ZeocinR) ORF under the control of the *S. cerevisiae* TEF1 promoter and *S. cerevisiae* CYC termination sequence.

Figure 14:
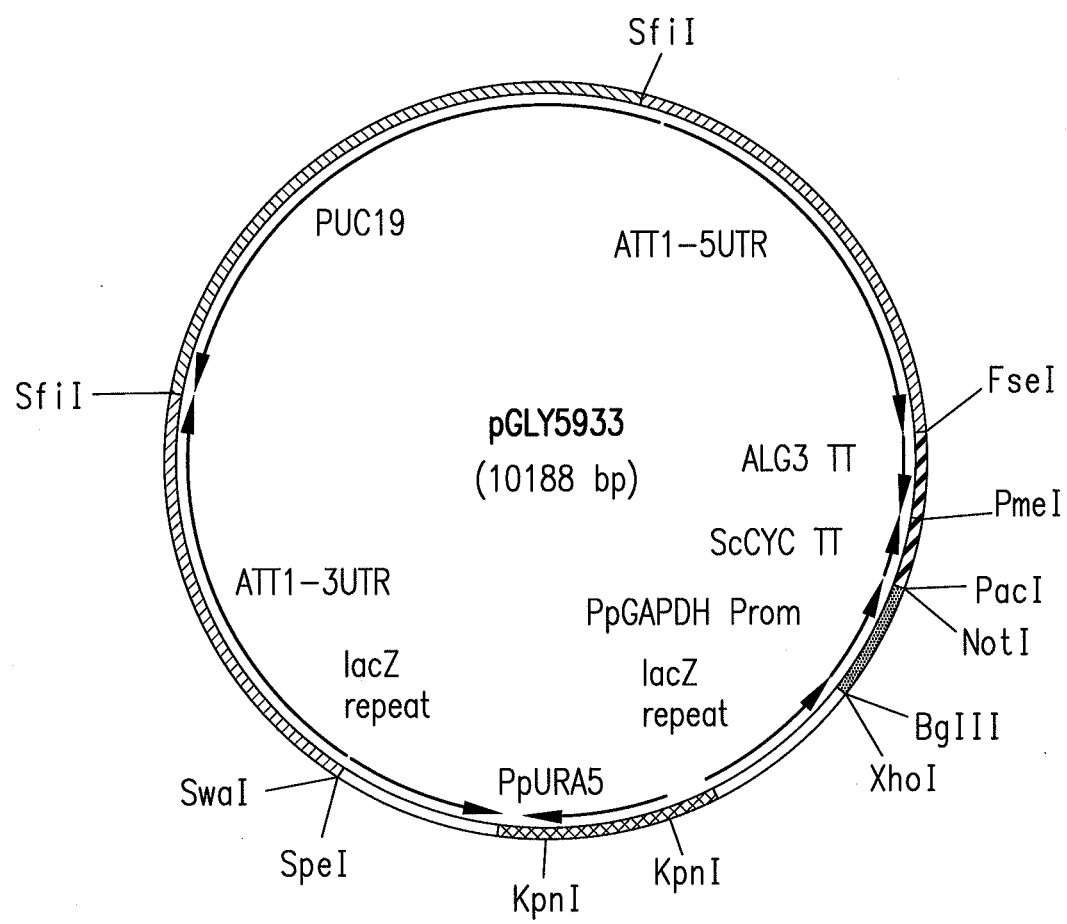

FIG. 14 shows a map of plasmid pGLY5933. The plasmid contains an expression cassette for selection comprising the *P. pastoris* URA5 gene or transcription unit (PpURA5) flanked by lacZ repeats (lacZ repeat) flanked on one side with the 5' nucleotide sequence of the *P. pastoris* ATT1 gene (ATT1-5UTR') and on the other side with the 3' nucleotide sequence of the *P. pastoris* ATT1 gene (ATT1-3UTR).

Figure 15:
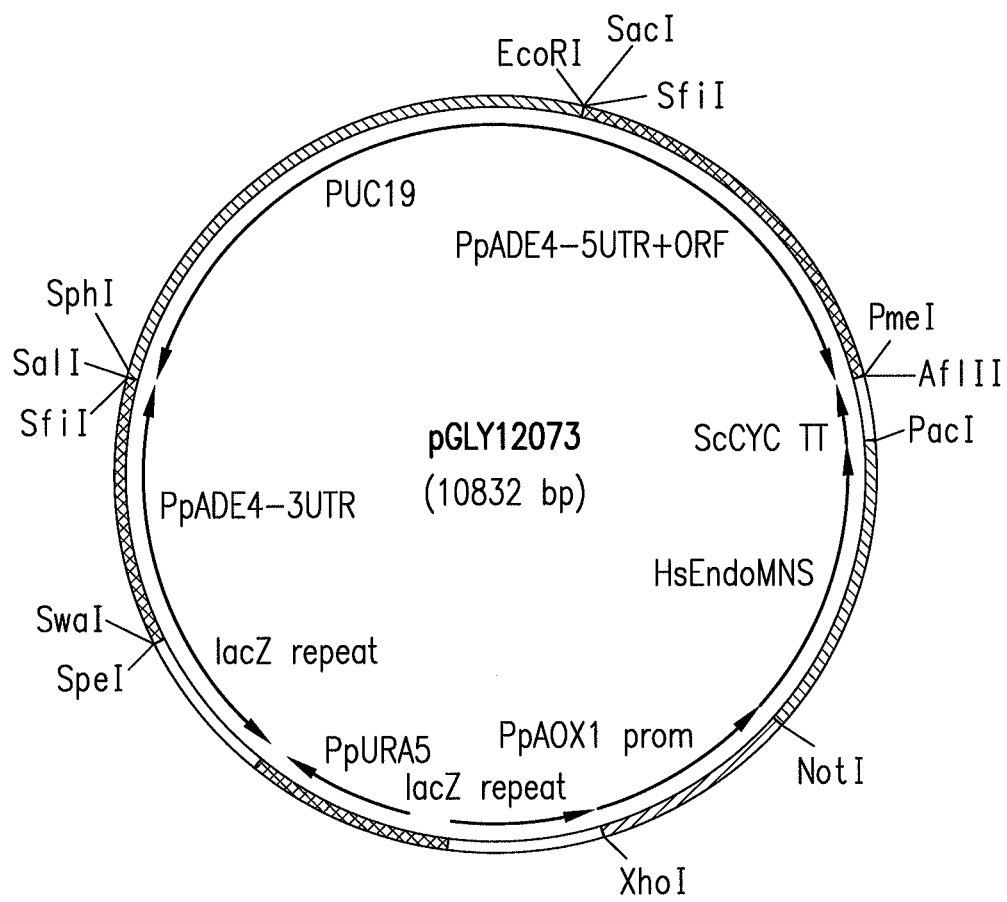

FIG. 15 shows a map of plasmid pGLY12073. The plasmid contains an expression cassette comprising the *P. pastoris* URA5 gene or transcription unit (PpURA5) flanked by lacZ repeats (lacZ repeat) for selection adjacent to an expression cassette encoding the full-length human endomannosidase operably linked to the *P. pastoris* AOX1 promoter and the *S. cerevisiae* CYC transcription termination sequence. The expression cassettes are flanked on one side with the 5' nucleotide sequence of the *P. pastoris* ADE4 gene and on the other side with the 3' nucleotide sequence of the *P. pastoris* ADE4 gene.

Figure 16:
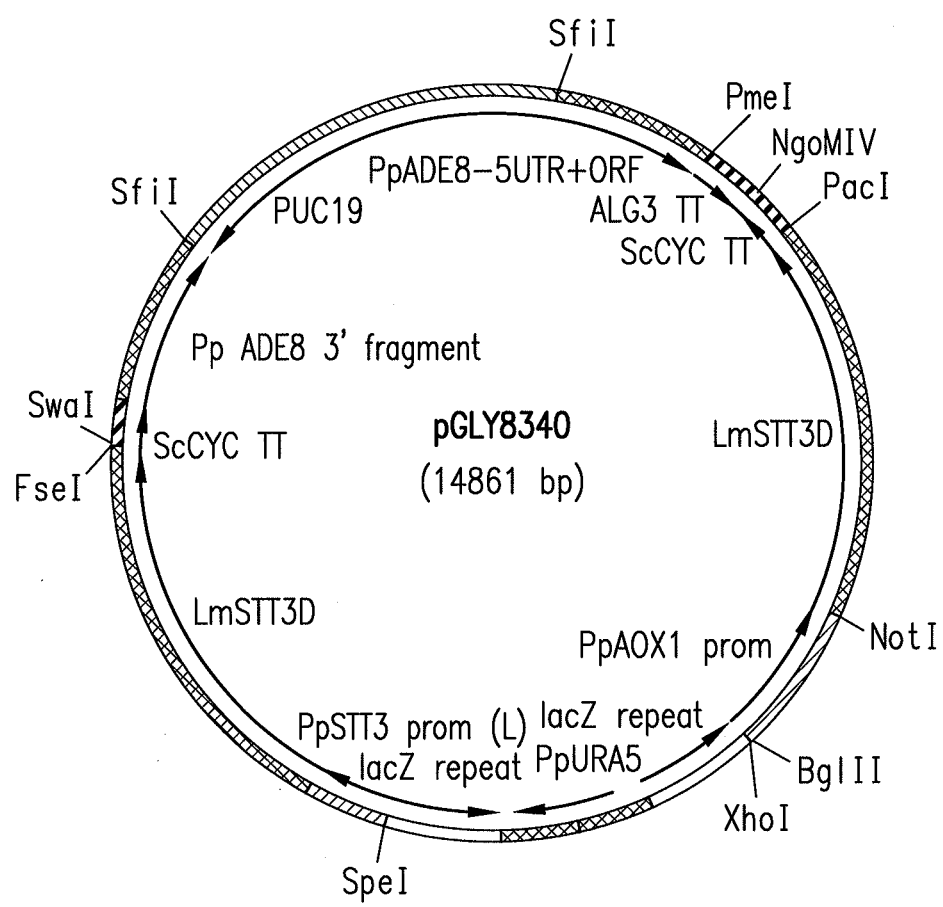

FIG. 16 shows a map of plasmid pGLY8340 encoding two LmSTT3D ORFs. One LmSTT3D ORF is operably linked to the *Pichia pastoris* alcohol oxidase I (AOX1) promoter and *S. cerevisiae* CYC transcription termination sequence. The other LmSTT3D ORF is operably linked to the *P. pastoris* STT3 promoter and the *S. cerevisiae* CYC transcription termination sequence. The plasmid targets the ADE8 locus. The plasmid contains an expression cassette comprising the *P. pastoris* URA5 gene or transcription unit (PpURA5) flanked by lacZ repeats (lacZ repeat) for selection situated between the two LmSTT3D ORFs.

Figure 17:
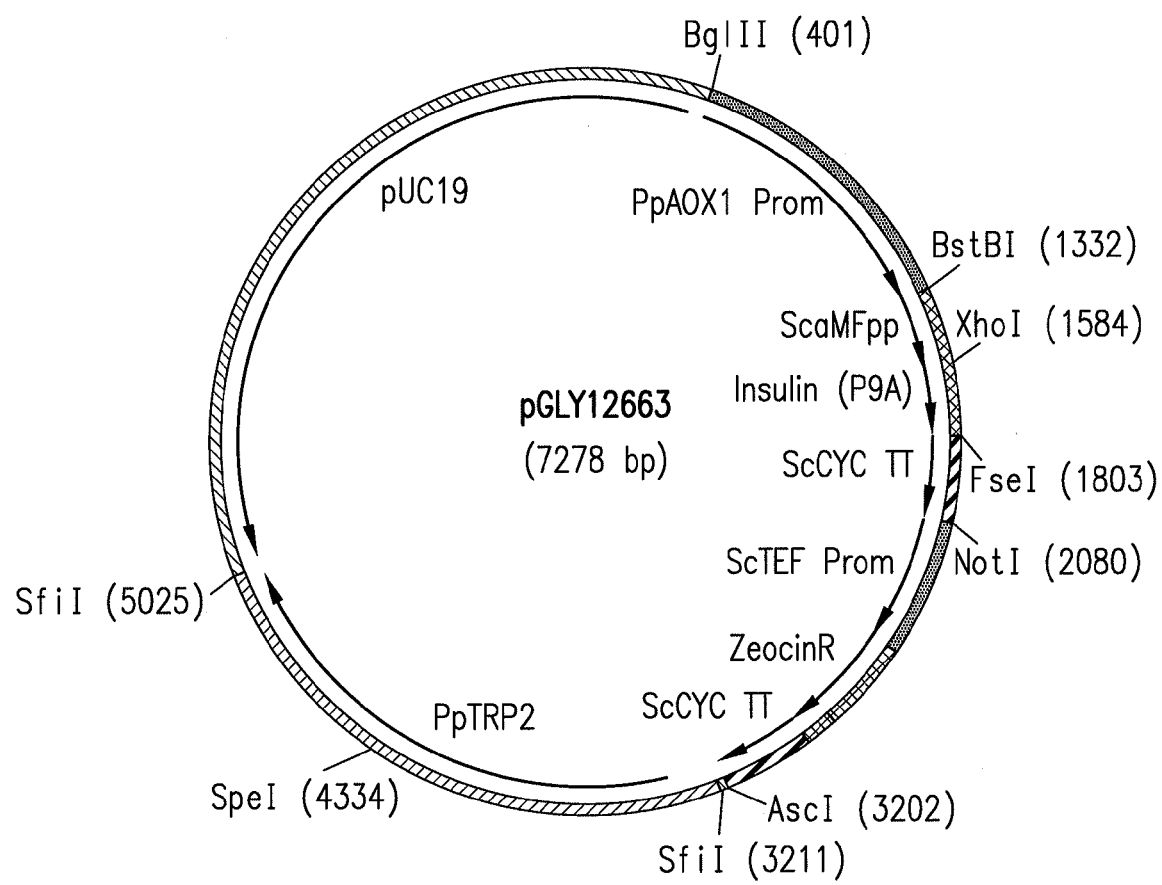

FIG. 17 shows a map of plasmid pGLY12663. The plasmid may target the TRP2 or AOX1p locus. The plasmid further includes an expression cassette encoding an insulin precursor fusion protein comprising a *S. cerevisiae* alpha mating factor signal sequence and propeptide fused to an N-terminal spacer peptide fused to the human insulin B-chain with NGT(−2) tripeptide addition and a P28N substitution fused to a C-peptide consisting of the amino acid sequence AAK fused to the human insulin A-chain. Selection of transformants uses zeocin resistance encoded by the zeocin resistance protein (ZeocinR) ORF under the control of the *S. cerevisiae* TEF1 promoter and *S. cerevisiae* CYC termination sequence.

DETAILED DESCRIPTION OF THE INVENTION

The present invention provides host cells and methods for increasing yield and N-glycosylation site occupancy as well as N-glycan quality, either complex or paucimannose ($Man_3GlcNAc_2$) in recombinant host cells that do not display with respect to a glycoprotein dolichyl-P-Man:$Man_5GlcNAc_2$-PP-dolichyl alpha-1,3 mannosyltransferase activity (Alg3p) activity. The increase in N-glycosylation site occupancy and N-glycan quality in recombinant host cells that do not display Alg3p activity is achieved by rendering the host cell to not display osteosarcoma 9 (OS-9) family gene protein activity and further expressing in the host cell a nucleic acid molecule encoding a *Trypanosoma brucei* STT3B protein integrated into the genome of the host cell. Host cells that do not display Alg3p or Os-9p activity or do not display ALG3 or OS-9 gene expression are designated herein as alg3Δ os-9Δ. OS-9 gene family includes genes or open reading frames encoding proteins of similar structure found in the genome of organisms including without limitation *Saccharomyces cerevisiae*, *Pichia pastoris*, *Schizosaccharomyces pombe*, *Caenorhabditis elegans*, and *Homo sapiens*.

In general, the yeast host cells herein lack detectable or have a disruption of expression of the ALG3 gene encoding Alg3p and lack detectable or have a disruption of expression of the YOS9 gene encoding Yos9p. Lack of detectable or disruption of expression may be achieved by a deletion or disruption of the ALG3 and/or YOS9 genes, mutation of the ALG3 and/or YOS9 genes such that the Alg3p and/or Yos9p lack detectable activity, small molecule inhibitors of the Alg3p and/or Yos9p which reduce or abrogate activity of the Alg3p and/or Yos9p, siRNA inhibitors of the Alg3p and/or Yos9p, or antisense RNA inhibitors of the Alg3p and/or Yos9p, or combinations thereof. Yeast host cells that do not display Alg3p or Yos9p activity or do not display ALG3 or YOS9 gene expression are designated herein as alg3Δ yos9Δ.

YOS9 is a yeast homolog of the human gene OS-9, which is overexpressed in osteosarcomas (Friedman et al., J. Biol. Chem. 277: 35274-35281 (2002); GenBank Accession No. CAY70383). The YOS9 gene encodes Yos9p, a lectin protein, which has been shown in *Saccharomyces cerevisiae* to be involved in the ER-associated degradation (ERAD) pathway, a quality control pathway in the ER that detects and targets misfolded glycoproteins for degradation in the cytosol (See Kim et al., Mol. Cell. 16: 741-751 (2005). Quan et al., Mol. Cell 32: 870-877 (2008) has shown that in the ERAD pathway, misfolded glycoproteins are modified to contain N-glycans that have a terminal α1,6-linked mannose. Yos9p is a sensor protein that recognizes N-glycans containing these terminal α1,6-linked mannose residues and targets glycoproteins that have them for degradation. In alg3Δ strains, the $Man_5GlcNAc_2$ oligosaccharide that is transferred to the N-linked glycosylation site also has a terminal α1,6-linked mannose residues, which may render the glycoprotein a substrate for the ERAD pathway (Clerc et al., J. Cell Biol. 184: 159-172 (2009)). The *Saccharomyces cerevisiae* Yos9p protein has the amino acid sequence shown in SEQ ID NO:40, which is encoded by the YOS9 nucleotide sequence shown in SEQ ID NO:41. The *Pichia pastoris* Yos9p protein has the amino acid sequence shown in SEQ ID NO:42, which is encoded by the YOS9 nucleotide sequence shown in SEQ ID NO:43. The *Aspergillus fumigates* Yos9p protein has the amino acid sequence shown in SEQ ID NO:44, which is encoded by the YOS9 nucleotide sequence shown in SEQ ID NO:45. The *Schizosaccharomyces pombe* Yos9p protein has the amino acid sequence shown in SEQ ID NO:46, which is encoded by the YOS9 nucleotide sequence shown in SEQ ID NO:47.

In the present invention, disruption or deletion of YOS9 gene expression in recombinant host cells that lack detectable or have a disruption of ALG3 gene expression (i.e., alg3Δ host cells) and further include a nucleic acid molecule encoding a *Trypanosoma brucei* STT3 protein results in a host cell that is capable of producing recombinant heterologous glycoproteins in which the yield of the recombinant glycoproteins is increased compared to host cells that express the host cell's endogenous YOS9. Thus, the yield of paucimannose N-glycans in such host cells further modified to include an α1,2-mannosidase activity targeted to the ER or Golgi apparatus or the yield of complex N-glycans when these host cells are further modified to include one more glycosylation enzymes to enable the host cells to produce glycoproteins that have human-like N-glycosylation patterns or that have predominantly particular N-glycan structures is increased compared to host cells that express the host cell's endogenous YOS9. In particular embodiments, the *Trypanosoma brucei* STT3 protein is the *Trypanosoma brucei* STT3B protein or the *Trypanosoma brucei* STT3A protein or the *Trypanosoma brucei* STT3C protein.

Figure 1:
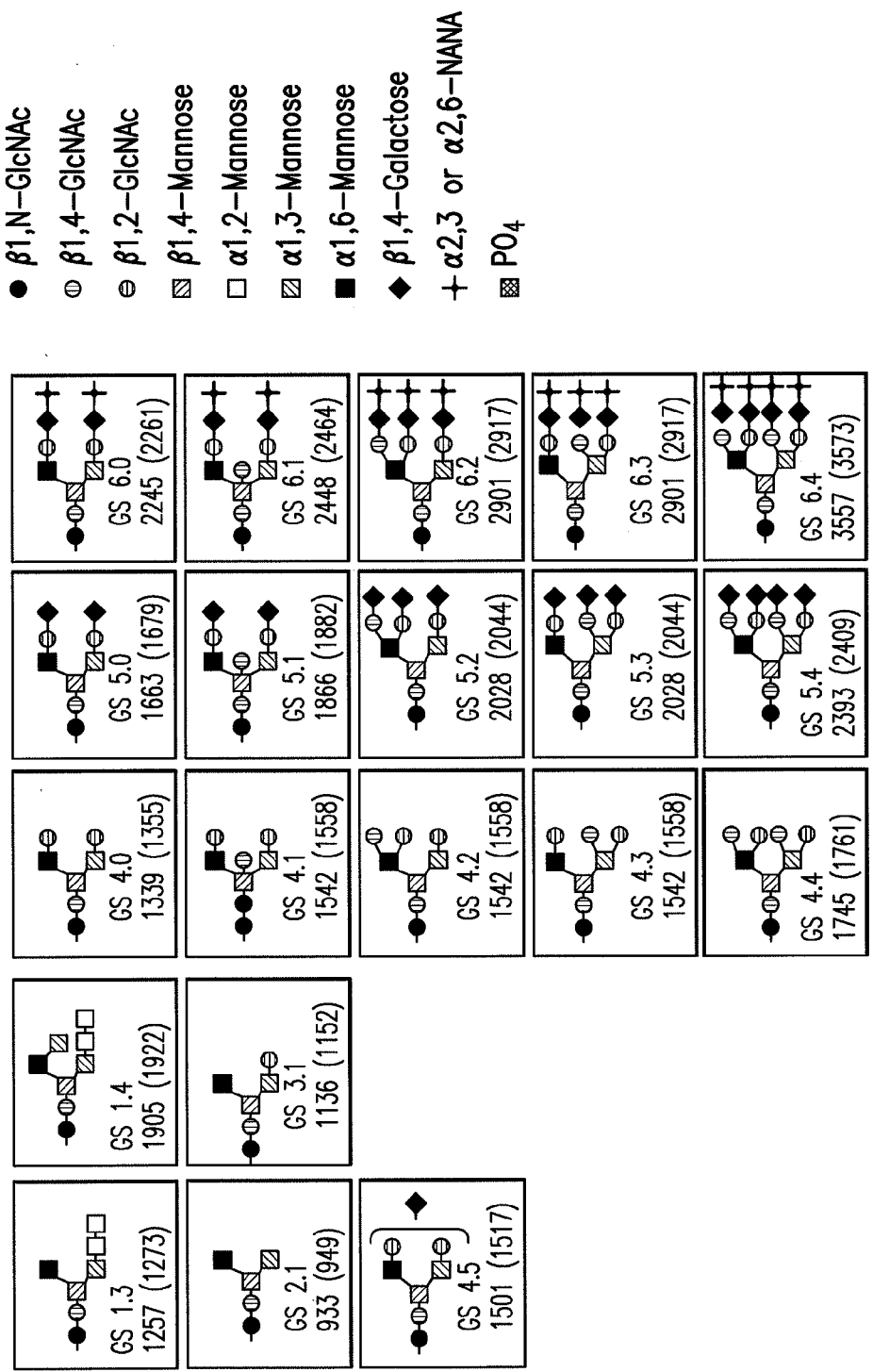
FIG. 1 shows examples of N-glycan structures that can be attached to the asparagine residue in the motif Asn-Xaa-Ser/Thr wherein Xaa is any amino acid other than proline or attached to any amino acid in vitro. Recombinant host cells can be genetically modified to produce glycoproteins that have predominantly particular N-glycan species.

The construction of host cells that do not display Alg3p protein activity or lack or have a disruption of expression from the ALG3 gene has been described in Published U.S. Application No. 20050170452 or US20100227363, which are incorporated herein by reference. Alg3p is $Man_5GlcNAc_2$-PP-dolichyl alpha-1,3 mannosyltransferase that transferase a mannose residue to the mannose residue of the alpha-1,6 arm of lipid-linked $Man_5GlcNAc_2$ (FIG. 1, GS 1.3) in an alpha-1,3 linkage to produce lipid-linked $Man_6GlcNAc_2$ (FIG. 1, GS 1.4), a precursor for the synthesis of lipid-linked $Glc_3Man_9GlcNAc_2$, which is then transferred by an oligosaccharyltransferase to an aspargine residue of a glycoprotein followed by removal of the glucose (Glc) residues. In host cells that lack Alg3p protein activity, the lipid-linked $Man_5GlcNAc_2$ oligosaccharide may be transferred by an oligosaccharyltransferase to an aspargine residue of a glycoprotein. In such host cells that further include an α1,2-mannosidase, the $Man_5GlcNAc_2$ oligosaccharide attached to the glycoprotein is trimmed to a trimannose (paucimannose) $Man_3GlcNAc_2$ structure (FIG. 1, GS 2.1). The $Man_5GlcNAc_2$ (GS 1.3) structure is distinguishable from the $Man_5GlcNAc_2$ (GS 2.0) shown in FIG. 1, and which is produced in host cells that express the $Man_5GlcNAc_2$-PP-dolichyl alpha-1,3 mannosyltransferase (Alg3p).

The N-glycosylation site occupancy of glycoproteins comprising paucimannose N-glycans or complex N-glycans produced in the alg3Δ yos9Δ host cells may be substantially increased by expressing in the host cells a nucleic acid molecule encoding a *Trypanosoma brucei* STT3B protein integrated into the genome of the host cell. The *Trypanosoma brucei* STT3 protein is overexpressed constitutively or inducibly in the recombinant alg3Δ yos9Δ host cell in which the host cell continues to express its endogenous genes encoding the proteins comprising its oligosaccharyltransferase (OTase) complex, which includes the expression of the endogenous host cell STT3 gene. Thus, the host cell expresses both the *Trypanosoma brucei* STT3 protein and the endogenous host cell OTase complex, including the endogenous host cell SST3 protein. Furthermore, with respect to recombinant yeast, filamentous fungus, algal, or plant host cells, the host cells can further be genetically engineered to produce glycoproteins that comprise a mammalian or human-like glycosylation pattern comprising complex and/or hybrid N-glycans and not glycoproteins that have the host cells' endogenous glycosylation pattern.

In further embodiments, the host further includes integrated into the genome of the host cell one or more nucleic acid molecules wherein each said molecule encodes one or more heterologous single-subunit oligosaccharyltransferases which in particular embodiments, at least one of which is capable of functionally suppressing the lethal phenotype of a mutation of at least one essential protein of the yeast oligosaccharyltransferase (OTase) complex. Published International Application No. WO2011106389, which is incorporated herein by reference, discloses methods for increasing the N-glycosylation site occupancy of a glycoprotein produced in recombinant lower eukaryote host cells genetically engineered to express the glycoprotein. In particular, the method provides recombinant host cells that overexpress a heterologous single-subunit oligosaccharyltransferase, which in particular embodiments is capable of functionally suppressing the lethal phenotype of a mutation of at least one essential protein of the yeast oligosaccharyltransferase (OTase) complex.

Nasab et al., Molecular Biology of the Cell 19: 3758-3768 (2008) expressed each of the four *Leishmania major* STT3 proteins individually in *Saccharomyces cerevisiae* and found that three of them, LmSTT3A protein, LmSTT3B protein, and LmSTT3D protein, were able to complement a deletion of the yeast STT3 locus. In addition, LmSTT3D expression suppressed the lethal phenotype of single and double deletions in genes encoding various essential OTase subunits. The LmSTT3 proteins did not incorporate into the yeast OTase complex but instead formed a homodimeric enzyme, capable of replacing the endogenous, multimeric enzyme of the yeast cell. The results indicate that while these single-subunit oligosaccharyltransferases may resemble the prokaryotic enzymes, they use substrates typical for eukaryote glycosylation: that is, the N—X—S/T N-glycosylation recognition site and dolicholpyrophosphate-linked high mannose oligosaccharides.

Therefore in particular embodiments of the present invention, the open reading frame encoding at least one heterologous single-subunit oligosaccharyltransferase (for example, selected from the group consisting of LmSTT3A protein, LmSTT3B protein, or LmSTT3D) is overexpressed constitutively or inducibly in the recombinant alg3Δ yos9Δ host cell in which the host cell expresses the *Trypanosoma brucei* STT3 protein and continues to express its endogenous genes encoding the proteins comprising its oligosaccharyltransferase (OTase) complex, which includes the expression of the endogenous host cell STT3 gene. Thus, the host cell expresses the *Trypanosoma brucei* STT3 protein, the heterologous single-subunit oligosaccharyltransferase, and the endogenous host cell OTase complex, including the endogenous host cell SST3 protein. Furthermore, with respect to recombinant yeast, filamentous fungus, algal, or plant host cells, the host cells can further be genetically engineered to produce glycoproteins that comprise a mammalian or human-like glycosylation pattern comprising complex and/or hybrid N-glycans and not glycoproteins that have the host cells' endogenous glycosylation pattern.

The present invention has been exemplified herein using *Pichia pastoris* alg3Δ yos9Δ host cells genetically engineered to produce mammalian- or human-like complex N-glycans and that express at least the *Trypanosoma brucei* STT3B; however, the present invention may be applied to other yeast host cells (including but not limited to *Saccharomyces cerevisiae, Schizosaccharomyces pombe, Ogataea minuta*, and *Pichia pastoris*) or filamentous fungi (including but not limited to *Tricoderma reesei*) that produce glycoproteins that have yeast or fungal N-glycans (either hypermannosylated N-glycans or high mannose N-glycans) or genetically engineered to produce glycoproteins that have mammalian- or human-like high mannose, complex, or hybrid N-glycans to improve the overall N-glycosylation site occupancy of glycoproteins produced in the host cell. Furthermore, the present invention can also be applied to plant and mammalian expression system to improve the overall N-glycosylation site occupancy of glycoproteins produced in these plant or mammalian expression systems, particularly glycoproteins that have more than two N-linked glycosylation sites.

The applicants have also discovered that particular combinations of exogenous OSTs will vary in ability to effect an increase in N-glycan site occupancy in particular proteins or classes of proteins. For example, as shown in Table 1, in the alg3Δ yos9Δ host cell the *Trypanosoma brucei* STT3C protein had little or no effect on N-glycan site occupancy of an anti-Her2 antibody expressed in the host cell compared to the effect of the *Trypanosoma brucei* STT3B protein or the *Trypanosoma brucei* STT3A protein. However, as shown in Table 3, N-glycan site occupancy of an insulin molecule modified to comprise N-glycosylation sites was increased in an alg3Δ yos9Δ host cell comprising the *Lieshmania major* STT3D when the host cell was further modified to express the the *Trypanosoma brucei* STT3C protein. This result was unexpected since the *Trypanosoma brucei* STT3C protein alone in the alg3Δ yos9Δ host cell had no apparent or significant affect on N-glycan site occupancy.

Therefore, the present invention provides a recombinant host cell that does not display dolichyl-P-Man:Man$_5$GlcNAc$_2$-PP-dolichyl alpha-1,3 mannosyltransferase activity (Alg3p) activity and does not display an osteosarcoma 9 (OS-9) family gene or homolog thereof activity and which further includes a first nucleic acid molecule encoding a *Trypanosoma brucei* STT3A protein, *Trypanosoma brucei* STT3B protein, or *Trypanosoma brucei* STT3C protein and a second nucleic acid molecule encoding a heterologous recombinant protein. In further embodiments, the first nucleic acid molecule encoding the *Trypanosoma brucei* STT3A protein, *Trypanosoma brucei* STT3B protein, or *Trypanosoma brucei* STT3C protein is integrated into the genome of the host cell. In further embodiments, the second nucleic acid encoding the heterologous recombinant protein is also integrated into the genome of the host cell. Integration into the host cell genome may be achieved by double-crossover homologous recombination or single-crossover homologous recombination. In the embodiments herein, the nucleic acid molecule encoding the *Trypanosoma brucei* STT3A protein, *Trypanosoma brucei* STT3B protein, or *Trypanosoma brucei* STT3C protein comprises an open reading frame (ORF) encoding the *Trypanosoma brucei* STT3 protein operably linked to a constitutive or inducible promoter and the nucleic acid molecule encoding the heterologous recombinant protein comprises an ORF operably linked to a constitutive or inducible promoter. In further embodiments, the host cell further includes a nucleic acid molecule encoding at least one heterologous single-subunit oligosaccharyltransferase (for example, selected from the group consisting of LmSTT3A protein, LmSTT3B protein, and LmSTT3D) operably linked to a constitutive or inducible promoter.

In particular aspects, the recombinant host cell does not express the dolichyl-P-Man:Man$_5$GlcNAc$_2$-PP-dolichyl alpha-1,3 mannosyltransferase activity (ALG3) gene and does not express the osteosarcoma 9 (OS-9) family gene or homolog thereof gene and which further includes a nucleic acid molecule encoding a *Trypanosoma brucei* STT3A protein, *Trypanosoma brucei* STT3B protein, or *Trypanosoma brucei* STT3C protein integrated into the genome of the host cell and a second nucleic acid molecule encoding a heterologous recombinant protein. In the embodiments herein, the nucleic acid molecule encoding the *Trypanosoma brucei* STT3A protein, *Trypanosoma brucei* STT3B protein, or *Trypanosoma brucei* STT3C protein comprises an ORF encoding the *Trypanosoma brucei* STT3 protein operably linked to a constitutive or inducible promoter and the nucleic acid molecule encoding the heterologous recombinant protein comprises an ORF operably linked to a constitutive or inducible promoter. In further embodiments, the host cell further includes a nucleic acid molecule encoding at least one heterologous single-subunit oligosaccharyltransferase (for example, selected from the group consisting of LmSTT3A protein, LmSTT3B protein, and LmSTT3D) operably linked to a constitutive or inducible promoter.

In particular aspects of the above, the host cell is a lower eukaryote. In further aspects, the lower eukaryote is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Ogataea minuta, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum*, and *Neurospora crassa*. Various yeasts, such as *Ogataea minuta, Kluyveromyces lactis, Pichia pastoris, Pichia methanolica*, and *Hansenula polymorpha* are particularly suitable for cell culture because they are able to grow to high cell densities and secrete large quantities of recombinant protein. Likewise, filamentous fungi, such as *Aspergillus niger, Fusarium* sp, *Neurospora crassa* and others can be used to produce glycoproteins of the invention at an industrial scale.

In further still aspects, the host cell is deficient in the activity of one or more enzymes selected from the group consisting of mannosyltransferases and phosphomannosyltransferases. In further still aspects, the host cell does not express an enzyme selected from the group consisting of 1,6 mannosyltransferase, 1,3 mannosyltransferase, and 1,2 mannosyltransferase.

In a particular aspect of any one of the above host cells, the host cell is a yeast host cell, including but not limited to, *Pichia pastoris, Shizosaccharomyces pombe, Ogataea minuta*, and *Saccharomyces cerevisiae*. In particular aspects, the host cell is an och1 mutant of *Pichia pastoris, Shizosaccharomyces pombe, Ogataea minuta*, or *Saccharomyces cerevisiae*. In yeast, the osteosarcoma 9 (OS-9) family gene is the YOS9 gene, which encodes Yos9p protein. Thus, the present invention provides recombinant yeast host cells that do not display a Man$_5$GlcNAc$_2$-PP-dolichyl alpha-1,3 mannosyltransferase activity (Alg3p) activity and a Yos9p protein or homolog thereof activity and which further includes a first nucleic acid molecule encoding a *Trypanosoma brucei*

STT3A protein, *Trypanosoma brucei* STT3B protein, or *Trypanosoma brucei* STT3C protein and a second nucleic acid molecule encoding a heterologous recombinant protein. In further embodiments, the host cell further includes a nucleic acid molecule encoding at least one heterologous single-subunit oligosaccharyltransferase (for example, selected from the group consisting of LmSTT3A protein, LmSTT3B protein, or LmSTT3D) operably linked to a constitutively or inducible promoter.

In particular aspects of the recombinant yeast host cell, the expression of the dolichyl-P-Man:Man$_5$GlcNAc$_2$-PP-dolichyl alpha-1,3 mannosyltransferase activity (ALG3) gene and the YOS9 gene or homolog thereof are disrupted and the host cell further includes a first nucleic acid molecule encoding a *Trypanosoma brucei* STT3A protein, *Trypanosoma brucei* STT3B protein, or *Trypanosoma brucei* STT3C protein and a second nucleic acid molecule encoding a heterologous recombinant protein. In further embodiments, the host cell further includes a nucleic acid molecule encoding at least one heterologous single-subunit oligosaccharyltransferase (for example, selected from the group consisting of LmSTT3A protein, LmSTT3B protein, or LmSTT3D) operably linked to a constitutively or inducible promoter.

Further provided are methods for producing recombinant glycoproteins using the host cells disclosed herein. In general, the method comprises providing a recombinant host cell that does not display Alg3p activity and osteosarcoma 9 (OS-9) family gene or homolog thereof activity which further includes a first nucleic acid molecule encoding a *Trypanosoma brucei* STT3A protein, *Trypanosoma brucei* STT3B protein, or *Trypanosoma brucei* STT3C protein and a second nucleic acid molecule encoding a heterologous recombinant protein and cultivating or fermenting the host cell in a medium for a time sufficient to express the recombinant glycoprotein. In further embodiments, the recombinant glycoprotein is secreted into to the medium where it can be recovered and purified from other components in the medium. In particular aspects, the host cell further includes a nucleic acid molecule encoding at least one heterologous single-subunit oligosaccharyltransferase (for example, selected from the group consisting of LmSTT3A protein, LmSTT3B protein, or LmSTT3D) operably linked to a constitutively or inducible promoter.

In particular aspects of the method, the host cell is a lower eukaryote. In further aspects, the lower eukaryote is selected from the group consisting of *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Ogataea minuta*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, and *Neurospora crassa*. Various yeasts, such as *Ogataea minuta*, *Kluyveromyces lactis*, *Pichia pastoris*, *Pichia methanolica*, and *Hansenula polymorpha* are particularly suitable for cell culture because they are able to grow to high cell densities and secrete large quantities of recombinant protein. Likewise, filamentous fungi, such as *Aspergillus niger*, *Fusarium* sp, *Neurospora crassa* and others can be used to produce glycoproteins of the invention at an industrial scale.

In further still aspects, the host cell is deficient in the activity of one or more enzymes selected from the group consisting of mannosyltransferases and phosphomannosyltransferases. In further still aspects, the host cell does not express an enzyme selected from the group consisting of 1,6 mannosyltransferase, 1,3 mannosyltransferase, and 1,2 mannosyltransferase.

In a particular aspect of any one of the above method, the host cell is a yeast host cell, including but not limited to, *Pichia pastoris*, *Shizosaccharomyces pombe*, *Ogataea minuta*, and *Saccharomyces cerevisiae*. In particular aspects, the host cell is an och1 mutant of *Pichia pastoris*, *Shizosaccharomyces pombe*, *Ogataea minuta*, or *Saccharomyces cerevisiae*. In yeast, the osteosarcoma 9 (OS-9) family gene is the YOS9 gene, which encodes Yos9p protein.

Thus, the present invention further provides a method for producing a recombinant glycoprotein comprising providing recombinant yeast host cell that does not display a Man$_5$GlcNAc$_2$-PP-dolichyl alpha-1,3 mannosyltransferase activity (Alg3p) activity and does not display a Yos9p protein or homolog thereof activity and which further includes a first nucleic acid molecule encoding a *Trypanosoma brucei* STT3A protein, *Trypanosoma brucei* STT3B protein, or *Trypanosoma brucei* STT3C protein and a second nucleic acid molecule encoding a heterologous recombinant protein. The recombinant host cell is cultivated or fermented in a medium for a time sufficient to express the recombinant glycoprotein. In further embodiments, the recombinant glycoprotein is secreted into to the medium where it can be recovered and purified from other components in the medium. In further embodiments, the host cell further includes a nucleic acid molecule encoding at least one heterologous single-subunit oligosaccharyltransferase (for example, selected from the group consisting of LmSTT3A protein, LmSTT3B protein, or LmSTT3D). In further aspects, the ORF encoding the STT3 protein is operably linked to a constitutive or inducible promoter. In further aspects, the nucleic acid molecule encoding the STT3 protein is integrated into the host cell genome.

In particular aspects of the method, provided is a recombinant yeast host cell in which expression of the dolichyl-P-Man:Man$_5$GlcNAc$_2$-PP-dolichyl alpha-1,3 mannosyltransferase activity (ALG3) gene and expression of the YOS9 gene or homolog thereof gene has been disrupted and the host cell further includes a first nucleic acid molecule encoding a *Trypanosoma brucei* STT3A protein, *Trypanosoma brucei* STT3B protein, or *Trypanosoma brucei* STT3C protein and a second nucleic acid molecule encoding a heterologous recombinant glycoprotein protein. The recombinant host cell is cultivated or fermented in a medium for a time sufficient to express the recombinant glycoprotein. In further embodiments, the recombinant glycoprotein is secreted into to the medium where it can be recovered and purified from other components in the medium. In further embodiments, the host cell further includes a nucleic acid molecule encoding at least one heterologous single-subunit oligosaccharyltransferase (for example, selected from the group consisting of LmSTT3A protein, LmSTT3B protein, or LmSTT3D). In further aspects, the ORF encoding the STT3 protein is operably linked to a constitutive or inducible promoter. In further aspects, the nucleic acid molecule encoding the STT3 protein is integrated into the host cell genome.

In particular aspects of the method, provided is a recombinant yeast host cell in which the genes encoding the dolichyl-P-Man:Man$_5$GlcNAc$_2$-PP-dolichyl alpha-1,3 mannosyltransferase activity (ALG3) gene and the YOS9 gene or homolog thereof gene have been deleted or disrupted and the host cell further includes a first nucleic acid molecule encoding a *Trypanosoma brucei* STT3A protein, *Trypanosoma brucei* STT3B protein, or *Trypanosoma brucei* STT3C protein and a second nucleic acid molecule encoding a heterologous recombinant glycoprotein protein. The recombinant host cell is cultivated or fermented in a medium for a time sufficient to express the recombinant glycoprotein. In further embodiments, the recombinant glycoprotein is secreted into to the medium where it can be recovered and purified from other components in the medium. In further embodiments, the host cell further includes a nucleic acid molecule encoding at least one heterologous single-subunit oligosaccharyltransferase (for example, selected from the group consisting of LmSTT3A protein, LmSTT3B protein, or LmSTT3D).

In particular aspects of the method, provided is a recombinant yeast host cell in which the genes encoding the dolichyl-P-Man:$Man_5GlcNAc_2$-PP-dolichyl alpha-1,3 mannosyltransferase activity (ALG3) gene and the YOS9 gene or homolog thereof gene have been deleted or disrupted and the host cell further includes a first nucleic acid molecule encoding a *Trypanosoma brucei* STT3B protein and a second nucleic acid molecule encoding a heterologous recombinant glycoprotein protein. The recombinant host cell is cultivated or fermented in a medium for a time sufficient to express the recombinant glycoprotein. In further embodiments, the recombinant glycoprotein is secreted into to the medium where it can be recovered and purified from other components in the medium. In further embodiments, the host cell further includes a nucleic acid molecule encoding at least one heterologous single-subunit oligosaccharyltransferase (for example, selected from the group consisting of LmSTT3A protein, LmSTT3B protein, or LmSTT3D).

In particular aspects of the method, provided is a recombinant yeast host cell in which the genes encoding the dolichyl-P-Man:$Man_5GlcNAc_2$-PP-dolichyl alpha-1,3 mannosyltransferase activity (ALG3) gene and the YOS9 gene or homolog thereof gene have been deleted or disrupted and the host cell further includes one or more nucleic acid molecules encoding a *Trypanosoma brucei* STT3A protein, *Trypanosoma brucei* STT3B protein, and *Trypanosoma brucei* STT3C protein and a nucleic acid molecule encoding a heterologous recombinant glycoprotein protein. The recombinant host cell is cultivated or fermented in a medium for a time sufficient to express the recombinant glycoprotein. In further embodiments, the recombinant glycoprotein is secreted into to the medium where it can be recovered and purified from other components in the medium. In further embodiments, the host cell further includes a nucleic acid molecule encoding at least one heterologous single-subunit oligosaccharyltransferase (for example, selected from the group consisting of LmSTT3A protein, LmSTT3B protein, or LmSTT3D).

In particular aspects of the method, provided is a recombinant yeast host cell in which expression of the dolichyl-P-Man:$Man_5GlcNAc_2$-PP-dolichyl alpha-1,3 mannosyltransferase activity (ALG3) gene and the YOS9 gene or homolog thereof gene has been disrupted and the host cell further includes a first nucleic acid molecule encoding a *Trypanosoma brucei* STT3C protein, a second nucleic acid molecule encoding a heterologous recombinant protein, and a third nucleic acid molecule encoding at least one heterologous single-subunit oligosaccharyltransferase (for example, selected from the group consisting of LmSTT3A protein, LmSTT3B protein, or LmSTT3D). The recombinant host cell is cultivated or fermented in a medium for a time sufficient to express the recombinant glycoprotein. In further embodiments, the recombinant glycoprotein is secreted into to the medium where it can be recovered and purified from other components in the medium.

In particular aspects of the method, provided is a recombinant yeast host cell in which expression of the dolichyl-P-Man:$Man_5GlcNAc_2$-PP-dolichyl alpha-1,3 mannosyltransferase activity (ALG3) gene and the YOS9 gene or homolog thereof gene has been disrupted and the host cell further includes a first nucleic acid molecule encoding a *Trypanosoma brucei* STT3C protein, a second nucleic acid molecule encoding a heterologous recombinant protein, and a third nucleic acid molecule encoding an LmSTT3D protein. The recombinant host cell is cultivated or fermented in a medium for a time sufficient to express the recombinant glycoprotein. In further embodiments, the recombinant glycoprotein is secreted into to the medium where it can be recovered and purified from other components in the medium.

In particular aspects of the method, provided is a recombinant yeast host cell in which the genes encoding the dolichyl-P-Man:$Man_5GlcNAc_2$-PP-dolichyl alpha-1,3 mannosyltransferase activity (ALG3) gene and the YOS9 gene or homolog thereof has been disrupted or deleted and the host cell further includes a first nucleic acid molecule encoding a *Trypanosoma brucei* STT3C protein, a second nucleic acid molecule encoding a heterologous recombinant protein, and a third nucleic acid molecule encoding an LmSTT3D protein. The recombinant host cell is cultivated or fermented in a medium for a time sufficient to express the recombinant glycoprotein. In further embodiments, the recombinant glycoprotein is secreted into to the medium where it can be recovered and purified from other components in the medium.

The above recombinant host cells may further include any combination of the following genetic manipulations to provide host cells that are capable of expressing glycoproteins in which the N-glycosylation pattern is mammalian-like or human-like or humanized or where a particular N-glycan species is predominant. This may achieved by eliminating selected endogenous glycosylation enzymes and/or supplying exogenous enzymes as described by Gerngross et al., U.S. Pat. No. 7,449,308, the disclosure of which is incorporated herein by reference, and general methods for reducing O-glycosylation in yeast have been described in International Application No. WO2007061631. In this manner, glycoprotein compositions can be produced in which a specific desired glycoform is predominant in the composition. If desired, additional genetic engineering of the glycosylation can be performed, such that the glycoprotein can be produced with or without core fucosylation. Use of lower eukaryotic host cells such as yeast are further advantageous in that these cells are able to produce relatively homogenous compositions of glycoprotein, such that the predominant glycoform of the glycoprotein may be present as greater than thirty mole percent of the glycoprotein in the composition. In particular aspects, the predominant glycoform may be present in greater than forty mole percent, fifty mole percent, sixty mole percent, seventy mole percent and, most preferably, greater than eighty mole percent of the glycoprotein present in the composition. Such can be achieved by eliminating selected endogenous glycosylation enzymes and/or supplying exogenous enzymes as described by Gerngross et al., U.S. Pat. No. 7,029,872 and U.S. Pat. No. 7,449,308, the disclosures of which are incorporated herein by reference. For example, a host cell can be selected or engineered to be depleted in α1,6-mannosyl transferase activities, which would otherwise add mannose residues onto the N-glycan on a glycoprotein. For example, in yeast such an α1,6-mannosyl transferase activity is encoded by the OCH1 gene and deletion or disruption of the OCH1 inhibits the production of high mannose or hypermannosylated N-glycans in yeast such as *Pichia pastoris* or *Saccharomyces cerevisiae*. (See for example, Gerngross et al. in U.S. Pat. No. 7,029,872; Contreras et al. in U.S. Pat. No. 6,803,225; and Chiba et al. in EP1211310B1 the disclosures of which are incorporated herein by reference).

In one embodiment, the host cell further includes an α1,2-mannosidase catalytic domain fused to a cellular targeting signal peptide not normally associated with the catalytic domain and selected to target the α1,2-mannosidase activity to the ER or Golgi apparatus of the host cell. Passage of a recombinant glycoprotein through the ER or Golgi apparatus of the host cell produces a recombinant glycoprotein comprising a $Man_3GlcNAc_2$ glycoform, for example, a recombinant glycoprotein composition comprising predominantly a $Man_3GlcNAc_2$ glycoform. For example, U.S. Published Patent Application No. 2005/0170452, the disclosures of which is incorporated herein by reference, discloses lower eukaryote host cells capable of producing a glycoprotein comprising a $Man_3GlcNAc_2$ glycoform.

In a further embodiment, the immediately preceding host cell further includes an N-acetylglucosaminyltransferase I (GlcNAc transferase I or GnT I) catalytic domain fused to a cellular targeting signal peptide not normally associated with the catalytic domain and selected to target GlcNAc transferase I activity to the ER or Golgi apparatus of the host cell. Passage of the recombinant glycoprotein through the ER or Golgi apparatus of the host cell produces a recombinant glycoprotein comprising a $GlcNAcMan_3GlcNAc_2$ glycoform, for example a recombinant glycoprotein composition comprising predominantly a $GlcNAcMan_3GlcNAc_2$ glycoform. U.S. Pat. No. 7,029,872, U.S. Pat. No. 7,449,308, and U.S. Published Patent Application No. 2005/0170452, the disclosures of which are all incorporated herein by reference, disclose lower eukaryote host cells capable of producing a glycoprotein comprising a $GlcNAcMan_3GlcNAc_2$ glycoform. The glycoprotein produced in the above cells can be treated in vitro with a hexaminidase to produce a recombinant glycoprotein comprising a $Man_3GlcNAc_2$ glycoform.

In a further embodiment, the immediately preceding host cell further includes N-acetylglucosaminyltransferase II (GlcNAc transferase II or GnT II) catalytic domain fused to a cellular targeting signal peptide not normally associated with the catalytic domain and selected to target GlcNAc transferase II activity to the ER or Golgi apparatus of the host cell. Passage of the recombinant glycoprotein through the ER or Golgi apparatus of the host cell produces a recombinant glycoprotein comprising a $GlcNAc_2Man_3GlcNAc_2$ glycoform, for example a recombinant glycoprotein composition comprising predominantly a $GlcNAc_2Man_3GlcNAc_2$ glycoform. U.S. Pat. Nos. 7,029,872 and 7,449,308 and U.S. Published Patent Application No. 2005/0170452, the disclosures of which are all incorporated herein by reference, disclose lower eukaryote host cells capable of producing a glycoprotein comprising a $GlcNAc_2Man_3GlcNAc_2$ glycoform. The glycoprotein produced in the above cells can be treated in vitro with a hexosaminidase that removes the terminal GlcNAc residues to produce a recombinant glycoprotein comprising a $Man_3GlcNAc_2$ glycoform or the hexosaminidase can be co-expressed with the glycoprotein in the host cell to produce a recombinant glycoprotein comprising a $Man_3GlcNAc_2$ glycoform.

In a further embodiment, the immediately preceding host cell further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising a $GalGlcNAc_2Man_3GlcNAc_2$ or $Gal_2GlcNAc_2Man_3GlcNAc_2$ glycoform, or mixture thereof for example a recombinant glycoprotein composition comprising predominantly a $GalGlcNAc_2Man_3GlcNAc_2$ glycoform or $Gal_2GlcNAc_2Man_3GlcNAc_2$ glycoform or mixture thereof. U.S. Pat. No. 7,029,872 and U.S. Published Patent Application No. 2006/0040353, the disclosures of which are incorporated herein by reference, discloses lower eukaryote host cells capable of producing a glycoprotein comprising a $Gal_2GlcNAc_2Man_3GlcNAc_2$ glycoform. The glycoprotein produced in the above cells can be treated in vitro with a galactosidase to produce a recombinant glycoprotein comprising a $GlcNAc_2Man_3GlcNAc_2$ glycoform, for example a recombinant glycoprotein composition comprising predominantly a $GlcNAc_2Man_3GlcNAc_2$ glycoform or the galactosidase can be co-expressed with the glycoprotein in the host cell to produce a recombinant glycoprotein comprising the $GlcNAc_2Man_3GlcNAc_2$ glycoform, for example a recombinant glycoprotein composition comprising predominantly a $GlcNAc_2Man_3GlcNAc_2$ glycoform.

In a further embodiment, the immediately preceding host cell further includes a sialyltransferase catalytic domain fused to a cellular targeting signal peptide not normally associated with the catalytic domain and selected to target sialyltransferase activity to the ER or Golgi apparatus of the host cell. Passage of the recombinant glycoprotein through the ER or Golgi apparatus of the host cell produces a recombinant glycoprotein comprising predominantly a $Sia_2Gal_2GlcNAc_2Man_3GlcNAc_2$ glycoform or $SiaGal_2GlcNAc_2Man_3GlcNAc_2$ glycoform or mixture thereof. For lower eukaryote host cells such as yeast and filamentous fungi, it is useful that the host cell further include a means for providing CMP-sialic acid for transfer to the N-glycan. U.S. Published Patent Application No. 2005/0260729, the disclosure of which is incorporated herein by reference, discloses a method for genetically engineering lower eukaryotes to have a CMP-sialic acid synthesis pathway and U.S. Published Patent Application No. 2006/0286637, the disclosure of which is incorporated herein by reference, discloses a method for genetically engineering lower eukaryotes to produce sialylated glycoproteins. The glycoprotein produced in the above cells can be treated in vitro with a neuraminidase to produce a recombinant glycoprotein comprising predominantly a $Gal_2GlcNAc_2Man_3GlcNAc_2$ glycoform or $GalGlcNAc_2Man_3GlcNAc_2$ glycoform or mixture thereof or the neuraminidase can be co-expressed with the glycoprotein in the host cell to produce a recombinant glycoprotein comprising predominantly a $Gal_2GlcNAc_2Man_3GlcNAc_2$ glycoform or $GalGlcNAc_2Man_3GlcNAc_2$ glycoform or mixture thereof.

In a further aspect, the above host cell capable of making glycoproteins having a $Man_5GlcNAc_2$ glycoform can further include a mannosidase III catalytic domain fused to a cellular targeting signal peptide not normally associated with the catalytic domain and selected to target the mannosidase III activity to the ER or Golgi apparatus of the host cell. Passage of the recombinant glycoprotein through the ER or Golgi apparatus of the host cell produces a recombinant glycoprotein comprising a Man$_3$GlcNAc$_2$ glycoform, for example a recombinant glycoprotein composition comprising predominantly a Man$_3$GlcNAc$_2$ glycoform. U.S. Pat. No. 7,625,756, the disclosures of which are all incorporated herein by reference, discloses the use of lower eukaryote host cells that express mannosidase III enzymes and are capable of producing glycoproteins having predominantly a Man$_3$GlcNAc$_2$ glycoform.

Any one of the preceding host cells can further include one or more GlcNAc transferase selected from the group consisting of GnT III, GnT IV, GnT V, GnT VI, and GnT IX to produce glycoproteins having bisected (GnT III) and/or multiantennary (GnT IV, V, VI, and IX)N-glycan structures such as disclosed in U.S. Pat. No. 7,598,055 and U.S. Published Patent Application No. 2007/0037248, the disclosures of which are all incorporated herein by reference.

In general yeast and filamentous fungi are not able to make glycoproteins that have N-glycans that include fucose. Therefore, the N-glycans disclosed herein will lack fucose unless the host cell is specifically modified to include a pathway for synthesizing GDP-fucose and a fucosyltransferase. Therefore, in particular aspects where it is desirable to have glycoproteins in which the N-glycan includes fucose, any one of the aforementioned host cells is further modified to include a fucosyltransferase and a pathway for producing fucose and transporting fucose into the ER or Golgi. Examples of methods for modifying Pichia pastoris to render it capable of producing glycoproteins in which one or more of the N-glycans thereon are fucosylated are disclosed in Published International Application No. WO 2008112092, the disclosure of which is incorporated herein by reference. In particular aspects of the invention, the Pichia pastoris host cell is further modified to include a fucosylation pathway comprising a GDP-mannose-4,6-dehydratase, GDP-keto-deoxy-mannose-epimerase/GDP-keto-deoxy-galactose-reductase, GDP-fucose transporter, and a fucosyltransferase. In particular aspects, the fucosyltransferase is selected from the group consisting of α1,2-fucosyltransferase, α1,3-fucosyltransferase, α1,4-fucosyltransferase, and α1,6-fucosyltransferase.

Various of the preceding host cells further include one or more sugar transporters such as UDP-GlcNAc transporters (for example, Kluyveromyces lactis and Mus musculus UDP-GlcNAc transporters), UDP-galactose transporters (for example, Drosophila melanogaster UDP-galactose transporter), and CMP-sialic acid transporter (for example, human sialic acid transporter). Because lower eukaryote host cells such as yeast and filamentous fungi lack the above transporters, it is preferable that lower eukaryote host cells such as yeast and filamentous fungi be genetically engineered to include the above transporters.

Host cells further include Pichia pastoris that are genetically engineered to eliminate glycoproteins having phosphomannose residues by deleting or disrupting one or both of the phosphomannosyltransferase genes PNO1 and MNN4B (See for example, U.S. Pat. Nos. 7,198,921 and 7,259,007; the disclosures of which are all incorporated herein by reference), which in further aspects can also include deleting or disrupting the MNN4A gene. Disruption includes disrupting the open reading frame encoding the particular enzymes or disrupting expression of the open reading frame or abrogating translation of RNAs encoding one or more of the β-mannosyltransferases and/or phosphomannosyltransferases using interfering RNA, antisense RNA, or the like. The host cells can further include any one of the aforementioned host cells modified to produce particular N-glycan structures.

Host cells further include lower eukaryote cells (e.g., yeast such as Pichia pastoris) that are genetically modified to control O-glycosylation of the glycoprotein by deleting or disrupting one or more of the protein O-mannosyltransferase (Dol-P-Man:Protein (Ser/Thr) Mannosyl Transferase genes) (PMTs) (See U.S. Pat. No. 5,714,377; the disclosure of which is incorporated herein by reference) or grown in the presence of Pmtp inhibitors and/or an α1,2 mannosidase as disclosed in Published International Application No. WO 2007061631 the disclosure of which is incorporated herein by reference. Disruption includes disrupting the open reading frame encoding the Pmtp or disrupting expression of the open reading frame or abrogating translation of RNAs encoding one or more of the Pmtps using interfering RNA, antisense RNA, or the like. The host cells can further include any one of the aforementioned host cells modified to produce particular N-glycan structures.

Pmtp inhibitors include but are not limited to a benzylidene thiazolidinediones. Examples of benzylidene thiazolidinediones that can be used are 5-[[3,4-bis(phenylmethoxy)phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo-3-thiazolidineacetic Acid.

In particular embodiments, the function or expression of at least one endogenous PMT gene is reduced, disrupted, or deleted. For example, in particular embodiments the function or expression of at least one endogenous PMT gene selected from the group consisting of the PMT1, PMT2, PMT3, and PMT4 genes is reduced, disrupted, or deleted; or the host cells are cultivated in the presence of one or more PMT inhibitors. In further embodiments, the host cells include one or more PMT gene deletions or disruptions and the host cells are cultivated in the presence of one or more Pmtp inhibitors. In particular aspects of these embodiments, the host cells also express a secreted α-1,2-mannosidase.

PMT deletions or disruptions and/or Pmtp inhibitors control O-glycosylation by reducing O-glycosylation occupancy; that is by reducing the total number of O-glycosylation sites on the glycoprotein that are glycosylated. The further addition of an α-1,2-mannosidase that is secreted by the cell controls O-glycosylation by reducing the mannose chain length of the O-glycans that are on the glycoprotein. Thus, combining PMT deletions or disruptions and/or Pmtp inhibitors with expression of a secreted α-1,2-mannosidase controls O-glycosylation by reducing occupancy and chain length. In particular circumstances, the particular combination of PMT deletions or disruptions, Pmtp inhibitors, and α-1,2-mannosidase is determined empirically as particular heterologous glycoproteins (antibodies, for example) may be expressed and transported through the Golgi apparatus with different degrees of efficiency and thus may require a particular combination of PMT deletions or disruptions, Pmtp inhibitors, and α-1,2-mannosidase. In another aspect, genes encoding one or more endogenous mannosyltransferase enzymes are deleted. The deletion(s) can be in combination with providing the secreted α-1,2-mannosidase and/or PMT inhibitors or can be in lieu of providing the secreted α-1,2-mannosidase and/or PMT inhibitors.

Thus, the control of O-glycosylation can be useful for producing particular glycoproteins in the host cells disclosed herein in better total yield or in yield of properly assembled glycoprotein. The reduction or elimination of O-glycosylation appears to have a beneficial effect on the assembly and transport of glycoproteins such as whole antibodies as they traverse the secretory pathway and are transported to the cell surface. Thus, in cells in which O-glycosylation is controlled, the yield of properly assembled glycoproteins such as antibody fragments is increased over the yield obtained in host cells in which O-glycosylation is not controlled.

To reduce or eliminate the likelihood of N-glycans and O-glycans with β-linked mannose residues, which are resistant to α-mannosidases, the recombinant glycoengineered *Pichia pastoris* host cells are genetically engineered to eliminate glycoproteins having α-mannosidase-resistant N-glycans by deleting or disrupting one or more of the β-mannosyltransferase genes (e.g., BMT1, BMT2, BMT3, and BMT4)(See, U.S. Pat. No. 7,465,577, U.S. Pat. No. 7,713,719, and Published International Application No. WO2011046855, each of which is incorporated herein by reference). The deletion or disruption of BMT2 and one or more of BMT1, BMT3, and BMT4 also reduces or eliminates detectable cross reactivity to antibodies against host cell protein.

In particular embodiments, the host cells do not display Alg3p protein activity or have a deletion or disruption of expression from the ALG3 gene (e.g., deletion or disruption of the open reading frame encoding the Alg3p to render the host cell alg3Δ) as described in Published U.S. Application No. 20050170452 or US20100227363, which are incorporated herein by reference. Alg3p is Man5GlcNAc2-PP-dolichyl alpha-1,3 mannosyltransferase that transferase a mannose residue to the mannose residue of the alpha-1,6 arm of lipid-linked Man5GlcNAc2 (FIG. 1, GS 1.3) in an alpha-1,3 linkage to produce lipid-linked Man6GlcNAc2 (FIG. 1, GS 1.4), a precursor for the synthesis of lipid-linked Glc3Man9GlcNAc2, which is then transferred by an oligosaccharyltransferase to an asparagine residue of a glycoprotein followed by removal of the glucose (Glc) residues. In host cells that lack Alg3p protein activity, the lipid-linked $Man_5GlcNAc_2$ oligosaccharide may be transferred by an oligosaccharyltransferase to an asparagine residue of a glycoprotein. In such host cells that further include an α1,2-mannosidase, the $Man_5GlcNAc_2$ oligosaccharide attached to the glycoprotein is trimmed to a tri-mannose (paucimannose) Man3GlcNAc2 structure (FIG. 1, GS 2.1). The $Man_5GlcNAc_2$ (GS 1.3) structure is distinguishable from the $Man_5GlcNAc_2$ (GS 2.0) shown in FIG. 1, and which is produced in host cells that express the $Man_5GlcNAc_2$-PP-dolichyl alpha-1,3 mannosyltransferase (Alg3p).

Therefore, provided is a method for producing an N-glycosylated insulin or insulin analogue and compositions of the same in a lower eukaryote host cell, comprising a deletion or disruption ALG3 gene (alg3Δ) and includes a nucleic acid molecule encoding an insulin or insulin analogue having at least one N-glycosylation site; and culturing the host cell under conditions for expressing the insulin or insulin analogue to produce the N-glycosylated insulin or insulin analogue having predominantly a $Man_5GlcNAc_2$ (GS 1.3) structure. In further embodiments, the host cell further expresses an endomannosidase activity (e.g., a full-length endomannosidase or a chimeric endomannosidase comprising an endomannosidase catalytic domain fused to a cellular targeting signal peptide not normally associated with the catalytic domain and selected to target the endomannosidase activity to the ER or Golgi apparatus of the host cell. See for example, U.S. Pat. No. 7,332,299) and/or glucosidase II activity (a full-length glucosidase II or a chimeric glucosidase II comprising a glucosidase II catalytic domain fused to a cellular targeting signal peptide not normally associated with the catalytic domain and selected to target the glucosidase II activity to the ER or Golgi apparatus of the host cell. See for example, U.S. Pat. No. 6,803,225). In particular aspects, the host cell further includes a deletion or disruption of the ALG6 (α1,3-glucosylatransferase) gene (alg6Δ) or an overexpression of the ALG6 gene (See for example, De Pourcq et al., PloSOne 2012; 7(6):e39976. Epub 2012 Jun. 29, which discloses genetically engineering *Yarrowia lipolytica* to produce glycoproteins that have $Man_5GlcNAc_2$ (GS 1.3) or paucimannose N-glycan structures). The nucleic acid sequence encoding the *Pichia pastoris* ALG6 is disclosed in EMBL database, accession number CCCA38426. In further aspects, the host cell further includes a deletion or disruption of the OCH1 gene (och1Δ).

Further provided is a method for producing an N-glycosylated insulin or insulin analogue and compositions of the same in a lower eukaryote host cell, comprising a deletion or disruption of the ALG3 gene (alg3Δ) and includes a nucleic acid molecule encoding a chimeric α1,2-mannosidase comprising an α1,2-mannosidase catalytic domain fused to a cellular targeting signal peptide not normally associated with the catalytic domain and selected to target the α1,2-mannosidase activity to the ER or Golgi apparatus of the host cell to overexpress the chimeric α1,2-mannosidase and a nucleic acid molecule encoding the insulin or insulin analogue having at least one N-glycosylation site; and culturing the host cell under conditions for expressing the insulin or insulin analogue to produce the N-glycosylated insulin or insulin analogue having predominantly a $Man_3GlcNAc_2$ structure. In further embodiments, the host cell further expresses or overexpresses an endomannosidase activity (e.g., a full-length endomannosidase or a chimeric endomannosidase comprising an endomannosidase catalytic domain fused to a cellular targeting signal peptide not normally associated with the catalytic domain and selected to target the endomannosidase activity to the ER or Golgi apparatus of the host cell) and/or a glucosidase II activity (a full-length glucosidase II or a chimeric glucosidease II comprising a glucosidase II catalytic domain fused to a cellular targeting signal peptide not normally associated with the catalytic domain and selected to target the glucosidase II activity to the ER or Golgi apparatus of the host cell). In particular aspects, the host cell further includes a deletion or disruption of the ALG6 gene (alg6Δ). In further aspects, the host cell further includes a deletion or disruption of the OCH1 gene (och1Δ) Example 6 shows the construction of an alg3Δ *Pichia pastoris* host cell that overexpresses a full-length endomannosidase, which produced an insulin analogue that has paucimannose N-glycans. Similar host cells may be constructed in other yeast or filamentous fungi.

In further embodiments, the above alg3Δ host cells may further include additional mammalian or human glycosylation enzymes (e.g., GnT I, GnT II, galactosylatransferase, fucosyltransferase, sialyl transferase) as disclosed previously to produce N-glycosylated insulin or insulin analogue having predominantly particular hybrid or complex N-glycans.

Yield of glycoprotein can in some situations be improved by overexpressing nucleic acid molecules encoding mammalian or human chaperone proteins or replacing the genes encoding one or more endogenous chaperone proteins with nucleic acid molecules encoding one or more mammalian or human chaperone proteins. In addition, the expression of mammalian or human chaperone proteins in the host cell also appears to control O-glycosylation in the cell. Thus, further included are the host cells herein wherein the function of at least one endogenous gene encoding a chaperone protein has been reduced or eliminated, and a vector encoding at least one mammalian or human homolog of the chaperone protein is expressed in the host cell. Also included are host cells in which the endogenous host cell chaperones and the mammalian or human chaperone proteins are expressed. In further aspects, the lower eukaryotic host cell is a yeast or filamentous fungi host cell. Examples of the use of chaperones of host cells in which human chaperone proteins are introduced to improve the yield and reduce or control O-glycosylation of recombinant proteins has been disclosed in Published International Application No. WO2009105357 and WO2010019487 (the disclosures of which are incorporated herein by reference).

Therefore, the methods disclose herein can use any host cell that has been genetically modified to produce glycoproteins comprising at least N-glycan shown in FIG. 1. The methods disclose herein can use any host cell that has been genetically modified to produce glycoproteins wherein the predominant N-glycan is selected from the group consisting of complex N-glycans, hybrid N-glycans, and high mannose N-glycans wherein complex N-glycans are selected from the group consisting of $Man_3GlcNAc_2$ (paucimannose), $GlcNAc_{(1-4)}Man_3GlcNAc_2$, $Gal_{(1-4)}GlcNAc_{(1-4)}Man_3GlcNAc_2$, and $Sia_{(1-4)}Gal_{(1-4)}Man_3GlcNAc_2$. In further embodiments, the host cell produces glycoproteins that have predominantly an N-glycan structure consisting of the $Man_5GlcNAc_2$ (GS 1.3) structure. In general, the strains here will not be expected to produce the $Man_5GlcNAc_2$ (GS 2.0) structure shown in FIG. 1.

For genetically engineering yeast, selectable markers can be used to construct the recombinant host cells include drug resistance markers and genetic functions which allow the yeast host cell to synthesize essential cellular nutrients, e.g. amino acids. Drug resistance markers that are commonly used in yeast include chloramphenicol, kanamycin, methotrexate, G418 (geneticin), Zeocin, and the like. Genetic functions that allow the yeast host cell to synthesize essential cellular nutrients are used with available yeast strains having auxotrophic mutations in the corresponding genomic function. Common yeast selectable markers provide genetic functions for synthesizing leucine (LEU2), tryptophan (TRP1 and TRP2), proline (PRO1), uracil (URA3, URA5, URA6), histidine (HIS3), lysine (LYS2), adenine (ADE1 or ADE2), and the like. Other yeast selectable markers include the ARR3 gene from *S. cerevisiae*, which confers arsenite resistance to yeast cells that are grown in the presence of arsenite (Bobrowicz et al., Yeast, 13:819-828 (1997); Wysocki et al., J. Biol. Chem. 272:30061-30066 (1997)). A number of suitable integration sites include those enumerated in U.S. Pat. No. 7,479,389 (the disclosure of which is incorporated herein by reference) and include homologs to loci known for *Saccharomyces cerevisiae* and other yeast or fungi. Methods for integrating vectors into yeast are well known (See for example, U.S. Pat. No. 7,479,389, U.S. Pat. No. 7,514,253, U.S. Published Application No. 2009012400, and WO2009/085135; the disclosures of which are all incorporated herein by reference). Examples of insertion sites include, but are not limited to, *Pichia* ADE genes; *Pichia* TRP (including TRP1 through TRP2) genes; *Pichia* MCA genes; *Pichia* CYM genes; *Pichia* PEP genes; *Pichia* PRB genes; and *Pichia* LEU genes. The *Pichia* ADE1 and ARG4 genes have been described in Lin Cereghino et al., Gene 263:159-169 (2001) and U.S. Pat. No. 4,818,700 (the disclosure of which is incorporated herein by reference), the HIS3 and TRP1 genes have been described in Cosano et al., Yeast 14:861-867 (1998), HIS4 has been described in GenBank Accession No. X56180.

The transformation of the yeast cells is well known in the art and may for instance be effected by protoplast formation followed by transformation in a manner known per se. The medium used to cultivate the cells may be any conventional medium suitable for growing yeast organisms.

In particular embodiments of any one of the above host cells and methods using the host cells, the recombinant heterologous protein is a therapeutic protein or glycoprotein, which in particular embodiments may be for example, selected from the group consisting of erythropoietin (EPO); cytokines such as interferon α, interferon β, interferon γ, and interferon ω; and granulocyte-colony stimulating factor (GCSF); granulocyte macrophage-colony stimulating factor (GM-CSF); coagulation factors such as factor VIII, factor IX, and human protein C; antithrombin III; thrombin; soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4-Ig; transmembrane activator and calcium modulator and cyclophilin ligand; glucagon-like protein 1; insulin, and IL-2 receptor agonist.

In further embodiments of any one of the above host cells, the therapeutic glycoprotein is an antibody, examples of which, include but are not limited to, an anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, or anti-CD20 antibody.

The present invention further provides for an isolated nucleic acid molecule comprising at least 10, 20, 30, 40, 50, 60, 70, 80, 90, or 100 contiguous nucleotides of SEQ ID NO:19 or SEQ ID NO:20.

The present invention further provides for a plasmid vector comprising at least 10, 20, 30, 40, 50, 60, 70, 80, 90, or 100 contiguous nucleotides of SEQ ID NO:19 or SEQ ID NO:20. In a further aspect, the plasmid includes a selection marker.

The present invention further provides for a plasmid vector comprising at least at least 10, 20, 30, 40, 50, 60, 70, 80, 90, or 100 contiguous nucleotides of SEQ ID NO:19 or SEQ ID NO:20. In a further aspect, the plasmid includes a selection marker.

The present invention further provides for a plasmid vector comprising at least at least 10, 20, 30, 40, 50, 60, 70, 80, 90, or 100 contiguous nucleotides of SEQ ID NO:19 and at least at least 10, 20, 30, 40, 50, 60, 70, 80, 90, or 100 contiguous nucleotides SEQ ID NO:20.

The present invention further provides for a plasmid vector comprising at least at least 10, 20, 30, 40, 50, 60, 70, 80, 90, or 100 contiguous nucleotides of SEQ ID NO:19 and at least at least 10, 20, 30, 40, 50, 60, 70, 80, 90, or 100 contiguous nucleotides SEQ ID NO:20, wherein the plasmid further includes a selection marker.

The following examples are intended to promote a further understanding of the present invention.

EXAMPLE 1

Plasmids comprising expression cassettes having an open reading frame (ORF) encoding an STT3 protein operably linked to an inducible or constitutive promoter were constructed as follows.

Figure 2:
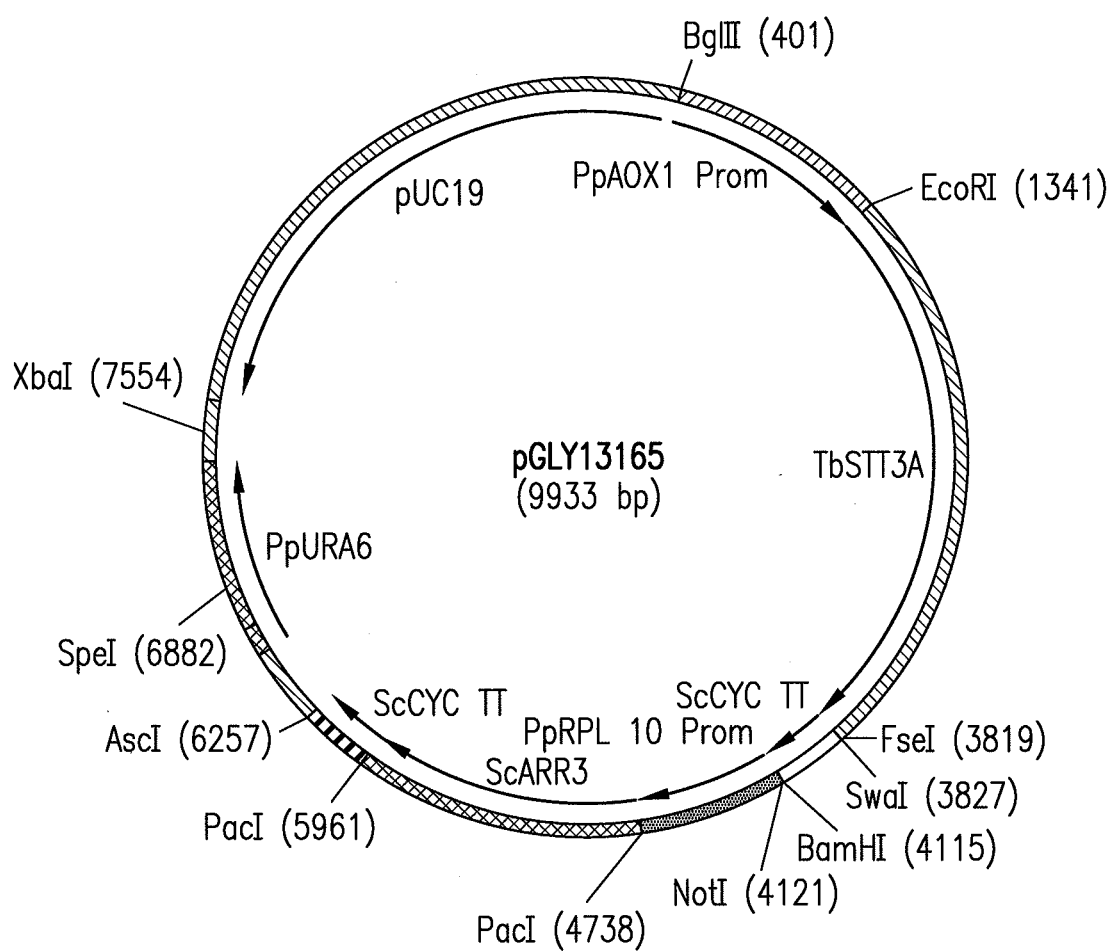
FIG. 2 shows a map of plasmid pGLY13165 encoding the TbSTT3A ORF under the control of the *Pichia pastoris* alcohol oxidase I (AOX1) promoter and *S. cerevisiae* CYC transcription termination sequence. The plasmid is a roll-in vector that targets the URA6 locus. The selection of transformants uses arsenic resistance encoded by the *S. cerevisiae* ARR3 ORF under the control of the *P. pastoris* RPL10 promoter and *S. cerevisiae* CYC transcription termination sequence.

Plasmid pGLY13165 (FIG. 2) is a roll-in integration plasmid that targets the URA6 locus (SEQ ID NO:7) in *P. pastoris*. The expression cassette encoding the TbSTT3A comprises a nucleic acid molecule encoding the TbSTT3A ORF codon-optimized for effective expression in *P. pastoris* (SEQ ID NO:12) operably linked at the 5' end to a nucleic acid molecule that has the inducible *P. pastoris* AOX1 promoter sequence (SEQ ID NO:3) and at the 3' end to a nucleic acid molecule that has the *P. pastoris* AOX1 transcription termination sequence (SEQ ID NO:17). For selecting transformants, the plasmid comprises an expression cassette encoding the *S. cerevisiae* ARR3 ORF (SEQ ID NO:5) in which the nucleic acid molecule encoding the ORF is operably linked at the 5' end to a nucleic acid molecule having the *P. pastoris* RPL10 promoter sequence (SEQ ID NO:6) and at the 3' end to a nucleic acid molecule having the *S. cerevisiae* CYC transcription termination sequence (SEQ ID NO:4)

Figure 3:
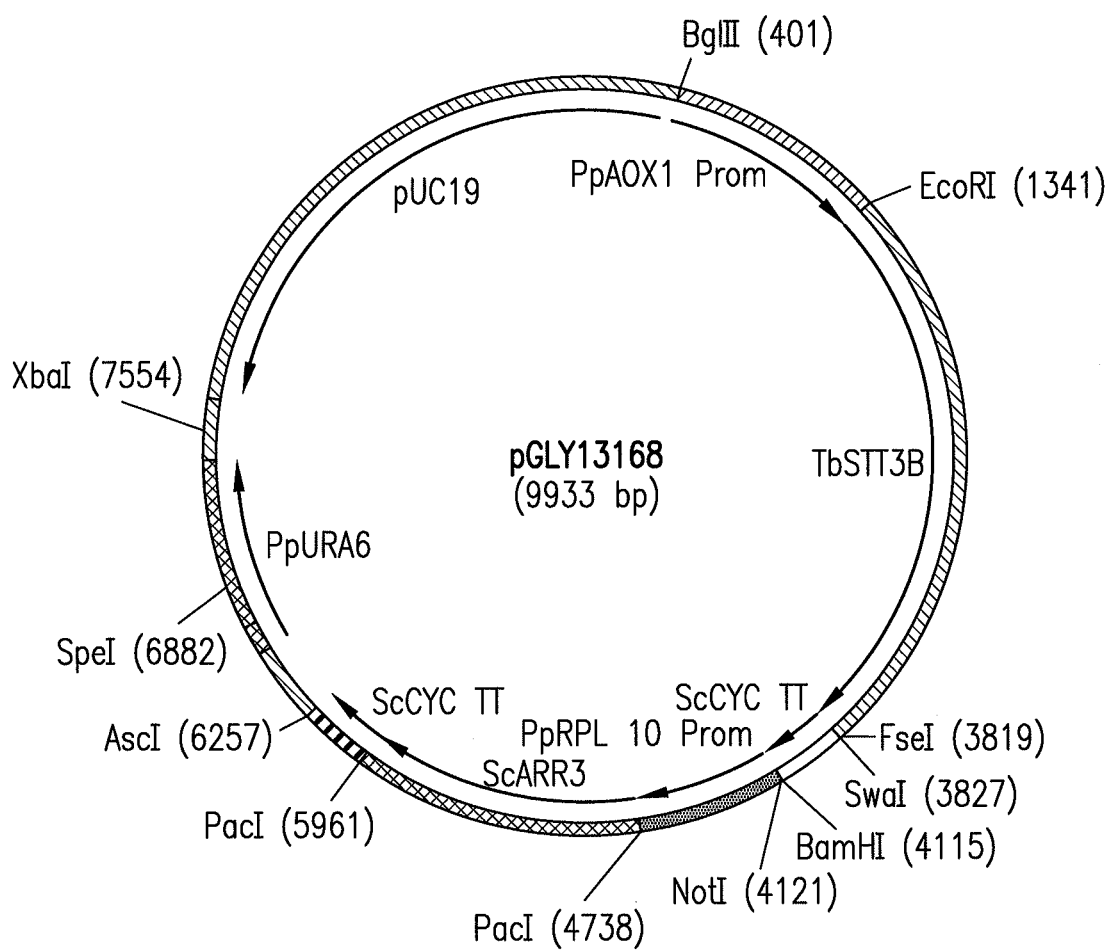
FIG. 3 shows a map of plasmid pGLY13168 encoding the TbSTT3B ORF under the control of the *Pichia pastoris* AOX1 promoter and *S. cerevisiae* CYC transcription termination sequence. The plasmid is a roll-in vector that targets the URA6 locus. The selection of transformants uses arsenic resistance encoded by the *S. cerevisiae* ARR3 ORF under the control of the *P. pastoris* RPL10 promoter and *S. cerevisiae* CYC transcription termination sequence.

Plasmid pGLY13168 (FIG. 3) is a roll-in integration plasmid that targets the URA6 locus (SEQ ID NO:7) in *P. pastoris*. The expression cassette encoding the TbSTT3B comprises a nucleic acid molecule encoding the TbSTT3B ORF codon-optimized for effective expression in *P. pastoris* (SEQ ID NO:13) operably linked at the 5' end to a nucleic acid molecule that has the inducible *P. pastoris* AOX1 promoter sequence (SEQ ID NO:3) and at the 3' end to a nucleic acid molecule that has the *P. pastoris* AOX1 transcription termination sequence (SEQ ID NO:17). For selecting transformants, the plasmid comprises an expression cassette encoding the *S. cerevisiae* ARR3 ORF (SEQ ID NO:5) in which the nucleic acid molecule encoding the ORF is operably linked at the 5' end to a nucleic acid molecule having the *P. pastoris* RPL10 promoter sequence (SEQ ID NO:6) and at the 3' end to a nucleic acid molecule having the *S. cerevisiae* CYC transcription termination sequence (SEQ ID NO:4).

Figure 4:
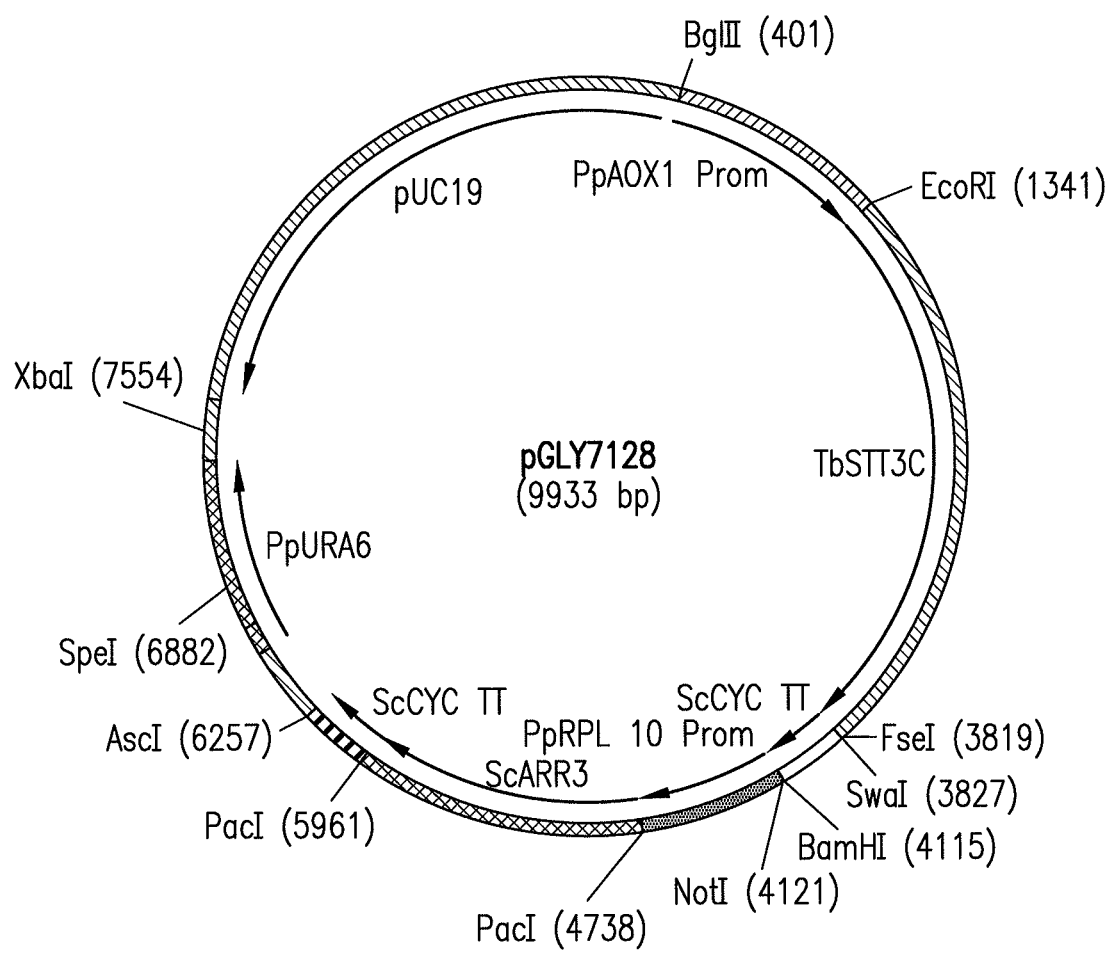
FIG. 4 shows a map of plasmid pGLY7128 encoding the TbSTT3C ORF under the control of the *Pichia pastoris* AOX1 promoter and *S. cerevisiae* CYC transcription termination sequence. The plasmid is a roll-in vector that targets the URA6 locus. The selection of transformants uses arsenic resistance encoded by the *S. cerevisiae* ARR3 ORF under the control of the *P. pastoris* RPL10 promoter and *S. cerevisiae* CYC transcription termination sequence.

Plasmid pGLY7128 (FIG. 4) is a roll-in integration plasmid that targets the URA6 locus in *P. pastoris*. The expression cassette encoding the TbSTT3C comprises a nucleic acid molecule encoding the TbSTT3C ORF codon-optimized for effective expression in *P. pastoris* (SEQ ID NO:14) operably linked at the 5' end to a nucleic acid molecule that has the inducible *P. pastoris* AOX1 promoter sequence (SEQ ID NO:3) and at the 3' end to a nucleic acid molecule that has the *S. cerevisiae* CYC transcription termination sequence (SEQ ID NO:4). For selecting transformants, the plasmid comprises an expression cassette encoding the *S. cerevisiae* ARR3 ORF (SEQ ID NO:5) in which the nucleic acid molecule encoding the ORF is operably linked at the 5' end to a nucleic acid molecule having the *P. pastoris* RPL10 promoter sequence (SEQ ID NO:6) and at the 3' end to a nucleic acid molecule having the *S. cerevisiae* CYC transcription termination sequence (SEQ ID NO:4).

The open reading frame encoding the LmSTT3D (SEQ ID NO:1) was codon-optimized for optimal expression in *P. pastoris* and synthesized by GeneArt AG, Brandenburg, Germany. The codon-optimized nucleic acid molecule encoding the LmSTT3D was designated pGLY6287 and has the nucleotide sequence shown in SEQ ID NO:2.

Figure 5:
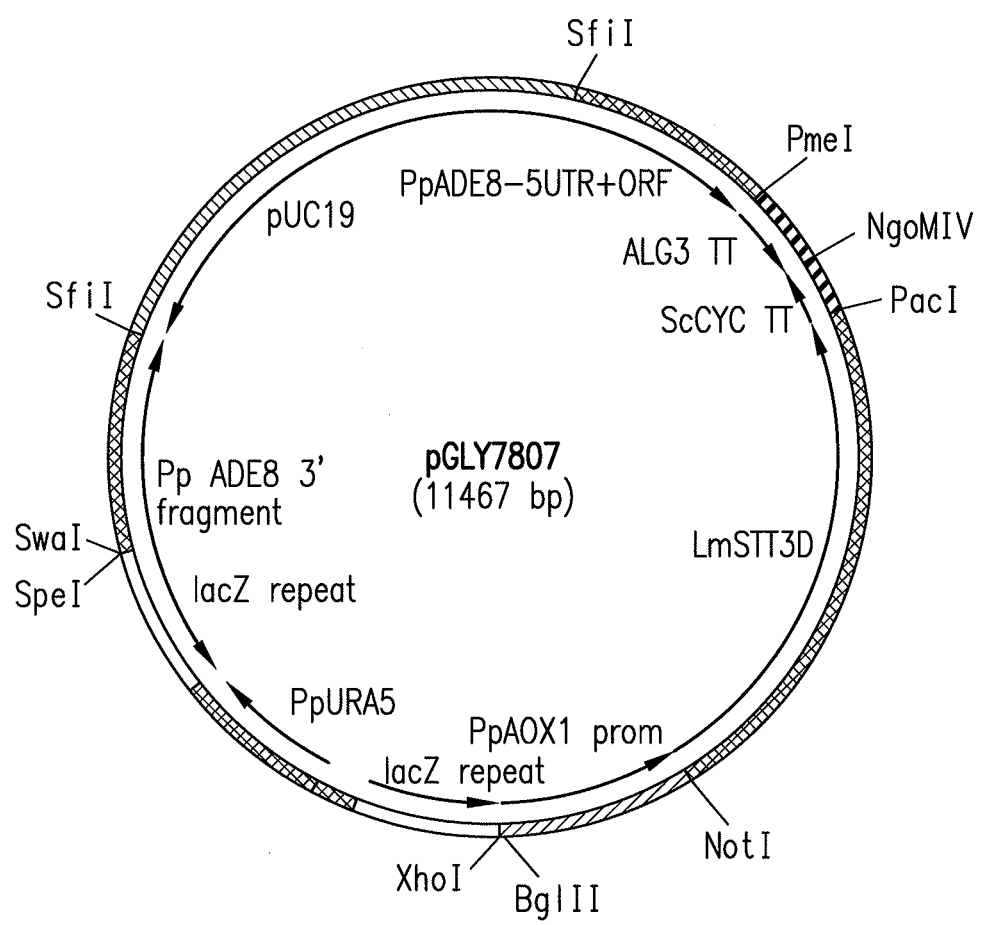
FIG. 5 shows a map of plasmid pGLY7807 encoding the LmSTT3D ORF under the control of the *Pichia pastoris* alcohol oxidase I (AOX1) promoter and *S. cerevisiae* CYC transcription termination sequence. The plasmid targets the ADE8 locus. The selection of transformants uses the URA5 expression cassette.

Plasmid pGLY7807 (FIG. 5) is a roll-in integration plasmid that targets the ADE8 locus in *P. pastoris*. The expression cassette encoding the LmSTT3D comprises a nucleic acid molecule encoding the LmSTT3D ORF codon-optimized for effective expression in *P. pastoris* operably linked at the 5' end to a nucleic acid molecule that has the inducible *P. pastoris* AOX1 promoter sequence (SEQ ID NO:3) and at the 3' end to a nucleic acid molecule that has the *S. cerevisiae* CYC transcription termination sequence (SEQ ID NO:4). For selecting transformants, the plasmid comprises an expression cassette encoding the plasmid further includes contains a nucleic acid molecule encoding a selection marker cassette comprising the *P. pastoris* URA5 gene or transcription unit (SEQ ID NO:38) flanked by nucleic acid molecules comprising lacZ repeats (SEQ ID NO:39). The expression and selection cassettes are adjacent and flanked on one side with *Pichia pastoris* ADE8 5' region (SEQ ID NO:61) and ORF and on the other side with the ADE8 3' region (SEQ ID NO:62).

EXAMPLE 2

Genetically engineered *Pichia pastoris* strains YGLY31886-31888 expressing the TbSTT3A, YGLY31889-31891 expressing TbSTT3B, and YGLY30626-30628 expressing TbSTT3C were constructed. These strains produce glycoproteins having galactose-terminated N-glycans. Briefly, the strains were constructed as follows.

In general, the strains were constructed from wild-type *Pichia pastoris* strain NRRL-Y 11430 using methods described earlier (See for example, U.S. Pat. No. 7,449,308; U.S. Pat. No. 7,479,389; U.S. Published Application No. 20090124000; Published PCT Application No. WO2009085135; Nett and Gerngross, Yeast 20:1279 (2003); Choi et al., Proc. Natl. Acad. Sci. USA 100:5022 (2003); Hamilton et al., Science 301:1244 (2003)). All plasmids were made in a pUC19 plasmid using standard molecular biology procedures. For nucleotide sequences that were optimized for expression in *P. pastoris*, the native nucleotide sequences were analyzed by the GENEOPTIMIZER software (GeneArt, Regensburg, Germany) and the results used to generate nucleotide sequences in which the codons were optimized for *P. pastoris* expression. Yeast strains were transformed by electroporation (using standard techniques as recommended by the manufacturer of the electroporator BioRad). From a series of transformations beginning with strain NRRL-Y 11430, strain YGLY8323 was produced. Strain YGLY8323 is capable of producing glycoproteins that have predominately galactose-terminated N-glycans. Construction of this strain from the wild-type NRRL-Y 11430 strain is described in detail in Example 2 of Published International Application No. WO2011106389 and which is incorporated herein by reference.

Figure 6:
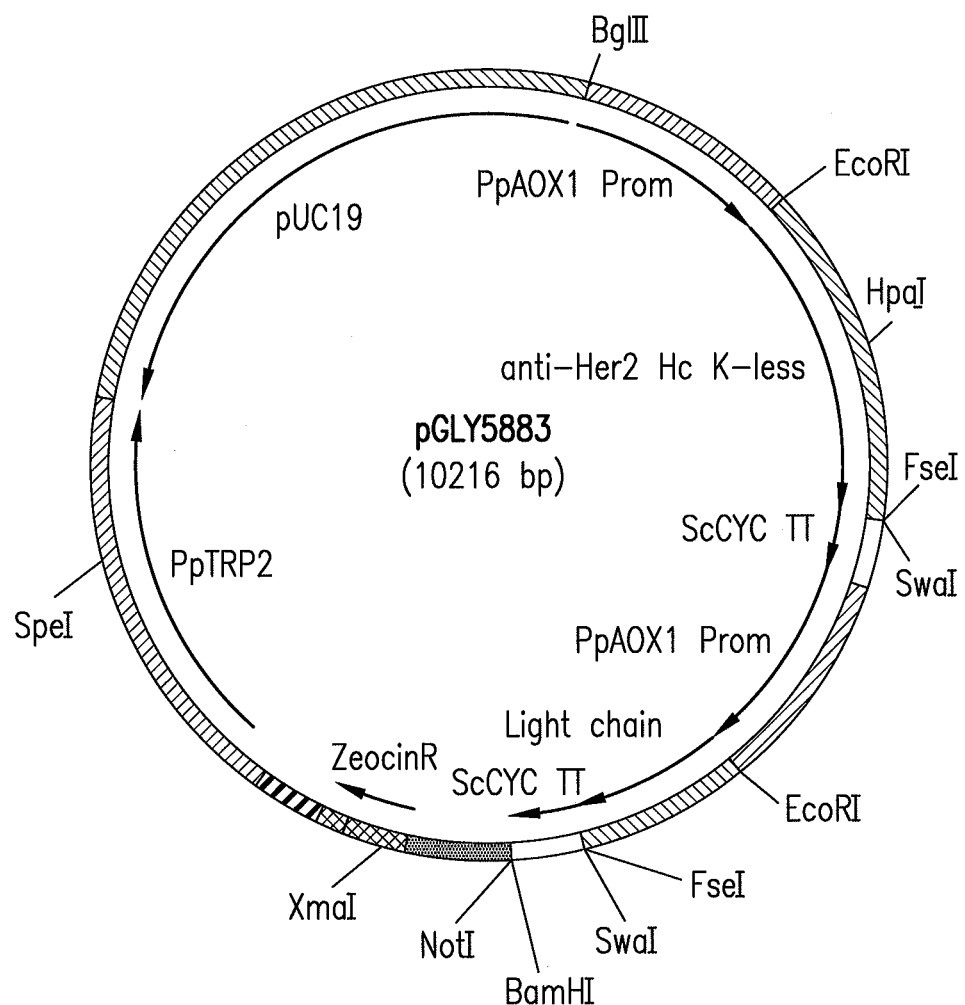
FIG. 6 shows a map of plasmid pGLY5883 encoding the light and heavy chains of an anti-Her2 antibody. The plasmid is a roll-in vector that targets the TRP2 locus. The ORFs encoding the light and heavy chains are under the control of a *P. pastoris* AOX1 promoter and the *P. pastoris* CIT1 transcription termination sequence. Selection of transformants uses zeocin resistance encoded by the zeocin resistance protein (ZeocinR) ORF under the control of the *P. pastoris* TEF1 promoter and *S. cerevisiae* CYC termination sequence.

Plasmid pGLY5883 (FIG. 6) is a roll-in integration plasmid encoding the light and heavy chains of an anti-Her2 antibody that targets the TRP2 locus in *P. pastoris*. The expression cassette encoding the anti-Her2 heavy chain comprises a nucleic acid molecule encoding the heavy chain ORF codon-optimized for effective expression in *P. pastoris* (SEQ ID NO:32) operably linked at the 5' end to a nucleic acid molecule encoding the *Saccharomyces cerevisiae* mating factor pre-signal sequence (SEQ ID NO:33) which in turn is fused at its N-terminus to a nucleic acid molecule that has the inducible *P. pastoris* AOX1 promoter sequence (SEQ ID NO:3) and at the 3' end to a nucleic acid molecule that has the *S. cerevisiae* CYC transcription termination sequence (SEQ ID NO:4). The expression cassette encoding the anti-Her2 light chain comprises a nucleic acid molecule encoding the light chain ORF codon-optimized for effective expression in *P. pastoris* (SEQ ID NO:35) operably linked at the 5' end to a nucleic acid molecule encoding the *Saccharomyces cerevisiae* mating factor pre-signal sequence (SEQ ID NO:33) which in turn is fused at its N-terminus to a nucleic acid molecule that has the inducible *P. pastoris* AOX1 promoter sequence (SEQ ID NO:3) and at the 3' end to a nucleic acid molecule that has the *S. cerevisiae* CYC transcription termination sequence (SEQ ID NO:4). For selecting transformants, the plasmid comprises an expression cassette encoding the Zeocin ORF in which the nucleic acid molecule encoding the ORF (SEQ ID NO:18) is operably linked at the 5' end to a nucleic acid molecule having the *S. cerevisiae* TEF promoter sequence (SEQ ID NO:36) and at the 3' end to a nucleic acid molecule having the *S. cerevisiae* CYC transcription termination sequence (SEQ ID NO:4). The plasmid further includes a nucleic acid molecule for targeting the TRP2 locus (SEQ ID NO:37). Strain YGLY12511 was generated by transforming pGLY5883, which encodes the anti-Her2 antibody, into YGLY8323. The strain YGLY12511 was selected from the strains produced. In this strain, the expression cassettes encoding the anti-Her2 heavy and light chains are targeted to the *Pichia pastoris* TRP2 locus (PpTRP2).

Figure 7:
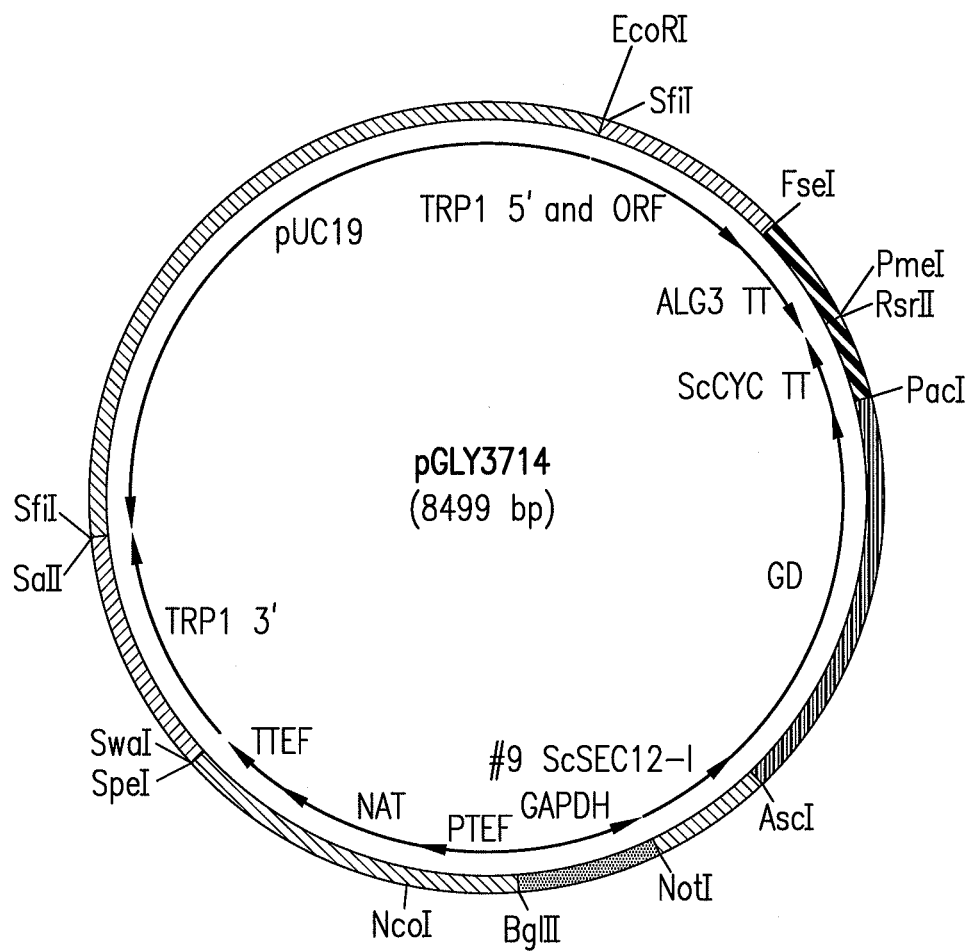
FIG. 7 shows a map of plasmid pGLY3714. Plasmid targets the TRP1 locus without disrupting expression of the locus and contains an expression cassettes encoding the mouse mannosidase IB catalytic domain (GD) fused at the N-terminus to *S. cerevisiae* SEC12 leader peptide (#9) operably linked to the *P. pastoris* GADPH promoter and the *S. cerevisiae* CYC termination sequence. The selection of transformants uses nourseothricin resistance encoded by the *Streptomyces nourcei* nourseothricin acetyltransferase (NAT) ORF under the control of the *Ashbya gossypii* TEF1 promoter (PTEF) and *Ashbya gossypii* TEF1 termination sequence (TTEF).

Plasmid pGLY3714 (FIG. 7) is an integration vector that targets the TRP1 locus and encodes the mouse mannosidase IB catalytic domain (GD) fused at the N-terminus to *S. cerevisiae* SEC12 leader peptide (9) to target the chimeric enzyme to the ER or Golgi, and an expression cassette comprising a nucleic acid molecule encoding the Nourseothricin resistance (NATR) expression cassette (originally from pAG25 from EROSCARF, Scientific Research and Development GmbH, Daimlerstrasse 13a, D-61352 Bad Homburg, Germany, See Goldstein et al., Yeast 15: 1541 (1999)). The NAT$^R$ expression cassette (SEQ ID NO:9) is operably regulated to the *Ashbya gossypii* TEF1 promoter (SEQ ID NO:10) and *A. gossypii* TEF1 termination sequences (SEQ ID NO:11). The expression cassette encoding the GD9 comprises a nucleic acid molecule encoding the mouse mannosidase IB catalytic domain (SEQ ID NO:51) fused at the 5' end to a nucleic acid molecule encoding the SEC12-m leader 9 (SEQ ID NO:52), which is operably linked at the 5' end to a nucleic acid molecule comprising the *P. pastoris* GADPH promoter (SEQ ID NO:8) and at the 3' end to a nucleic acid molecule comprising the *S. cerevisiae* CYC transcription termination sequence (SEQ ID NO:4). Plasmid pGLY1430 was linearized with SfiI and the linearized plasmid transformed into strain YGLY12511 to produce a number of strains by double-crossover homologous recombination. The strain YGLY14836 was selected from the strains produced.

Strain YGLY14836 was transformed with plasmid pGLY13168 encoding the *Trypanosoma brucei* STT3B protein to produce a number of trains of which YGLY33644-33647 was selected. As shown in Table 1, the N-glycosylation occupancy of anti-Her2 antibodies produced by YGLY33644-33647, which expresses the *T. brucei* STT3B was increased to about 99.6% compared to the N-glycosylation occupancy in the parental strain YGLY14386 lacking the *T. brucei* STT3B where occupancy was about 81.9%.

TABLE 1

| N-Glycan Site Occupancy | | | | |
|---|---|---|---|---|
| Strain (GS5.0) | ALG3 | YOS9 | TbSTT3 | N-glycan (mol %) |
| YGLY14836 | WT | WT | None | 81.9 |
| YGLY33644-33647 | WT | WT | AOX1P-TbSTT3B | 99.6 |

EXAMPLE 3

A strain capable of producing the paucimannose Man$_3$GlcNAc$_2$ (GS 2.1) structure was constructed to be used in an evaluation of the yield and quality of the N-glycosylation of an antibody expressed in the strain in the presence of various combinations of oligosaccharyltransferases. The strain was designated YGLY24541. Briefly, the strain was constructed as follows.

Construction of beginning strain YGLY16-3 is described in detail in Example 2 of Published International Application No. WO2011106389 and which is incorporated herein by reference. Plasmid pGLY3419 is an integration vector that contains the expression cassette comprising the *P. pastoris* URA5 gene flanked by lacZ repeats flanked on one side with the 5' nucleotide sequence of the *P. pastoris* BMT1 gene (SEQ ID NO:23) and on the other side with the 3' nucleotide sequence of the *P. pastoris* BMT1 gene (SEQ ID NO:24). Plasmid pGLY3419 was linearized and the linearized plasmid transformed into strain YGLY16-3 to produce a number of strains in which the URA5 expression cassette has been inserted into the BMT4 locus by double-crossover homologous recombination. The strain YGLY6697 was selected from the strains produced, and counterselected in the presence of 5-FOA to produce strain YGLY6719 in which the URA5 gene has been lost and only the lacZ repeats remain. The strain has disruptions of the BMT2 and BMT1 genes.

Figure 8:
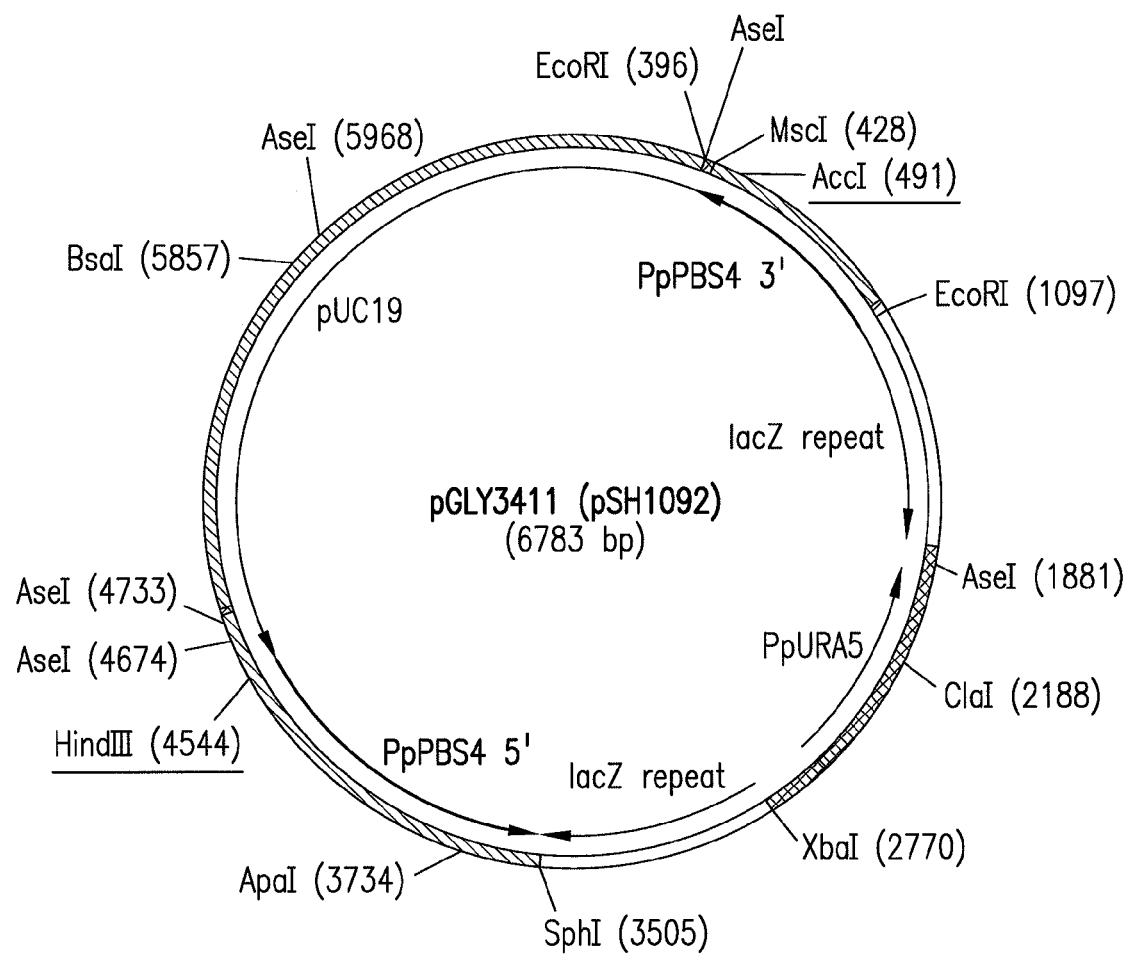
FIG. 8 shows a map of plasmid pGLY3411 (pSH1092). The plasmid is an integration vector that contains the expression cassette for selection comprising the *P. pastoris* URA5 gene or transcription unit (PpURA5) flanked by lacZ repeats (lacZ repeat) flanked on one side with the 5' nucleotide sequence of the *P. pastoris* BMT4 gene (PpPBS4 5') and on the other side with the 3' nucleotide sequence of the *P. pastoris* BMT4 gene (PpPBS4 3').

Plasmid pGLY3411 (FIG. 8) is an integration vector that contains the expression cassette comprising the *P. pastoris* URA5 gene flanked by lacZ repeats flanked on one side with the 5' nucleotide sequence of the *P. pastoris* BMT4 gene (SEQ ID NO:25) and on the other side with the 3' nucleotide sequence of the *P. pastoris* BMT4 gene (SEQ ID NO:26). Plasmid pGLY3411 was linearized and the linearized plasmid transformed into strain YGLY6719 to produce a number of strains in which the URA5 expression cassette has been inserted into the BMT4 locus by double-crossover homologous recombination. The strain YGLY6743 was selected from the strains produced, and counterselected in the presence of 5-FOA to produce strain YGLY6773 in which the URA5 gene has been lost and only the lacZ repeats remain. The strain has disruptions of the BMT2, BMT1, and BMT4 genes.

Figure 9:
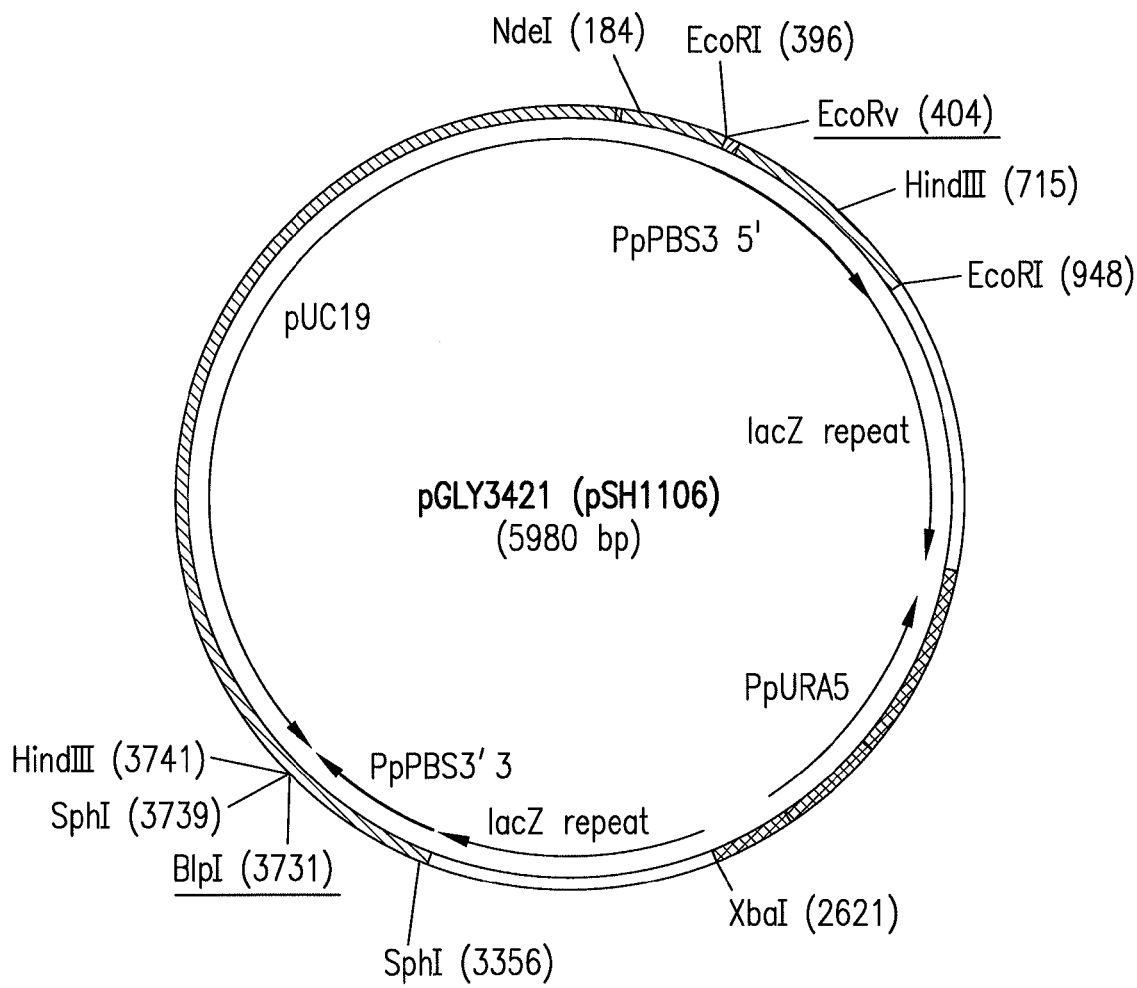
FIG. 9 shows a map of plasmid pGLY3421 (pSH1106). The plasmid contains an expression cassette for selection comprising the *P. pastoris* URA5 gene or transcription unit (PpURA5) flanked by lacZ repeats (lacZ repeat) flanked on one side with the 5' nucleotide sequence of the *P. pastoris* BMT3 gene (PpPBS3 5') and on the other side with the 3' nucleotide sequence of the *P. pastoris* BMT3 gene (PpPBS3 3').

Plasmid pGLY3421 (FIG. 9) is an integration vector that contains the expression cassette comprising the *P. pastoris* URA5 gene flanked by lacZ repeats flanked on one side with the 5' nucleotide sequence of the *P. pastoris* BMT3 gene (SEQ ID NO:27) and on the other side with the 3' nucleotide sequence of the *P. pastoris* BMT3 gene (SEQ ID NO:28). Plasmid pGLY3421 was linearized and the linearized plasmid transformed into strain YGLY6733 to produce a number of strains in which the URA5 expression cassette has been inserted into the BMT4 locus by double-crossover homologous recombination. The strain YGLY7754 was selected from the strains produced, and counterselected in the presence of 5-FOA to produce strain YGLY8252 in which the URA5 gene has been lost and only the lacZ repeats remain. The strain has disruptions of the BMT2, BMT1, BMT4, and BMT3 genes.

Figure 10:
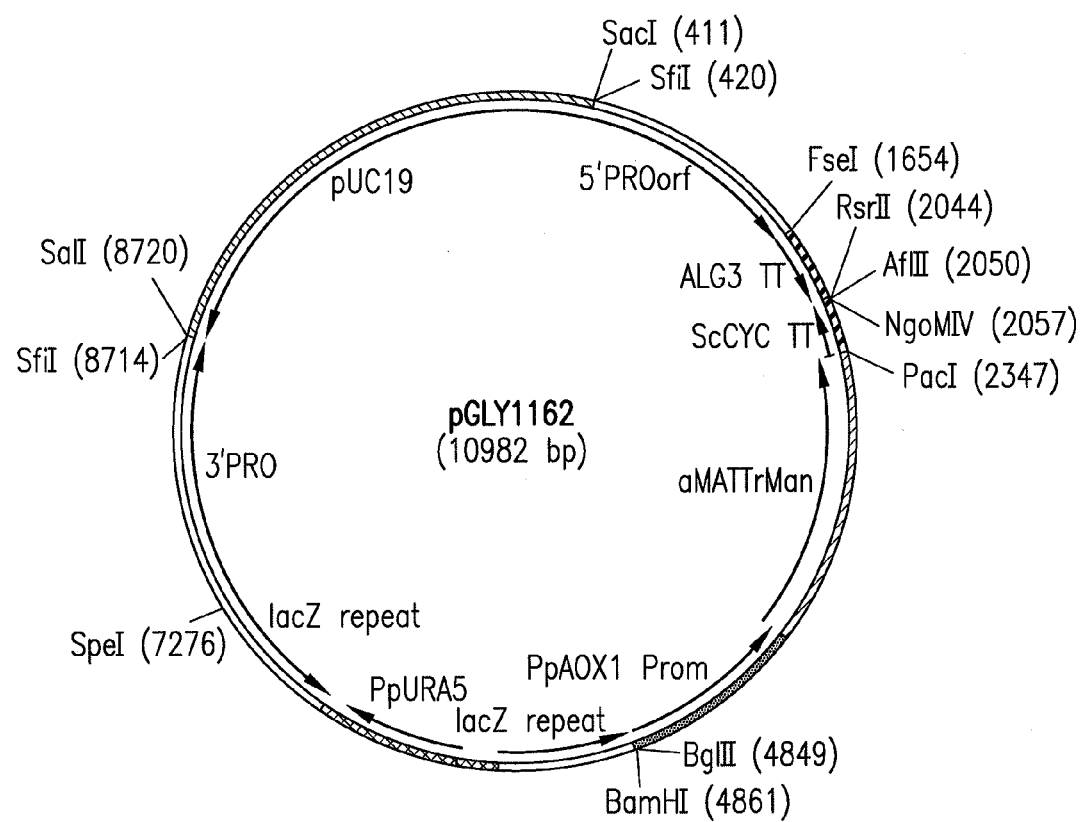
FIG. 10 shows a map of plasmid pGLY1162 cassettes encoding the *T. reesei* α-1,2-mannosidase catalytic domain fused at the N-terminus to *S. cerevisiae* αMATpre signal peptide (aMATTrMan) to target the chimeric protein to the secretory pathway and secretion from the cell operably linked to the *P. pastoris* AOX1 promoter and the *S. cerevi-* siae CYC termination sequence. The selection of transformants uses the URA5 expression cassette.

Plasmid pGLY1162 (FIG. 10) is an integration vector that targets the PRO1 locus without disrupting expression of the locus and contains expression cassettes encoding the *T. reesei* α-1,2-mannosidase catalytic domain fused at the N-terminus to *S. cerevisiae* αMATpre signal peptide (aMAT-TrMan) to target the chimeric protein to the secretory pathway and secretion from the cell. The expression cassette encoding the aMATTrMan comprises a nucleic acid molecule encoding the *T. reesei* catalytic domain (SEQ ID NO:29) fused at the 5' end to a nucleic acid molecule (SEQ ID NO:33) encoding the *S. cerevisiae* αMATpre signal peptide, which is operably linked at the 5' end to a nucleic acid molecule comprising the *P. pastoris* AOX1 promoter (SEQ ID NO:3) and at the 3' end to a nucleic acid molecule comprising the *S. cerevisiae* CYC transcription termination sequence (SEQ ID NO:4). The cassette is flanked on one side by a nucleic acid molecule comprising a nucleotide sequence from the 5' region and complete ORF of the PRO1 gene (SEQ ID NO:30) followed by a *P. pastoris* ALG3 termination sequence and on the other side by a nucleic acid molecule comprising a nucleotide sequence from the 3' region of the PRO1 gene (SEQ ID NO:31). Plasmid pGLY1162 was linearized and the linearized plasmid transformed into strain YGLY8252 to produce a number of strains in which the URA5 expression cassette has been inserted into the PRO1 locus by double-crossover homologous recombination. The strain YGLY8292 was selected from the strains produced, and counterselected in the presence of 5-FOA to produce strain YGLY9060 in which the URA5 gene has been lost and only the lacZ repeats remain.

Plasmid pGLY7140 (FIG. 11) is a knock-out vector that targets the YOS9 locus and contains a nucleic acid molecule comprising the *P. pastoris* URA5 gene (SEQ ID NO:38) or transcription unit flanked by nucleic acid molecules comprising lacZ repeats (SEQ ID NO:39) which in turn is flanked on one side by a nucleic acid molecule comprising a nucleotide sequence from the 5' region of the YOS9 gene (SEQ ID NO:19) and on the other side by a nucleic acid molecule comprising a nucleotide sequence from the 3' region of the YOS9 gene (SEQ ID NO:20). Strain YGLY9060 was transformed with plasmid pGLY7140 linearized with SfiI to produce a number of strains in which the URA5 gene flanked by the lacZ repeats has been inserted into the YOS9 locus by double-crossover homologous recombination. Strain YGLY23328 was selected from the strains produced. The strain was counterselected in the presence of 5-FOA to produce strain YGLY23360 in which the URA5 gene has been lost and only the lacZ repeats remain.

Plasmid pGLY5508 (FIG. 12) is a knock-out vector that targets the ALG3 locus and contains a nucleic acid molecule comprising the *P. pastoris* URA5 gene or transcription unit flanked by nucleic acid molecules comprising lacZ repeats which in turn is flanked on one side by a nucleic acid molecule comprising a nucleotide sequence from the 5' region of the ALG3 gene (SEQ ID NO:21) and on the other side by a nucleic acid molecule comprising a nucleotide sequence from the 3' region of the ALG3 gene (SEQ ID NO:22). Strain YGLY24540-YGLY24542 was generated by transforming pGLY5508 linearized with SfiI into strain YGLY23360 to produce a number of strains in which the URA5 gene flanked by the lacZ repeats has been inserted into the ALG3 locus by double-crossover homologous recombination. Strain YGLY24540-YGLY24542 was selected from the strains produced.

EXAMPLE 4

Strain YGLY24540-YGLY24542 produced in Example 3 was used for the construction of several strains that express an antibody to evaluate the N-glycosylation of antibodies produced in the presence of various oligosaccharyltransferases. Construction of these strains is as follows.

Plasmid pGLY6833 (FIG. 13) is a roll-in integration plasmid encoding the light and heavy chains of an anti-Her2 antibody that targets the TRP2 locus in *P. pastoris*. The expression cassette encoding the anti-Her2 heavy chain comprises a nucleic acid molecule encoding the heavy chain ORF codon-optimized for effective expression in *P. pastoris* (SEQ ID NO:15) operably linked at the 5' end to a nucleic acid molecule (SEQ ID NO:33) encoding the *Saccharomyces cerevisiae* mating factor pre-signal sequence which in turn is fused at its N-terminus to a nucleic acid molecule that has the inducible *P. pastoris* AOX1 promoter sequence (SEQ ID NO:3) and at the 3' end to a nucleic acid molecule that has the *P. pastoris* CIT1transcription termination sequence (SEQ ID NO:34). The expression cassette encoding the anti-Her2 light chain comprises a nucleic acid molecule encoding the light chain ORF codon-optimized for effective expression in *P. pastoris* (SEQ ID NO:16) operably linked at the 5' end to a nucleic acid molecule encoding the *Saccharomyces cerevisiae* mating factor pre-signal sequence (SEQ ID NO:33) which in turn is fused at its N-terminus to a nucleic acid molecule that has the inducible *P. pastoris* AOX1 promoter sequence (SEQ ID NO:3) and at the 3' end to a nucleic acid molecule that has the *P. pastoris* CIT1 transcription termination sequence (SEQ ID NO:34). For selecting transformants, the plasmid comprises an expression cassette encoding the Zeocin ORF in which the nucleic acid molecule encoding the ORF (SEQ ID NO:18) is operably linked at the 5' end to a nucleic acid molecule having the *S. cerevisiae* TEF promoter sequence (SEQ ID NO:36) and at the 3' end to a nucleic acid molecule having the *S. cerevisiae* CYC transcription termination sequence. The plasmid further includes a nucleic acid molecule for targeting the TRP2 locus (SEQ ID NO:37). Plasmid pGLY6833 was transformed into strain YGLY24541 to produce a number of strains that express the anti-Her2 antibody of which strain YGLY26362 was selected.

Strain YGLY26362 was transformed with pGLY13165, which encodes the *T. brucei* STT3A, to produce strain YGLY31886-31888; or pGLY13168, which encodes the *T. brucei* STT3B, to produce strain YGLY31889-31891; or pGLY7128, which encodes the *T. brucei* STT3C, to produce strain YGLY30626-30628.

As shown in Table 2, the N-glycosylation occupancy of anti-Her2 antibodies produced in the strain expressing the *T. brucei* STT3B was enhanced over the parent strain lacking the *T. brucei* STT3B, or in strains that expressed either *T. brucei* STT3A or *T. brucei* STT3C.

TABLE 2

| N-Glycan Site Occupancy | | | | |
|---|---|---|---|---|
| Strain (GS2.1) | ALG3 | YOS9 | TbSTT3 | N-glycan (mol %) |
| YGLY26362 | Knock-out | Knock-out | None | 15.3 |
| YGLY31886-31888 | Knock-out | Knock-out | AOX1P-TbSTT3A | 60.2 |
| YGLY31889-31891 | Knock-out | Knock-out | AOX1P-TbSTT3B | 99.8 |
| YGLY30626-30628 | Knock-out | Knock-out | AOX1P-TbSTT3C | 17.3 |

EXAMPLE 5

This example shows the effect various oligosyltransferases have on the N-glycosylation of insulin modified to comprise N-glycosylation sites. The glycosylated insulin precursor can be processed in vitro to glycosylated insulin analog 210-2-B. 210-B-2 is a heterodimer comprising a native insulin A-chain and a B-chain (des(B30)) having the amino acid sequence N*GTFVNQHLCGSHLVEALYLVCGERGFFYTN*K (SEQ ID NO:54) wherein the Asn residues N* at positions 1 and 31 (B-2 & B28) are each covalently linked in a β1 linkage to a Man$_3$GlcNAc$_2$ (paucimannose)N-glycan.

Strain YGLY24540-24542 was generated as shown in Example 3 and then transformed with pGLY7807 encoding the LmSTT3D (Example 1) to produce a number of strains of which strain YGLY29308 was selected. Strain YGLY29308 was counter-selected on 5-FOA to produce a number of strains of which strain YGLY29345 was selected.

Strain YGLY29345 was transformed with plasmid pGLY5933 (FIG. 14), which disrupts the ATT1 gene. Disruption of the ATT1 gene may provide improve cell fitness during fermentation. The salient features of the plasmid is that it comprises the URA5 expression cassette described above flanked on one end with a nucleic acid molecule comprising the 5' or upstream region of the ATT1 gene (SEQ ID NO:48) and the other end with a nucleic acid molecule encoding the 3' or downstream region of the ATT1 gene (SEQ ID NO:49). YGLY24586 was transformed with plasmid pGLY5933 resulted in a number of strains of which strain YGLY27303 was selected. The strain was counter-selected on 5-FOA to produce strain YGLY30609.

Plasmid pGLY12073 (FIG. 15) is a roll-in integration plasmid that targets the ADE4 locus in P. pastoris and encodes the human endomannosidase ORF. The expression cassette encoding the full-length human endomannosidase comprises a nucleic acid molecule encoding full-length human endomannosidase ORF codon-optimized for effective expression in P. pastoris (SEQ ID NO:50) operably linked at the 5' end to a nucleic acid molecule that has the inducible P. pastoris AOX1 promoter sequence (SEQ ID NO:3) and at the 3' end the S. cerevisiae CYC transcription termination sequence (SEQ ID NO:4). For selecting transformants, the plasmid includes the URA5 expression cassette as described previously. The expression and selection cassettes are adjacent and flanked on one side with Pichia pastoris ADE4 5' region (SEQ ID NO:59) and ORF and on the other side with the ADE4 3' region (SEQ ID NO:60). Strain YGLY30609 was transformed with plasmid pGLY12073 to generate a number of strains of which strain YGLY31595 was selected. The strain was counter-selected on 5-FOA to produce strain YGLY31747.

Plasmid pGLY8340 (FIG. 16) is a roll-in integration plasmid that targets the ADE8 locus in P. pastoris and comprises two expression cassettes encoding the LmSTT3D. The first expression cassette encoding the LmSTT3D comprises a nucleic acid molecule encoding the LmSTT3D ORF codon-optimized for effective expression in P. pastoris operably linked at the 5' end to a nucleic acid molecule that has the inducible P. pastoris AOX1 promoter sequence (SEQ ID NO:3) and at the 3' end to a nucleic acid molecule that has the S. cerevisiae CYC transcription termination sequence (SEQ ID NO:4). The second expression cassette encoding the LmSTT3D comprises a nucleic acid molecule encoding the LmSTT3D ORF codon-optimized for effective expression in P. pastoris operably linked at the 5' end to a nucleic acid molecule that has the P. pastoris STT3 promoter sequence (SEQ ID NO:53) and at the 3' end to a nucleic acid molecule that has the S. cerevisiae CYC transcription termination sequence (SEQ ID NO:4). For selecting transformants, the plasmid comprises an expression cassette encoding the plasmid further includes contains a nucleic acid molecule encoding a selection marker cassette comprising the P. pastoris URA5 gene or transcription unit (SEQ ID NO:38) flanked by nucleic acid molecules comprising lacZ repeats (SEQ ID NO:39). The expression and selection cassettes are adjacent and flanked on one side with Pichia pastoris ADE8 5' region (SEQ ID NO:61) and ORF and on the other side with the ADE8 3' region (SEQ ID NO:62). Strain YGLY31747 was transformed with pGLY8340 to produce a number of strains of which strain YGLY31777 was selected.

Plasmid pGLY12663 (FIG. 17), which is a roll-in integration plasmid that targets the TRP2 or AOX1p loci, includes an expression cassette encoding an insulin precursor fusion protein comprising a S. cerevisiae alpha mating factor signal sequence and propeptide (SEQ ID NO:55) fused to an N-terminal spacer peptide (SEQ ID NO:56) fused to the human insulin B-chain with NGT(−2) tripeptide addition and a P28N substitution (SEQ ID NO:57) fused to a C-peptide consisting of the amino acid sequence AAK fused to the human insulin A-chain (SEQ ID NO:58). Strain YGLY31777 was transformed with plasmid pGLY12663 to produce a number strains of which strain YGLY31816 was selected.

Strain YGLY31816 was transformed with pGLY13165, which encodes the T. brucei STT3A, to produce strain YGLY33996; or pGLY13168, which encodes the T. brucei STT3B, to produce strain YGLY33997; or pGLY7128, which encodes the T. brucei STT3C, to produce strain YGLY34727.

As shown in Table 3, in strains that express both the LmSTT3D and the TbSTT3C, the N-glycosylated insulin molecule had about 90% N-glycosylation site occupancy. This was unexpected because the results shown in Table 2 suggested that TbSTT3C would have little or no effect on N-glycosylation occupancy.

TABLE 3

| Strain (GS2.1) | ALG3 | YOS9 | LmSTT3D | TbSTT3 | N-glycan (mol %) |
|---|---|---|---|---|---|
| YGLY31816 | Knockout | Knockout | PpSTT3p-LmSTT3D AOX1p-LmSTT3D | None | 78-80% |
| YGLY33996 | Knockout | Knockout | PpSTT3p-LmSTT3D AOX1p-LmSTT3D | AOX1P-TbSTT3A | 76.9 |
| YGLY33997 | Knockout | Knockout | PpSTT3p-LmSTT3D AOX1p-LmSTT3D | AOX1P-TbSTT3B | 78.9 |
| YGLY34727 | Knockout | Knockout | PpSTT3p-LmSTT3D AOX1p-LmSTT3D | AOX1P-TbSTT3C | 89.4 |

N-Glycan Site Occupancy (Insulin)

EXAMPLE 6

Microchip CE-SDS sample preparation is as follows. IgG sample (100-200 μg) was concentrated to about 100 μL and buffer exchanged with 100 mM Tris-HCl pH 9.0 with 1% SDS. Then the sample along with 2 μL of 10 kDa internal standard provided by Beckman is reduced by addition of 5 μL beta mercaptoethanol and boiled for 3 minutes.

Separation Methods by Labchip GXII (Caliper Life Science, CA) is as follows.

The reduced sample is resolved over a bare-fused silica capillary (30.2 cm, 50 μm I.D.) according to the method recommended by manufacturer for reduced IgG in the reverse polarity orientation with a detection window of 20.2 cm from the inlet. For each cycle, the capillary is first preconditioned with 0.1 N NaOH, 0.1 N HCl, HPLC graded water and SDSMW Gel Buffer, provided by manufacturer. Samples are electrokinetically introduced by applying voltage at 5 kV for 20 seconds. Electrophoresis is performed at constant voltage, with an applied field strength of 497 volts/cm with capillary temperature maintained at 25° C. using recirculating liquid coolant. The current generated is approximately 27 μAmps. The peak detection is recorded at 2 Hz at 220 nm of 10 nm bandwidth. The occupancy is determined by percentage of the corrected peak areas corresponding to the glycosylated heavy chain.

N-glycosylation Occupancy analysis was as follows.

Antibody sample (5 μL) at approximately 1-2 mg/mL is added to 7 μL of sample buffer provided with HT Protein Express Labchip® Kit supplemented with 50 mM 2-mercaptoethanol (Sigma-Aldrich; St. Louis, Mo., USA). The sample mixture is then incubated at 75 C for 15 minutes. Prior to microchip analysis, deionized HPLC grade water (35 μL) is added to the sample mixture and added onto the instrument for size separation. The N-glycosylation occupancy is determined by percentage of the corrected peak areas corresponding to the glycosylated heavy chain (GHC). The ratio of heavy and light chains (H:L) is calculated from total corrected peak area of GHC and nonglycosylated heavy (NGHC) against that of light chain. The impurity is reported as the total corrected peak area of protein bands that do not belong to GHC, NGHC or light chain.

The DasGip Protocol for growing the recombinant host cells is substantially as follows.

The inoculum seed flasks are inoculated from yeast patches (isolated from a single colony) on agar plates into 0.1 L of 4% BSGY in a 0.5-L baffled flask. Seed flasks are grown at 180 rpm and 24° C. (Innova 44, New Brunswick Scientific) for 48 hours. Cultivations were done in 1 L (fedbatch-pro, DASGIP BioTools) bioreactors. Vessels are charged with 0.54 L of 0.22 μm filtered 4% BSGY media and autoclaved at 121° C. for 45 minutes. After sterilization and cooling; the aeration, agitation and temperatures are set to 0.7 vvm, 400 rpm and 24° C. respectively. The pH is adjusted to and controlled at 6.5 using 30% ammonium hydroxide. Inoculation of a prepared bioreactor occurred aseptically with 60 mL from a seed flask. Agitation is ramped to maintain 20% dissolved oxygen (DO) saturation. After the initial glycerol charge is consumed, denoted by a sharp increase in the dissolved oxygen, a 50% w/w glycerol solution containing 5 mg/L biotin and 32.3 mg/L PMTi-4 is triggered to feed at 3.68 mL/hr for eight hours. During the glycerol fed-batch phase 0.375 mL of PTM2 salts are injected manually. Completion of the glycerol fed-batch is followed by a 0.5 hour starvation period and initiation of the induction phase. A continuous feed of a 50% v/v methanol solution containing 2.5 mg/L biotin and 6.25 mL/L PTM2 salts is started at a flat rate of 2.16 mL/hour. Injections of 0.25 mL of 1.9 mg/mL PMTi-4 (in methanol) are added after each 24 hours of induction. In general, individual fermentations are harvested within 36-110 hours of induction. The culture broth is clarified by centrifugation (Sorvall Evolution RC, Thermo Scientific) at 8500 rpm for 40 min and the resulting supernatant was submitted for purification.

4% BSGY with 100 mM Sorbitol

| Component | Concentration (g/L) |
|---|---|
| $KH_2PO_4$ (monobasic) | 11.9 |
| $K_2HPO_4$ (dibasic) | 2.5 |
| Sorbitol | 18.2 |
| Yeast Extract | 10 |
| Soytone | 20 |
| Glycerol | 40 |
| YNB | 13.4 |
| Biotin | 20 (ml/L) |
| Anti-foam | 8 drops/L* |

Solution to be autoclaved once made

PTM2 Salts

| Component | Concentration (g/L) |
|---|---|
| $CuSO_4$—$5H_2O$ | 1.50 |
| NaI | 0.08 |
| $MnSO_4$—$H_2O$ | 1.81 |
| $H_3BO_4$ | 0.02 |
| $FeSO_4$—$7H_2O$ | 6.50 |
| $ZnCl_2$ | 2.00 |
| $CoCl_2$—$6H_2O$ | 0.50 |
| $Na_2MoO_4$—$2H_2O$ | 0.20 |
| Biotin (dry stock) | 0.20 |
| 98% $H_2SO_4$ | 5 mL/L |

Dissolve in 80% of the desired total volume of DI water.
Once dissolved make up to final total volume with DI water
Filter under vacuum through 0.22 micron filter into sterile bottle.
Label with Solution Name, Batch Number, and Date. Store at 4° C.

PMTi-4 is a PMT inhibitor disclosed in U.S. Published Application No. 20110076721 as Example 4 compound. PMTi-4 has the structure

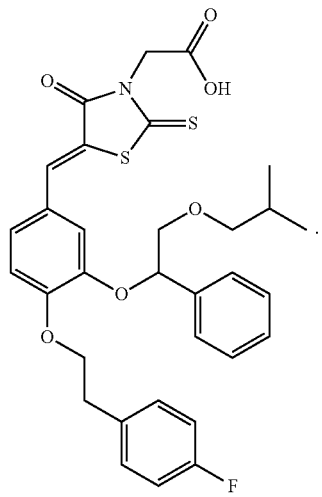 [SMILES: CC(C)COCC(Oc1cc(/C=C2\SC(=S)N(CC(=O)O)C2=O)ccc1OCCc1ccc(F)cc1)c1ccccc1]

SEQUENCES

Sequences that were used to produce some of the strains disclosed in the Examples are provided in the following table.

BRIEF DESCRIPTION OF THE SEQUENCES

| SEQ ID NO: | Description | Sequence |
|---|---|---|
| 1 | Leishmania major STT3D (protein) | MGKRKGNSLGDSGSAATASREASAQAEDAASQTKTASP PAKVILLPKTLTDEKDFIGIFPFPFWPVHFVLTVVALFVLA ASCFQAFTVRMISVQIYGYLIHEFDPWFNYRAAEYMSTH GWSAFFSWFDYMSWYPLGRPVGSTTYPGLQLTAVAIHR ALAAAGMPMSLNNVCVLMPAWFGAIATATLAFCTYEA SGSTVAAAAAALSFSIIPAHLMRSMAGEFDNECIAVAAM LLTFYCWVRSLRTRSSWPIGVLTGVAYGYMAAAWGGYI FVLNMVAMHAGISSMVDWARNTYNPSLLRAYTLFYVV GTAIAVCVPPVGMSPFKSLEQLGALLVLVFLCGLQVCEV LRARAGVEVRSRANFKIRVRVFSVMAGVAALAISVLAPT GYFGPLSVRVRALFVEHTRTGNPLVDSVAEHQPASPEA MWAFLHVCGVTWGLGSIVLAVSTFVHYSPSKVFWLLNS GAVYYFSTRMARLLLLSGPAACLSTGIFVGTILEAAVQLS FWDSDATKAKKQQKQAQRHQRGAGKGSGRDDAKNAT TARAFCDVFAGSSLAWGHRMVLSIAMWALVTTTAVSFF SSEFASHSTKFAEQSSNPMIVFAAVVQNRATGKPMNLLV DDYLKAYEWLRDSTPEDARVLAWWDYGYQITGIGNRTS LADGNTWNHEHIATIGKMLTSPVVEAHSLVRHMADYVL IWAGQSGDLMKSPHMARIGNSVYHDICPDDPLCQQFGF HRNDYSRPTPMMRASLLYNLHEAGKRKGVKVNPSLFQE VYSSKYGLVRIFKVMNVSAESKKWVADPANRVCHPPGS WICPGQYPPAKEIQEMLAHRVPFDQVTNADRKNNVGSY QEEYMRRMRESENRR |
| 2 | Leishmania major STT3D (DNA) | ATGGGTAAAAGAAAGGGAAACTCCTTGGGAGATTCTG GTTCTGCTGCTACTGCTTCCAGAGAGGCTTCTGCTCAA GCTGAAGATGCTGCTTCCCAGACTAAGACTGCTTCTCC ACCTGCTAAGGTTATCTTGTTGCCAAAGACTTTGACTG ACGAGAAGGACTTCATCGGTATCTTCCCATTTCCATTC TGGCCAGTTCACTTCGTTTTGACTGTTGTTGCTTTGTTC GTTTTGGCTGCTTCCTGTTTCCAGGCTTTCACTGTTAGA ATGATCTCCGTTCAAATCTACGGTTACTTGATCCACGA ATTTGACCCATGGTTCAACTACAGAGCTGCTGAGTAC ATGTCTACTCACGGATGGAGTGCTTTTTTCTCCTGGTT CGATTACATGTCCTGGTATCCATTGGGTAGACCAGTTG GTTCTACTACTTACCCAGGATTGCAGTTGACTGCTGTT GCTATCCATAGAGCTTTGGCTGCTGCTGGAATGCCAAT GTCCTTGAACAATGTTTGTGTTTTGATGCCAGCTTGGT TTGGTGCTATCGCTACTGCTACTTTGGCTTTCTGTACTT ACGAGGCTTCTGGTTCTACTGTTGCTGCTGCAGCT GCTTTGTCCTTCTCCATTATCCCTGCTCACTTGATGAG ATCCATGGCTGGTGAGTTCGACAACGAGTGTATTGCT GTTGCTGCTATGTTGTTGACTTTCTACTGTTGGGTTCGT TCCTTGAGAACTAGATCCTCCTGGCCAATCGGTGTTTT GACAGGTGTTGCTTACGGTTACATGGCTGCTGCTTGGG GAGGTTACATCTTCGTTTTGAACATGGTTGCTATGCAC GCTGGTATCTCTTCTATGGTTGACTGGGCTAGAAACAC TTACAACCCATCCTTGTTGAGAGCTTACACTTTGTTCT ACGTTGTTGGTACTGCTATCGCTGTTTGTGTTCCACCA GTTGGAATGTCTCCATTCAAGTCCTTGGAGCAGTTGGG AGCTTTGTTGGTTTTGGTTTTCTTGTGTGGATTGCAAGT TTGTGAGGTTTTGAGAGCTAGAGCTGGTGTTGAAGTTA GATCCAGAGCTAATTTCAAGATCAGAGTTAGAGTTTTC TCCGTTATGGCTGGTGTTGCTGCTTTGGCTATCTCTGTT TTGGCTCCAACTGGTTACTTTGGTCCATTGTCTGTTAG AGTTAGAGCTTTGTTTGTTGAGCACACTAGAACTGGTA ACCCATTGGTTGACTCCGTTGCTGAACATCAACCAGCT TCTCCAGAGGCTATGTGGGCTTTCTTGCATGTTTGTGG TGTTACTTGGGGATTGGGTTCCATTGTTTTGGCTGTTTC CACTTTCGTTCACTACTCCCCATCTAAGGTTTTCTGGTT GTTGAACTCCGGTGCTGTTTACTACTTCTCCACTAGAA TGGCTAGATTGTTGTTGTTGTCCGGTCCAGCTGCTTGT TTGTCCACTGGTATCTTCGTTGGTACTATCTTGGAGGC TGCTGTTCAATTGTCTTTCTGGGACTCCGATGCTACTA AGGCTAAGAAGCAGCAAAAGCAGGCTCAAAGACACC AAAGAGGTGCTGGTAAAGGTTCTGGTAGAGATGACGC TAAGAACGCTACTACTGCTAGAGCTTTCTGTGACGTTT TCGCTGGTTCTTCTTTGGCTTGGGGTCACAGAATGGTT TTGTCCATTGCTATGTGGGCTTTGGTTACTACTACTGC TGTTTCCTTCTTCTCCTCCGAATTTGCTTCTCACTCCAC TAAGTTCGCTGAACAATCCTCCAACCCAATGATCGTTT TCGCTGCTGTTGTTCAGAACAGAGCTACTGGAAAGCC AATGAACTTGTTGGTTGACGACTACTTGAAGGCTTACG AGTGGTTGAGAGACTCTACTCCAGAGGACGCTAGAGT TTTGGCTTGGTGGGACTACGGTTACCAAATCACTGGTA |

BRIEF DESCRIPTION OF THE SEQUENCES

| SEQ ID NO: | Description | Sequence |
|---|---|---|
| | | TCGGTAACAGAACTTCCTTGGCTGATGGTAACACTTGG AACCACGAGCACATTGCTACTATCGGAAAGATGTTGA CTTCCCCAGTTGTTGAAGCTCACTCCCTTGTTAGACAC ATGGCTGACTACGTTTTGATTTGGGCTGGTCAATCTGG TGACTTGATGAAGTCTCCACACATGGCTAGAATCGGT AACTCTGTTTACCACGACATTTGTCCAGATGACCCATT GTGTCAGCAATTCGGTTTCCACAGAAACGATTACTCCA GACCAACTCCAATGATGAGAGCTTCCTTGTTGTACAAC TTGCACGAGGCTGGAAAAAGAAAGGGTGTTAAGGTTA ACCCATCTTTGTTCCAAGAGGTTTACTCCTCCAAGTAC GGACTTGTTAGAATCTTCAAGGTTATGAACGTTTCCGC TGAGTCTAAGAAGTGGGTTGCAGACCCAGCTAACAGA GTTTGTCACCCACCTGGTTCTTGGATTTGTCCTGGTCA ATACCCACCTGCTAAAGAAATCCAAGAGATGTTGGCT CACAGAGTTCCATTCGACCAGGTTACAAACGCTGACA GAAAGAACAATGTTGGTTCCTACCAAGAGGAATACAT GAGAAGAATGAGAGAGTCCGAGAACAGAAGATAATA G |
| 3 | Pp AOX1 promoter | AACATCCAAAGACGAAAGGTTGAATGAAACCTTTTTG CCATCCGACATCCACAGGTCCATTCTCACACATAAGTG CCAAACGCAACAGGAGGGGATACACTAGCAGCAGAC CGTTGCAAACGCAGGACCTCCACTCCTCTTCTCCTCAA CACCCACTTTTGCCATCGAAAAACCAGCCCAGTTATTG GGCTTGATTGGAGCTCGCTCATTCCAATTCCTTCTATT AGGCTACTAACACCATGACTTTATTAGCCTGTCTATCC TGGCCCCCCTGGCGAGGTTCATGTTTGTTTATTTCCGA ATGCAACAAGCTCCGCATTACACCCGAACATCACTCC AGATGAGGGCTTTCTGAGTGTGGGGTCAAATAGTTTC ATGTTCCCCAAATGGCCCAAAACTGACAGTTTAAACG CTGTCTTGGAACCTAATATGACAAAAGCGTGATCTCAT CCAAGATGAACTAAGTTTGGTTCGTTGAAATGCTAAC GGCCAGTTGGTCAAAAAGAAACTTCCAAAAGTCGGCA TACCGTTTGTCTTGTTTGGTATTGATTGACGAATGCTC AAAAATAATCTCATTAATGCTTAGCGCAGTCTCTCTAT CGCTTCTGAACCCCGGTGCACCTGTGCCGAAACGCAA ATGGGGAAACACCCGCTTTTTGGATGATTATGCATTGT CTCCACATTGTATGCTTCCAAGATTCTGGTGGGAATAC TGCTGATAGCCTAACGTTCATGATCAAAATTTAACTGT TCTAACCCCTACTTGACAGCAATATATAAACAGAAGG AAGCTGCCCTGTCTTAAACCTTTTTTTTTATCATCATTA TTAGCTTACTTTCATAATTGCGACTGGTTCCAATTGAC AAGCTTTTGATTTTAACGACTTTTAACGACAACTTGAG AAGATCAAAAAACAACTAATTATTCGAAACG |
| 4 | ScCYC TT | ACAGGCCCCTTTTCCTTTGTCGATATCATGTAATTAGT TATGTCACGCTTACATTCACGCCCTCCTCCCACATCCG CTCTAACCGAAAAGGAAGGAGTTAGACAACCTGAAGT CTAGGTCCCTATTTATTTTTTTTAATAGTTATGTTAGTA TTAAGAACGTTATTTATATTTCAAATTTTTCTTTTTTTT CTGTACAAACGCGTGTACGCATGTAACATTATACTGA AAACCTTGCTTGAGAAGGTTTTGGGACGCTCGAAGGC TTTAATTTGCAAGCTGCCGGCTCTTAAG |
| 5 | ScARR3 ORF | ATGTCAGAAGATCAAAAAAGTGAAAATTCCGTACCTT CTAAGGTTAATATGGTGAATCGCACCGATATACTGAC TACGATCAAGTCATTGTCATGGCTTGACTTGATGTTGC CATTTACTATAATTCTCTCCATAATCATTGCAGTAATA ATTTCTGTCTATGTGCCTTCTTCCCGTCACACTTTTGAC GCTGAAGGTCATCCCAATCTAATGGGAGTGTCCATTCC TTTGACTGTTGGTATGATTGTAATGATGATTCCCCCGA TCTGCAAAGTTTCCTGGGAGTCTATTCACAAGTACTTC TACAGGAGCTATATAAGGAAGCAACTAGCCCTCTCGT TATTTTTGAATTGGGTCATCGGTCCTTTGTTGATGACA GCATTGGCGTGGATGGCGCTATTCGATTATAAGGAAT ACCGTCAAGGCATTATTATGATCGGAGTAGCTAGATG CATTGCCATGGTGCTAATTTGGAATCAGATTGCTGGAG GAGACAATGATCTCTGCGTCGTGCTTGTTATTACAAAC TCGCTTTTACAGATGGTATTATATGCACCATTGCAGAT ATTTTACTGTTATGTTATTCTCATGACCACCTGAATA CTTCAAATAGGGTATTATTCGAAGAGGTTGCAAAGTC TGTCGGAGTTTTTCTCGGCATACCACTGGGAATTGGCA TTATCATACGTTTGGGAAGTCTTACCATAGCTGGTAAA AGTAATTATGAAAAATACATTTTGAGATTTATTTCTCC |

| SEQ ID NO: | Description | Sequence |
|---|---|---|
|  |  | ATGGGCAATGATCGGATTTCATTACACTTTATTTGTTA<br>TTTTTATTAGTAGAGGTTATCAATTTATCCACGAAATT<br>GGTTCTGCAATATTGTGCTTTGTCCCATTGGTGCTTTA<br>CTTCTTTATTGCATGGTTTTTGACCTTCGCATTAATGAG<br>GTACTTATCAATATCTAGGAGTGATACACAAAGAGAA<br>TGTAGCTGTGACCAAGAACTACTTTTAAAGAGGGTCT<br>GGGGAAGAAAGTCTTGTGAAGCTAGCTTTTCTATTAC<br>GATGACGCAATGTTTCACTATGGCTTCAAATAATTTTG<br>AACTATCCCTGGCAATTGCTATTTCCTTATATGGTAAC<br>AATAGCAAGCAAGCAATAGCTGCAACATTTGGGCCGT<br>TGCTAGAAGTTCCAATTTTATTGATTTTGGCAATAGTC<br>GCGAGAATCCTTAAACCATATTATATATGGAACAATA<br>GAAATTAA |
| 6 | PpRPL10 promoter | GTTCTTCGCTTGGTCTTGTATCTCCTTACACTGTATCTT<br>CCCATTTGCGTTTAGGTGGTTATCAAAAACTAAAAGG<br>AAAAATTTCAGATGTTTATCTCTAAGGTTTTTTCTTTTT<br>ACAGTATAACACGTGATGCGTCACGTGGTACTAGATT<br>ACGTAAGTTATTTTGGTCCGGTGGGTAAGTGGGTAAG<br>AATAGAAAGCATGAAGGTTTACAAAAACGCAGTCACG<br>AATTATTGCTACTTCGAGCTTGGAACCACCCCAAAGAT<br>TATATTGTACTGATGCACTACCTTCTCGATTTTGCTCCT<br>CCAAGAACCTACGAAAAACATTTCTTGAGCCTTTTCAA<br>CCTAGACTACACATCAAGTTATTTAAGGTATGTTCCGT<br>TAACATGTAAGAAAAGGAGAGGATAGATCGTTTATGG<br>GGTACGTCGCCTGATTCAAGCGTGACCATTCGAAGAA<br>TAGGCCTTCGAAAGCTGAATAAAGCAAATGTCAGTTG<br>CGATTGGTATGCTGACAAATTAGCATAAAAAGCAATA<br>GACTTTCTAACCACCTGTTTTTTTCCTTTTACTTTATTT<br>ATATTTTGCCACCGTACTAACAAGTTCAGACAAA |
| 7 | URA6 region | CAAATGCAAGAGGACATTAGAAATGTGTTTGGTAAGA<br>ACATGAAGCCGGAGGCATACAAACGATTCACAGATTT<br>GAAGGAGGAAAACAAACTGCATCCACCGGAAGTGCC<br>AGCAGCCGTGTATGCCAACCTTGCTCTCAAAGGCATTC<br>CTACGGATCTGAGTGGGAAATATCTGAGATTCACAGA<br>CCCACTATTGGAACAGTACCAAACCTAGTTTGGCCGA<br>TCCATGATTATGTAATGCATATAGTTTTTGTCGATGCT<br>CACCCGTTTCGAGTCTGTCTCGTATCGTCTTACGTATA<br>AGTTCAAGCATGTTTACCAGGTCTGTTAGAAACTCCTT<br>TGTGAGGGCAGGACCTATTCGTCTCGGTCCCGTTGTTT<br>CTAAGAGACTGTACAGCCAAGCGCAGAATGGTGGCAT<br>TAACCATAAGAGGATTCTGATCGGACTTGGTCTATTGG<br>CTATTGGAACCACCCTTTACGGGACAACCAACCCTAC<br>CAAGACTCCTATTGCATTTGTGGAACCAGCCACGGAA<br>AGAGCGTTTAAGGACGGAGACGTCTCTGTGATTTTTGT<br>TCTCGGAGGTCCAGGAGCTGGAAAAGGTACCCAATGT<br>GCCAAACTAGTGAGTAATTACGGATTTGTTCACCTGTC<br>AGCTGGAGACTTGTTACGTGCAGAACAGAAGAGGGAG<br>GGGTCTAAGTATGGAGAGATGATTTCCCAGTATATCA<br>GAGATGGACTGATAGTACCTCAAGAGGTCACCATTGC<br>GCTCTTGGAGCAGGCCATGAAGGAAAACTTCGAGAAA<br>GGGAAGACACGGTTCTTGATTGATGGATTCCCTCGTA<br>AGATGGACCAGGCCAAAACTTTTGAGGAAAAAGTCGC<br>AAAGTCCAAGGTGACACTTTTCTTTGATTGTCCCGAAT<br>CAGTGCTCCTTGAGAGATTACTTAAAAGAGGACAGAC<br>AAGCGGAAGAGGATGATAATGCGGAGAGTATCAA<br>AAAAAGATTCAAAACATTCGTGGAAACTTCGATGCCT<br>GTGGTGGACTATTTCGGGAAGCAAGGACGCGTTTTGA<br>AGGTATCTTGTGACCACCCTGTGGATCAAGTGTATTCA<br>CAGGTTGTGTCGGTGCTAAAAGAGAAGGGGATCTTTG<br>CCGATAACGAGACGGAGAATAAATAA |
| 8 | PpGAPDH promoter | TTTTTGTAGAAATGTCTTGGTGTCCTCGTCCAATCAGG<br>TAGCCATCTCTGAAATATCTGGCTCCGTTGCAACTCCG<br>AACGACCTGCTGGCAACGTAAAATTCTCCGGGGTAAA<br>ACTTAAATGTGGAGTAATGGAACCAGAAACGTCTCTT<br>CCCTTCTCTCTCCTTCCACCGCCCGTTACCGTCCCTAG<br>GAAATTTTACTCTGCTGGAGAGCTTCTTCTACGGCCCC<br>CTTGCAGCAATGCTCTTCCCAGCATTACGTTGCGGGTA<br>AAACGGAGGTCGTGTACCCGACCTAGCAGCCCAGGGA<br>TGGAAAAGTCCCGGCCGTGCTGGCAATAATAGCGGG<br>CGGACGCATGTCATGAGATTATTGGAAACCACCAGAA |

BRIEF DESCRIPTION OF THE SEQUENCES

| SEQ ID NO: | Description | Sequence |
|---|---|---|
| | | TCGAATATAAAAGGCGAACACCTTTCCCAATTTTGGTT TCTCCTGACCCAAAGACTTTAAATTTAATTTATTTGTC CCTATTTCAATCAATTGAACAACTATCAAAACACA |
| 9 | NatR ORF | ATGGGTACCACTCTTGACGACACGGCTTACCGGTACC GCACCAGTGTCCCGGGGGACGCCGAGGCCATCGAGGC ACTGGATGGGTCCTTCACCACCGACACCGTCTTCCGCG TCACCGCCACCGGGGACGGCTTCACCCTGCGGGAGGT GCCGGTGGACCCGCCCCTGACCAAGGTGTTCCCCGAC GACGAATCGGACGACGAATCGGACGACGGGGAGGAC GGCGACCCGGACTCCCGGACGTTCGTCGCGTACGGGG ACGACGGCGACCTGGCGGGCTTCGTGGTCATCTCGTA CTCGGCGTGGAACCGCCGGCTGACCGTCGAGGACATC GAGGTCGCCCCGGAGCACCGGGGGCACGGGGTCGGG CGCGCGTTGATGGGGCTCGCGACGGAGTTCGCCGGCG AGCGGGGCGCCGGGCACCTCTGGCTGGAGGTCACCAA CGTCAACGCACCGGCGATCCACGCGTACCGGCGGATG GGGTTCACCCTCTGCGGCCTGGACACCGCCCTGTACG ACGGCACCGCCTCGGACGGCGAGCGGCAGGCGCTCTA CATGAGCATGCCCTGCCCC |
| 10 | Ashbya gossypii TEF1 promoter | GATCTGTTTAGCTTGCCTCGTCCCCGCCGGGTCACCCG GCCAGCGACATGGAGGCCCAGAATACCCTCCTTGACA GTCTTGACGTGCGCAGCTCAGGGGCATGATGTGACTG TCGCCCGTACATTTAGCCCATACATCCCCATGTATAAT CATTTGCATCCATACATTTTGATGGCCGCACGGCGCGA AGCAAAAATTACGGCTCCTCGCTGCAGACCTGCGAGC AGGGAAACGCTCCCCTCACAGACGCGTTGAATTGTCC CCACGCCGCGCCCCTGTAGAGAAATATAAAAGGTTAG GATTTGCCACTGAGGTTCTTCTTTCATATACTTCCTTTT AAAATCTTGCTAGGATACAGTTCTCACATCACATCCGA ACATAAACAACC |
| 11 | Ashbya gossypii TEF1 termination sequence | TAATCAGTACTGACAATAAAAAGATTCTTGTTTTCAAG AACTTGTCATTTGTATAGTTTTTTTATATTGTAGTTGTT CTATTTTAATCAAATGTTAGCGTGATTTATATTTTTTT CGCCTCGACATCATCTGCCCAGATGCGAAGTTAAGTG CGCAGAAAGTAATATCATGCGTCAATCGTATGTGAAT GCTGGTCGCTATACTGCTGTCGATTCGATACTAACGCC GCCATCCAGTGTCGAAAAC |
| 12 | Trypanosoma brucei STT3A (DNA) | ATGACCAAGGGAGGAAAAGTTGCTGTTACAAAGGGTA GTGCCCAATCTGACGGTGCTGGAGAGGGAGGAATGAG TAAAGCCAAGAGTTCAACTACATTTGTTGCTACCGGTG GAGGTAGTCTTCCAGCTTGGGCCTTGAAAGCTGTTTCT ACTATTGTCTCCGCCGTTATTTTGATCTACTCTGTCCAT AGAGCTTATGATATTAGATTGACCTCCGTTAGATTGTA CGGTGAACTTATCCACGAGTTCGACCCTTGGTTTAACT ACAGAGCCACTCAATATTTGTCTGATAATGGATGGAG AGCATTTTTCCAGTGGTACGACTATATGTCCTGGTATC CATTGGGAAGACCTGTTGGTACCACTATTTTTCCTGGT ATGCAATTGACTGGAGTCGCTATCCATAGAGTTCTTGA AATGTTGGGAAGAGGAATGTCAATTAACAACATCTGT GTCTACATTCCTGCCTGGTTTGGTAGTATCGCAACAGT TCTTGCTGCCTTGATTGCTTACGAGTCTTCCAACTCATT GAGTGTCATGGCATTCACCGCTTACTTTTTCTCTATCG TTCCAGCACACTTGATGAGATCCATGGCTGGTGAATTT GATAATGAGTGTGTTGCTATGGCAGCTATGTTGCTTAC TTTCTACATGTGGGTTAGATCCCTTAGATCAAGTTCTT CCTGGCCTATTGGAGCATTGGCTGGTGTCGCTTACGGA TATATGGTTTCTACATGGGGAGGTTATATCTTCGTCTT GAACATGGTTGCCTTTCATGCATCCGTCTGTGTTTTGC TTGATTGGGCTAGAGGTATCTACTCTGTCTCCTTGCTT AGAGCCTATTCTTTGTTTTTCGTTATTGGAACTGCCTTG GCAATCTGCGTCCCACCTGTTGAATGGACACCTTTTAG ATCCCTTGAGCAATTGACCGCCCTTTTTGTCTTCGTTTT TATGTGGGCACTTCATTACTCTGAATATTTGAGAGAGA GAGCTAGAGCCCCTATTCACTCAAGTAAAGCCTTGCA GATTAGAGCAAGAATCTTCATGGGTACTTTGTCATTGC TTTTGATTGTTGCAAGTCTTTTGGCTCCATTTGGATTTT TCAAACCTACAGCTTACAGAGTCAGAGCCTTGTTCGTT AAGCACACCAGAACTGGTAACCCATTGGTCGATTCAG TTGCTGAACATAGACCTACAACCGCAGGTGCTTACCTT AGATATTTTCACGTTTGTTACCCATTGTGGGGATGCGG |

BRIEF DESCRIPTION OF THE SEQUENCES

| SEQ ID NO: | Description | Sequence |
|---|---|---|
| | | AGGTTTGTCCATGCTTGTTTTCATGAAGAAAGACAGAT<br>GGAGAGCAATTGTCTTTTTGGCTTCACTTAGTACAGTT<br>ACCATGTATTTCTCAGCTAGAATGAGTAGACTTTTGCT<br>TTTGGCCGGTCCTGCCGCAACTGCCTGTGCAGGAATGT<br>TCATTGGAGGTTTGTTTGATCTTGCTTTGTCTCAATTCG<br>GAGATTTGCATTCCCCAAAGGACGCCTCTGGAGATTC<br>CGACCCTGCTGGAGGTTCCAAAAGAGCCAAGGGTAAA<br>GTTGTCAATGAACCATCTAAGAGAGCTATTTTCTCCCA<br>CAGATGGTTTCAAAGATTGGTCCAGTCACTTCCAGTTC<br>CTTTGAGAAGAGGTATCGCAGTTGTCGTTTTGGTTTGT<br>CTTTTCGCTAACCCTATGAGACATTCTTTTGAAAAGTC<br>CTGCGAGAAAATGGCTCACGCCTTGTCTTCCCCAAGA<br>ATTATCGCCGTTACTGATTTGCCTAATGGTGAAAGAGT<br>CTTGGCAGATGACTACTATGTTTCATACCTTTGGTTGA<br>GAAACAATACCCCAGAGGATGCTAGAATTTTGAGTTG<br>GTGGGACTACGGTTATCAAATTACTGGAATCGGTAAC<br>AGAACTACATTGGCAGATGGTAATACATGGTCTCATA<br>AGCACATTGCTACCATCGGAAAAATGTTGACTTCACCT<br>GTTAAAGAAAGTCATGCACTTATTAGACACTTGGCTG<br>ACTACGTTTTGATCTGGGCTGGAGAGGATAGAGGAGA<br>CCTTTTGAAATCTCCACATATGGCTAGAATCGGTAACT<br>CAGTTTACAGAGATATGTGTAGTGAAGATGACCCTAG<br>ATGCAGACAATTCGGATTTGAGGGTGGTGACTTGAAC<br>AAGCCAACTCCTATGATGCAGAGATCCCTTTTGTACAA<br>TTTGCACAGATTTGGTACTGATGGAGGTAAAACACAA<br>CTTGACAAGAACATGTTCCAGTTGGCTTACGTCTCCAA<br>GTATGGATTGGTTAAAATCTACAAAGTCGTTAACGTTT<br>CAGAAGAGAGTAAAGCTTGGGTCGCCGATCCAAAGAA<br>TAGAGTTTGTGACCCACCTGGTTCTTGGATTTGCGCCG<br>GACAATACCCACCTGCAAAAGAAATCCAGGATATGTT<br>GGCTAAGAGATTTCATTATGAGTAATGA |
| 13 | *Trypanosoma brucei* STT3B (DNA) | ATGACCAAGGGAGGAAAGGTTGCTGTTACTAAAGGTT<br>CTGCTCAATCCGACGGTGCTGGAGAGGGAGGAATGTC<br>AAAAGCCAAGAGTAGTACTACATTTGTTGCTACCGGT<br>GGAGGTTCTCTTCCAGCATGGGCTTTGAAGGCCGTTTC<br>AACTGTTGTCAGTGCAGTTATTTTGATCTACTCCGTCC<br>ATAGAGCTTACGATATCAGATTGACATCAGTTAGACTT<br>TATGGTGAATTGATCCACGAGTTTGACCCTTGGTTCAA<br>CTACAGAGCAACCCAATATTTGTCCGATAATGGATGG<br>AGAGCTTTCTTTCAGTGGTACGACTATATGTCATGGTA<br>CCCATTGGGAAGACCTGTTGGTACCACTATTTTTCCTG<br>GTATGCAATTGACTGGAGTTGCTATCCATAGAGTCTTG<br>GAAATGCTTGGAAGAGGAATGTCAATTAACAACATCT<br>GTGTTTACATCCCTGCTTGGTTTGGTTCTATCGCCACT<br>GTCTTGGCTGCCCTTATTGCTTACGAGTCTTCCAACTC<br>ATTGAGTGTTATGGCCTTCACAGCATACTTTTTCTCTA<br>TTGTCCCAGCTCACTTGATGAGATCAATGGCCGGTGA<br>ATTTGATAATGAGTGTGTTGCTATGGCAGCTATGTTGC<br>TTACTTTCTATATGTGGGTTAGATCCCTTAGATCAAGT<br>TCTTCCTGGCCTATTGGAGCCTTGGCAGGTGTTGCTTA<br>CGGATATATGGTCTCAACTTGGGGAGGTTACATCTTTG<br>TTTTGAACATGGTCGCTTTCCATGCCTCTGTTTGTGTCT<br>TGCTTGATTGGGCCAGAGGTACATACTCTGTTTCCTTG<br>CTTAGAGCATATTCTTTGTTTTTCGTCATTGGAACCGC<br>TTTGGCCATCTGCGTTCCACCTGTCGAATGGACTCCTT<br>TTAGATCCTTGGAGCAACTTACAGCCTTGTTCGTTTTT<br>GTCTTCATGTGGGCACTTCATTACTCTGAATATTTGAG<br>AGAGAGAGCAAGAGCTCCTATTCACTCTAGTAAGGCA<br>TTGCAGATTAGAGCTAGAATCTTTATGGGTACTCTTAG<br>TTTGCTTTTGATTGTTGCTATCTACTTGTTCTCCACAGG<br>ATATTTTAGACCATTCTCTTCCAGAGTTAGAGCTTTGT<br>TCGTCAAACACACTAGAACAGGTAATCCATTGGTTGA<br>TAGTGTCGCCGAACATCACCCTGCATCTAACGATGACT<br>TTTTCGGATACTTGCATGTTTGTTACAACGGTTGGATC<br>ATCGGATTTTTCTTTATGTCAGTTAGTTGTTTCTTTCAC<br>TGCACTCCAGGAATGTCATTTCTTTTGCTTTACAGTAT<br>CCTTGCTTACTACTTCTCTTTGAAGATGTCCAGATTGC<br>TTTTGCTTTCTGCACCTGTTGCTTCCATTTTGACCGGTT<br>ACGTTGTCGGATCTATCGTTGATTGGCCGCAGACTGT<br>TTTGCTGCCAGTGGTACTGAACATGCTGATTCTAAGGA<br>GCACCAAGGAAAAGCCAGAGGAAAGGGTCAAAAAGA<br>ACAGATTACTGTTGAGTGTGGTTGCCATAACCCTTTTT<br>ACAAGCTTTGGTGTAATTCCTTCTCAAGTAGATTGGTT |

BRIEF DESCRIPTION OF THE SEQUENCES

| SEQ ID NO: | Description | Sequence |
|---|---|---|
| | | GTCGGAAAATTCTTTGTTGTCGTTGTCCTTTCAATTTGC |
| | | GGTCCAACTTTCTTGGGTTCTAACTTCAGAATCTATTC |
| | | CGAACAATTCGCAGATTCAATGTCTTCCCCTCAGATTA |
| | | TCATGAGAGCCACTGTTGGAGGTAGAAGAGTCATTTT |
| | | GGATGACTACTATGTTTCTTACTTGTGGCTTAGAAACA |
| | | ATACACCAGAGGATGCTAGAATTTTGTCCTGGTGGGA |
| | | CTACGGTTATCAAATTACCGGAATCGGTAACAGAACA |
| | | ACCTTGGCTGATGGTAACACTTGGAATCATGAACACA |
| | | TTGCCACAATCGGAAAGATGTTGACCTCACCTGTTAA |
| | | AGAGAGTCATGCACTTATTAGACACTTGGCTGACTAC |
| | | GTTTTGATCTGGGCTGGATATGATGGTTCTGACTTGCT |
| | | TAAGTCCCCACATATGGCTAGAATTGGTAATTCCGTTT |
| | | ACAGAGATATCTGTTCAGAAGATGACCCTTTGTGCAC |
| | | ACAATTTGGTTTCTATTCAGGAGACTTTAGTAAACCAA |
| | | CCCCTATGATGCAGAGATCCTTGCTTTACAACTTGCAC |
| | | AGATTTGGTACCGATGGAGGTAAAACTCAACTTGACA |
| | | AGAACATGTTCCAGTTGGCTTACGTTTCTAAGTATGGA |
| | | TTGGTCAAAATCTACAAAGTTATGAACGTCTCTGAAG |
| | | AGTCCAAAGCCTGGGTTGCAGATCCAAAGAATAGAAA |
| | | ATGTGACGCTCCTGGTTCTTGGATTTGCACTGGACAAT |
| | | ACCCACCTGCAAAGGAAATTCAGGATATGCTTGCTAA |
| | | AAGAATCGATTATGAACAATTGGAGGACTTTAACAGA |
| | | AGAAATAGATCCGACGCTTACTATAGAGCCTACATGA |
| | | GACAGATGGGTTAATGA |
| 14 | Trypanosoma brucei STT3C (DNA) | ATGACTAAGGGTGGTAAAGTTGCTGTTACTAAGGGTT |
| | | CTGCTCAATCTGATGGTGCTGGTGAAGGTGGAATGTCT |
| | | AAGGCTAAGTCCTCCACTACTTTCGTTGCTACTGGTGG |
| | | TGGTTCTTTGCCAGCTTGGGCTTTGAAGGCTGTTTCCA |
| | | CTGTTGTTTCCGCTGTTATCTTGATCTACTCCGTTCACA |
| | | GAGCTTACGACATCAGATTGACTTCAGTTAGATTGTAC |
| | | GGTGAGTTGATCCACGAATTTGACCCATGGTTCAACTA |
| | | CAGAGCTACTCAGTACTTGTCTGACAACGGATGGAGA |
| | | GCTTTCTTCCAGTGGTACGATTACATGTCCTGGTATCC |
| | | ATTGGGTAGACCAGTTGGTACTACTATCTTCCCAGGAA |
| | | TGCAGTTGACTGGAGTTGCTATCCACAGAGTTTTGGAG |
| | | ATGTTGGGTAGAGGAATGTCCATCAACAACATCTGTG |
| | | TTTACATCCCAGCTTGGTTTGGTTCCATTGCTACTGTTT |
| | | TGGCTGCTTTGATCGCTTACGAATCCTCTAACTCCTTG |
| | | TCCGTTATGGCTTTCACTGCTTACTTTTTCTCCATCGTT |
| | | CCTGCTCATTTGATGAGATCCATGGCTGGTGAGTTCGA |
| | | CAACGAGTGTGTTGCTATGGCTGCTATGTTGTTGACTT |
| | | TCTACATGTGGGTTCGTTCCTTGAGATCCTCTTCCTCTT |
| | | GGCCAATTGGTGCTTTGGCTGGTGTTGCTTACGGTTAC |
| | | ATGGTTTCCACTTGGGGAGGTTACATCTTCGTTTTGAA |
| | | CATGGTTGCTTTCCACGCTTCCGTTTGTGTTTTGTTGGA |
| | | CTGGGCTAGAGGAACTTACTCCGTTTCCTTGTTGAGAG |
| | | CTTACTCCTTGTTCTTCGTTATCGGTACTGCTTTGGCTA |
| | | TTTGTGTTCCACCAGTTGAGTGGACTCCATTCAGATCC |
| | | TTGGAGCAGTTGACTGCTTTGTTCGTTTTCGTTTTCATG |
| | | TGGGCTTTGCACTACTCTGAGTACTTGAGAGAGAGAG |
| | | CTAGAGCACCAATTCACTCCTCCAAGGCTTTGCAAATC |
| | | AGAGCTAGAATCTTCATGGGAACTTTGTCCTTGTTGTT |
| | | GATCGTTGCTATCTACTTGTTCTCCACTGGTTACTTCA |
| | | GATCCTTCTCATCCAGAGTTAGAGCTTTGTTTGTTAAG |
| | | CACACTAGAACTGGTAACCCATTGGTTGACTCCGTTGC |
| | | TGAACACAGACCAACTACTGCTGGTGCTTTCTTGAGAC |
| | | ACTTGCATGTTTGTTACAATGGATGGATCATCGGTTTT |
| | | TTCTTCATGTCCGTTTCTTGTTTCTTCCACTGTACTCCA |
| | | GGAATGTCCTTCTTGTTGTTGTACTCCATCTTGGCTTAC |
| | | TACTTCTCATTGAAGATGTCCAGATTGTTGTTGTTGTC |
| | | CGCTCCAGTTGCTTCTATCTTGACTGGTTACGTTGTTG |
| | | GTTCCATCGTTGATTTGGCTGCTGATTGTTTCGCTGCTT |
| | | CTGGTACTGAACACGCTGACTCCAAAGAACACCAGGG |
| | | TAAAGCTAGAGGAAAGGGACAGAAGAGACAGATCAC |
| | | TGTTGAGTGTGGTTGTCACAACCCATTCTACAAGTTGT |
| | | GGTGTAACTCATTCTCCTCCAGATTGGTTGTTGGAAAG |
| | | TTCTTCGTTGTTGTTGTTTTGTCCATCTGTGGTCCAACT |
| | | TTCTTGGGTTCCGAGTTCAGAGCACACTGTGAGAGATT |
| | | CTCCGTTTCCGTTGCTAACCCAAGAATCATCTCCTCCA |
| | | TCAGACACTCTGGTAAGTTGGTTTTGGCTGACGACTAC |
| | | TACGTTTCCTACTTGTGGTTGAGAAACAACACTCCAGA |
| | | GGACGCTAGAATTTTGTCTTGGTGGGACTACGGTTACC |
| | | AAATCACTGGTATCGGTAACAGAACTACTTTGGCTGA |

| SEQ ID NO: | Description | Sequence |
|---|---|---|
| | | CGGTAACACTTGGAACCACGAGCACATTGCTACTATC<br>GGAAAGATGTTGACTTCCCCAGTTAAAGAGTCCCACG<br>CTTTGATTAGACACTTGGCTGACTACGTTTTGATTTGG<br>GCTGGTGAAGATAGAGGAGACTTGAGAAAGTCCAGAC<br>ACATGGCTAGAATCGGTAACTCCGTTTACAGAGACAT<br>GTGTTCTGAGGACGACCCATTGTGTACTCAGTTCGGTT<br>TCTACTCCGGTGATTTCAACAAGCCAACTCCAATGATG<br>CAGAGATCCTTGTTGTACAACTTGCACAGATTCGGTAC<br>TGATGGTGGAAAGACTCAGTTGGACAAGAACATGTTC<br>CAGTTGGCTTACGTTTCCAAGTACGGATTGGTCAAAAT<br>CTACAAGGTTATGAACGTTTCCGAAGAGTCTAAGGCT<br>TGGGTTGCAGACCCAAAGAATAGAAAGTGTGACGCTC<br>CTGGTTCTTGGATTTGTGCTGGTCAATACCCACCTGCT<br>AAAGAAATCCAGGACATGTTGGCTAAGAGAATCGACT<br>ACGAGCAATTGGAGGACTTCAACAGAAGAAATAGATC<br>CGACGCTTACTACAGAGCTTACATGAGACAGATGGGT<br>TAATAG |
| 15 | Anti-Her2 Heavy chain (VH + IgG1 constant region) (DNA) | GAGGTTCAGTTGGTTGAATCTGGAGGAGGATTGGTTC<br>AACCTGGTGGTTCTTTGAGATTGTCCTGTGCTGCTTCC<br>GGTTTCAACATCAAGGACACTTACATCCACTGGGTTA<br>GACAAGCTCCAGGAAAGGGATTGGAGTGGGTTGCTAG<br>AATCTACCCAACTAACGGTTACACAAGATACGCTGAC<br>TCCGTTAAGGGAAGATTCACTATCTCTGCTGACACTTC<br>CAAGAACACTGCTTACTTGCAGATGAACTCCTTGAGA<br>GCTGAGGATACTGCTGTTTACTACTGTTCCAGATGGGG<br>TGGTGATGGTTTCTACGCTATGGACTACTGGGGTCAAG<br>GAACTTTGGTTACTGTTTCCTCCGCTTCTACTAAGGGA<br>CCATCTGTTTTCCCATTGGCTCCATCTTCTAAGTCTACT<br>TCCGGTGGTACTGCTGCTTTGGGATGTTTGGTTAAAGA<br>CTACTTCCCAGAGCCAGTTACTGTTTCTTGGAACTCCG<br>GTGCTTTGACTTCTGGTGTTCACACTTTCCCAGCTGTTT<br>TGCAATCTTCCGGTTTGTACTCTTTGTCCTCCGTTGTTA<br>CTGTTCCATCCTCTTCCTTGGGTACTCAGACTTACATCT<br>GTAACGTTAACCACAAGCCATCCAACACTAAGGTTGA<br>CAAGAAGGTTGAGCCAAAGTCCTGTGACAAGACACAT<br>ACTTGTCCACCATGTCCAGCTCCAGAATTGTTGGGTGG<br>TCCATCCGTTTTCTTGTTCCCACCAAAGCCAAAGGACA<br>CTTTGATGATCTCCAGAACTCCAGAGGTTACATGTGTT<br>GTTGTTGACGTTTCTCACGAGGACCCAGAGGTTAAGTT<br>CAACTGGTACGTTGACGGTGTTGAAGTTCACAACGCT<br>AAGACTAAGCCAAGAGAAGAGCAGTACAACTCCACTT<br>ACAGAGTTGTTTCCGTTTTGACTGTTTTGCACCAGGAC<br>TGGTTGAACGGTAAAGAATACAAGTGTAAGGTTTCCA<br>ACAAGGCTTTGCCAGCTCCAATCGAAAAGACTATCTC<br>CAAGGCTAAGGGTCAACCAAGAGAGCCACAGGTTTAC<br>ACTTTGCCACCATCCAGAGAAGAGATGACTAAGAACC<br>AGGTTTCCTTGACTTGTTTGGTTAAAGGATTCTACCCA<br>TCCGACATTGCTGTTGAGTGGGAATCTAACGGTCAAC<br>CAGAGAACAACTACAAGACTACTCCACCAGTTTTGGA<br>TTCTGATGGTTCCTTCTTCTTGTACTCCAAGTTGACTGT<br>TGACAAGTCCAGATGGCAACAGGGTAACGTTTTCTCC<br>TGTTCCGTTATGCATGAGGCTTTGCACAACCACTACAC<br>TCAAAAGTCCTTGTCTTTGTCCCCTGGTTAA |
| 16 | Anti-Her2 light chain (VL + Kappa constant region) (DNA) | GACATCCAAATGACTCAATCCCCATCTTCTTTGTCTGC<br>TTCCGTTGGTGACAGAGTTACTATCACTTGTAGAGCTT<br>CCCAGGACGTTAATACTGCTGTTGCTTGGTATCAACAG<br>AAGCCAGGAAAGGCTCCAAAGTTGTTGATCTACTCCG<br>CTTCCTTCTTGTACTCTGGTGTTCCATCCAGATTCTCTG<br>GTTCCAGATCCGGTACTGACTTCACTTTGACTATCTCC<br>TCCTTGCAACCAGAAGATTTCGCTACTTACTACTGTCA<br>GCAGCACTACACTACTCCACCAACTTTCGGACAGGGT<br>ACTAAGGTTGAGATCAAGAGAACTGTTGCTGCTCCAT<br>CCGTTTTCATTTTCCCACCATCCGACGAACAGTTGAAG<br>TCTGGTACAGCTTCCGTTGTTTGTTTGTTGAACAACTT<br>CTACCCAAGAGAGGCTAAGGTTCAGTGGAAGGTTGAC<br>AACGCTTTGCAATCCGGTAACTCCCAAGAATCCGTTAC<br>TGAGCAAGACTCTAAGGACTCCACTTACTCCTTGTCCT<br>CCACTTTGACTTTGTCCAAGGCTGATTACGAGAAGCAC<br>AAGGTTTACGCTTGTGAGGTTACACATCAGGGTTTGTC<br>CTCCCCAGTTACTAAGTCCTTCAACAGAGGAGAGTGTT<br>AA |

BRIEF DESCRIPTION OF THE SEQUENCES

| SEQ ID NO: | Description | Sequence |
|---|---|---|
| 17 | PpAOX1 TT | TCAAGAGGATGTCAGAATGCCATTTGCCTGAGAGATG CAGGCTTCATTTTGATACTTTTTTATTTGTAACCTATAT AGTATAGGATTTTTTTTGTCATTTTGTTTCTTCTCGTAC GAGCTTGCTCCTGATCAGCCTATCTCGCAGCTGATGAA TATCTTGTGGTAGGGGTTTGGGAAAATCATTCGAGTTT GATGTTTTTCTTGGTATTTCCCACTCCTCTTCAGAGTAC AGAAGATTAAGTGAGACGTTCGTTTGTGCA |
| 18 | Sequence of the Sh ble ORF (Zeocin resistance marker): | ATGGCCAAGTTGACCAGTGCCGTTCCGGTGCTCACCG CGCGCGACGTCGCCGGAGCGGTCGAGTTCTGGACCGA CCCGGCTCGGGTTCTCCCGGGACTTCGTGGAGGACGAC TTCGCCGGTGTGGTCCGGGACGACGTGACCCTGTTCAT CAGCGCGGTCCAGGACCAGGTGGTGCCGGACAACACC CTGGCCTGGGTGTGGGTGCGCGGCCTGGACGAGCTGT ACGCCGAGTGGTCGGAGGTCGTGTCCACGAACTTCCG GGACGCCTCCGGGCCGGCCATGACCGAGATCGGCGAG CAGCCGTGGGGGCGGGAGTTCGCCCTGCGCGACCCGG CCGGCAACTGCGTGCACTTCGTGGCCGAGGAGCAGGA CTGA |
| 19 | Sequence of the 5'-Region used for knock out of YOS9 | CCATAGCCTCTGATTGATGTAAGCACCGACAGTACCT GGCTCTAACTTGTTAGAGGTTTTGGTGGTCAAGACATA TCTGTTATCACAAATAACATAATGGTTATCGGGAAAG TCATTGGGATGAACAGCAAGTGTGTTCATGATGGCAA ATTCATTACCCGGAGAGTTGACTATCTTCAATACATGC ACCTTTGGAGCATTTCTCTTTGTGAATCCCAGTTTTTCC ATGGTTGTGGCAAAGTGTAGAGATGTTAAGTGCAGCG AGCAAAGACAAGTAGATAGACTGTATGGTGTTCTGAT GTTATAGTTGTAGTGAATAATCTATAAATGCCTTATTT GAAGGTTTATGTAATAGATTTACCCGTGTGTAGCAAGT GTACTGCTAAGAGGTACTATAAAGTTATTCATGTGGAT ATATTCAGTAGATAATAACAAAGCTACAAGGAGATCA AGAAACCATATGAGTTGTTCGTCACATAAGAGATTAC GTAATGACAAATCGGGGAACTAGTACCAATTCTGTCT TAAAGTAGTGTCTCTCTAAGCATAACGACCTATTTGAT AACTGGGCTGAACTCCAAGCAGCCTGATGATGTTGAC CTGACTTATTCAGAAGGGCTATTGGTTTTGATTTCCAG ATATTAGCATAATTAGCAATGCCGGAACAATATACAT CCAATATTTTTGAATGAATGAACGGTTATCAACATTTA CTTCTGCCTCCTCGTCTATGACTTCCTTGAGTTCCAGCT TGTTATCGGATCTGATTTTTTTGATTTTCTTTTCTTTTCT TGGTAGTTTGGGAATTGGTGCCTGTCGAATTTGTTCAA CTATTAGGTTAAGACCTTTCTGACTAGCATCGAAGAA GGCTACATTTTCGATGTCGTTGTGTTTGTTGATAGTCA GCTTGATATCCTGTGCAATTGGAGAACTTAGTCTTTTG TAATTGAAGCAGCCTTCGTCCAAACATATTCTGTAAAG ATCACTTGGCAGGTCTAGTTGTTCACCGGTGTGCAATT TCCATTTTGAGTCAAATTCTAGTGTGGCCAAGTTGAAC GAGTTCTGAGCGAAATCAATAGCCTTCAACTGATACG CAAATGTAGACCCCAAGAAAAGAAACAACGTGACGA GGCTTTGTAGGGTAGTAGCCATTGTCGAATAGTTGAG GATAAGTAGACGGCGAGTTATTCTCCTTGATAAATGCT ATCGCGATGGATAGTGATTACAGTGCGATAATATTAT CCTTTTCATCCACGTCAACCATGGTTAACAGGCCATTG GACATTATGATAAAGGTCCTGCTATTCCTGCTCTCCCT ATCAAGTCTTGTGAAAGCTTTGGATGATTCCATTGATA AGAATTCTGTGGTAAGTCTTTTAATTTTTGTTTTCACA AGATCATGCCGTGCTAACTGGGTACTATAGTATACC |
| 20 | Sequence of the 3'-Region used for knock out of YOS9 | GGTTCCTATTCACTGAAGACAGAATACCTCATGACACT CCAAACTTTAGAGTGTATAACGGAGTTAATGTGAATT AAGACAATTTATATACTCAGTAAAATAAATACTAGTA CTTACGTCTTTTTTAGTCAGAGCACTAACTCTGCTGG AAGGGTTCTTCGTGTAAATTGGTACAGACGCTGGTAA AGTACCACTATACGTTGTTTGACAAATAGGTAGTTTGA AGCTGACATCAAGTTTCAAGTCCTTAGGAGTCACATTG CGAGTTTGAATGACCAATTGTATTAATCTCTTAATCTT GAAGTACAATCTCTTCTCTTTGAGACTGGGTTTCAAGA CAGTGACGGGATTAGCAGGATCGATTTTGGGTGATGC CTTATACCTTTCTTGACGTAATTGTGACAGATCTATTA GCAACTTGCTTATAAGTTCTTGCTCTTTGTTGGAACGG ATAGCCTCTATCTCATCCTCCTCAACGAAGCTTCCCGG AGTCCAGGAGAGGAGGTTGTCTAGCTTGATCTTATAG TCTTCGGATCCATTGACCTGGACTTCCTTATCTGTGTTT |

-continued

| SEQ ID NO: | Description | Sequence |
|---|---|---|
| | | TCAAGTTTAGTTGATGTATCTGTCCCCGTATGGCCATT CTTAGTCTCCTGGTCAACAGGTGCCGGAAGCTCTTTTT CAATTCTTTTTGGTTCGTCCTTCTGAAGTTCATTATCCG TCTCATTTTTAGATGGTCTGCTCAGTTTTTCTGCTATAT CACCAAGCTTTCTAAAACCAGCTTGCTCCAGCCACCTC AGGCCCTTCAATTCACTGGAGATTGCAGATTTTTCTTC GTCTATTGTAGGTGCAAAACTGAAATCGTTACCCTTAT TGTGGGTGAGCCATTGACCCATCGGTAACGCGTACCA GTTCAAATGAAAGAGGTTTGGCAATAAATCCGTAGGT TTGGTGGCTGGGTGAGGTTCATTGTTGTATTGAGGAGA AATCTTGTTAAGCGGCTGTGAACTAATGGAAGGGACA TGGGGGATTACTTTCGTCAGATTAAAATCGCCTTCATT CACTACAGCTTCTCTAGCATCCAAGCTTGATTTATTAT TCAGGGACGAAAACAATGGCGCATTAGGTGTGATGAA TGTAGTTAAACATTCTCCGTTGGATGAAACAAAAAAT GTGGACACTTTATTGAAGTCTTTTGTCATCGATTCTTC AAACTCACTGGTGTAATCATCTAAAACACGAGAGTCA ACGCTTTCTCTTAGTTGTCTGTAGTTGAACAAAAATCT TCCTGCCTCTCTGATCAATAACTCAACCATCGACTTGT AGAACAAATCAATCTTGACGTAGTCTTCCGAATCTCTG TTCCGTTCGTTTATAAGTATCAGGCACACTAAAGTTAG GTCGTGAAATATGGAATAAATAGTCTTGTAGTGACCA CTCTTTATTCTGTCGCTGATGGTAACCAGCTCTGTAGG TTTGAGATCCTTACCATCAACAAGCTGATAGTATGATC CAGCTATCAAGGAAGGATCCTGGAC |
| 21 | Sequence of the 5'-Region used for knock out of ALG3 | AACCTTCATGGAACGATTCGGATACGGAAAAACCTGA GATAGTTTTAACTAGAGTAGATGCAAGATTTCACGATT CTAAAGACCGAGAAGGAGATGTCTGATGTCGGTAACT ACTATCCGGTAAATGATATTAGCACACTATATGCTACT AGCGAGTCTGGAACCAATTCTACTATCCATTGATGCTC TATTAGGGATGGAGAATTCAATCAACCCCTCTAATTCT GATTTCAGATGTTCCAACAGCGAAGTAGCCCTTGACA AGTTCTCAACATCACTCATCTTAGCTACATTCACGTAT GCTTTGATAAAAAACTCTCTACTTTTGTCAATGAGCTC TAGCCTAGTCTCTGGTTCTATCGTTTCCTCTTTGGTCTC CAGATTACTCTCTGGATTAGAATCTACATCCATCTTCA TATCTATGTCCATGTCCAGCTCAATTTTCATACCGTCA GTATTCTTAGATTCGATAGCAGTATCTGATCTGGTAGA TCCATTAGTTGCTGCAGCGGTATTTTCTTTGGAATTTG GAGCACTTTCCTGTTTCTGTTTCATAAAGACTCGGTAG ATTGCAATGACTATATCGTTTCTGTAGAACTTGTAACC ATGAGTCCAAAATTGGGTTTCAGGCATGTATCCTAGCT CATCTAAATATCCAACCACATCATCCGTGCTACATATA GTAGACTCGTAGAGTGTCTGTGAAGAAACGGCTCTTTT TCCTGCCAAAGGAACGTCCGATATTTGAAGGGTCCAT ATACGATTTTCCTTATTAAGAGCTTCAAGATGTTTCTT ATTAAACAATTCAAAGTCTTTTAATTCAATTGTGTTAT CAATAGGATCCTCAACGTCCTGTTTCCATTCGGTGGAC ATTCTCATCTTGTATTGTTCGATTTGGTTGACTTTTCCA GTCTGGAACTCAGGACTATAAGGAAACTTTGGAGTTA AAATAACAGTATAAGTTGAGAGCCTTGCGGGCACCAT ACCCGTTAGAGACTTCAACGTCTCCAAGATCAACTGC AGTTGAGACTCTTGGATTCTAGATACCAGAGACACCT GTTGTACCATATAATTAAGTGACTGGGCTGGCTTGGAT ACAGGATTTCGAGAAGTGCTTCGAATTATCAGACCGA AGGCAGTTGATATTTTGTGCCTCAGCCTTAATGTTCCC TATAACTTAAGGCTATACACAGCTTTATGATTAATGAA TCTGGGCTGCTGGTGACGAATTTCGTCAATGACCAGTT GCCTACGGGCGATAATTATTTTTTCAGTTGGATGAAAG AACGGAAAAACCCGGTCAGATTCAAAAAGAATATTGA TAATCTTTGTCTAGCACAACTGAAATGCTTGGAAACTC TCCCAAGCATGAATCAGACCTGAGATTGTATTAGACG AAAAAATTGTAGTATAGAGTTATAGACATATAGGTTG TGGCAATATCCTGTGCAAGCCAATATCTCACAGAAAT AAACGTACACACCAGATACAACTATTTCGAAAAGCAC ACTTTGAGCGCAACAGTGATTGTCCTAACAGTATAGG TTTCTAAGGCCCCAGCAGACCATGACGGCAAATTATTT ATTTCCCCTCGTATTTGCCTTATCTCCTTTTGTTCTCAT TCTTATCTTGGCTACTGTAATTATCTGGATAACCCTCG ATACTTCGCTTGGTTTCTACCTCACAACATATCCCTAC C |

BRIEF DESCRIPTION OF THE SEQUENCES

| SEQ ID NO: | Description | Sequence |
|---|---|---|
| 22 | Sequence of the 3'-Region used for knock out of ALG3 | ATTTACAATTAGTAATATTAAGGTGGTAAAAACATTC GTAGAATTGAAATGAATTAATATAGTATGACAATGGT TCATGTCTATAAATCTCCGGCTTCGGTACCTTCTCCCC AATTGAATACATTGTCAAAATGAATGGTTGAACTATT AGGTTCGCCAGTTTCGTTATTAAGAAAACTGTTAAAAT CAAATTCCATATCATCGGTTCCAGTGGGAGGACCAGT TCCATCGCCAAAATCCTGTAAGAATCCATTGTCAGAA CCTGTAAAGTCAGTTTGAGATGAAATTTTTCCGGTCTT TGTTGACTTGGAAGCTTCGTTAAGGTTAGGTGAAACA GTTTGATCAACCAGCGGCTCCCGTTTTCGTCGCTTAGT AGCAGCATTATTACCAGGAATGCCGCCTGTAGAGTTTT GATGTGTCCTAGCTGCAATTGGAGTCTGTGGAGTAGT GGGAGTCGGGGGCTCAGTAGCTTTCTTTGCCTTCTTTT TAGCTGGCTCCTTTTTCTTTCGTACAGGTGCGACATTA TTTGGTGTAGACCCCGCAGAAGTGTTACCAGTACTATG TGCAGTGTTTTGAGTTTGTGTACCAGGTGAAGTTCCGG GAGTATTCTTCGTGACCACTGCAGAGTTCTGGGGAGG GAGCATTACATTCACATTAAATTTTGGTTCGGGCGGTG TGTGCTCTGGAATTGGATCAAAGTTAGAAAAATGCCC GCTTCCCTTCTTACATGCCATGTCATGACGCTGTTTGTT CTGTTTCTCAAGCATCATTAGCTCTTTCTGATACTCCTG TATACCTACAATTTTAGAAGCACTTGATTGAGACTGTT GCGATTGCTGGTGTTGGCTCTGTGATTGTGGTTGTGCT ATTTGCTGATGTTGTGACCCTGGAGTTGGAACTAGCTC CGGCTGCTGAATAGAAGAAGGCGGAGAATGTTGCGGT TGAGATGCAGGTAAAGGCTGCTGATAAACAGGACCAG GTTGCGAGAATCTAGGTGTGGTGGACGAGTGAGGAGT ACCGGCGGCAGAAGTAGAGTGAGGCAGAGGAGCCAT |
| 23 | Sequence of the 5'-Region used for knock out of BMT1 | CATATGGTGAGAGCCGTTCTGCACAACTAGATGTTTTC GAGCTTCGCATTGTTTCCTGCAGCTCGACTATTGAATT AAGATTTCCGGATATCTCCAATCTCACAAAAACTTATG TTGACCACGTGCTTTCCTGAGGCGAGGTGTTTTATATG CAAGCTGCCAAAAATGGAAAACGAATGGCCATTTTTC GCCCAGGCAAATTATTCGATTACTGCTGTCATAAAGA CAGTGTTGCAAGGCTCACATTTTTTTTAGGATCCGAG ATAAAGTGAATACAGGACAGCTTATCTCTATATCTTGT ACCATTCGTGAATCTTAAGAGTTCGGTTAGGGGGACT CTAGTTGAGGGTTGGCACTCACGTATGGCTGGGCGCA GAAATAAAATTCAGGCGCAGCAGCACTTATCGATG |
| 24 | Sequence of the 3'-Region used for knock out of BMT1 | GAATTCACAGTTATAAATAAAAACAAAAACTCAAAAA GTTTGGGCTCCACAAAATAACTTAATTTAAATTTTTGT CTAATAAATGAATGTAATTCCAAGATTATGTGATGCA AGCACAGTATGCTTCAGCCCTATGCAGCTACTAATGTC AATCTCGCCTGCGAGCGGGCCTAGATTTTCACTACAA ATTTCAAAACTACGCGGATTTATTGTCTCAGAGAGCA ATTTGGCATTTCTGAGCGTAGCAGGAGGCTTCATAAG ATTGTATAGGACCGTACCAACAAATTGCCGAGGCACA ACACGGTATGCTGTGCACTTATGTGGCTACTTCCCTAC AACGGAATGAAACCTTCCTCTTTCCGCTTAAACGAGA AAGTGTGTCGCAATTGAATGCAGGTGCCTGTGCGCCTT GGTGTATTGTTTTTGAGGGCCCAATTTATCAGGCGCCT TTTTTCTTGGTTGTTTTCCCTTAGCCTCAAGCAAGGTTG GTCTATTTCATCTCCGCTTCTATACCGTGCCTGATACT GTTGGATGAGAACACGACTCAACTTCCTGCTGCTCTGT ATTGCCAGTGTTTTGTCTGTGATTTGGATCGGAGTCCT CCTTACTTGGAATGATAATAATCTTGGCGGAATCTCCC TAAACGGAGGCAAGGATTCTGCCTATGATGATCTGCT ATCATTGGGAAGCTT |
| 25 | Sequence of the 5'-Region used for knock out of BMT4 | AAGCTTGTTCACCGTTGGGACTTTTCCGTGGACAATGT TGACTACTCCAGGAGGGATTCCAGCTTTCTCTACTAGC TCAGCAATAATCAATGCAGCCCCAGGCGCCCGTTCTG ATGGCTTGATGACCGTTGTATTGCCTGTCACTATAGCC AGGGGTAGGGTCCATAAAGGAATCATAGCAGGGAAA TTAAAAGGGCATATTGATGCAATCACTCCCAATGGCT CTCTTGCCATTGAAGTCTCCATATCAGCACTAACTTCC AAGAAGGACCCCTTCAAGTCTGACGTGATAGAGCACG CTTGCTCTGCCACCTGTAGTCCTCTCAAAACGTCACCT TGTGCATCAGCAAAGACTTTACCTTGCTCCAATACTAT GACGGAGGCAATTCTGTCAAAATTCTCTCTCAGCAATT CAACCAACTTGAAAGCAAATTGCTGTCTCTTGATGATG GAGACTTTTTTCCAAGATTGAAATGCAATGTGGGACG |

BRIEF DESCRIPTION OF THE SEQUENCES

| SEQ ID NO: | Description | Sequence |
|---|---|---|
| | | ACTCAATTGCTTCTTCCAGCTCCTCTTCGGTTGATTGA GGAACTTTTGAAACCACAAAATTGGTCGTTGGGTCAT GTACATCAAACCATTCTGTAGATTTAGATTCGACGAA AGCGTTGTTGATGAAGGAAAAGGTTGGATACGGTTTG TCGGTCTCTTTGGTATGGCCGGTGGGGTATGCAATTGC AGTAGAAGATAATTGGACAGCCATTGTTGAAGGTAGA GAAAAGGTCAGGGAACTTGGGGGTTATTTATACCATT TTACCCCACAAATAACAACTGAAAAGTACCCATTCCA TAGTGAGAGGTAACCGACGGAAAAAGACGGGCCCAT GTTCTGGGACCAATAGAACTGTGTAATCCATTGGGAC TAATCAACAGACGATTGGCAATATAATGAAATAGTTC GTTGAAAAGCCACGTCAGCTGTCTTTTCATTAACTTTG GTCGGACACAACATTTTCTACTGTTGTATCTGTCCTAC TTTGCTTATCATCTGCCACAGGGCAAGTGGATTTCCTT CTCGCGCGGCTGGGTGAAAACGGTTAACGTGAA |
| 26 | Sequence of the 3'-Region used for knock out of BMT4 | GCCTTGGGGGACTTCAAGTCTTTGCTAGAAACTAGAT GAGGTCAGGCCCTCTTATGGTTGTGTCCCAATTGGGCA ATTTCACTCACCTAAAAAGCATGACAATTATTTAGCGA AATAGGTAGTATATTTTCCCTCATCTCCCAAGCAGTTT CGTTTTTGCATCCATATCTCTCAAATGAGCAGCTACGA CTCATTAGAACCAGAGTCAAGTAGGGGTGAGCTCAGT CATCAGCCTTCGTTTCTAAAACGATTGAGTTCTTTTGT TGCTACAGGAAGCGCCCTAGGGAACTTTCGCACTTTG GAAATAGATTTTGATGACCAAGAGCGGGAGTTGATAT TAGAGAGGCTGTCCAAAGTACATGGGATCAGGCCGGC CAAATTGATTGGTGTGACTAAACCATTGTGTACTTGGA CACTCTATTACAAAAGCGAAGATGATTTGAAGTATTA CAAGTCCCGAAGTGTTAGAGGATTCTATCGAGCCCAG AATGAAATCATCAACCGTTATCAGCAGATTGATAAAC TCTTGGAAAGCGGTATCCCATTTTCATTATTGAAGAAC TACGATAATGAAGATGTGAGAGACGGCGACCCTCTGA ACGTAGACGAAGAAACAAATCTACTTTTGGGGTACAA TAGAGAAAGTGAATCAAGGGAGGTATTTGTGGCCATA ATACTCAACTCTATCATTAATG |
| 27 | Sequence of the 5'-Region used for knock out of BMT3 | GATATCTCCCTGGGGACAATATGTGTTGCAACTGTTCG TTGTTGGTGCCCCAGTCCCCCAACCGGTACTAATCGGT CTATGTTCCCGTAACTCATATTCGGTTAGAACTAGAAC AATAAGTGCATCATTGTTCAACATTGTGGTTCAATTGT CGAACATTGCTGGTGCTTATATCTACAGGGAAGACGA TAAGCCTTTGTACAAGAGAGGTAACAGACAGTTAATT GGTATTTCTTTGGGAGTCGTTGCCCTCTACGTTGTCTC CAAGACATACTACATTCTGAGAAACAGATGGAAGACT CAAAAATGGGAGAAGCTTAGTGAAGAAGAGAAAGTT GCCTACTTGGACAGAGCTGAGAAGGAGAACCTGGGTT CTAAGAGGCTGGACTTTTTGTTCGAGAGTTAAACTGCA TAATTTTTTCTAAGTAAATTTCATAGTTATGAAATTTCT GCAGCTTAGTGTTTACTGCATCGTTTACTGCATCACCC TGTAAATAATGTGAGCTTTTTTCCTTCCATTGCTTGGT ATCTTCCTTGCTGCTGTTT |
| 28 | Sequence of the 3'-Region used for knock out of BMT3 | ACAAAACAGTCATGTACAGAACTAACGCCTTTAAGAT GCAGACCACTGAAAAGAATTGGGTCCCATTTTTCTTGA AAGACGACCAGGAATCTGTCCATTTTGTTTACTCGTTC AATCCTCTGAGAGTACTCAACTGCAGTCTTGATAACG GTGCATGTGATGTTCTATTTGAGTTACCACATGATTTT GGCATGTCTTCCGAGCTACGTGGTGCCACTCCTATGCT CAATCTTCCTCAGGCAATCCCGATGGCAGACGACAAA GAAATTTGGGTTTCATTCCCAAGAACGAGAATATCAG ATTGCGGGTGTTCTGAAACAATGTACAGGCCAATGTT AATGCTTTTTGTTAGAGAAGGAACAAACTTTTTTGCTG AGC |
| 29 | DNA encodes Tr ManI catalytic domain | CGCGCCGGATCTCCCAACCCTACGAGGGCGGCAGCAG TCAAGGCCGCATTCCAGACGTCGTGGAACGCTTACCA CCATTTTGCCTTTCCCCATGACGACCTCCACCCGGTCA GCAACAGCTTTGATGATGAGAGAAACGGCTGGGGCTC GTCGGCAATCGATGGCTTGGACACGGCTATCCTCATG GGGGATGCCGACATTGTGAACACGATCCTTCAGTATG TACCGCAGATCAACTTCACCACGACTGCGGTTGCCAA CCAAGGCATCTCCGTGTTCGAGACCAACATTCGGTAC CTCGGTGGCCTGCTTTCTGCCTATGACCTGTTGCGAGG TCCTTTTCAGCTCCTTGGCGACAAACCAGACCCTGGTAA |

| SEQ ID NO: | Description | Sequence |
|---|---|---|
| | | ACAGCCTTCTGAGGCAGGCTCAAACACTGGCCAACGG<br>CCTCAAGGTTGCGTTCACCACTCCCAGCGGTGTCCCGG<br>ACCCTACCGTCTTCTTCAACCCTACTGTCCGGAGAAGT<br>GGTGCATCTAGCAACAACGTCGCTGAAATTGGAAGCC<br>TGGTGCTCGAGTGGACACGGTTGAGCGACCTGACGGG<br>AAACCCGCAGTATGCCCAGCTTGCGCAGAAGGGCGAG<br>TCGTATCTCCTGAATCCAAAGGGAAGCCCGGAGGCAT<br>GGCCTGGCCTGATTGGAACGTTTGTCAGCACGAGCAA<br>CGGTACCTTTCAGGATAGCAGCGGCAGCTGGTCCGGC<br>CTCATGGACAGCTTCTACGAGTACCTGATCAAGATGT<br>ACCTGTACGACCCGGTTGCGTTTGCACACTACAAGGA<br>TCGCTGGGTCCTTGCTGCCGACTCGACCATTGCGCATC<br>TCGCCTCTCACCCGTCGACGCGCAAGGACTTGACCTTT<br>TTGTCTTCGTACAACGGACAGTCTACGTCGCCAAACTC<br>AGGACATTTGGCCAGTTTTGCCGGTGGCAACTTCATCT<br>TGGGAGGCATTCTCCTGAACGAGCAAAAGTACATTGA<br>CTTTGGAATCAAGCTTGCCAGCTCGTACTTTGCCACGT<br>ACAACCAGACGGCTTCTGGAATCGGCCCCGAAGGCTT<br>CGCGTGGGTGGACAGCGTGACGGGCGCCGGCGGCTCG<br>CCGCCCTCGTCCCAGTCCGGGTTCTACTCGTCGGCAGG<br>ATTCTGGGTGACGGCACCGTATTACATCCTGCGGCCG<br>GAGACGCTGGAGAGCTTGTACTACGCATACCGCGTCA<br>CGGGCGACTCCAAGTGGCAGGACCTGGCGTGGGAAGC<br>GTTCAGTGCCATTGAGGACGCATGCCGCGCCGGCAGC<br>GCGTACTCGTCCATCAACGACGTGACGCAGGCCAACG<br>GCGGGGGTGCCTCTGACGATATGGAGAGCTTCTGGTT<br>TGCCGAGGCGCTCAAGTATGCGTACCTGATCTTTGCGG<br>AGGAGTCGGATGTGCAGGTGCAGGCCAACGGCGGGA<br>ACAAATTTGTCTTTAACACGGAGGCGCACCCCTTTAGC<br>ATCCGTTCATCATCACGACGGGGCGGCCACCTTGCTTA<br>A |
| 30 | Sequence of the 5'-region that was used to knock into the PpPRO1 locus: | GAAGGGCCATCGAATTGTCATCGTCTCCTCAGGTGCC<br>ATCGCTGTGGGCATGAAGAGAGTCAACATGAAGCGGA<br>AACCAAAAAAGTTACAGCAAGTGCAGGCATTGGCTGC<br>TATAGGACAAGGCCGTTTGATAGGACTTTGGGACGAC<br>CTTTTCCGTCAGTTGAATCAGCCTATTGCGCAGATTTT<br>ACTGACTAGAACGGATTTGGTCGATTACACCCAGTTTA<br>AGAACGCTGAAAATACATTGGAACAGCTTATTAAAAT<br>GGGTATTATTCCTATTGTCAATGAGAATGACACCCTAT<br>CCATTCAAGAAATCAAATTTGGTGACAATGACACCTT<br>ATCCGCCATAACAGCTGGTATGTGTCATGCAGACTAC<br>CTGTTTTTGGTGACTGATGTGGACTGTCTTTACACGGA<br>TAACCCTCGTACGAATCCGGACGCTGAGCCAATCGTG<br>TTAGTTAGAAATATGAGGAATCTAAACGTCAATACCG<br>AAAGTGGAGGTTCCGCCGTAGGAACAGGAGGAATGA<br>CAACTAAATTGATCGCAGCTGATTTGGGTGTATCTGCA<br>GGTGTTACAACGATTATTTGCAAAAGTGAACATCCCG<br>AGCAGATTTTGGACATTGTAGAGTACAGTATCCGTGCT<br>GATAGAGTCGAAAATGAGGCTAAATATCTGGTCATCA<br>ACGAAGAGGAAACTGTGGAACAATTTCAAGAGATCAA<br>TCGGTCAGAACTGAGGGAGTTGAACAAGCTGGACATT<br>CCTTTGCATACACGTTTCGTTGGCCACAGTTTTAATGC<br>TGTTAATAACAAAGAGTTTTGGTTACTCCATGGACTAA<br>AGGCCAACGGAGCCATTATCATTGATCCAGGTTGTTAT<br>AAGGCTATCACTAGAAAAAACAAAGCTGGTATTCTTC<br>CAGCTGGAATTATTTCCGTAGAGGGTAATTTCCATGAA<br>TACGAGTGTGTTGATGTTAAGGTAGGACTAAGAGATC<br>CAGATGACCCACATTCACTAGACCCCAATGAAGAACT<br>TTACGTCGTTGGCCGTGCCCGTTGTAATTACCCCAGCA<br>ATCAAATCAACAAAATTAAGGGTCTACAAAGCTCGCA<br>GATCGAGCAGGTTCTAGGTTACGCTGACGGTGAGTAT<br>GTTGTTCACAGGGACAACTTGGCTTTCCCAGTATTTGC<br>CGATCCAGAACTGTTGGATGTTGTTGAGAGTACCCTGT<br>CTGAACAGGAGAGAGAATCCAAACCAAATAAATAG |
| 31 | Sequence of the 3'-region that was used to knock into the PpPRO1 locus: | AATTTCACATATGCTGCTTGATTATGTAATTATACCTT<br>GCGTTCGATGGCATCGATTTCCTCTTCTGTCAATCGCG<br>CATCGCATTAAAAGTATACTTTTTTTTTTTTCCTATAGT<br>ACTATTCGCCTTATTATAAACTTTGCTAGTATGAGTTC<br>TACCCCCAAGAAAGAGCCTGATTTGACTCCTAAGAAG<br>AGTCAGCCTCCAAAGAATAGTCTCGGTGGGGGTAAAG<br>GCTTTAGTGAGGAGGGTTTCTCCCAAGGGGACTTCAG<br>CGCTAAGCATATACTAAATCGTCGCCCTAACACCGAA |

| SEQ ID NO: | Description | Sequence |
|---|---|---|
| | | GGCTCTTCTGTGGCTTCGAACGTCATCAGTTCGTCATC ATTGCAAAGGTTACCATCCTCTGGATCTGGAAGCGTTG CTGTGGGAAGTGTGTTGGGATCTTCGCCATTAACTCTT TCTGGAGGGTTCCACGGGCTTGATCCAACCAAGAATA AAATAGACGTTCCAAAGTCGAAACAGTCAAGGAGACA AAGTGTTCTTTCTGACATGATTTCCACTTCTCATGCAG CTAGAAATGATCACTCAGAGCAGCAGTTACAAACTGG ACAACAATCAGAACAAAAGAAGAAGATGGTAGTCG ATCTTCTTTTTCTGTTTCTTCCCCCGCAAGAGATATCCG GCACCCAGATGTACTGAAAACTGTCGAGAAACATCTT GCCAATGACAGCGAGATCGACTCATCTTTACAACTTC AAGGTGGAGATGTCACTAGAGGCATTTATCAATGGGT AACTGGAGAAAGTAGTCAAAAAGATAACCCGCCTTTG AAACGAGCAAATAGTTTTAATGATTTTTCTTCTGTGCA TGGTGACGAGGTAGGCAAGGCAGATGCTGACCACGAT CGTGAAAGCGTATTCGACGAGGATGATATCTCCATTG ATGATATCAAAGTTCCGGGAGGGATGCGTCGAAGTTT TTTATTACAAAAGCATAGAGACCAACAACTTTCTGGA CTGAATAAAACGGCTCACCAACCAAAACAACTTACTA AACCTAATTTCTTCACGAACAACTTTATAGAGTTTTTG GCATTGTATGGGCATTTTGCAGGTGAAGATTTGGAGG AAGACGAAGATGAAGATTTAGACAGTGGTTCCGAATC AGTCGCAGTCAGTGATAGTGAGGGAGAATTCAGTGAG GCTGACAACAATTTGTTGTATGATGAAGAGTCTCTCCT ATTAGCACCTAGTACCTCCAACTATGCGAGATCAAGA ATAGGAAGTATTCGTACTCCTACTTATGGATCTTTCAG TTCAAATGTTGGTTCTTCGTCTATTCATCAGCAGTTAA TGAAAAGTCAAATCCCGAAGCTGAAGAAACGTGGACA GCACAAGCATAAAACACAATCAAAAATACGCTCGAAG AAGCAAACTACCACCGTAAAAGCAGTGTTGCTGCTAT TAAA |
| 32 | Anti-Her2 Heavy chain (VH + IgG1 constant region) (DNA) | GAGGTTCAGTTGGTTGAATCTGGAGGAGGATTGGTTC AACCTGGTGGTTCTTTGAGATTGTCCTGTGCTGCTTCC GGTTTCAACATCAAGGACACTTACATCCACTGGGTTA GACAAGCTCCAGGAAAGGGATTGGAGTGGGTTGCTAG AATCTACCCAACTAACGGTTACACAAGATACGCTGAC TCCGTTAAGGGAAGATTCACTATCTCTGCTGACACTTC CAAGAACACTGCTTACTTGCAGATGAACTCCTTGAGA GCTGAGGATACTGCTGTTTACTACTGTTCCAGATGGGG TGGTGATGGTTTCTACGCTATGGACTACTGGGGTCAAG GAACTTTGGTTACTGTTTCCTCCGCTTCTACTAAGGGA CCATCTGTTTTCCCATTGGCTCCATCTTCTAAGTCTACT TCCGGTGGTACTGCTGCTTTGGGATGTTTGGTTAAAGA CTACTTCCCAGAGCCAGTTACTGTTTCTTGGAACTCCG GTGCTTTGACTTCTGGTGTTCACACTTTCCCAGCTGTTT TGCAATCTTCCGGTTTGTACTCTTTGTCCTCCGTTGTTA CTGTTCCATCCTCTTCCTTGGGTACTCAGACTTACATCT GTAACGTTAACCACAAGCCATCCAACACTAAGGTTGA CAAGAAGGTTGAGCCAAAGTCCTGTGACAAGACACAT ACTTGTCCACCATGTCCAGCTCCAGAATTGTTGGGTGG TCCATCCGTTTTCTTGTTCCCACCAAAGCCAAAGGACA CTTTGATGATCTCCAGAACTCCAGAGGTTACATGTGTT GTTGTTGACGTTTCTCACGAGGACCCAGAGGTTAAGTT CAACTGGTACGTTGACGGTGTTGAAGTTCACAACGCT AAGACTAAGCCAAGAGAAGAGCAGTACAACTCCACTT ACAGAGTTGTTTCCGTTTTGACTGTTTTGCACCAGGAC TGGTTGAACGGTAAAGAATACAAGTGTAAGGTTTCCA ACAAGGCTTTGCCAGCTCCAATCGAAAAGACTATCTC CAAGGCTAAGGGTCAACCAAGAGAGCCACAGGTTTAC ACTTTGCCACCATCCAGAGAAGAGATGACTAAGAACC AGGTTTCCTTGACTTGTTTGGTTAAAGGATTCTACCCA TCCGACATTGCTGTTGAGTGGGAATCTAACGGTCAAC CAGAGAACAACTACAAGACTACTCCACCAGTTTTGGA TTCTGATGGTTCCTTCTTCTTGTACTCCAAGTTGACTGT TGACAAGTCCAGATGGCAACAGGGTAACGTTTTCTCC TGTTCCGTTATGCATGAGGCTTTGCACAACCACTACAC TCAAAAGTCCTTGTCTTTGTCCCCTGGTTAA |
| 33 | Saccharomyces cerevisiae mating factor pre-signal peptide (DNA) | ATGAGATTCCCATCCATCTTCACTGCTGTTTTGTTCGCT GCTTCTTCTGCTTTGGCT |

| SEQ ID NO: | Description | Sequence |
|---|---|---|
| 34 | PpCITI TT | CCGGCCATTTAAATATGTGACGACTGGGTGATCCGGG<br>TTAGTGAGTTGTTCTCCCATCTGTATATTTTTCATTTAC<br>GATGAATACGAAATGAGTATTAAGAAATCAGGCGTAG<br>CAATATGGGCAGTGTTCAGTCCTGTCATAGATGGCAA<br>GCACTGGCACATCCTTAATAGGTTAGAGAAAATCATT<br>GAATCATTTGGGTGGTGAAAAAAAATTGATGTAAACA<br>AGCCACCCACGCTGGGAGTCGAACCCAGAATCTTTTG<br>ATTAGAAGTCAAACGCGTTAACCATTACGCTACGCAG<br>GCATGTTTCACGTCCATTTTTGATTGCTTTCTATCATAA<br>TCTAAAGATGTGAACTCAATTAGTTGCAATTTGACCAA<br>TTCTTCCATTACAAGTCGTGCTTCCTCCGTTGATGCAA<br>C |
| 35 | Anti-Her2 light chain (VL + Kappa constant region)(DNA) | GACATCCAAATGACTCAATCCCCATCTTCTTTGTCTGC<br>TTCCGTTGGTGACAGAGTTACTATCACTTGTAGAGCTT<br>CCCAGGACGTTAATACTGCTGTTGCTTGGTATCAACAG<br>AAGCCAGGAAAGGCTCAAAGTTGTTGATCTACTCCG<br>CTTCCTTCTTGTACTCTGGTGTTCCATCCAGATTCTCTG<br>GTTCCAGATCCGGTACTGACTTCACTTTGACTATCTCC<br>TCCTTGCAACCAGAAGATTTCGCTACTTACTACTGTCA<br>GCAGCACTACACTACTCCACCAACTTTCGGACAGGGT<br>ACTAAGGTTGAGATCAAGAGAACTGTTGCTGCTCCAT<br>CCGTTTTCATTTTCCCACCATCCGACGAACAGTTGAAG<br>TCTGGTACAGCTTCCGTTGTTTGTTTGTTGAACAACTT<br>CTACCCAAGAGAGGCTAAGGTTCAGTGGAAGGTTGAC<br>AACGCTTTGCAATCCGGTAACTCCCAAGAATCCGTTAC<br>TGAGCAAGACTCTAAGGACTCCACTTACTCCTTGTCCT<br>CCACTTTGACTTTGTCCAAGGCTGATTACGAGAAGCAC<br>AAGGTTTACGCTTGTGAGGTTACACATCAGGGTTTGTC<br>CTCCCCAGTTACTAAGTCCTTCAACAGAGGAGAGTGTT<br>AA |
| 36 | ScTEF1 promoter | GATCCCCCACACACCATAGCTTCAAAATGTTTCTACTC<br>CTTTTTTACTCTTCCAGATTTTCTCGGACTCCGCGCATC<br>GCCGTACCACTTCAAAACACCCAAGCACAGCATACTA<br>AATTTCCCCTCTTTCTTCCTCTAGGGTGTCGTTAATTAC<br>CCGTACTAAAGGTTTGGAAAAGAAAAAAGAGACCGCC<br>TCGTTTCTTTTTCTTCGTCGAAAAAGGCAATAAAAATT<br>TTTATCACGTTTCTTTTTCTTGAAAATTTTTTTTTTTGA<br>TTTTTTTTCTCTTTCGATGACCTCCCATTGATATTTAAGT<br>TAATAAAACGGTCTTCAATTTCTCAAGTTTCAGTTTCAT<br>TTTTCTTGTTCTATTACAACTTTTTTTTACTTCTTGCTCA<br>TTAGAAAGAAAGCATAGCAATCTAATCTAAGTTTTAA<br>TTACAAA |
| 37 | Sequence of the PpTRP2 gene integration locus: | GGTTTCTCAATTACTATATACTACTAACCATTTACCTG<br>TAGCGTATTTCTTTTCCCTCTTCGCGAAAGCTCAAGGG<br>CATCTTCTTGACTCATGAAAAATATCTGGATTTCTTCT<br>GACAGATCATCACCCTTGAGCCCAACTCTCTAGCCTAT<br>GAGTGTAAGTGATAGTCATCTTGCAACAGATTATTTTG<br>GAACGCAACTAACAAAGCAGATACACCCTTCAGCAGA<br>ATCCTTTCTGGATATTGTGAAGAATGATCGCCAAAGTC<br>ACAGTCCTGAGACAGTTCCTAATCTTTACCCCATTTAC<br>AAGTTCATCCAATCAGACTTCTTAACGCCTCATCTGGC<br>TTATATCAAGCTTACCAACAGTTCAGAAACTCCCAGTC<br>CAAGTTTCTTGCTTGAAAGTGCGAAGAATGGTGACAC<br>CGTTGACAGGTACACCTTTATGGGACATTCCCCCAGA<br>AAAATAATCAAGACTGGGCCTTTAGAGGGTGCTGAAG<br>TTGACCCCTTGGTGCTTCTGGAAAAAGAACTGAAGGG<br>CACCAGACAAGCGCAACTTCCTGGTATTCCTCGTCTAA<br>GTGGTGGTGCCATAGGATACATCTCGTACGATTGTATT<br>AAGTACTTTGAACCAAAAACTGAAAGAAAACTGAAAG<br>ATGTTTTGCAACTTCCGGAAGCAGCTTTGATGTTGTTC<br>GACACGATCGTGGCTTTTGACAATGTTTATCAAAGATT<br>CCAGGTAATTGGAAACGTTTCTCTATCCGTTGATGACT<br>CGGACGAAGCTATTCTTGAGAAATATTATAAGACAAG<br>AGAAGAAGTGGAAAAGATCAGTAAAGTGGTATTTGAC<br>AATAAAAACTGTTCCCTACTATGAACAGAAAGATATTA<br>TTCAAGGCCAAACGTTCACCTCTAATATTGGTCAGGA<br>AGGGTATGAAAACCATGTTCGCAAGCTGAAAGAACAT<br>ATTCTGAAAGGAGACATCTTCCAAGCTGTTCCCTCTCA<br>AAGGGTAGCCAGGCCGACCTCATTGCACCCTTTCAAC<br>ATCTATCGTCATTTGAGAACTGTCAATCCTTCTCCATA<br>CATGTTCTATATTGACTATCTAGACTTCCAAGTTGTTG |

| SEQ ID NO: | Description | Sequence |
|---|---|---|
| | | GTGCTTCACCTGAATTACTAGTTAAATCCGACAACAAC<br>AACAAAATCATCACACATCCTATTGCTGGAACTCTTCC<br>CAGAGGTAAAACTATCGAAGAGGACGACAATTATGCT<br>AAGCAATTGAAGTCGTCTTTGAAAGACAGGGCCGAGC<br>ACGTCATGCTGGTAGATTTGGCCAGAAATGATATTAA<br>CCGTGTGTGTGAGCCCACCAGTACCACGGTTGATCGTT<br>TATTGACTGTGGAGAGATTTTCTCATGTGATGCATCTT<br>GTGTCAGAAGTCAGTGGAACATTGAGACCAAACAAGA<br>CTCGCTTCGATGCTTTCAGATCCATTTTCCCAGCAGGA<br>ACCGTCTCCGGTGCTCCGAAGGTAAGAGCAATGCAAC<br>TCATAGGAGAATTGGAAGGAGAAAAGAGAGGTGTTTA<br>TGCGGGGGCCGTAGGACACTGGTCGTACGATGGAAAA<br>TCGATGGACACATGTATTGCCTTAAGAACAATGGTCG<br>TCAAGGACGGTGTCGCTTACCTTCAAGCCGGAGGTGG<br>AATTGTCTACGATTCTGACCCCTATGACGAGTACATCG<br>AAACCATGAACAAAATGAGATCCAACAATAACACCAT<br>CTTGGAGGCTGAGAAAATCTGGACCGATAGGTTGGCC<br>AGAGACGAGAATCAAAGTGAATCCGAAGAAAACGAT<br>CAATGAACGGAGGACGTAAGTAGGAATTTATG |
| 38 | Sequence of the PpURA5 auxotrophic marker: | TCTAGAGGGACTTATCTGGGTCCAGACGATGTGTATC<br>AAAAGACAAATTAGAGTATTTATAAAGTTATGTAAGC<br>AAATAGGGGCTAATAGGGAAAGAAAAATTTTGGTTCT<br>TTATCAGAGCTGGCTCGCGCGCAGTGTTTTTCGTGCTC<br>CTTTGTAATAGTCATTTTTGACTACTGTTCAGATTGAA<br>ATCACATTGAAGATGTCACTGGAGGGGTACCAAAAAA<br>GGTTTTTGGATGCTGCAGTGGCTTCGCAGGCCTTGAAG<br>TTTGGAACTTTCACCTTGAAAAGTGGAAGACAGTCTCC<br>ATACTTCTTTAACATGGGTCTTTTCAACAAAGCTCCAT<br>TAGTGAGTCAGCTGGCTGAATCTTATGCTCAGGCCATC<br>ATTAACAGCAACCTGGAGATAGACGTTGTATTTGGAC<br>CAGCTTATAAAGGTATTCCTTTGGCTGCTATTACCGTG<br>TTGAAGTTGTACGAGCTGGGCGGCAAAAAATACGAAA<br>ATGTCGGATATGCGTTCAATAGAAAAGAAAAGAAAGA<br>CCACGGAGAAGGTGGAAGCATCGTTGGAGAAAGTCTA<br>AAGAATAAAAGAGTACTGATTATCGATGATGTGATGA<br>CTGCAGGTACTGCTATCAACGAAGCATTTGCTATAATT<br>GGAGCTGAAGGTGGGAGAGTTGAAGGTTGTATTATTG<br>CCCTAGATAGAATGGAGACTACAGGAGATGACTCAAA<br>TACCAGTGCTACCCAGGCTGTTAGTCAGAGATATGGT<br>ACCCCTGTCTTGAGTATAGTGACATTGGACCATATTGT<br>GGCCCATTTGGGCGAAACTTTCACAGCAGACGAGAAA<br>TCTCAAATGGAAACGTATAGAAAAAAGTATTTGCCCA<br>AATAAGTATGAATCTGCTTCGAATGAATGAATTAATC<br>CAATTATCTTCTCACCATTATTTTCTTCTGTTTCGGAGC<br>TTTGGGCACGGCGGCGGATCC |
| 39 | Sequence of the part of the Ec lacZ gene that was used to construct the PpURA5 blaster (recyclable auxotrophic marker) | CCTGCACTGGATGGTGGCGCTGGATGGTAAGCCGCTG<br>GCAAGCGGTGAAGTGCCTCTGGATGTCGCTCCACAAG<br>GTAAACAGTTGATTGAACTGCCTGAACTACCGCAGCC<br>GGAGAGCGCCGGGCAACTCTGGCTCACAGTACGCGTA<br>GTGCAACCGAACGCGACCGCATGGTCAGAAGCCGGGC<br>ACATCAGCGCCTGGCAGCAGTGGCGTCTGGCGGAAAA<br>CCTCAGTGTGACGCTCCCCGCCGCGTCCCACGCCATCC<br>CGCATCTGACCACCAGCGAAATGGATTTTTGCATCGA<br>GCTGGGTAATAAGCGTTGGCAATTTAACCGCCAGTCA<br>GGCTTTCTTTCACAGATGTGGATTGGCGATAAAAAAC<br>AACTGCTGACGCCGCTGCGCGATCAGTTCACCCGTGC<br>ACCGCTGGATAACGACATTGGCGTAAGTGAAGCGACC<br>CGCATTGACCCTAACGCCTGGGTCGAACGCTGGAAGG<br>CGGCGGGCCATTACCAGGCCGAAGCAGCGTTGTTGCA<br>GTGCACGGCAGATACACTTGCTGATGCGGTGCTGATT<br>ACGACCGCTCACGCGTGGCAGCATCAGGGGAAAACCT<br>TATTTATCAGCCGGAAAACCTACCGGATTGATGGTAG<br>TGGTCAAATGGCGATTACCGTTGATGTTGAAGTGGCG<br>AGCGATACACCGCATCCGGCGCGGATTGGCCTGAACT<br>GCCAG |
| 40 | ScYos9p (protein) | MQAKIIYALSAISALIPLGSSLLAPIEDPIVSNKYLISYIDED<br>DWSDRILQNQSVMNSGYIVNMGDDLECFIQNASTQLND<br>VLEDSNEHSNSEKTALLTKTLNQGVKTIFDKLNERCIFYQ<br>AGFWIYEYCPGIEFVQFHGRVNTKTGEIVNRDESLVYRL<br>GKPKANVEEREFELLYDDVGYYISEIIGSGDICDVTGAER<br>MVEIQYVCGGSNSGPSTIQWVRETKICVYEAQVTIPELC |

| SEQ ID NO: | Description | Sequence |
|---|---|---|
| | | NLELLAKNEDQKNASPILCRMPAKSKIGSNSIDLITKYEPI FLGSGIYFLRPFNTDERDKLMVTDNAMSNWDEITETYYQ KFGNAINKMLSLRLVSLPNGHILQPGDSCVWLAEVVDM KDRFQTTLSLNILNSQRAEIFFNKTFTFNEDNGNFLSYKIG DHGESTELGQITHSNKADINTAEIRSDEYLINTDNELFLRI SKEIAEVKELLNEIVSPHEMEVIFENMRNQPNNDFELAL MNKLKSSLNDDNKVEQINNARMDDDESTSHTTRDIGEA GSQTTGNTESEVTNVAAGVFIEHDEL |
| 41 | ScYOS9 DNA | ATGCAAGCTAAAATTATATATGCTCTGAGCGCAATTTC TGCGTTGATTCCGTTAGGATCATCACTATTAGCACCTA TAGAAGACCCCATAGTATCGAATAAGTACCTCATATC TTACATCGATGAGGACGACTGGAGTGATAGGATATTA CAAAATCAGTCTGTCATGAACTCGGGATATATAGTGA ATATGGGCGACGACCTTGAATGCTTTATTCAAAATGC AAGCACTCAATTGAATGATGTATTGGAAGACTCAAAT GAGCATAGCAATAGTGAAAAGACAGCATTATTAACTA AAACCCTGAATCAAGGTGTTAAGACAATTTTCGATAA ATTAAATGAACGGTGCATCTTCTACCAAGCCGGATTTT GGATTTACGAGTACTGTCCTGGCATAGAATTTGTTCAG TTCCATGGTAGAGTAAATACAAAAACTGGTGAAATAG TAAATCGAGATGAATCTTTGGTCTACCGCCTGGGAAA ACCAAAAGCAAATGTAGAAGAGAGAGAATTTGAACT ACTTTATGACGATGTAGGATATTACATCAGCGAAATT ATAGGGTCAGGTGATATTTGCGATGTGACGGGGGCTG AAAGAATGGTTGAAATACAATATGTCTGTGGCGGCTC AAACTCTGGACCATCGACTATTCAATGGGTGAGAGAA ACAAAAATTTGTGTTTATGAAGCCCAAGTTACCATACC TGAATTGTGCAATTTAGAATTACTAGCCAAAAATGAA GACCAAAAGAACGCCTCACCTATACTTTGCAGGATGC CCGCAAAATCAAAAATTGGTAGTAACTCTATTGATTTA ATCACCAAATATGAACCGATTTTTTTAGGTTCTGGAAT ATACTTTCTAAGGCCCTTTAACACCGACGAAAGAGAC AAATTAATGGTTACTGACAATGCCATGTCAAATTGGG ATGAGATTACGGAAACATATTACCAGAAATTTGGAAA TGCCATAAACAAATGCTTAGTTTGAGATTAGTATCGT TACCTAATGGACATATTCTCCAGCCTGGTGACTCATGT GTTTGGTTGGCGGAAGTGGTTGATATGAAAGATCGGT TTCAAACCACTTTATCGTTGAACATACTTAATTCACAG AGAGCAGAGATATTTTTCAACAAGACGTTTACATTTA ATGAAGATAATGGAAACTTCCTATCATACAAAATTGG GGATCATGGCGAGTCAACTGAACTTGGTCAAATAACC CACTCAAACAAAGCAGATATAAATACCGCAGAAATTC GGTCAGATGAATACTTAATTAACACTGATAATGAGCT ATTCTTGAGGATTTCTAAGGAGATAGCAGAAGTGAAA GAATTATTAAACGAAATCGTAAGTCCACATGAAATGG AAGTAATATTTGAAAACATGAGAAATCAACCGAATAA TGATTTTGAACTGGCGTTGATGAACAAGTTGAAATCCT CATTAAATGATGATAACAAAGTTGAGCAGATAAACAA CGCAAGGATGGATGATGATGAAAGCACTAGTCATACA ACCAGAGACATCGGGGAAGCTGGATCACAAACGACA GGGAATACTGAATCGGAGGTAACAAACGTAGCAGCTG GTGTTTTCATCGAACATGATGAGCTTTAA |
| 42 | PpYos9p (protein) | MIKVLLFLLSLSSLVKALDDSIDKNSVYTINYLNHAISPTS EKIVTLRSTDDQYFECLFNDEIDTDQKLHQKQILKTLPAQ YNLSEIPELQTEINSAFNILENYNLNDAQPTKDRYWTYQI INGKLYQYNGNLRIVLANIPKNLTREDIVLEKNMHQSVF LSLSLQNGAICDLTFTPRKTNIRFQYVNKLNTLGIVSADEI QTCEYEILINVPKFKDTIFQYGFLEPLKKIDCYSSDSSMIN LADYQISVLSHKWFLGAKDFRLILITDVSNPPVISIEELNLI FQTFPKYGPPELGITGEISPHDTFIFRIPVYSYNRTKFGDV LVEQNIRGEKRFLFTEDRIPHDTPNFRVYNGVNVN |
| 43 | PpYOS9 (DNA) | ATGATAAAGGTCCTGCTATTCCTGCTCTCCCTATCAAG TCTTGTGAAAGCTTTGGATGATTCCATTGATAAGAATT CTGTGGTAAGTCTTTTAATTTTTGTTTTCACAAGATCAT GCCGTGCTAACTGGGTACTATAGTATACCATAAACTA CTTAAATCATGCCATCTCACCCACCTCAGAAAAAATA GTGACATTAAGATCAACGGACGATCAATATTTTGAGT GTTTGTTTAATGATGAAATTGATACTGACCAGAAACTA CATCAAAAGCAGATTCTGAAAACTCTTCCAGCTCAAT ACAACTTGAGTGAAATACCAGAACTTCAAACTGAAAT AAACTCTGCATTCAATATACTTGAAAACTATAACCTCA |

| SEQ ID NO: | Description | Sequence |
|---|---|---|
| | | ACGATGCTCAGCCAACCAAGGACAGATATTGGACATA<br>TCAAATAATAAATGGAAAATTGTACCAATATAACGGG<br>AACTTGCGAATTGTCCTGGCTAATATACCCAAGAATCT<br>GACGAGGGAAGACATAGTTCTGGAGAAGAATATGCAC<br>CAATCGGTGTTTTTATCACTCAGCTTACAAAACGGTGC<br>CATTTGTGATTTGACTTTCACTCCTAGAAAGACAAATA<br>TACGGTTTCAATACGTTAACAAGCTCAACACTCTAGG<br>AATTGTCTCCGCCGATGAAATACAGACCTGCGAATAT<br>GAAATTCTTATCAATGTTCCTAAGTTCAAAGATACCAT<br>TTTTCAGTACGGATTTTTGGAGCCTTTGAAGAAGATTG<br>ATTGCTACTCGAGTGATAGCTCAATGATAAATTTGGCA<br>GACTACCAAATATCTGTCCTTTCCCATAAATGGTTCTT<br>AGGGGCCAAAGATTTCAGGTTGATTTTGATCACTGAT<br>GTGTCTAACCCTCCCGTGATATCAATAGAAGAACTGA<br>ATCTCATATTTCAAACATTTCCTAAATACGGTCCCCCA<br>GAGCTCGGGATCACTGGTGAGATTTCACCCCATGACA<br>CTTTTATCTTCAGAATTCCTGTGTACAGCTACAATAGG<br>ACAAAATTCGGTGACGTACTGGTTGAGCAGAATATCA<br>GGGGAGAGAAAAGGTTCCTATTCACTGAAGACAGAAT<br>ACCTCATGACACTCCAAACTTTAGAGTGTATAACGGA<br>GTTAATGTGAATTAA |
| 44 | AfYos9p (protein) | MIRRIRTLTPLLVLACAGSGAWASKKAFNIQDDLLAYPQ<br>FQVFFPDEYILDARARELLQNQQESSSASADKTFSEGND<br>AQVYLGSRKDQSEDVNKETIEGSGFTYEEMLLEGQRYL<br>CSIPQVDNGNRDQTNGAESTSKEDEQREIARATDRGLEL<br>LREMEGKCMYYISGWWSYSFCYKKQIKQFHALPSGPGV<br>PNYPPIEDSTTHSFVLGRFPNSGDDEDLEGDAEHKKTTTD<br>VAELQTKGGSRYLVQRLGGGTKCDLTGKDRKIEVQFHC<br>HPQSTDRIGWIKELTTCSYLMVIYTPRLCNDVAFLPPQQD<br>EAHAIECREILSEEEVSDWEANREYHLAQQLVESAITPEF<br>PVVGDIEVGAHKWVGSEGKQIEKGRVASIGEEKIEVVAK<br>RQNGEITRLSKEELKKYGLDPEKIETLKSRLEELAKGKD<br>WTLEIVESNGERGLVGTVDSNDDEKEDHAAQGSISQPAQ<br>GTTADKGESNAETGEEKKKADEKIDHYEPEKSGPTTDDA<br>DDGSEEIFFKDEL |
| 45 | AfYOS9 (DNA) | ATGATTCGACGTATACGGACTCTTACCCCATTGCTGGT<br>GCTGGCTTGTGCTGGTTCCGGCGCATGGGCCAGCAAG<br>AAGGCGTTCAACATACAAGATGATCTACTTGCATATC<br>CTCAATTTCAAGTCTTCTTCCCTGATGAATACATTCTT<br>GATGCGCGAGCAAGGGAGTTATTACAGAATCAACAAG<br>AGAGCTCTTCGGCTTCCGCTGATAAGACATTCTCCGAA<br>GGCAATGATGCGCAAGTATATCTGGGAAGCCGAAAAG<br>ATCAATCTGAAGACGTCAATAAAGAGACGATAGAAGG<br>ATCTGGGTTCACATACGAGGAGATGCTCCTTGAGGGA<br>CAGAGATATCTCTGTTCCATTCCGCAAGTCGACAACG<br>GAAACAGGGACCAGACGAACGGAGCGGAAAGCACCA<br>GTAAAGAGGATGAACAGCGAGAAATTGCACGCGCGA<br>CGGACCGTGGCCTGGAACTTCTGCGCGAGATGGAAGG<br>CAAATGCATGTACTACATATCCGGATGGTGGTCATACT<br>CATTCTGCTACAAGAAGCAAATCAAGCAGTTTCATGC<br>ACTACCGTCCGGTCCAGGCGTGCCCAACTACCCGCCG<br>ATAGAAGACTCTACGACCCATTCTTTCGTGCTGGGCAG<br>GTTTCCCAACAGCGGCGACGACGAGGATTTGGAGGGG<br>GATGCGGAGCACAAAAAGACAACTACAGATGTCGCCG<br>AGCTCCAGACTAAAGGCGGGTCGCGGTACTTAGTGCA<br>GCGGCTGGGGGGCGGAACCAAGTGCGACTTGACAGGC<br>AAAGACCGGAAGATCGAAGTGCAGTTCCACTGCCATC<br>CGCAATCTACAGATCGGATCGGTTGGATCAAGGAACT<br>TACTACTTGCTCATATCTCATGGTGATCTACACTCCGC<br>GCTTGTGCAATGATGTCGCATTTCTGCCGCCTCAGCAG<br>GACGAGGCTCACGCGATCGAATGCCGCGAGATTCTCT<br>CCGAGGAAGAGGTTTCCGACTGGGAAGCAAACCGGG<br>AATATCATTTGGCTCAGCAGCTCGTCGAATCAGCGATT<br>ACACCCGAGTTTCCTGTTGTCGGGGATATCGAGGTCG<br>GGGCGCACAAGTGGGTGGGATCGGAAGGCAAGCAGA<br>TCGAGAAGGGTCGAGTGGCATCCATTGGAGAAGAGAA<br>GATCGAGGTAGTTGCCAAGCGCCAAAATGGAGAGATC<br>ACAAGGTTGTCCAAGGAGGAGTTGAAGAAATACGGTC<br>TTGATCCTGAGAAGATTGAGACGCTGAAAAGCCGCCT<br>CGAGGAGCTTGCCAAGGGTAAGGACTGGACACTGGAG<br>ATTGTCGAGTCTAACGGCGAGCGTGGCTTAGTCGGAA<br>CTGTCGACTCCAACGACGATGAGAAAGAGGATCACGC |

BRIEF DESCRIPTION OF THE SEQUENCES

| SEQ ID NO: | Description | Sequence |
|---|---|---|
| | | CGCACAGGGCTCTATATCGCAGCCGGCACAGGGAACT ACAGCTGACAAGGGGAATCCAATGCAGAGACAGGA GAGGAAAAGAAGAAGGCAGACGAGAAGATAGACCAT TACGAGCCAGAAAAATCAGGGCCGACCACTGATGATG CCGACGACGGCAGCGAGGAAATCTTCTTCAAGGATGA GCTCTAG |
| 46 | SpYos9p (protein) | MFPHLILPAIGSSKVRTMVLPFAFVGFFIFPICLASLLDWN DAYEYPKYSFEWSNVSILEGDIDSIKEKTEKTKLSSLFYA GKHEYFCVYPNASLIKQNSTTEPSYDLQELRIQGTEKINE LANVFLIENRGYWTYDYVYGQHVRQYHLEPQQGSDKV LANPMYILGTAPNTQTKKNLEENWAIGFVEGKAYLQTTF RNGTMCDITKRPRHVILSYECSTNSDTPEITQYQEVSSCA YSMTIHVPGLCSLPAFKIQEDIPSEKIVCYNVIKEKSNEVD HKDSQHVVDEVAQTSPPEVKEVETQSS |
| 47 | SpYOS9 (DNA) | ATGTTTCCACATTTGATTCTACCTGCAATCGGCTCATC TAAAGTTAGGACTATGGTGCTACCATTTGCTT TTGTGGGGTTTTTTATTTTTCCAATATGTTTAGCTTCTT TGTTAGACTGGAATGATGCATATGAATATCC TAAATATTCGTTTGAATGGAGTAATGTGTCAATATTAG AGGGCGACATTGACTCAATTAAAGAAAAAACTGAAAA AACTAAATTATCGTCATTATTCTATGCTGGAAAGCATG AATATTTTTGTGTATATCCCAATGCGTCTCTTATAAAA CAAAATAGCACAACCGAACCAAGCTATGATTTACAAG AATTGCGGATACAAGGGACTGAAAAAATCAATGAGCT TGCTAATGTATTTTTAATCGAGAATCGTGGTTATTGGA CTTATGACTATGTCTACGGTCAACACGTGCGTCAATAT CATTTGGAGCCGCAGCAAGGTTCTGACAAAGTCCTTG CTAACCCTATGTATATACTTGGTACGGCACCTAACACT CAAACTAAAAAGAATTTGGAAGAAAATTGGGCTATTG GATTTGTTGAAGGTAAAGCATATTTGCAAACAACTTTC CGAAATGGGACTATGTGCGACATTACTAAGAGACCAA GACACGTAATTCTAAGTTATGAATGCAGTACAAATTC GGATACTCCTGAAATTACTCAATATCAAGAAGTTTCA AGCTGTGCATATTCAATGACTATTCACGTTCCCGGTTT ATGCTCATTACCTGCTTTCAAAATTCAAGAGGACATAC CCTCTGAAAAAATTGTGTGCTATAATGTAATTAAAGA AAAATCAAACGAAGTCGACCATAAGGATTCCCAGCAC GTTGTTGATGAAGTTGCTCAAACATCTCCGCCTGAGGT GAAGGAGGTAGAGACGCAATCAAGTTAG |
| 48 | *Pichia pastoris* ATT1 5' region in pGLY5933 | GGCCGGGACTACATGAGGCCGATTCTTCAAGCCAGGG AAATTAATTGCTTGAACCGGAAAATCATTAAGGCAGG CAACGAAAAATCCAACTCCTTGGTTGAATTGACTCAA AAGTTTATCTTACGGAGAAAAGCTAAAGACATCAATA CGAATTTCCTTCCGCCAAAAACTGAACTGATACTGATG GTTCCAATGACTGAATTACAACAGGAGCTATACAAGG ATATAATTGAAACTAACCAAGCCAAGCTTGGCTTGAT CAACGACAGAAACTTTTTCTTCAAAAAATTTTGATTC TTCGTAAAATATGCAATTCACCCTCCCTGCTGAAAGAC GAACCTGATTTTGCCAGATACAATCTCGGCAATAGATT CAATAGCGGTAAGATCAAGCTAACAGTACTGCTTTTA CGAAAGCTGTTTGAAACCACCAATGAGAAGTGTGTGA TTGTTTCAAACTTCACTAAAACTTTGGACGTACTTCAG CTAATCATAGAGCACAACAATTGGAAATACCACCGAC TAGATGGTTCGAGTAAAGGACGGGACAAAATCGTACG AGATTTTAACGAGTCGCCTCAAAAAGATCGATTCATC ATGTTGCTTTCTTCCAAGGCAGGGGAGTGGGGCTCA ACTTAATTGGAGCCTCACGCTTAATTCTTTTTGATAAC GACTGGAATCCCAGTGTTGACATTCAAGCAATGGCTA GAGTGCATCGAGACGGGCAGAAAAGGCACACCTTTAT CTATCGTTTGTATACGAAAGGCACAATTGACGAAAAG ATCCTACAAAGGCAATTGATGAAACAAAATCTGAGCG ACAAATTCCTGGATGATAATGATAGCAGCAAGGATGA TGTGTTTAACGACTACGATCTCAAAGATTGTTTACTG TAGATCTTGACACGAATTGTAGTACACACGATTTGATG GAATGTTTATGTAATGGGCGGCTGAGAGATCCGACTC CCGTCTTGGAAGCAGAAGAATGCAAGACAAAACCGTT GGAGGCCGTTGACGACACGGATGATGGTTGGATGTCA GCTCTGGATTTCAAACAGTTATCACAAAAAGAGGAGA CAGGTGCTGTGTCAACAATGCGTCAATGTCTGCTCGG ATATCAACACATTGATCCAAAGATTTTGGAACCAACA GAACCTGTAGGGGACGATTGGTATTGGCAAACATCC |

BRIEF DESCRIPTION OF THE SEQUENCES

| SEQ ID NO: | Description | Sequence |
|---|---|---|
| | | TCGCGGAGTCCTCAGGCTTGGCTAAATCTGCATTGTCA TCTGAAAAGAAACCCAAGAAACCAGTGGTGAACTTTA TCTTTGTGTCAGGCCAAGACTAAGCTGGAAGAACGGA ACTTTAATCGAAGGAAAAATTAAATGTCAAAGTGGGT CGATCAGGAGATAATCCATGCTTCACGTGATTTTTCTT AATAAACGCCGGAAAAACTTTCTTTTTTGTGACCAAA ATTATCCGATCTGAAAAAAAATTACGCATGCGTGAAG TAGGATGAGAGACTTACTGTTGAACTTTGTGAGACGA GGGGAAAAGGAATATCCTGATCGTAAACAAAAAGTT TTCCAGCCCAATCGGGAACATCTGCGAAGTGTTGGAA TTCAACCCCTCTTTCGAAAATGTTCCATTTTACCCAAA ATTATTGTTATTAAATAATACATGTGTTACTAGCAAAG TCTGCGCTTTCCATGTCTCAGATTCGGCAGATAACAAA GTTGACACGTTCTTGCGAGATACGCATGAATCTTTTGG CTGCTTTTTGTGAAAGAGAAATGGTGCCATATATTGCA GACGCCCCTGAAAGATTAGTGTGCGGCTGAGTCTTTTT TTTTTCTCAACCAGCTTTTTCTTTTTATTGGGTACCATC GCGCACGCAGGACTCATGCTCCATTAGACTTCTGAAC CACCTGACTTAATATTCATGGACGGACGCTTTTATCCT TAAATTGTTCATCCATTCCTCAATTTTTCCGTTTGCCCT CCCTGTACTATTAAATTACAAAAGCTGATCTTTTTCAA GTGTTTCTCTTTGAATCGCTC |
| 49 | *Pichia pastoris* ATT1 3' region in pGLY5933: | GGACCCTGAAGACGAAGACATGTCTGCCTTAGAGTTT ACCGCAGTTCGATTCCCCAACTTTTCAGCTACGACAAC AGCCCCGCCTCCTACTCCAGTCAATTGCAACAGTCCTG AAAACATCAAGACCTCCACTGTGGACGATTTTTTGAA AGCTACTCAAGATCCAAATAACAAAGAGATACTCAAC GACATTTACAGTTTGATTTTTGATGACTCCATGGATCC TATGAGCTTCGGAAGTATGGAACCAAGAAACGATTTG GAAGTTCCGGACACTATAATGGATTAATTTGCAGCGG GCCTGTTTGTATAGTCTTTGATTGTGTATAATAGAATT ACTACGCGTATATCCCGATCTGGAAGTAACATGGAAG TTTCCCATTTTCGCGCAGTCTCCTACTCGTATCCTCCCC ACCCCTTACCGATGACGCAAAAGGTCACTAGATAAGC ATAGCATAGTTTCATCCCTTGCTCTTTCCTTGTACCAA CAGATCATGGCTGGGAATCTCAAGGATATTCTATCCTT GTCGAGGAAGACAGCAAGGAATCTGAAGCAGGCTCTG GATGAGCTTGCGGAGCAGGTGATCAACCACCAACGGA GACGACCAGCTCTGGTCCGAGTTCCTATCAACAACAA CCTTAGGCGCAAGAGCCAGCAGTCCTTTTTGAATCGC AGGTCATTCCATCTTTGGACCAGCAAGTACAACCCAT ACTTTTGGAGGGGAGGCAGAAGCAACGTTCTGGACCA GCTTAACCGTGAAGCTTTAAGGTACAGATCGTCTTTTG CGAAACCCGGATTTTATCCAAGTGGGCTGTATCAGTC AACTTTCCCTCAAAGAGGTAGTAGGATGTTTTCCACCT GCGCCTACTCATGTCAGCAGGAGGCAGTCAAAAACTT GACTTCCGCTGTTCGTGCTTTGTTACAAAGTGGTGCTA ATTTCGGCAGTCAAATGAAACAAATGAAACACTGTTC GCAAAAGAAGAAGCACTTCTCTAAATTTTCTAAGAGG CTTACTTCTTCCACTGCCGCTGGGTCTGGCAAGAATGC TGAACAAGCTCCTTCTGGTTTGGCCGAAGGATCCGCTG TTGTTTTTAGCCTTGAACGTCAAAGTCACAATACTGAG TTGGAAGGAATCTTGGATCAAGAACTTCTTCCATTCT CGAGGAAGAAATGGTTCAACATGAGCGTCACCTGGCT ATTATTAGAGAAGAAATCCAGAGAATTAGTGAGAATC TAGGATCATTACCATTAATCATGTCTGGTCACAAGATT GAGGTATTTTTCCCCAATTGTGACACTGTTAAATGTGA GCAACTGATGAGAGATTTGGCTATTACGAAAGGGGTT GTGAGGCGTCATGATTCTACTGCTGAGCATTCAAGCTC CAGGTCATTTGTTCCAGAAGATTGCTTGTATTCCTCAG GGTCAAGTTCACCGAATCCTTTATCCTCAACTTCTTCG AAATCATTTGATAGAGTCTCATTGGACTACATTTCCTC TCGGTCTACATCTGATCAAACCACTGGTTCTGAGTACA CATCTCTGTCTCAACAATATCACCTGGTTAGCAATTAC AACCCTGTACTATCCTCAGCCCCGGGTTCTTCGAGGGT CTTGGAGCTGAATACTCCCGAGTCCACTATGGAAGGC AGTACAGATCTGGAGTATTTAACGCGAGACGATGTGT TGCTGTTAAATGTCTAATCTAGACCTATCCTTCATTCT ATATAGCTTAGTTGAGTTTTACGTAAGCCCTAGTTTTT GTTAATTCTTATCGATTTATGGTTAGTGTACCACTCAA CTCACGATGATATATCCCAGGAGCTGTTTGTGCATTAT AACTACCAATCCT |

BRIEF DESCRIPTION OF THE SEQUENCES

| SEQ ID NO: | Description | Sequence |
|---|---|---|
| 50 | DNA encodes *Homo sapiens* endomannosidase (codon-optimized for expression in *Pichia pastoris*) | ATGGCTAAGTTCAGAAGAAGAACCTGTATTATCCTTG CTTTGTTTATTTTGTTTATCTTTTCCCTTATGATGGGAT TGAAGATGTTGAGACCTAACACCGCCACTTTTGGTGC ACCATTCGGACTTGATTTGCTTCCTGAATTGCATCAAA GAACTATCCATTTGGGTAAAAACTTCGATTTCCAGAA ATCAGACAGAATCAATAGTGAAACAAACACCAAGAAT TTGAAGTCAGTTGAGATCACAATGAAGCCTAGTAAAG CTTCTGAATTGAATCTTGATGAGCTTCCACCTTTGAAC AACTATTTGCATGTTTTCTACTATAGTTGGTACGGTAA CCCACAATTCGATGGAAAGTATATCCATTGGAATCAC CCAGTCTTGGAACATTGGGACCCTAGAATTGCTAAAA ACTACCCACAGGGTAGACACAATCCACCTGATGACAT TGGTTCTTCCTTTTATCCTGAATTGGGATCTTACTCAA GTAGAGATCCATCCGTTATTGAGACTCACATGAGACA AATGAGATCAGCTAGTATCGGTGTTTTGGCCCTTTCTT GGTATCCACCTGATGTCAACGACGAAAATGGAGAGCC AACTGATAACCTTGTTCCTACAATTTTGGACAAGGCTC ATAAATACAACTTGAAGGTCACTTTCCACATTGAACCT TATTCCAATAGAGATGACCAGAACATGTACAAGAACG TTAAGTACATCATCGATAAGTACGGTAACCATCCAGC ATTCTACAGATACAAGACTAAGACAGGAAATGCTTTG CCTATGTTCTACGTCTATGACTCTTACATTACTAAGCC AGAGAAATGGGCTAACTTGCTTACTACATCTGGTTCCA GATCAATTAGAAATTCTCCTTACGATGGACTTTTTATC GCCTTGCTTGTTGAAGAGAAGCATAAGTACGATATCTT GCAATCCGGTTTCGACGGAATCTACACTTATTTTGCCA CAAACGGTTTCACCTACGGATCTTCCCACCAGAATTGG GCATCTTTGAAGTTGTTTTGTGATAAGTACAATTTGAT TTTCATCCCATCAGTCGGTCCTGGATATATTGACACTT CTATCAGACCATGGAACACCCAAAACACTAGAAACAG AATTAATGGTAAATACTACGAAATCGGACTTTCCGCT GCCTTGCAAACCAGACCTTCCTTGATTTCAATCACT TCTTTTAACGAATGGCATGAGGGTACTCAGATTGAAA AGGCTGTTCCAAAAAGAACATCAAATACCGTCTACTT GGATTATAGACCACACAAGCCTGGATTGTACCTTGAG TTGACAAGAAAATGGTCTGAAAAGTATTCCAAAGAGA GAGCAACCTACGCTCTTGACAGACAATTGCCAGTTTCT TAATGA |
| 51 | Mouse mannosidase 1B catalytic domain | GATCCAGAAGACATGGAGATCAAGAAGAAAAGAGAC AAAATTAAAGAGATGATGAAACATGCCTGGGATAATT ACAGAACATACGGATGGGACATAATGAACTAAGGCC TATTGCAAGGAAAGGCCATTCCACTAACATATTCGGA AGCTCACAGATGGGTGCCACCATAGTGGATGCTTTGG ATACCCTTTATATCATGGGGCTTCATGATGAATTCATG GATGGGCAAAGATGGATTGAAGAAAACCTTGATTTCA GTGTGAATTCAGAAGTGTCTGTCTTTGAAGTTAACATT CGCTTTATTGGAGGGCTCCTCGCTGCATATTACCTGTC AGGAGAGGAAATATTCAAGACTAAAGCAGTGCAGTTG GCTGAGAAACTCCTTCCTGCCTTTAACACACCTACTGG GATTCCCTGGGCAATGGTGAACCTGAAAAGTGGAGTA GGTCGAAACTGGGGCTGGGCGTCTGCAGGCAGCAGCA TCCTGGCTGAGTTCGGCACCCTGCACATGGAGTTTGTG CACCTCAGCTACTTGACCGGTGACTTGACTTACTATAA TAAGGTCATGCACATTCGGAAACTACTGCAGAAAATG GAACGCCCAAATGGTCTTTATCCAAATTATTTAAACCC AAGAACAGGGCGCTGGGGTCAGTATCACACATCAGTT GGTGGTCTGGGAGATAGTTTTTATGAATACTTACTGAA AGCATGGCTGATGTCAGATAAAACAGACCACGAGGCA AGAAGGATGTATGACGATGCTGTTGAGGCTATAGAAA AACATCTTATTAAGAAGTCCCGAGGAGGTCTGGTTTTT ATTGGAGAATGGAAGAATGGACACTTGGAAAGGAAG ATGGGGCACTTGGCCTGCTTTGCTGGGGAATGTTTGC CCTTGGAGCAGATGGTTCCAGAAAGGATAAAGCTGGC CACTACTTAGAACTAGGGGCAGAAATTGCACGAACAT GTCATGAGTCATATGACAGAACTGCATTGAAACTAGG TCCGGAGTCATTCAAGTTTGATGGTGCAGTGGAAGCC GTGGCTGTGCGGCAGGCTGAAAAGTATTACATCCTTC GTCCAGAAGTAATTGAAACCTATTGGTATCTATGGCG ATTTACCCACGACCCAAGATACAGGCAGTGGGGCTGG GAAGCAGCACTGGCTATTGAAGTCGTGCCGGGTCA GCGGTGGGTTTTCTGGTGTCAAGGATGTATACGCCCCG ACCCCTGTGCATGACGACGTGCAGCAGAGCTTTTTTCT TGCTGAAACATTAAAATACTTGTACCTGCTGTTCTCTG |

| SEQ ID NO: | Description | Sequence |
|---|---|---|
| | | GCGATGACCTTCTACCTTTAGACCACTGGGTGTTTAAC<br>ACAGAGGCGCACCCTCTGCCGGTGTTGCGCTTAGCCA<br>ACAGCACTCTTTCAGGTAATCCTGCTGTCCGATGA |
| 52 | SEC12 leader 9 | ATGAACACTATCCACATAATAAAATTACCGCTTAACT<br>ACGCCAACTACACCTCAATGAAACAAAAAATCTCTAA<br>ATTTTTCACCAACTTCATCCTTATTGTGCTGCTTTCTTA<br>CATTTTACAGTTCTCCTATAAGCACAATTTGCATTCCA<br>TGCTTTTCAATTACGCGAAGGACAATTTTCTAACGAAA<br>AGAGACACCATCTCTTCGCCCTACGTAGTTGATGAAG<br>ACTTACATCAAACAACTTTGTTTGGCAACCACGGTACA<br>AAAACATCTGTACCTAGCGTAGATTCCATAAAAGTGC<br>ATGGCGTGCATGAGACGAGTTCTGTGAATGGAACTGA<br>AGTCTTATGTACTGAAAGTAACATTATTAATACTGGAG<br>GGGCAGAGTTTGAGATCACCAACGCAACTTTTCGAGA<br>AATAGATGATGCT |
| 53 | PpSTT3 promoter | ACCAGTCTTGAAGATTCAGACGTAGACATGGATAAAT<br>TTGTTGACGCTATGGATATTTCACCGTTGCCAGATGCC<br>GCAGATTCGTCATTTTCTACGGTTAAAGCTTCCAGACA<br>GAGTTCACTAACCACAAGAAAACTAATTCCGTCCAAA<br>CAAAGTAAGAGCCTTCTAAGCTCTTTGAAGAACGCTG<br>AAGCTCAACCAGATGAAACAGAATAGTTCCACCCTT<br>AGGTGCACCCTCACGAATGAATTTGGTAGAACCTAAT<br>ATGGTGCTTGAAGATAATAATAAATAGATCAATCAAC<br>TCACCGAACAAATGATTATATAATTGGGCTCTCCTTTC<br>CTGCTAGCCCTTGCACTTCCCTTCCCTAGTAAATACAT<br>CCGAGAGCATCCTTCGCGAATACCTTCCAACACATAA<br>ACAGTACACTACTCCGCCGAAAAAGACACGTTGGAGC<br>GACTAGCTTAAAATACTCTCCACCGCCAAATCCTCCCT<br>CAACGGATCTCCAACA |
| 54 | Insulin analogue B chain (des B30): Asn at 1 and 31 beta-1 linked to a paucimannose N-glycan | <u>N*</u>GTFVNQHLCGSHLVEALYLVCGERGFFYT<u>N*</u>K |
| 55 | Sc alpha mating factor signal sequence and pro-peptide | MRFPSIFTAVLFAASSALAAPVNTTTEDETAQIPAEAVIG<br>YSDLEGDFDVAVLPFSNSTNNGLLFINTTIASIAAKEEGV<br>SLEKR |
| 56 | N-terminal spacer | EEAEAEAEAK |
| 57 | B-chain | NGTFVNQHLCGSHLVEALYLVCGERGFFYTNK |
| 58 | A-chain | GIVEQCCTSICSLYQLENYCN |
| 59 | PpADE4-5UTR + ORF | TACACGATCACAAGTTGTGTATAGTCTTTTCTTTAAAC<br>TGATCGTAGACCAGACCACCACAGCGTAGCCAAATGT<br>TATTTATTCATTAATCGAAAAAGTTTTGGTTCAGGCGC<br>GACAAGGTAGTAAGAAAAAAATTCTGCATGAATTGAT<br>TCTTCACTTGGTACTTGATTCATTGAACAATATAAACA<br>CAGATAATGTGTGGGATTCTTGGAATTGTATTGGCTGA<br>TCAGTCAGAAGATGTTGCAGCTGAATTGTTAGATGGA<br>GCCATGTTTTTGCAACATAGGGGACAAGATGCCGCAG<br>GTATTGTGACCTGTGCAGGAGGACGTTTTTATCAATGC<br>AAAGGTAATGGAATGGCCAAGGACGTACTTACGGAGC<br>AACGTATGAAAGGGCTGGTAGGTAATATGGGAATTGC<br>GCAGCTAAGATATCCGACTGCTGGTTCTAGTGCCATG<br>AGCGAAGCGCAGCCGTTTTATGTTAACAGTCCATACG<br>GAATTGCACTTTCTCATAATGGTAATCTTGTGAATGGA<br>CGTAATCTCCGCCAGAAATTAGATGATGTTCTTCATCG<br>CCATATAAATACAGATAGTGATAGCGAGTTACTGTTG<br>AACATTTTTGCTGCTGAGTTGGCTCAGTACGACAAGA<br>AAAGAGTTAACTCAGAAGACATTTTCAAGGCCCTCGT<br>TGGTGTCTACAGAGAATGTCGTGGAGCTTATGCTTGTG<br>TCAGTATGTTGGCCGGCTATGGTATTATTGGATTTCGT<br>GATCCTCATGGTATCAGACCTTTAGTCGTCGGAGAAC<br>GTGTGAGAGTGTCCCAAACTCCCGGTGACACTCACTT |

| SEQ ID NO: | Description | Sequence |
|---|---|---|
| | | GCAATGCGATTATATGCTTGCCTCTGAGAGTGTAGTTT<br>TAAAGGCTCATGGATTTCACAACTTTAGGGATATTTTA<br>CCAGGTGAAGCTGTTATTATCACAAAGAGAGGGCCTC<br>CGGAGTTTTGTCAAATTGTTCCTGCGAAAGCCTACACT<br>CCGGATATTTTTGAATACGTTTATTTTGCTAGACCTGA<br>TTCGATTATGGATGGAATATCTGTCTACCGAAGCCGTT<br>TGGCAATGGGGCGCAAACTAGCCCAGAAAATCACCTC<br>TCGTTTTACCAGTCAGTCCTTAAACGTAGTTAGAGAAA<br>TTGATGTGGTGATACCTGTTCCAGATACATCTCGACCT<br>TCAGCTCTGGAATGTGCCGTGACGCTTGGCATACCAT<br>TCAGAGAAGGTTTTGTCAAAAATCGTTATGTGGGCCG<br>TACCTTCATTATGCCGAACCAGAAGGAAAGAACTTCG<br>TCTGTGCGACGTAAATTAAACGCTATGTCTTCTGAGTT<br>TGCTGGTCGTAACGTTTTGTTAATTGACGACTCGATCG<br>TAAGAGGAACCACGTCCAAGGAAATCGTTAACATGGC<br>AAGAGAAGCTGGCGCTAACAAAGTATACTTTGCATCA<br>TGCTCTCCAGTCATACGATACAATCATATATATGGCAT<br>TGACCTCGCAGATTCACGTGCTTTGGTGGGATTTGGTC<br>GATCAGAAAGGGAGGTATCTGACTTGATAGGTGCTGA<br>CGATGTAATTTACCAGTCACTTGATGATTTGAAATCCT<br>GTTGTGTTCAGGAGCCCGAACTCCCATCCGAGTTACCC<br>TCAACTAGGATTGCATTCACCCAACCACCTCCGAAGA<br>TTAATGGATTTGAGGTGGGTGTATTCACCGGAGTTTAT<br>GTAACTGGAGAGGAAGATCATTATCTCAAGGAGTTAG<br>AACAGGTAAGAGCTAAAAATGAGCGATCACGTATTAA<br>TGGCTGTGGTATAGACGTTAAAGCGGAGACTGATATT<br>TCTTTGTTTAATAGAGGGGAGAGTTGA |
| 60 | PpADE4-3UTR | TAGTAAAGAGCATATCAGTTGCAAATCTCATACTTAC<br>ATCTGTCCAATTCGTCAATCATGCAACTAGTGTGTCTA<br>ACCGCTAATGTGCAACCAAATCCAATTAATGGAAGAA<br>TAAAGTCTTCCGTAAATTGGTTTGCTTCGCAAATCTCT<br>CGATATATGAGGTATTAAAGAAAGTAAGAATATGAAA<br>TCGTAACTGGTAATAGATGGATGTATCTAGAATCAAC<br>CAACTAATAAGACAAACATTGTTTGCAGCGCTATCAT<br>GTCTTTTACAGTAAGTCTTTTCTGTCAAGTGGATAAAC<br>GGGTCAAAAATTATAATGATGTACGTACGTTCGCCTTC<br>GCACCATAAACGACGAGGCCTAATTTTTACTATATAAT<br>AACAAAAGTTAAGACAGTAATACCCTGTCGCTTTACA<br>TCAGACAAAATCATGTTGTTGAGTAGTCAGTCATTGAT<br>TCATGAGTTCATTTCTAAATACTTGAAATCCAATATGA<br>ACTACCTCACAATTTAAAAAGGAAGATAATCAATCCT<br>ATTATTCGCTGGCCACCGTAATGCCATATTCGGATCAG<br>ATGAAAACGAAGCATAGGTTGAATATAAGCAATCTAA<br>CTTCGTTCAGCATTTGCTCTGAAAAATACACCAAAAA<br>AACATGCGATTTAGATTGTGATGCTGCTCTTGACCCTG<br>CCCTATGTTTCAAACTACGGATCACTTTCTTAAAAAAG<br>CCGGGCTGCATATTTCCAGATAATCATGACGCATCCAC<br>CTCGTTACAATGTACCTAAACTAAAAGACAACGACAG<br>CCCCCTTGGTTGTGCAGATCATCATCTCCTATCAAACA<br>GCACACAAAAAACTGGGTAATAAGTTTAGAACGAGTT<br>ACAAAATGTCTTCCTCCTTTTGCAATTCTAATCTACGC<br>GGAATCTGTCACCCTCTTAGGTTTATTCTCTTACAGTA<br>CTTCCCCTAGAATCCCGACAAGAGCTAAACAAAAACT<br>TAGGCCAGAAAGCAAAGTTCCCTTAGCATATAATTTA<br>CCTAGCTTTGTTAGGCTATTTCGAACTTGATTCCGTTC<br>AATCGCCCACTCCACTTCATCTTCGACATTATCTTCCA<br>TCAATTCTCCTTCTACAGAAACATAGGCTGACCCATCT<br>AAAGAAGATCTTTCAGTAATGTCTTGTTTCTTTTGTTG<br>CAGTGGTGAGCCATTTTGACTTCGTGAAAGTTTCT<br>TTAGAATAGTTGTTTCCAGA |
| 61 | PpADE8-<br>5UTR + ORF | AACCCAACTGCTCTGCTGTTATCCTCATGCATGATGTTGAG<br>ACACATGTCTTTGAACAGCTATGCCGACAAGATCGAAAACT<br>CTGTCTTGAAGACCATTGCTTCTGGACCAGAGCACAGAACT<br>AAGGACTTGAAAGGAACCTCCTCGACTTCAAACTTCACCGA<br>ACAAGTTATCAAGAACTTGTAATAGTGAACGGTTATGAAA<br>ATGAATGCTTCATGACTTGAGGCTCCTTTCGTTAGAAATAT<br>AGATAGATGTAGCAGTCTTTTGAAACGGTTGAAAAATGTAT<br>TAACGATCTTTACTAGTAATTATGGTTTGCAGTTCGCACTTT<br>TTTTTTTCAGCCTTTATCATCGATCACACTAGGAAAAAAAA<br>ATCAAGCTAGTCTAGTAACGATGACGCCTAAGATATTAGTA<br>CTCATTTCTGGTAATGGAAGCAACCTCCAGGCTCTCATTAA<br>TGCCAAGGAGCAAGGCCAGCTGAAAGCAGAAATATCTTTG |

-continued

| SEQ ID NO: | Description | Sequence |
|---|---|---|
| | | GTCATATCCTCAAGTAGTAAGGCATTTGGCATCGAAAGAGC CAGGAAACACAACATTCCAGTCCGAGTGCATGAGCTGAAG TCATACTACCAGGGAATTCCCAAAGAGGAGAAAGCCAAAC GAGCCGAAAAGAGAAACGATTTTGATCAAGACCTGGTCAA GATCATATTGAGCGAGAAGCCTGATCTTGTTGTTTGTGCCG GCTGGATGCTTATACTAGGTGAAAAATTCTTACAACCTTTA CAAGAGAAGAACATCTCCATCATAAACTTGCATCCATCCTT GCCTGGAGCCTTTGAGGGAATTAATGCAATCGAAAGATCTT ATAATGCCGGTCAGAATGGCGAAATTACTAAGGGTGGTAT CATGATCCATCGGGTTATTCTGGAGGTTGATAGAGGACAAC CTCTCATAGTGAGAGAAATAGATGTTATCAAAGGAGAGAC GCTAGAGTCGTGGGAGGCAAGAATCCATTCTTTAGAACACC AAGCAATAGTGGATGGAACTAACAAGGCATTGGACGAGTT GAAATAA |
| 62 | PpADE8-3UTR | GGGTCACATATAAGCCAATTAATTTCTTCAATTTCTTTTATC CGTTAACAGTATGTTGTATATCTTTATGCTTCAGTATCTACC TCCATTGGAACCACAGTTTCCTCAATATCGACAAGATTGTA GATACTCTCTTTCAACACCGCAGTAGTGCCTCTAGCAAACT TGTATGACTTAACCTTGGCTTCACGGACGTTAGGCTTCAGA TAGTTTCTGTACAATTGGGCATCTTTTCCAACTTCCATGACA CAAAGGTCCACGTTAGAACCGGATCCCAAATCATTCCAGAT ACCTGCCTCAATAGCTTCTGTGCACAGCTTCATTGCCTCTTC CTTAGTCAAGCCTTCTTTCCAGTTGCTCTCCAAGACAGCCA TGGCCGCCAGCGAACCTGATCCCAAAGATTGATAGAATCC AATATCGGTGGATCCATGCGCATGGATAGAAAACAAGTGG GCTCCTGTAGGATCAACACCACCGACGATTAGATAGGCTCC AATGTGACCTTGGTACTTGAACAGATGTTGTTTCAGCATCG TCAATGCTGTGACCACTCGAGGTTTCCTTTCTGTAGACATG GCATGCAATTCTAGATTTGATCCAATCAGTTGTGTAACCAT CTCTGTATCAGCAGCGGTACCTGCTCCTGCACACCATATAG TAGGTGACAACCTGTGTAGCTTTTCACAATTCTTGTCAGCC ACGATAGGACCTGACGTAGCTCTGGTATCGGCAGCGATCAC AACACCTCCTTCAAATTTAACTCCCACAATGGTGGTTCCTG TGGAAGTTGCCTTCGGAGAGCCAAATCCCTTAGCTGAAAGG AATTGATTTCTTTGGTGGTTATCGAAACTGAGGCCTGCCAT ATTCGTGTGATGGTATGGTGAACGAGTTTGTCAAGTGGGTT GAATTTGCCTTCAGGATATTACGATTCGAGAAGTACATTCT ATCGATGTCGGATGTGAGATACATACATTAAAACTCATACG TCAAAGGTATGCAACTACGGCTCTCAAGAACCTTTTATATA CAGGACGTTAGTTGACCACCTTGTCACATCTATGGCACAGT TCGTGATCT |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A host cell that does not display dolichyl —P—Man:Man5GlcNAc2-PP-dolichyl alpha-1,3 mannosyltransferase (alg3p) activity, Att1p activity, and osteosarcoma 9 (OS-9) protein activity comprising a nucleic acid molecule encoding a *Trypanosoma brucei* STT3 protein integrated into the genome of the host cell, wherein the host cell is a yeast or filamentous fungus and the OS-9 protein activity is Yos9p activity.

2. The host cell of claim 1, wherein the host cell further includes a nucleic acid molecule encoding a heterologous protein.

3. The host cell of claim 1, wherein the host cell is genetically engineered to produce glycoproteins comprising one or more mammalian- or human-like N-glycans.

4. A host cell comprising:
(a) a disruption in expression of the endogenous dolichyl-P-Man:Man5GlcNAc2-PP-dolichyl alpha-1,3 mannosyltransferase (ALG3) gene;
(b) a disruption in the expression of endogenous osteosarcoma 9 (OS-9) family gene;
(c) disruption in expression of an endogenous gene encoding ATT; and
(d) a nucleic acid molecule encoding a *Trypanosoma brucei* STT3 protein integrated into the genome of the host cell, wherein the host cell is a yeast or filamentous fungus and the OS-9 family gene is a YOS9 gene.

5. The host cell of claim 4, wherein the disruption in the expression of the endogenous dolichyl-P-Man:Man5GlcNAc2-PP-dolichyl alpha-1,3 mannosyltransferase (ALG3) and endogenous osteosarcoma 9 (OS-9) family gene or homolog is achieved by deleting or disrupting the gene.

6. The host cell of claim 4, wherein the host cell further includes a nucleic acid molecule encoding a heterologous protein.

7. The host cell of claim 4, wherein the host cell is genetically engineered to produce glycoproteins comprising one or more mammalian- or human-like N-glycans.

8. A method for producing a heterologous glycoprotein, comprising;
(a) providing a host cell that does not display dolichyl-P-Man:Man5GlcNAc2-PP-dolichyl alpha-1,3 mannosyltransferase (Alg3p) activity, osteosarcoma 9 (OS-9) protein activity, Att1p activity, and having integrated into the genome of the host cell a nucleic acid molecule encoding a *Trypanosoma brucei* STT3 protein and a nucleic acid molecule encoding the heterologous glycoprotein; and
(b) culturing the host cell under conditions for expressing the heterologous glycoprotein to produce the heterologous glycoprotein, wherein the host cell is a yeast or filamentous fungus and the OS-9 family gene is a YOS9 gene.

9. The method of claim 8, wherein the host cell is genetically engineered to produce glycoproteins comprising one or more mammalian- or human-like N-glycans.

\* \* \* \* \*

SEQUENCE LISTING

<160> NUMBER OF SEQ ID NOS: 62

<210> SEQ ID NO 1
<211> LENGTH: 857
<212> TYPE: PRT
<213> ORGANISM: Leishmania major

<400> SEQUENCE: 1

Met Gly Lys Arg Lys Gly Asn Ser Leu Gly Asp Ser Gly Ser Ala Ala
1               5                   10                  15

Thr Ala Ser Arg Glu Ala Ser Ala Gln Ala Glu Asp Ala Ala Ser Gln
            20                  25                  30

Thr Lys Thr Ala Ser Pro Pro Ala Lys Val Ile Leu Leu Pro Lys Thr
        35                  40                  45

Leu Thr Asp Glu Lys Asp Phe Ile Gly Ile Phe Pro Pro Phe Trp
    50                  55                  60

```
Pro Val His Phe Val Leu Thr Val Val Ala Leu Phe Val Leu Ala Ala
 65                  70                  75                  80

Ser Cys Phe Gln Ala Phe Thr Val Arg Met Ile Ser Val Gln Ile Tyr
                 85                  90                  95

Gly Tyr Leu Ile His Glu Phe Asp Pro Trp Phe Asn Tyr Arg Ala Ala
                100                 105                 110

Glu Tyr Met Ser Thr His Gly Trp Ser Ala Phe Phe Ser Trp Phe Asp
            115                 120                 125

Tyr Met Ser Trp Tyr Pro Leu Gly Arg Pro Val Gly Ser Thr Thr Tyr
        130                 135                 140

Pro Gly Leu Gln Leu Thr Ala Val Ala Ile His Arg Ala Leu Ala Ala
145                 150                 155                 160

Ala Gly Met Pro Met Ser Leu Asn Asn Val Cys Val Leu Met Pro Ala
                165                 170                 175

Trp Phe Gly Ala Ile Ala Thr Ala Thr Leu Ala Phe Cys Thr Tyr Glu
                180                 185                 190

Ala Ser Gly Ser Thr Val Ala Ala Ala Ala Ala Leu Ser Phe Ser
                195                 200                 205

Ile Ile Pro Ala His Leu Met Arg Ser Met Ala Gly Glu Phe Asp Asn
        210                 215                 220

Glu Cys Ile Ala Val Ala Ala Met Leu Leu Thr Phe Tyr Cys Trp Val
225                 230                 235                 240

Arg Ser Leu Arg Thr Arg Ser Ser Trp Pro Ile Gly Val Leu Thr Gly
                245                 250                 255

Val Ala Tyr Gly Tyr Met Ala Ala Ala Trp Gly Gly Tyr Ile Phe Val
                260                 265                 270

Leu Asn Met Val Ala Met His Ala Gly Ile Ser Ser Met Val Asp Trp
        275                 280                 285

Ala Arg Asn Thr Tyr Asn Pro Ser Leu Leu Arg Ala Tyr Thr Leu Phe
        290                 295                 300

Tyr Val Val Gly Thr Ala Ile Ala Val Cys Val Pro Pro Val Gly Met
305                 310                 315                 320

Ser Pro Phe Lys Ser Leu Glu Gln Leu Gly Ala Leu Leu Val Leu Val
                325                 330                 335

Phe Leu Cys Gly Leu Gln Val Cys Glu Val Leu Arg Ala Arg Ala Gly
                340                 345                 350

Val Glu Val Arg Ser Arg Ala Asn Phe Lys Ile Arg Val Arg Val Phe
                355                 360                 365

Ser Val Met Ala Gly Val Ala Ala Leu Ala Ile Ser Val Leu Ala Pro
        370                 375                 380

Thr Gly Tyr Phe Gly Pro Leu Ser Val Arg Val Arg Ala Leu Phe Val
385                 390                 395                 400

Glu His Thr Arg Thr Gly Asn Pro Leu Val Asp Ser Val Ala Glu His
                405                 410                 415

Gln Pro Ala Ser Pro Glu Ala Met Trp Ala Phe Leu His Val Cys Gly
                420                 425                 430

Val Thr Trp Gly Leu Gly Ser Ile Val Leu Ala Val Ser Thr Phe Val
        435                 440                 445

His Tyr Ser Pro Ser Lys Val Phe Trp Leu Asn Ser Gly Ala Val
        450                 455                 460

Tyr Tyr Phe Ser Thr Arg Met Ala Arg Leu Leu Leu Leu Ser Gly Pro
465                 470                 475                 480
```

Ala Ala Cys Leu Ser Thr Gly Ile Phe Val Gly Thr Ile Leu Glu Ala
            485                 490                 495

Ala Val Gln Leu Ser Phe Trp Asp Ser Asp Ala Thr Lys Ala Lys Lys
        500                 505                 510

Gln Gln Lys Gln Ala Gln Arg His Gln Arg Gly Ala Gly Lys Gly Ser
        515                 520                 525

Gly Arg Asp Asp Ala Lys Asn Ala Thr Thr Ala Arg Ala Phe Cys Asp
        530                 535                 540

Val Phe Ala Gly Ser Ser Leu Ala Trp Gly His Arg Met Val Leu Ser
545                 550                 555                 560

Ile Ala Met Trp Ala Leu Val Thr Thr Thr Ala Val Ser Phe Phe Ser
                565                 570                 575

Ser Glu Phe Ala Ser His Ser Thr Lys Phe Ala Glu Gln Ser Ser Asn
                580                 585                 590

Pro Met Ile Val Phe Ala Ala Val Val Gln Asn Arg Ala Thr Gly Lys
            595                 600                 605

Pro Met Asn Leu Leu Val Asp Asp Tyr Leu Lys Ala Tyr Glu Trp Leu
            610                 615                 620

Arg Asp Ser Thr Pro Glu Asp Ala Arg Val Leu Ala Trp Trp Asp Tyr
625                 630                 635                 640

Gly Tyr Gln Ile Thr Gly Ile Gly Asn Arg Thr Ser Leu Ala Asp Gly
                645                 650                 655

Asn Thr Trp Asn His Glu His Ile Ala Thr Ile Gly Lys Met Leu Thr
                660                 665                 670

Ser Pro Val Val Glu Ala His Ser Leu Val Arg His Met Ala Asp Tyr
            675                 680                 685

Val Leu Ile Trp Ala Gly Gln Ser Gly Asp Leu Met Lys Ser Pro His
            690                 695                 700

Met Ala Arg Ile Gly Asn Ser Val Tyr His Asp Ile Cys Pro Asp Asp
705                 710                 715                 720

Pro Leu Cys Gln Gln Phe Gly Phe His Arg Asn Asp Tyr Ser Arg Pro
                725                 730                 735

Thr Pro Met Met Arg Ala Ser Leu Leu Tyr Asn Leu His Glu Ala Gly
                740                 745                 750

Lys Arg Lys Gly Val Lys Val Asn Pro Ser Leu Phe Gln Glu Val Tyr
            755                 760                 765

Ser Ser Lys Tyr Gly Leu Val Arg Ile Phe Lys Val Met Asn Val Ser
            770                 775                 780

Ala Glu Ser Lys Lys Trp Val Ala Asp Pro Ala Asn Arg Val Cys His
785                 790                 795                 800

Pro Pro Gly Ser Trp Ile Cys Pro Gly Gln Tyr Pro Pro Ala Lys Glu
                805                 810                 815

Ile Gln Glu Met Leu Ala His Arg Val Pro Phe Asp Gln Val Thr Asn
                820                 825                 830

Ala Asp Arg Lys Asn Asn Val Gly Ser Tyr Gln Glu Glu Tyr Met Arg
            835                 840                 845

Arg Met Arg Glu Ser Glu Asn Arg Arg
        850                 855

<210> SEQ ID NO 2
<211> LENGTH: 2577
<212> TYPE: DNA
<213> ORGANISM: Leishmania major

<400> SEQUENCE: 2

```
atgggtaaaa gaaagggaaa ctccttggga gattctggtt ctgctgctac tgcttccaga      60
gaggcttctg ctcaagctga agatgctgct tcccagacta agactgcttc tccacctgct     120
aaggttatct tgttgccaaa gactttgact gacgagaagg acttcatcgg tatcttccca     180
tttccattct ggccagttca cttcgttttg actgttgttg ctttgttcgt tttggctgct     240
tcctgtttcc aggctttcac tgttagaatg atctccgttc aaatctacgg ttacttgatc     300
cacgaatttg acccatggtt caactacaga gctgctgagt acatgctac tcacggatgg      360
agtgcttttt tctcctggtt cgattacatg tcctggtatc cattgggtag accagttggt     420
tctactactt acccaggatt gcagttgact gctgttgcta tccatagagc tttggctgct     480
gctggaatgc caatgtcctt gaacaatgtt tgtgttttga tgccagcttg gtttggtgct     540
atcgctactg ctactttggc tttctgtact tacgaggctt ctggttctac tgttgctgct     600
gctgcagctg ctttgtcctt ctccattatc cctgctcact tgatgagatc catggctggt     660
gagttcgaca acgagtgtat tgctgttgct gctatgttgt tgactttcta ctgttgggtt     720
cgttccttga aactagatc ctcctggcca atcggtgttt tgacaggtgt tgcttacggt     780
tacatggctg ctgcttgggg aggttacatc ttcgttttga catggttgc tatgcacgct      840
ggtatctctt ctatggttga ctgggctaga aacacttaca acccatcctt gttgagagct     900
tacactttgt tctacgttgt tggtactgct atcgctgttt gtgttccacc agttggaatg     960
tctccattca gtccttgga gcagttggga gctttgttgg ttttggtttt cttgtgtgga    1020
ttgcaagttt gtgaggtttt gagagctaga gctggtgttg aagttagatc cagagctaat    1080
ttcaagatca gagttagagt tttctccgtt atggctggtg ttgctgcttt ggctatctct    1140
gttttggctc caactggtta ctttggtcca ttgtctgtta gagttagagc tttgtttgtt    1200
gagcacacta gaactggtaa cccattggtt gactccgttg ctgaacatca accagcttct    1260
ccagaggcta tgtgggcttt cttgcatgtt tgtggtgtta cttggggatt gggttccatt    1320
gttttggctg tttccacttt cgttcactac tccccatcta aggtttcctg ttgttgaac     1380
tccggtgctg tttactactt ctccactaga atggctagat tgttgttgtt gtccggtcca    1440
gctgcttgtt tgtccactgg tatcttcgtt ggtactatct tggaggctgc tgttcaattg    1500
tctttctggg actccgatgc tactaaggct aagaagcagc aaaagcaggc tcaaagacac    1560
caaagaggtg ctggtaaagg ttctggtaga gatgacgcta agaacgctac tactgctaga    1620
gcttctgtg acgttttcgc tggttcttct ttggcttggg gtcacagaat ggttttgtcc     1680
attgctatgt gggctttggt tactactact gctgtttcct tcttctcctc cgaatttgct    1740
tctcactcca ctaagttcgc tgaacaatcc tccaacccaa tgatcgttt cgctgctgtt     1800
gttcagaaca gagctactgg aaagccaatg aacttgttgg ttgacgacta cttgaaggct    1860
tacgagtggt tgagagactc tactccagag gacgctagag ttttggcttg gtgggactac    1920
ggttaccaaa tcactggtat cggtaacaga acttccttgg ctgatggtaa cacttggaac    1980
cacgagcaca ttgctactat cggaaagatg ttgacttccc cagttgttga agctcactcc    2040
cttgttagac acatggctga ctacgttttg atttggctg tcaatctgg tgacttgatg     2100
aagtctccac acatggctag aatcggtaac tctgtttacc acgacatttg tccagatgac    2160
ccattgtgtc agcaattcgg tttccacaga aacgattact ccagaccaac tccaatgatg    2220
agagcttcct tgttgtacaa cttgcacgag gctggaaaaa gaaagggtgt taaggttaac    2280
ccatctttgt tccaagaggt ttactcctcc aagtacggac ttgttagaat cttcaaggtt    2340
```

```
atgaacgttt ccgctgagtc taagaagtgg gttgcagacc cagctaacag agtttgtcac    2400
ccacctggtt cttggatttg tcctggtcaa tacccacctg ctaaagaaat ccaagagatg    2460
ttggctcaca gagttccatt cgaccaggtt acaaacgctg acagaaagaa caatgttggt    2520
tcctaccaag aggaatacat gagaagaatg agagagtccg agaacagaag ataatag      2577
```

```
<210> SEQ ID NO 3
<211> LENGTH: 934
<212> TYPE: DNA
<213> ORGANISM: Artificial Sequence
<220> FEATURE:
<223> OTHER INFORMATION: AOX1 promoter

<400> SEQUENCE: 3
aacatccaaa gacgaaaggt tgaatgaaac cttttgcca tccgacatcc acaggtccat      60
tctcacacat aagtgccaaa cgcaacagga ggggatacac tagcagcaga ccgttgcaaa    120
cgcaggacct ccactcctct tctcctcaac acccactttt gccatcgaaa accagccca    180 gttattgggc ttgattggag ctcgctcatt ccaattcctt ctattaggct actaacacca    240
tgactttatt agcctgtcta tcctggcccc cctggcgagg ttcatgtttg tttatttccg    300
aatgcaacaa gctccgcatt acacccgaac atcactccag atgagggctt tctgagtgtg    360
gggtcaaata gtttcatgtt ccccaaatgg cccaaaactg acagtttaaa cgctgtcttg    420
gaacctaata tgacaaaagc gtgatctcat ccaagatgaa ctaagtttgg ttcgttgaaa    480
tgctaacggc cagttggtca aaagaaact tccaaaagtc ggcataccgt ttgtcttgtt    540
tggtattgat tgacgaatgc tcaaaaataa tctcattaat gcttagcgca gtctctctat    600
cgcttctgaa ccccggtgca cctgtgccga aacgcaaatg gggaaacacc cgcttttgg     660 atgattatgc attgtctcca cattgtatgc ttccaagatt ctggtgggaa tactgctgat    720
agcctaacgt tcatgatcaa aatttaactg ttctaaccc tacttgacag caatatataa    780
acagaaggaa gctgccctgt cttaaaccct tttttttatc atcattatta gcttactttc    840
ataattgcga ctggttccaa ttgacaagct tttgatttta acgacttta acgacaactt    900 gagaagatca aaaacaact aattattcga aacg                                934
```

```
<210> SEQ ID NO 4
<211> LENGTH: 293
<212> TYPE: DNA
<213> ORGANISM: Artificial Sequence
<220> FEATURE:
<223> OTHER INFORMATION: ScCYC TT

<400> SEQUENCE: 4
acaggcccct ttcctttgt cgatatcatg taattagtta tgtcacgctt acattcacgc      60
cctcctccca catccgctct aaccgaaaag gaaggagtta gacaacctga agtctaggtc    120
cctatttatt ttttttaata gttatgttag tattaagaac gttatttata tttcaaattt    180
ttcttttttt tctgtacaaa cgcgtgtacg catgtaacat tatactgaaa accttgcttg    240
agaaggtttt gggacgctcg aaggctttaa tttgcaagct gccggctctt aag           293
```

```
<210> SEQ ID NO 5
<211> LENGTH: 1215
<212> TYPE: DNA
<213> ORGANISM: Artificial Sequence
<220> FEATURE:
<223> OTHER INFORMATION: ScARR3 ORF
```

<400> SEQUENCE: 5

```
atgtcagaag atcaaaaaag tgaaaattcc gtaccttcta aggttaatat ggtgaatcgc      60
accgatatac tgactacgat caagtcattg tcatggcttg acttgatgtt gccatttact     120
ataattctct ccataatcat tgcagtaata atttctgtct atgtgccttc ttcccgtcac     180
acttttgacg ctgaaggtca tcccaatcta atgggagtgt ccattccttt gactgttggt     240
atgattgtaa tgatgattcc cccgatctgc aaagtttcct gggagtctat tcacaagtac     300
ttctacagga gctatataag gaagcaacta gccctctcgt tatttttgaa ttgggtcatc     360
ggtcctttgt tgatgacagc attggcgtgg atggcgctat tcgattataa ggaataccgt     420
caaggcatta ttatgatcgg agtagctaga tgcattgcca tggtgctaat ttggaatcag     480
attgctggag agacaatga tctctgcgtc gtgcttgtta ttacaaactc gcttttacag     540
atggtattat atgcaccatt gcagatattt tactgttatg ttatttctca tgaccacctg     600
aatacttcaa atagggtatt attcgaagag gttgcaaagt ctgtcggagt ttttctcggc     660
ataccactgg gaattggcat tatcatacgt ttgggaagtc ttaccatagc tggtaaaagt     720
aattatgaaa atacatttt gagatttatt tctccatggg caatgatcgg atttcattac     780
actttatttg ttatttttat tagtagaggt tatcaattta tccacgaaat tggttctgca     840
atattgtgct ttgtcccatt ggtgctttac ttctttattg catggttttt gaccttcgca     900
ttaatgaggt acttatcaat atctaggagt gatacacaaa gagaatgtag ctgtgaccaa     960
gaactacttt taagagggt ctggggaaga aagtcttgtg aagctagctt ttctattacg    1020
atgacgcaat gtttcactat ggcttcaaat aattttgaac tatccctggc aattgctatt    1080
tccttatatg gtaacaatag caagcaagca atagctgcaa catttgggcc gttgctagaa    1140
gttccaattt tattgatttt ggcaatagtc gcgagaatcc ttaaaccata ttatatatgg    1200
aacaatagaa attaa                                                    1215
```

<210> SEQ ID NO 6
<211> LENGTH: 600
<212> TYPE: DNA
<213> ORGANISM: Artificial Sequence
<220> FEATURE:
<223> OTHER INFORMATION: PpRPL10 promoter

<400> SEQUENCE: 6

```
gttcttcgct tggtcttgta tctccttaca ctgtatcttc ccatttgcgt ttaggtggtt      60
atcaaaaact aaaaggaaaa atttcagatg tttatctcta aggtttttc ttttttacagt    120
ataacacgtg atgcgtcacg tggtactaga ttacgtaagt tattttggtc cggtgggtaa     180
gtgggtaaga atagaaagca tgaaggttta caaaaacgca gtcacgaatt attgctactt     240
cgagcttgga accacccccaa agattatatt gtactgatgc actaccttct cgattttgct     300
cctccaagaa cctacgaaaa acatttcttg agccttttca acctagacta cacatcaagt     360
tatttaaggt atgttccgtt aacatgtaag aaaaggagag gatagatcgt ttatggggta     420
cgtcgcctga ttcaagcgtg accattcgaa gaataggcct tcgaaagctg aataaagcaa     480
atgtcagttg cgattggtat gctgacaaat tagcataaaa agcaatagac tttctaacca     540
cctgtttttt tccttttact ttatttatat tttgccaccg tactaacaag ttcagacaaa     600
```

<210> SEQ ID NO 7
<211> LENGTH: 1144
<212> TYPE: DNA
<213> ORGANISM: Artificial Sequence

```
<220> FEATURE:
<223> OTHER INFORMATION: URA6 region

<400> SEQUENCE: 7
caaatgcaag aggacattag aaatgtgttt ggtaagaaca tgaagccgga ggcatacaaa      60
cgattcacag atttgaagga ggaaaacaaa ctgcatccac cggaagtgcc agcagccgtg     120
tatgccaacc ttgctctcaa aggcattcct acggatctga gtgggaaata tctgagattc     180
acagacccac tattggaaca gtaccaaacc tagtttggcc gatccatgat tatgtaatgc     240
atatagtttt tgtcgatgct cacccgtttc gagtctgtct cgtatcgtct tacgtataag     300
ttcaagcatg tttaccaggt ctgttagaaa ctcctttgtg agggcaggac ctattcgtct     360
cggtcccgtt gtttctaaga gactgtacag ccaagcgcag aatggtggca ttaaccataa     420
gaggattctg atcggacttg gtctattggc tattggaacc acccctttacg ggacaaccaa    480 ccctaccaag actcctattg catttgtgga accagccacg gaaagagcgt taaggacgg     540 agacgtctct gtgattttg ttctcggagg tccaggagct ggaaaaggta cccaatgtgc     600
caaactagtg agtaattacg gatttgttca cctgtcagct ggagacttgt tacgtgcaga    660
acagaagagg gaggggtcta agtatggaga gatgattcc cagtatatca gagatggact    720
gatagtacct caagaggtca ccattgcgct cttggagcag gccatgaagg aaaacttcga    780
gaaagggaag acacggttct tgattgatgg attccctcgt aagatggacc aggccaaaac    840
ttttgaggaa aaagtcgcaa agtccaaggt gacacttttc tttgattgtc ccgaatcagt    900
gctccttgag agattactta aaagaggaca gacaagcgga agagaggatg ataatgcgga    960
gagtatcaaa aaaagattca aaacattcgt ggaaacttcg atgcctgtgg tggactattt   1020
cgggaagcaa ggacgcgttt tgaaggtatc ttgtgaccac cctgtggatc aagtgtattc   1080
acaggttgtg tcggtgctaa aagagaaggg gatctttgcc gataacgaga cggagaataa   1140
ataa                                                                1144

<210> SEQ ID NO 8
<211> LENGTH: 486
<212> TYPE: DNA
<213> ORGANISM: Artificial Sequence
<220> FEATURE:
<223> OTHER INFORMATION: PpGAPDH promoter

<400> SEQUENCE: 8
tttttgtaga aatgtcttgg tgtcctcgtc caatcaggta gccatctctg aaatatctgg     60
ctccgttgca actccgaacg acctgctggc aacgtaaaat tctccggggt aaaacttaaa    120
tgtggagtaa tggaaccaga aacgtctctt cccttctctc tcttccacc gcccgttacc    180 gtccctagga aatttactc tgctggagag cttcttctac ggccccttg cagcaatgct    240 cttcccagca ttacgttgcg ggtaaaacgg aggtcgtgta cccgacctag cagcccaggg    300
atggaaaagt cccggccgtc gctggcaata atagcgggcg gacgcatgtc atgagattat    360
tggaaaccac cagaatcgaa tataaaaggc gaacaccttt cccaattttg gtttctcctg    420
acccaaagac tttaaattta atttatttgt ccctatttca atcaattgaa caactatcaa    480
aacaca                                                              486

<210> SEQ ID NO 9
<211> LENGTH: 573
<212> TYPE: DNA
<213> ORGANISM: Artificial Sequence
<220> FEATURE:
```

<223> OTHER INFORMATION: NatR ORF

<400> SEQUENCE: 9

| | | |
|---|---|---|
| atgggtacca ctcttgacga cacggcttac cggtaccgca ccagtgtccc ggggacgcc | 60 | |
| gaggccatcg aggcactgga tgggtccttc accaccgaca ccgtcttccg cgtcaccgcc | 120 | |
| accggggacg gcttcaccct gcgggaggtg ccggtggacc cgcccctgac caaggtgttc | 180 | |
| cccgacgacg aatcggacga cgaatcggac gacggggagg acggcgaccc ggactcccgg | 240 | |
| acgttcgtcg cgtacgggga cgacggcgac ctggcgggct cgtggtcat ctcgtactcg | 300 | |
| gcgtggaacc gccggctgac cgtcgaggac atcgaggtcg ccccggagca ccggggcac | 360 | |
| ggggtcgggc gcgcgttgat ggggctcgcg acggagttcg ccggcgagcg gggcgccggg | 420 | |
| cacctctggc tggaggtcac caacgtcaac gcaccggcga tccacgcgta ccggcggatg | 480 | |
| gggttcaccc tctgcggcct ggacaccgcc ctgtacgacg gcaccgcctc ggacggcgag | 540 | |
| cggcaggcgc tctacatgag catgccctgc ccc | 573 | |

<210> SEQ ID NO 10
<211> LENGTH: 388
<212> TYPE: DNA
<213> ORGANISM: Artificial Sequence
<220> FEATURE:
<223> OTHER INFORMATION: Ashbya gossypii TEF1 promoter

<400> SEQUENCE: 10

| | | |
|---|---|---|
| gatctgttta gcttgcctcg tccccgccgg gtcacccggc cagcgacatg gaggcccaga | 60 | |
| ataccctcct tgacagtctt gacgtgcgca gctcaggggc atgatgtgac tgtcgcccgt | 120 | |
| acatttagcc catacatccc catgtataat catttgcatc catacatttt gatggccgca | 180 | |
| cggcgcgaag caaaaattac ggctcctcgc tgcagacctg cgagcaggga acgctcccc | 240 | |
| tcacagacgc gttgaattgt ccccacgccg cgcccctgta gagaaatata aaaggttagg | 300 | |
| atttgccact gaggttcttc tttcatatac ttccttttaa aatcttgcta ggatacagtt | 360 | |
| ctcacatcac atccgaacat aaacaacc | 388 | |

<210> SEQ ID NO 11
<211> LENGTH: 247
<212> TYPE: DNA
<213> ORGANISM: Artificial Sequence
<220> FEATURE:
<223> OTHER INFORMATION: Ashbya gossypii TEF1 termination sequence

<400> SEQUENCE: 11

| | | |
|---|---|---|
| taatcagtac tgacaataaa aagattcttg ttttcaagaa cttgtcattt gtatagtttt | 60 | |
| tttatattgt agttgttcta ttttaatcaa atgttagcgt gatttatatt ttttttcgcc | 120 | |
| tcgacatcat ctgcccagat gcgaagttaa gtgcgcagaa agtaatatca tgcgtcaatc | 180 | |
| gtatgtgaat gctggtcgct atactgctgt cgattcgata ctaacgccgc catccagtgt | 240 | |
| cgaaaac | 247 | |

<210> SEQ ID NO 12
<211> LENGTH: 2409
<212> TYPE: DNA
<213> ORGANISM: Trypanosoma brucei

<400> SEQUENCE: 12

| | | |
|---|---|---|
| atgaccaagg gaggaaaagt tgctgttaca aagggtagtg cccaatctga cggtgctgga | 60 | |
| gagggaggaa tgagtaaagc caagagttca actacatttg ttgctaccgg tggaggtagt | 120 | |

```
cttccagctt gggccttgaa agctgtttct actattgtct ccgccgttat tttgatctac    180
tctgtccata gagcttatga tattagattg acctccgtta gattgtacgg tgaacttatc    240
cacgagttcg acccttggtt taactacaga gccactcaat atttgtctga taatggatgg    300
agagcatttt tccagtggta cgactatatg tcctggtatc cattgggaag acctgttggt    360
accactattt ttcctggtat gcaattgact ggagtcgcta tccatagagt tcttgaaatg    420
ttgggaagag gaatgtcaat taacaacatc tgtgtctaca ttcctgcctg gtttggtagt    480
atcgcaacag ttcttgctgc cttgattgct tacgagtctt ccaactcatt gagtgtcatg    540
gcattcaccg cttactttt ctctatcgtt ccagcacact tgatgagatc catggctggt    600
gaatttgata atgagtgtgt tgctatggca gctatgttgc ttactttcta catgtgggtt    660
agatccctta gatcaagttc ttcctggcct attggagcat tggctggtgt cgcttacgga    720
tatatggttt ctacatgggg aggttatatc ttcgtcttga acatggttgc ctttcatgca    780
tccgtctgtg ttttgcttga ttgggctaga ggtatctact ctgtctcctt gcttagagcc    840
tattctttgt ttttcgttat tggaactgcc ttggcaatct gcgtcccacc tgttgaatgg    900 acaccttta gatcccttga gcaattgacc gccctttttg tcttcgtttt tatgtgggca    960
cttcattact ctgaatattt gagagagaga gctagagccc ctattcactc aagtaaagcc   1020
ttgcagatta gagcaagaat cttcatgggt actttgtcat tgcttttgat tgttgcaagt   1080
cttttggctc catttggatt tttcaaacct acagcttaca gagtcagagc cttgttcgtt   1140
aagcacacca gaactggtaa cccattggtc gattcagttg ctgaacatag acctacaacc   1200
gcaggtgctt accttagata ttttcacgtt tgttacccat tgtggggatg cggaggtttg   1260
tccatgcttg ttttcatgaa gaaagacaga tggagagcaa ttgtcttttt ggcttcactt   1320
agtacagtta ccatgtattt ctcagctaga atgagtagac ttttgctttt ggccggtcct   1380
gccgcaactg cctgtgcagg aatgttcatt ggaggtttgt ttgatcttgc tttgtctcaa   1440
ttcggagatt tgcattcccc aaaggacgcc tctggagatt ccgaccctgc tggaggttcc   1500
aaaagagcca agggtaaagt tgtcaatgaa ccatctaaga gagctatttt ctcccacaga   1560
tggtttcaaa gattggtcca gtcacttcca gttcctttga aagaggtat cgcagttgtc   1620 gttttggttt gtcttttcgc taaccctatg agacattctt ttgaaaagtc ctgcgagaaa   1680
atggctcacg ccttgtcttc cccaagaatt atcgccgtta ctgatttgcc taatggtgaa   1740
agagtcttgg cagatgacta ctatgtttca tacctttggt tgagaaacaa taccccagag   1800
gatgctagaa ttttgagttg gtgggactac ggttatcaaa ttactggaat cggtaacaga   1860
actacattgg cagatggtaa tacatggtct cataagcaca ttgctaccat cggaaaaatg   1920
ttgacttcac ctgttaaaga aagtcatgca cttattagac acttggctga ctacgttttg   1980
atctgggctg gagaggatag aggagacctt ttgaaatctc cacatatggc tagaatcggt   2040
aactcagttt acagagatat gtgtagtgaa gatgacccta gatgcagaca attcggatt    2100 gagggtggtg acttgaacaa gccaactcct atgatgcaga gatccctttt gtacaatttg   2160
cacagatttg gtactgatgg aggtaaaaca caacttgaca gaacatgtt ccagttggct    2220 tacgtctcca gtatggatt ggttaaaatc tacaaagtcg ttaacgtttc agaagagagt    2280
aaagcttggg tcgccgatcc aaagaataga gtttgtgacc cacctggttc ttggatttgc   2340
gccggacaat accccctgc aaaagaaatc caggatatgt tggctaagag atttcattat   2400
gagtaatga                                                          2409
```

<210> SEQ ID NO 13
<211> LENGTH: 2469
<212> TYPE: DNA
<213> ORGANISM: Trypanosoma brucei

<400> SEQUENCE: 13

| | | | | | |
|---|---|---|---|---|---|
| atgaccaagg | gaggaaaggt | tgctgttact | aaaggttctg | ctcaatccga | cggtgctgga | 60 |
| gagggaggaa | tgtcaaaagc | caagagtagt | actacatttg | ttgctaccgg | tggaggttct | 120 |
| cttccagcat | gggctttgaa | ggccgtttca | actgttgtca | gtgcagttat | tttgatctac | 180 |
| tccgtccata | gagcttacga | tatcagattg | acatcagtta | gactttatgg | tgaattgatc | 240 |
| cacgagtttg | acccttggtt | caactacaga | gcaacccaat | atttgtccga | taatggatgg | 300 |
| agagctttct | ttcagtggta | cgactatatg | tcatggtacc | cattgggaag | acctgttggt | 360 |
| accactattt | ttcctggtat | gcaattgact | ggagttgcta | ccatagagt | cttggaaatg | 420 |
| cttggaagag | gaatgtcaat | taacaacatc | tgtgtttaca | tccctgcttg | gtttggttct | 480 |
| atcgccactg | tcttggctgc | ccttattgct | tacgagtctt | ccaactcatt | gagtgttatg | 540 |
| gccttcacag | catactttt | ctctattgtc | ccagctcact | tgatgagatc | aatggccggt | 600 |
| gaatttgata | atgagtgtgt | tgctatggca | gctatgttgc | ttactttcta | tatgtgggtt | 660 |
| agatcccta | gatcaagttc | ttcctggcct | attggagcct | tggcaggtgt | tgcttacgga | 720 |
| tatatggtct | caacttgggg | aggttacatc | tttgttttga | acatggtcgc | tttccatgcc | 780 |
| tctgtttgtg | tcttgcttga | ttgggccaga | ggtacatact | ctgtttcctt | gcttagagca | 840 |
| tattctttgt | ttttcgtcat | tggaaccgct | ttggccatct | gcgttccacc | tgtcgaatgg | 900 |
| actccttta | gatccttgga | gcaacttaca | gccttgttcg | ttttgtctt | catgtgggca | 960 |
| cttcattact | ctgaatattt | gagagagaga | gcaagagctc | ctattcactc | tagtaaggca | 1020 |
| ttgcagatta | gagctagaat | ctttatgggt | actcttagtt | tgcttttgat | tgttgctatc | 1080 |
| tacttgttct | ccacaggata | ttttagacca | ttctcttcca | gagttagagc | tttgttcgtc | 1140 |
| aaacacacta | gaacaggtaa | tccattggtt | gatagtgtcg | ccgaacatca | ccctgcatct | 1200 |
| aacgatgact | ttttcggata | cttgcatgtt | tgttacaacg | gttggatcat | cggattttc | 1260 |
| tttatgtcag | ttagttgttt | cttcactgc | actccaggaa | tgtcatttct | tttgctttac | 1320 |
| agtatccttg | cttactactt | ctcttttgaag | atgtccagat | gcttttgct | ttctgcacct | 1380 |
| gttgcttcca | ttttgaccgg | ttacgttgtc | ggatctatcg | ttgatttggc | cgcagactgt | 1440 |
| tttgctgcca | gtggtactga | acatgctgat | tctaaggagc | accaaggaaa | agccagagga | 1500 |
| aagggtcaaa | agaacagat | tactgttgag | tgtggttgcc | ataacccttt | ttacaagctt | 1560 |
| tggtgtaatt | ccttctcaag | tagattggtt | gtcggaaaat | tctttgttgt | cgttgtcctt | 1620 |
| tcaatttgcg | gtccaacttt | cttgggttct | aacttcagaa | tctattccga | acaattcgca | 1680 |
| gattcaatgt | cttcccctca | gattatcatg | agagccactg | ttggaggtag | aagagtcatt | 1740 |
| ttggatgact | actatgtttc | ttacttgtgg | cttagaaaca | atacaccaga | ggatgctaga | 1800 |
| attttgtcct | ggtgggacta | cggttatcaa | attaccggaa | tcggtaacag | aacaaccttg | 1860 |
| gctgatggta | acacttggaa | tcatgaacac | attgccacaa | tcggaaagat | gttgacctca | 1920 |
| cctgttaaag | agagtcatgc | acttattaga | cacttggctg | actacgtttt | gatctgggct | 1980 |
| ggatatgatg | ttctgactt | gcttaagtcc | ccacatatgg | ctagaattgg | taattccgtt | 2040 |
| tacagagata | tctgttcaga | agatgaccct | tgtgcacac | aatttggttt | ctattcagga | 2100 |
| gactttagta | aaccaacccc | tatgatgcag | agatccttgc | tttacaactt | gcacagattt | 2160 |

```
ggtaccgatg gaggtaaaac tcaacttgac aagaacatgt tccagttggc ttacgtttct    2220
aagtatggat tggtcaaaat ctacaaagtt atgaacgtct ctgaagagtc caaagcctgg    2280
gttgcagatc caagaatag aaaatgtgac gctcctggtt cttggatttg cactggacaa    2340
tacccacctg caaaggaaat tcaggatatg cttgctaaaa gaatcgatta tgaacaattg    2400
gaggacttta acagaagaaa tagatccgac gcttactata gagcctacat gagacagatg    2460
ggttaatga                                                            2469

<210> SEQ ID NO 14
<211> LENGTH: 2469
<212> TYPE: DNA
<213> ORGANISM: Trypanosoma brucei

<400> SEQUENCE: 14
atgactaagg gtggtaaagt tgctgttact aagggttctg ctcaatctga tggtgctggt      60
gaaggtggaa tgtctaaggc taagtcctcc actactttcg ttgctactgg tggtggttct     120
ttgccagctt gggctttgaa ggctgtttcc actgttgttt ccgctgttat cttgatctac     180
tccgttcaca gagcttacga catcagattg acttcagtta gattgtacgg tgagttgatc     240
cacgaatttg acccatggtt caactacaga gctactcagt acttgtctga acggatgg      300 agagcttttct tccagtggta cgattacatg tcctggtatc cattgggtag accagttggt    360
actactatct tcccaggaat gcagttgact ggagttgcta tccacagagt tttggagatg    420
ttgggtagag aatgtccat caacaacatc tgtgtttaca tcccagcttg gtttggttcc    480
attgctactg ttttggctgc tttgatcgct tacgaatcct ctaactcctt gtccgttatg    540
gctttcactg cttactttt ctccatcgtt cctgctcatt tgatgagatc catggctggt    600
gagttcgaca cgagtgtgt tgctatggct gctatgttgt tgactttcta catgtgggtt    660
cgttccttga tcctcttc ctcttggcca attggtgctt tggctggtgt tgcttacggt      720
tacatggttt ccacttgggg aggttacatc ttcgttttga acatggttgc tttccacgct    780
tccgtttgtg ttttgttgga ctgggctaga ggaacttact ccgtttcctt gttgagagct    840
tactccttgt tcttcgttat cggtactgct ttggctattt gtgttccacc agttgagtgg    900
actccattca gatccttgga gcagttgact gctttgttcg ttttcgtttt catgtgggct    960
ttgcactact ctgagtactt gagagagaga gctagagcac caattcactc ctccaaggct    1020
ttgcaaatca gagctagaat cttcatggga actttgtcct tgttgttgat cgttgctatc    1080
tacttgttct ccactggtta cttcagatcc ttctcatcca gagttagagc tttgtttgtt    1140
aagcacacta gaactggtaa cccattggtt gactccgttg ctgaacacag accaactact    1200
gctggtgctt cttgagaca cttgcatgtt tgttacaatg gatggatcat cggttttttc    1260
ttcatgtccg tttcttgttt cttccactgt actccaggaa tgtccttctt gttgttgtac    1320
tccatcttgg cttactactt ctcattgaag atgtccagat tgttgttgtt gtccgctcca    1380
gttgcttcta tcttgactgg ttacgttgtt ggttccatcg ttgatttggc tgctgattgt    1440
ttcgctgctt ctggtactga acacgctgac tccaaagaac accagggtaa agctagagga    1500
aagggacaga agagacagat cactgttgag tgtggttgtc acaacccatt ctacaagttg    1560
tggtgtaact cattctcctc cagattggtt gttggaaagt tcttcgttgt tgttgttttg    1620
tccatctgtg gtccaacttt cttggggtcc gagttcagag cacactgtga gagattctcc    1680
gtttccgttg ctaacccaag aatcatctcc tccatcagac actctggtaa gttggttttg    1740
```

```
gctgacgact actacgtttc ctacttgtgg ttgagaaaca acactccaga ggacgctaga      1800
attttgtctt ggtgggacta cggttaccaa atcactggta tcggtaacag aactactttg      1860
gctgacggta acacttggaa ccacgagcac attgctacta tcggaaagat gttgacttcc      1920
ccagttaaag agtcccacgc tttgattaga cacttggctg actacgtttt gatttgggct      1980
ggtgaagata gaggagactt gagaaagtcc agacacatgg ctagaatcgg taactccgtt      2040
tacagagaca tgtgttctga ggacgaccca ttgtgtactc agttcggttt ctactccggt      2100
gatttcaaca agccaactcc aatgatgcag agatccttgt tgtacaactt gcacagattc      2160
ggtactgatg gtggaaagac tcagttggac aagaacatgt tccagttggc ttacgtttcc      2220
aagtacggat tggtcaaaat ctacaaggtt atgaacgttt ccgaagagtc taaggcttgg      2280
gttgcagacc caagaatag aaagtgtgac gctcctggtt cttggatttg tgctggtcaa      2340
tacccacctg ctaaagaaat ccaggacatg ttggctaaga gaatcgacta cgagcaattg      2400
gaggacttca acagaagaaa tagatccgac gcttactaca gagcttacat gagacagatg      2460
ggttaatag                                                              2469

<210> SEQ ID NO 15
<211> LENGTH: 1350
<212> TYPE: DNA
<213> ORGANISM: Artificial Sequence
<220> FEATURE:
<223> OTHER INFORMATION: Anti-Her2 Heavy chain (VH + IgG1 constant
      region)

<400> SEQUENCE: 15
gaggttcagt tggttgaatc tggaggagga ttggttcaac tggtggttc tttgagattg        60 tcctgtgctg cttccggttt caacatcaag gacacttaca tccactgggt tagacaagct      120
ccaggaaagg gattggagtg ggttgctaga atctacccaa ctaacggtta cacaagatac      180
gctgactccg ttaagggaag attcactatc tctgctgaca cttccaagaa cactgcttac      240
ttgcagatga actccttgag agctgaggat actgctgttt actactgttc cagatggggt      300
ggtgatggtt tctacgctat ggactactgg ggtcaaggaa cttttggttac tgtttcctcc      360 gcttctacta agggaccatc tgttttccca ttggctccat cttctaagtc tacttccggt      420
ggtactgctg ctttgggatg ttttggttaaa gactacttcc cagagccagt tactgttt ct      480 tggaactccg gtgctttgac ttctggtgtt cacactttcc cagctgtttt gcaatcttcc      540
ggtttgtact ctttgtcctc cgttgttact gttccatcct cttccttggg tactcagact      600
tacatctgta acgttaacca caagccatcc aacactaagg ttgacaagaa ggttgagcca      660
aagtcctgtg acaagacaca tacttgtcca ccatgtccag ctccagaatt gttgggtggt      720
ccatccgttt tcttgttccc accaaagcca aggacactt tgatgatctc cagaactcca      780
gaggttacat gtgttgttgt tgacgtttct cacgaggacc cagaggttaa gttcaactgg      840
tacgttgacg gtgttgaagt tcacaacgct aagactaagc caagagaaga gcagtacaac      900
tccacttaca gagttgtttc cgttttgact gttttgcacc aggactggtt gaacggtaaa      960
gaatacaagt gtaaggtttc caacaaggct ttgccagctc aatcgaaaa gactatctcc      1020 aaggctaagg gtcaaccaag agagccacag gtttacactt tgccaccatc cagagaagag      1080
atgactaaga accaggtttc cttgacttgt ttggttaaag gattctaccc atccgacatt      1140
gctgttgagt gggaatctaa cggtcaacca gagaacaact acaagactac tccaccagtt      1200
ttggattctg atggttcctt cttcttgtac tccaagttga ctgttgacaa gtccagatgg      1260
```

```
caacagggta acgttttctc ctgttccgtt atgcatgagg ctttgcacaa ccactacact    1320
caaaagtcct tgtctttgtc ccctggttaa                                     1350

<210> SEQ ID NO 16
<211> LENGTH: 645
<212> TYPE: DNA
<213> ORGANISM: Artificial Sequence
<220> FEATURE:
<223> OTHER INFORMATION: Anti-Her2 light chain (VL + Kappa constant
      region)

<400> SEQUENCE: 16
gacatccaaa tgactcaatc cccatcttct ttgtctgctt ccgttggtga cagagttact      60
atcacttgta gagcttccca ggacgttaat actgctgttg cttggtatca acagaagcca     120
ggaaaggctc caaagttgtt gatctactcc gcttccttct tgtactctgg tgttccatcc     180
agattctctg gttccagatc cggtactgac ttcactttga ctatctcctc cttgcaacca     240
gaagatttcg ctacttacta ctgtcagcag cactacacta ctccaccaac tttcggacag     300
ggtactaagg ttgagatcaa gagaactgtt gctgctccat ccgttttcat tttcccacca     360
tccgacgaac agttgaagtc tggtacagct tccgttgttt gtttgttgaa caacttctac     420
ccaagagagg ctaaggttca gtggaaggtt gacaacgctt gcaatccgg taactcccaa      480 gaatccgtta ctgagcaaga ctctaaggac tccacttact ccttgtcctc cactttgact     540
ttgtccaagg ctgattacga aagcacaag gtttacgctt gtgaggttac acatcagggt      600
ttgtcctccc cagttactaa gtccttcaac agaggagagt gttaa                     645

<210> SEQ ID NO 17
<211> LENGTH: 260
<212> TYPE: DNA
<213> ORGANISM: Artificial Sequence
<220> FEATURE:
<223> OTHER INFORMATION: PpAOX1 TT

<400> SEQUENCE: 17
tcaagaggat gtcagaatgc catttgcctg agagatgcag gcttcatttt gatacttttt      60
tatttgtaac ctatatagta taggattttt tttgtcattt tgtttcttct cgtacgagct     120
tgctcctgat cagcctatct cgcagctgat gaatatcttg tggtagggt ttgggaaaat      180 cattcgagtt tgatgttttt cttggtattt cccactcctc ttcagagtac agaagattaa     240
gtgagacgtt cgtttgtgca                                                 260

<210> SEQ ID NO 18
<211> LENGTH: 375
<212> TYPE: DNA
<213> ORGANISM: Artificial
<220> FEATURE:
<223> OTHER INFORMATION: Sh ble ORF (Zeocin resistance marker)

<400> SEQUENCE: 18
atggccaagt tgaccagtgc cgttccggtg ctcaccgcgc gcgacgtcgc cggagcggtc      60
gagttctgga ccgaccggct cgggttctcc cgggacttcg tggaggacga cttcgccggt     120
gtggtccggg acgacgtgac cctgttcatc agcgcggtcc aggaccaggt ggtgccggac     180
aacaccctgg cctgggtgtg ggtgcgcggc ctggacgagc tgtacgccga gtggtcggag     240
gtcgtgtcca cgaacttccg ggacgcctcc gggccggcca tgaccgagat cggcgagcag     300
ccgtgggggc gggagttcgc cctgcgcgac ccggccggca actgcgtgca cttcgtggcc     360
```

-continued gaggagcagg actga                                                         375

<210> SEQ ID NO 19
<211> LENGTH: 1430
<212> TYPE: DNA
<213> ORGANISM: Artificial Sequence
<220> FEATURE:
<223> OTHER INFORMATION: Sequence of the 5'-Region used for knock out of
      YOS9

<400> SEQUENCE: 19
ccatagcctc tgattgatgt aagcaccgac agtacctggc tctaacttgt tagaggtttt    60
ggtggtcaag acatatctgt tatcacaaat aacataatgg ttatcgggaa agtcattggg   120
atgaacagca agtgtgttca tgatggcaaa ttcattaccc ggagagttga ctatcttcaa   180
tacatgcacc tttggagcat ttctctttgt gaatcccagt ttttccatgg ttgtggcaaa   240
gtgtagagat gttaagtgca gcgagcaaag acaagtagat agactgtatg gtgttctgat   300
gttatagttg tagtgaataa tctataaatg ccttatttga aggtttatgt aatagattta   360
cccgtgtgta gcaagtgtac tgctaagagg tactataaag ttattcatgt ggatatattc   420
agtagataat aacaaagcta caaggagatc aagaaaccat atgagttgtt cgtcacataa   480
gagattacgt aatgacaaat cggggaacta gtaccaattc tgtcttaaag tagtgtctct   540
ctaagcataa cgacctattt gataactggg ctgaactcca agcagcctga tgatgttgac   600
ctgacttatt cagaagggct attggttttg atttccagat attagcataa ttagcaatgc   660
cggaacaata tacatccaat attttttgaat gaatgaacgg ttatcaacat ttacttctgc   720
ctcctcgtct atgacttcct tgagttccag cttgttatcg gatctgattt ttttgatttt   780
cttttctttt cttggtagtt tgggaattgg tgcctgtcga atttgttcaa ctattaggtt   840
aagacctttc tgactagcat cgaagaaggc tacattttcg atgtcgttgt gtttgttgat   900
agtcagcttg atatcctgtg caattggaga acttagtctt ttgtaattga agcagccttc   960
gtccaaacat attctgtaaa gatcacttgg caggtctagt tgttcaccgg tgtgcaattt  1020
ccattttgag tcaaattcta gtgtggccaa gttgaacgag ttctgagcga atcaatagc   1080 cttcaactga tacgcaaatg tagaccccaa gaaaagaaac aacgtgacga ggctttgtag  1140
ggtagtagcc attgtcgaat agttgaggat aagtagacgg cgagttattc tccttgataa  1200
atgctatcgc gatggatagt gattacagtg cgataatatt atcctttttca tccacgtcaa  1260 ccatggttaa caggccattg gacattatga taaaggtcct gctattcctg ctctccctat  1320
caagtcttgt gaaagctttg gatgattcca ttgataagaa ttctgtggta agtcttttaa  1380
tttttgtttt cacaagatca tgccgtgcta actgggtact atagtatacc               1430

<210> SEQ ID NO 20
<211> LENGTH: 1498
<212> TYPE: DNA
<213> ORGANISM: Artificial Sequence
<220> FEATURE:
<223> OTHER INFORMATION: Sequence of the 3'-Region used for knock out of
      YOS9

<400> SEQUENCE: 20
ggttcctatt cactgaagac agaatacctc atgcactcc aaactttaga gtgtataacg     60
gagttaatgt gaattaagac aatttatata ctcagtaaaa taaatactag tacttacgtc   120 ttttttttagt cagagcacta actctgctgg aagggttctt cgtgtaaatt ggtacagacg   180
ctggtaaagt accactatac gttgtttgac aaataggtag tttgaagctg acatcaagtt   240

-continued

```
tcaagtcctt aggagtcaca ttgcgagttt gaatgaccaa ttgtattaat ctcttaatct    300
tgaagtacaa tctcttctct ttgagactgg gtttcaagac agtgacggga ttagcaggat    360
cgattttggg tgatgcctta tacctttctt gacgtaattg tgacagatct attagcaact    420
tgcttataag ttcttgctct ttgttggaac ggatagcctc tatctcatcc tcctcaacga    480
agcttcccgg agtccaggag aggaggttgt ctagcttgat cttatagtct tcggatccat    540
tgacctggac ttccttatct gtgttttcaa gtttagttga tgtatctgtc cccgtatggc    600
cattcttagt ctcctggtca acaggtgccg gaagctcttt ttcaattctt tttggttcgt    660
ccttctgaag ttcattatcc gtctcatttt tagatggtct gctcagtttt tctgctatat    720
caccaagctt tctaaaacca gcttgctcca gccacctcag gcccttcaat tcactggaga    780
ttgcagattt ttcttcgtct attgtaggtg caaaactgaa atcgttaccc ttattgtggg    840
tgagccattg acccatcggt aacgcgtacc agttcaaatg aaagaggttt ggcaataaat    900
ccgtaggttt ggtggctggg tgaggttcat tgttgtattg aggagaaatc ttgttaagcg    960
gctgtgaact aatggaaggg acatggggga ttactttcgt cagattaaaa tcgccttcat   1020
tcactacagc ttctctagca tccaagcttg atttattatt cagggacgaa acaatggcg   1080 cattaggtgt gatgaatgta gttaaacatt ctccgttgga tgaaacaaaa aatgtggaca   1140
ctttattgaa gtcttttgtc atcgattctt caaactcact ggtgtaatca tctaaaacac   1200
gagagtcaac gctttctctt agttgtctgt agttgaacaa aaatcttcct gcctctctga   1260
tcaataactc aaccatcgac ttgtagaaca aatcaatctt gacgtagtct tccgaatctc   1320
tgttccgttc gtttataagt atcaggcaca ctaaagttag gtcgtgaaat atggaataaa   1380
tagtcttgta gtgaccactc tttattctgt cgctgatggt aaccagctct gtaggtttga   1440
gatccttacc atcaacaagc tgatagtatg atccagctat caaggaagga tcctggac    1498
```

<210> SEQ ID NO 21
<211> LENGTH: 1699
<212> TYPE: DNA
<213> ORGANISM: artificial sequence
<220> FEATURE:
<223> OTHER INFORMATION: Sequence of the 5'-Region used for knock out of ALG3

<400> SEQUENCE: 21

```
aaccttcatg gaacgattcg gatacggaaa aacctgagat agttttaact agagtagatg     60
caagatttca cgattctaaa gaccgagaag gagatgtctg atgtcggtaa ctactatccg    120
gtaaatgata ttagcacact atatgctact agcgagtctg gaaccaattc tactatccat    180
tgatgctcta ttagggatgg agaattcaat caacccctct aattctgatt tcagatgttc    240
caacagcgaa gtagcccttg acaagttctc aacatcactc atcttagcta cattcacgta    300
tgctttgata aaaaactctc tacttttgtc aatgagctct agcctagtct ctggttctat    360
cgtttcctct ttggtctcca gattactctc tggattagaa tctacatcca tcttcatatc    420
tatgtccatg tccagctcaa ttttcatacc gtcagtattc ttagattcga tagcagtatc    480
tgatctggta gatccattag ttgctgcagc ggtatttttct ttggaatttg agcactttc    540 ctgtttctgt ttcataaaga ctcggtagat tgcaatgact atatcgtttc tgtagaactt    600
gtaaccatga gtccaaaatt gggtttcagg catgtatcct agctcatcta aatatccaac    660
cacatcatcc gtgctacata tagtagactc gtagagtgtc tgtgaagaaa cggctcttt    720 tcctgccaaa ggaacgtccg atatttgaag ggtccatata cgattttcct tattaagagc    780
```

```
ttcaagatgt ttcttattaa acaattcaaa gtctttaat tcaattgtgt tatcaatagg      840
atcctcaacg tcctgtttcc attcggtgga cattctcatc ttgtattgtt cgatttggtt      900
gacttttcca gtctggaact caggactata aggaaacttt ggagttaaaa taacagtata      960
agttgagagc cttgcgggca ccatacccgt tagagacttc aacgtctcca agatcaactg     1020
cagttgagac tcttggattc tagataccag agacacctgt tgtaccatat aattaagtga     1080
ctgggctggc ttggatacag gatttcgaga agtgcttcga attatcagac cgaaggcagt     1140
tgatattttg tgcctcagcc ttaatgttcc ctataactta aggctataca cagctttatg     1200
attaatgaat ctgggctgct ggtgacgaat ttcgtcaatg accagttgcc tacgggcgat     1260
aattattttt tcagttggat gaaagaacgg aaaaacccgg tcagattcaa aaagaatatt     1320
gataatcttt gtctagcaca actgaaatgc ttggaaactc tcccaagcat gaatcagacc     1380
tgagattgta ttagacgaaa aaattgtagt atagagttat agacatatag gttgtggcaa     1440
tatcctgtgc aagccaatat ctcacagaaa taaacgtaca caccagatac aactatttcg     1500
aaaagcacac tttgagcgca acagtgattg tcctaacagt ataggtttct aaggccccag     1560
cagaccatga cggcaaatta tttatttccc ctcgtatttg ccttatctcc ttttgttctc     1620
attcttatct tggctactgt aattatctgg ataaccctcg atacttcgct tggtttctac     1680
ctcacaacat atccctacc                                                  1699

<210> SEQ ID NO 22
<211> LENGTH: 1052
<212> TYPE: DNA
<213> ORGANISM: artificial sequence
<220> FEATURE:
<223> OTHER INFORMATION: Sequence of the 3'-Region used for knock out of
      ALG3

<400> SEQUENCE: 22
atttacaatt agtaatatta aggtggtaaa aacattcgta gaattgaaat gaattaatat       60
agtatgacaa tggttcatgt ctataaatct ccggcttcgg taccttctcc ccaattgaat      120
acattgtcaa aatgaatggt tgaactatta ggttcgccag tttcgttatt aagaaaactg      180
ttaaaatcaa attccatatc atcggttcca gtgggaggac cagttccatc gccaaaatcc      240
tgtaagaatc cattgtcaga acctgtaaag tcagtttgag atgaaatttt tccggtcttt      300
gttgacttgg aagcttcgtt aaggttaggt gaaacagttt gatcaaccag cggctcccgt      360
tttcgtcgct tagtagcagc attattacca ggaatgccgc ctgtagagtt ttgatgtgtc      420
ctagctgcaa ttggagtctg tggagtagtg ggagtcgggg gctcagtagc tttctttgcc      480 ttcttttag ctggctcctt tttctttcgt acaggtgcga cattatttgg tgtagacccc      540
gcagaagtgt taccagtact atgtgcagtg ttttgagttt gtgtaccagg tgaagttccg      600
ggagtattct tcgtgaccac tgcagagttc tggggaggga gcattacatt cacattaaat      660
tttggttcgg gcggtgtgtg ctctggaatt ggatcaaagt tagaaaaatg cccgcttccc      720
ttcttacatg ccatgtcatg acgctgtttg ttctgtttct caagcatcat tagctctttc      780
tgatactcct gtatacctac aattttagaa gcacttgatt gagactgttg cgattgctgg      840
tgttggctct gtgattgtgg ttgtgctatt tgctgatgtt gtgaccctgg agttggaact      900
agctccggct gctgaataga agaaggcgga gaatgttgcg gttgagatgc aggtaaaggc      960
tgctgataaa caggaccagg ttgcgagaat ctaggtgtgg tggacgagtg aggagtaccg     1020
gcggcagaag tagagtgagg cagaggagcc at                                   1052
```

<210> SEQ ID NO 23
<211> LENGTH: 411
<212> TYPE: DNA
<213> ORGANISM: artificial sequence
<220> FEATURE:
<223> OTHER INFORMATION: Sequence of the 5'-Region used for knock out of
      BMT1

<400> SEQUENCE: 23

```
catatggtga gagccgttct gcacaactag atgttttcga gcttcgcatt gtttcctgca      60
gctcgactat tgaattaaga tttccggata tctccaatct cacaaaaact tatgttgacc     120
acgtgctttc ctgaggcgag gtgttttata tgcaagctgc aaaaatgga aaacgaatgg      180
ccatttttcg cccaggcaaa ttattcgatt actgctgtca taaagacagt gttgcaaggc     240
tcacattttt ttttaggatc cgagataaag tgaatacagg acagcttatc tctatatctt     300
gtaccattcg tgaatcttaa gagttcggtt aggggactc tagttgaggg ttggcactca      360
cgtatggctg ggcgcagaaa taaaattcag gcgcagcagc acttatcgat g              411
```

<210> SEQ ID NO 24
<211> LENGTH: 692
<212> TYPE: DNA
<213> ORGANISM: artificial sequence
<220> FEATURE:
<223> OTHER INFORMATION: Sequence of the 3'-Region used for knock out of
      BMT1

<400> SEQUENCE: 24

```
gaattcacag ttataaataa aaacaaaaac tcaaaaagtt tgggctccac aaaataactt      60
aatttaaatt tttgtctaat aaatgaatgt aattccaaga ttatgtgatg caagcacagt     120
atgcttcagc cctatgcagc tactaatgtc aatctcgcct gcgagcgggc ctagattttc     180
actacaaatt tcaaaactac gcggatttat tgtctcagag agcaatttgg catttctgag     240
cgtagcagga ggcttcataa gattgtatag gaccgtacca acaaattgcc gaggcacaac     300
acggtatgct gtgcacttat gtggctactt ccctacaacg gaatgaaacc ttcctctttc     360
cgcttaaacg agaaagtgtg tcgcaattga atgcaggtgc ctgtgcgcct tggtgtattg     420
tttttgaggg cccaatttat caggcgcctt ttttcttggt tgttttccct tagcctcaag     480
caaggttggt ctatttcatc tccgcttcta taccgtgcct gatactgttg gatgagaaca     540
cgactcaact tcctgctgct ctgtattgcc agtgttttgt ctgtgatttg gatcggagtc     600
ctccttactt ggaatgataa taatcttggc ggaatctccc taaacggagg caaggattct     660
gcctatgatg atctgctatc attgggaagc tt                                  692
```

<210> SEQ ID NO 25
<211> LENGTH: 1043
<212> TYPE: DNA
<213> ORGANISM: artificial sequence
<220> FEATURE:
<223> OTHER INFORMATION: Sequence of the 5'-Region used for knock out of
      BMT4

<400> SEQUENCE: 25

```
aagcttgttc accgttggga cttttccgtg gacaatgttg actactccag gagggattcc      60
agctttctct actagctcag caataatcaa tgcagcccca ggcgcccgtt ctgatggctt     120
gatgaccgtt gtattgcctg tcactatagc caggggtagg gtccataaag gaatcatagc     180
agggaaatta aaagggcata ttgatgcaat cactcccaat ggctctcttg ccattgaagt     240
```

```
ctccatatca gcactaactt ccaagaagga cccttcaag tctgacgtga tagagcacgc    300
ttgctctgcc acctgtagtc ctctcaaaac gtcaccttgt gcatcagcaa agactttacc    360
ttgctccaat actatgacgg aggcaattct gtcaaaattc tctctcagca attcaaccaa    420
cttgaaagca aattgctgtc tcttgatgat ggagactttt ttccaagatt gaaatgcaat    480
gtgggacgac tcaattgctt cttccagctc ctcttcggtt gattgaggaa cttttgaaac    540
cacaaaattg gtcgttgggt catgtacatc aaaccattct gtagatttag attcgacgaa    600
agcgttgttg atgaaggaaa aggttggata cggtttgtcg gtctctttgg tatggccggt    660
ggggtatgca attgcagtag aagataattg gacagccatt gttgaaggta gagaaaaggt    720
cagggaactt gggggttatt tataccattt taccccacaa ataacaactg aaaagtaccc    780
attccatagt gagaggtaac cgacggaaaa agacgggccc atgttctggg accaatagaa    840
ctgtgtaatc cattgggact aatcaacaga cgattggcaa tataatgaaa tagttcgttg    900
aaaagccacg tcagctgtct tttcattaac tttggtcgga cacaacattt tctactgttg    960
tatctgtcct actttgctta tcatctgcca cagggcaagt ggatttcctt ctcgcgcggc   1020
tgggtgaaaa cggttaacgt gaa                                           1043

<210> SEQ ID NO 26
<211> LENGTH: 695
<212> TYPE: DNA
<213> ORGANISM: artificial sequence
<220> FEATURE:
<223> OTHER INFORMATION: Sequence of the 3'-Region used for knock out of
      BMT4

<400> SEQUENCE: 26
gccttggggg acttcaagtc tttgctagaa actagatgag gtcaggcccct cttatggttg     60 tgtcccaatt gggcaatttc actcacctaa aaagcatgac aattatttag cgaaataggt    120
agtatatttt ccctcatctc ccaagcagtt tcgttttttgc atccatatct ctcaaatgag    180
cagctacgac tcattagaac cagagtcaag taggggtgag ctcagtcatc agccttcgtt    240
tctaaaacga ttgagttctt ttgttgctac aggaagcgcc ctagggaact ttcgcacttt    300
ggaaatagat tttgatgacc aagagcggga gttgatatta gagaggctgt ccaaagtaca    360
tgggatcagg ccggccaaat tgattggtgt gactaaacca ttgtgtactt ggacactcta    420
ttacaaaagc gaagatgatt tgaagtatta caagtcccga agtgttagag gattctatcg    480
agcccagaat gaaatcatca accgttatca gcagattgat aaactcttgg aaagcggtat    540
cccattttca ttattgaaga actacgataa tgaagatgtg agagacggcg accctctgaa    600
cgtagacgaa gaaacaaatc tacttttggg gtacaataga gaaagtgaat caagggaggt    660
atttgtggcc ataatactca actctatcat taatg                              695

<210> SEQ ID NO 27
<211> LENGTH: 546
<212> TYPE: DNA
<213> ORGANISM: artificial sequence
<220> FEATURE:
<223> OTHER INFORMATION: Sequence of the 5'-Region used for knock out of
      BMT3

<400> SEQUENCE: 27
gatatctccc tggggacaat atgtgttgca actgttcgtt gttggtgccc cagtcccca     60 accggtacta atcggtctat gttcccgtaa ctcatattcg gttagaacta gaacaataag    120
```

```
tgcatcattg ttcaacattg tggttcaatt gtcgaacatt gctggtgctt atatctacag    180
ggaagacgat aagcctttgt acaagagagg taacagacag ttaattggta tttctttggg    240
agtcgttgcc ctctacgttg tctccaagac atactacatt ctgagaaaca gatggaagac    300
tcaaaaatgg gagaagctta gtgaagaaga gaaagttgcc tacttggaca gagctgagaa    360
ggagaacctg ggttctaaga ggctggactt tttgttcgag agttaaactg cataattttt    420
tctaagtaaa tttcatagtt atgaaatttc tgcagcttag tgtttactgc atcgtttact    480
gcatcaccct gtaaataatg tgagcttttt tccttccatt gcttggtatc ttccttgctg    540
ctgttt                                                               546

<210> SEQ ID NO 28
<211> LENGTH: 378
<212> TYPE: DNA
<213> ORGANISM: artificial sequence
<220> FEATURE:
<223> OTHER INFORMATION: Sequence of the 3'-Region used for knock out of
      BMT3

<400> SEQUENCE: 28
acaaaacagt catgtacaga actaacgcct ttaagatgca gaccactgaa aagaattggg     60
tcccattttt cttgaaagac gaccaggaat ctgtccattt tgtttactcg ttcaatcctc    120
tgagagtact caactgcagt cttgataacg gtgcatgtga tgttctattt gagttaccac    180
atgattttgg catgtcttcc gagctacgtg gtgccactcc tatgctcaat cttcctcagg    240
caatcccgat ggcagacgac aaagaaattt gggtttcatt cccaagaacg agaatatcag    300
attgcgggtg ttctgaaaca atgtacaggc caatgttaat gctttttgtt agagaaggaa    360 caaactttt tgctgagc                                                  378

<210> SEQ ID NO 29
<211> LENGTH: 1494
<212> TYPE: DNA
<213> ORGANISM: artificial sequence
<220> FEATURE:
<223> OTHER INFORMATION: DNA encodes Tr ManI catalytic domain

<400> SEQUENCE: 29
cgcgccggat ctcccaaccc tacgagggcg gcagcagtca aggccgcatt ccagacgtcg     60
tggaacgctt accaccattt tgcctttccc catgacgacc tccacccggt cagcaacagc    120
tttgatgatg agagaaacgg ctggggctcg tcggcaatcg atggcttgga cacggctatc    180
ctcatggggg atgccgacat tgtgaacacg atccttcagt atgtaccgca gatcaacttc    240
accacgactg cggttgccaa ccaaggcatc tccgtgttcg agaccaacat tcggtacctc    300
ggtggcctgc tttctgccta tgacctgttg cgaggtcctt tcagctcctt ggcgacaaac    360
cagaccctgg taaacagcct tctgaggcag ctcaaacac tggccaacgg cctcaaggtt    420
gcgttcacca ctcccagcgg tgtcccggac cctaccgtct tcttcaaccc tactgtccgg    480
agaagtggtg catctagcaa caacgtcgct gaaattggaa gcctggtgct cgagtggaca    540
cggttgagcg acctgacggg aaacccgcag tatgcccagc ttgcgcagaa gggcgagtcg    600
tatctcctga atccaaaggg aagcccggag gcatggcctg gctgattgg aacgtttgtc    660 agcacgagca acggtacctt tcaggatagc agcggcagct ggtccggcct catggacagc    720
ttctacgagt acctgatcaa gatgtacctg tacgacccgg ttgcgtttgc acactacaag    780
gatcgctggg tccttgctgc cgactcgacc attgcgcatc tcgcctctca cccgtcgacg    840
```

```
cgcaaggact tgacctttt gtcttcgtac aacggacagt ctacgtcgcc aaactcagga    900
catttggcca gttttgccgg tggcaacttc atcttgggag gcattctcct gaacgagcaa    960
aagtacattg actttggaat caagcttgcc agctcgtact ttgccacgta caaccagacg   1020
gcttctggaa tcggcccga aggcttcgcg tgggtggaca gcgtgacggg cgccggcggc   1080
tcgccgccct cgtcccagtc cgggttctac tcgtcggcag gattctgggt gacggcaccg   1140
tattacatcc tgcggccgga gacgctggag agcttgtact acgcataccg cgtcacgggc   1200
gactccaagt ggcaggacct ggcgtgggaa gcgttcagtg ccattgagga cgcatgccgc   1260
gccggcagcg cgtactcgtc catcaacgac gtgacgcagg ccaacggcgg gggtgcctct   1320
gacgatatgg agagcttctg gtttgccgag gcgctcaagt atgcgtacct gatctttgcg   1380
gaggagtcgg atgtgcaggt gcaggccaac ggcgggaaca aatttgtctt taacacggag   1440
gcgcacccct ttagcatccg ttcatcatca cgacggggcg gccaccttgc ttaa         1494

<210> SEQ ID NO 30
<211> LENGTH: 1231
<212> TYPE: DNA
<213> ORGANISM: artificial sequence
<220> FEATURE:
<223> OTHER INFORMATION: Sequence of the 5'-region that was used to
      knock into the PpPRO1 locus

<400> SEQUENCE: 30
gaagggccat cgaattgtca tcgtctcctc aggtgccatc gctgtgggca tgaagagagt     60
caacatgaag cggaaaccaa aaagttaca gcaagtgcag gcattggctg ctataggaca    120
aggccgtttg ataggacttt gggacgacct tttccgtcag ttgaatcagc ctattgcgca   180 gatttactg actagaacgg atttggtcga ttacacccag tttaagaacg ctgaaaatac    240
attggaacag cttattaaaa tgggtattat tcctattgtc aatgagaatg acaccctatc    300
cattcaagaa atcaaatttg gtgacaatga caccttatcc gccataacag ctggtatgtg    360
tcatgcagac tacctgtttt tggtgactga tgtggactgt ctttacacgg ataaccctcg    420
tacgaatccg gacgctgagc caatcgtgtt agttagaaat atgaggaatc taaacgtcaa    480
taccgaaagt ggaggttccg ccgtaggaac aggaggaatg acaactaaat tgatcgcagc    540
tgatttgggt gtatctgcag gtgttacaac gattatttgc aaaagtgaac atcccgagca    600
gattttggac attgtagagt acagtatccg tgctgataga gtcgaaaatg aggctaaata    660
tctggtcatc aacgaagagg aaactgtgga acaatttcaa gagatcaatc ggtcagaact    720
gagggagttg aacaagctgg acattccttt gcatacacgt ttcgttggcc acagttttaa    780
tgctgttaat aacaaagagt tttggttact ccatggacta aaggccaacg gagccattat    840
cattgatcca ggttgttata aggctatcac tagaaaaaac aaagctggta ttcttccagc    900
tggaattatt tccgtagagg gtaatttcca tgaatacgag tgtgttgatg ttaaggtagg    960
actaagagat ccagatgacc cacattcact agacccaat gaagaactt acgtcgttgg    1020 ccgtgcccgt tgtaattacc ccagcaatca aatcaacaaa attaagggtc tacaaagctc   1080
gcagatcgag caggttctag ttacgctga cggtgagtat gttgttcaca gggacaactt    1140
ggctttccca gtatttgccg atccagaact gttggatgtt gttgagagta ccctgtctga    1200
acaggagaga gaatccaaac caaataaata g                                  1231

<210> SEQ ID NO 31
<211> LENGTH: 1425
<212> TYPE: DNA
```

<213> ORGANISM: artificial sequence
<220> FEATURE:
<223> OTHER INFORMATION: Sequence of the 3'-region that was used to
      knock into the PpPRO1 locus

<400> SEQUENCE: 31

```
aatttcacat atgctgcttg attatgtaat tataccttgc gttcgatggc atcgatttcc      60
tcttctgtca atcgcgcatc gcattaaaag tatacttttt ttttttttcct atagtactat    120
tcgcccttatt ataaactttg ctagtatgag ttctaccccc aagaaagagc ctgatttgac    180
tcctaagaag agtcagcctc caaagaatag tctcggtggg ggtaaaggct ttagtgagga    240
gggtttctcc caaggggact tcagcgctaa gcatatacta atcgtcgcc ctaacaccga     300
aggctcttct gtggcttcga acgtcatcag ttcgtcatca ttgcaaaggt taccatcctc    360
tggatctgga agcgttgctg tgggaagtgt gttgggatct tcgccattaa ctctttctgg    420
agggttccac gggcttgatc caaccaagaa taaaatagac gttccaaagt cgaaacagtc    480
aaggagacaa agtgttcttt ctgacatgat ttccacttct catgcagcta gaaatgatca    540
ctcagagcag cagttacaaa ctggacaaca atcagaacaa aaagaagaag atggtagtcg    600
atcttctttt tctgtttctt cccccgcaag agatatccgg cacccagatg tactgaaaac    660
tgtcgagaaa catcttgcca atgacagcga gatcgactca tctttacaac ttcaaggtgg    720
agatgtcact agaggcattt atcaatgggt aactggagaa agtagtcaaa aagataaccc    780
gcctttgaaa cgagcaaata gttttaatga ttttttcttct gtgcatggtg acgaggtagg    840
caaggcagat gctgaccacg atcgtgaaag cgtattcgac gaggatgata tctccattga    900
tgatatcaaa gttccgggag ggatgcgtcg aagttttta ttacaaaagc atagagacca    960
acaactttct ggactgaata aaacggctca ccaaccaaaa caacttacta aacctaattt   1020
cttcacgaac aactttatag agttttggc attgtatggg catttgcag gtgaagattt   1080
ggaggaagac gaagatgaag attagacag tggttccgaa tcagtcgcag tcagtgatag   1140
tgagggagaa ttcagtgagg ctgacaacaa tttgttgtat gatgaagagt ctctcctatt   1200
agcacctagt acctccaact atgcgagatc aagaatagga agtattcgta ctcctactta   1260
tggatctttc agttcaaatg ttggttcttc gtctattcat cagcagttaa tgaaaagtca   1320
aatcccgaag ctgaagaaac gtggacagca caagcataaa acacaatcaa aaatacgctc   1380
gaagaagcaa actaccaccg taaaagcagt gttgctgcta ttaaa                   1425
```

<210> SEQ ID NO 32
<211> LENGTH: 1350
<212> TYPE: DNA
<213> ORGANISM: artificial sequence
<220> FEATURE:
<223> OTHER INFORMATION: Anti-Her2 Heavy chain (VH + IgG1 constant
      region)

<400> SEQUENCE: 32

```
gaggttcagt tggttgaatc tggaggagga ttggttcaac ctggtggttc tttgagattg     60
tcctgtgctg cttccggttt caacatcaag gacacttaca tccactgggt tagacaagct    120
ccaggaaagg gattggagtg ggttgctaga atctacccaa ctaacggtta cacaagatac    180
gctgactccg ttaagggaag attcactatc tctgctgaca cttccaagaa cactgcttac    240
ttgcagatga actccttgag agctgaggat actgctgttt actactgttc cagatggggt    300
ggtgatggtt tctacgctat ggactactgg ggtcaaggaa ctttggttac tgtttcctcc    360
gcttctacta agggaccatc tgttttccca ttggctccat cttctaagtc tacttccggt    420
```

```
ggtactgctg ctttgggatg tttggttaaa gactacttcc cagagccagt tactgtttct    480
tggaactccg gtgctttgac ttctggtgtt cacactttcc cagctgtttt gcaatcttcc    540
ggtttgtact ctttgtcctc cgttgttact gttccatcct cttccttggg tactcagact    600
tacatctgta acgttaacca caagccatcc aacactaagg ttgacaagaa ggttgagcca    660
aagtcctgtg acaagacaca tacttgtcca ccatgtccag ctccagaatt gttgggtggt    720
ccatccgttt tcttgttccc accaaagcca aggacactt tgatgatctc cagaactcca    780
gaggttacat gtgttgttgt tgacgtttct cacgaggacc cagaggttaa gttcaactgg    840
tacgttgacg gtgttgaagt tcacaacgct aagactaagc caagagaaga gcagtacaac    900
tccacttaca gagttgtttc cgttttgact gttttgcacc aggactggtt gaacggtaaa    960
gaatacaagt gtaaggtttc caacaaggct ttgccagctc aatcgaaaa gactatctcc   1020 aaggctaagg gtcaaccaag agagccacag gtttacactt tgccaccatc cagagaagag   1080
atgactaaga accaggtttc cttgacttgt ttggttaaag gattctaccc atccgacatt   1140
gctgttgagt gggaatctaa cggtcaacca gagaacaact acaagactac tccaccagtt   1200
ttggattctg atggttcctt cttcttgtac tccaagttga ctgttgacaa gtccagatgg   1260
caacagggta acgttttctc ctgttccgtt atgcatgagg ctttgcacaa ccactacact   1320
caaaagtcct tgtctttgtc ccctggttaa                                   1350

<210> SEQ ID NO 33
<211> LENGTH: 57
<212> TYPE: DNA
<213> ORGANISM: artificial sequence
<220> FEATURE:
<223> OTHER INFORMATION: Saccharomyces cerevisiae mating factor
      pre-signal peptide

<400> SEQUENCE: 33
atgagattcc catccatctt cactgctgtt ttgttcgctg cttcttctgc tttggct        57

<210> SEQ ID NO 34
<211> LENGTH: 414
<212> TYPE: DNA
<213> ORGANISM: artificial sequence
<220> FEATURE:
<223> OTHER INFORMATION: PpCIT1 TT

<400> SEQUENCE: 34
ccggccattt aaatatgtga cgactgggtg atccgggtta gtgagttgtt ctcccatctg     60 tatattttc atttacgatg aatacgaaat gagtattaag aaatcaggcg tagcaatatg    120
ggcagtgttc agtcctgtca tagatggcaa gcactggcac atccttaata ggttagagaa    180
aatcattgaa tcatttgggt ggtgaaaaaa aattgatgta acaagccac ccacgctggg    240 agtcgaaccc agaatctttt gattagaagt caaacgcgtt aaccattacg ctacgcaggc    300
atgtttcacg tccattttg attgctttct atcataatct aaagatgtga actcaattag    360
ttgcaatttg accaattctt ccattacaag tcgtgcttcc tccgttgatg caac          414

<210> SEQ ID NO 35
<211> LENGTH: 645
<212> TYPE: DNA
<213> ORGANISM: artificial sequence
<220> FEATURE:
<223> OTHER INFORMATION: Anti-Her2 light chain (VL + Kappa constant
      region)
```

<400> SEQUENCE: 35

```
gacatccaaa tgactcaatc cccatcttct ttgtctgctt ccgttggtga cagagttact    60
atcacttgta gagcttccca ggacgttaat actgctgttg cttggtatca acagaagcca   120
ggaaaggctc caaagttgtt gatctactcc gcttccttct tgtactctgg tgttccatcc   180
agattctctg gttccagatc cggtactgac ttcactttga ctatctcctc cttgcaacca   240
gaagatttcg ctacttacta ctgtcagcag cactacacta ctccaccaac tttcggacag   300
ggtactaagg ttgagatcaa gagaactgtt gctgctccat ccgttttcat tttcccacca   360
tccgacgaac agttgaagtc tggtacagct tccgttgttt gtttgttgaa caacttctac   420
ccaagagagg ctaaggttca gtggaaggtt gacaacgctt gcaatccgg taactcccaa    480
gaatccgtta ctgagcaaga ctctaaggac tccacttact ccttgtcctc cactttgact   540
ttgtccaagg ctgattacga aagcacaag gtttacgctt gtgaggttac acatcagggt    600
ttgtcctccc cagttactaa gtccttcaac agaggagagt gttaa                   645
```

<210> SEQ ID NO 36
<211> LENGTH: 427
<212> TYPE: DNA
<213> ORGANISM: artificial sequence
<220> FEATURE:
<223> OTHER INFORMATION: ScTEF1 promoter

<400> SEQUENCE: 36

```
gatcccccac acaccatagc ttcaaaatgt ttctactcct tttttactct tccagatttt    60
ctcggactcc gcgcatcgcc gtaccacttc aaaacaccca agcacagcat actaaatttc   120
ccctctttct tcctctaggg tgtcgttaat tacccgtact aaaggtttgg aaaagaaaaa   180
agagaccgcc tcgtttcttt ttcttcgtcg aaaaaggcaa taaaaatttt tatcacgttt   240
cttttttcttg aaaatttttt tttttgattt tttttctcttt cgatgacctc ccattgatat   300
ttaagttaat aaacggtctt caatttctca gtttcagtt tcattttttct tgttctatta   360
caacttttttt tacttcttgc tcattagaaa gaaagcatag caatctaatc taagttttaa   420
ttacaaa                                                            427
```

<210> SEQ ID NO 37
<211> LENGTH: 1793
<212> TYPE: DNA
<213> ORGANISM: artificial sequence
<220> FEATURE:
<223> OTHER INFORMATION: Sequence of the PpTRP2 gene integration locus

<400> SEQUENCE: 37

```
ggtttctcaa ttactatata ctactaacca tttacctgta gcgtatttct tttccctctt    60
cgcgaaagct caagggcatc ttcttgactc atgaaaaata tctggatttc ttctgacaga   120
tcatcaccct tgagcccaac tctctagcct atgagtgtaa gtgatagtca tcttgcaaca   180
gattattttg gaacgcaact aacaaagcag atacacccctt cagcagaatc ctttctggat   240
attgtgaaga atgatcgcca aagtcacagt cctgagacag ttcctaatct ttaccccatt   300
tacaagttca tccaatcaga cttcttaacg ccctcatctgg cttatatcaa gcttaccaac   360
agttcagaaa ctcccagtcc aagtttcttg cttgaaagtg cgaagaatgg tgacaccgtt   420
gacaggtaca cctttatggg acattccccc agaaaaataa tcaagactgg gcctttagag   480
ggtgctgaag ttgacccctt ggtgcttctg gaaaagaaac tgaagggcac cagacaagcg   540
caacttcctg gtattcctcg tctaagtggt ggtgccatag gatacatctc gtacgattgt   600
```

```
attaagtact ttgaaccaaa aactgaaaga aaactgaaag atgttttgca acttccggaa      660
gcagctttga tgttgttcga cacgatcgtg gcttttgaca atgtttatca aagattccag      720
gtaattggaa acgtttctct atccgttgat gactcggacg aagctattct tgagaaatat      780
tataagacaa gagaagaagt ggaaaagatc agtaaagtgg tatttgacaa taaaactgtt      840
ccctactatg aacagaaaga tattattcaa ggccaaacgt tcacctctaa tattggtcag      900
gaagggtatg aaaaccatgt tcgcaagctg aaagaacata ttctgaaagg agacatcttc      960
caagctgttc cctctcaaag ggtagccagg ccgacctcat tgcacccttt caacatctat     1020
cgtcatttga gaactgtcaa tccttctcca tacatgttct atattgacta tctagacttc     1080
caagttgttg gtgcttcacc tgaattacta gttaaatccg acaacaacaa caaaatcatc     1140
acacatccta ttgctggaac tcttcccaga ggtaaaacta tcgaagagga cgacaattat     1200
gctaagcaat tgaagtcgtc tttgaaagac agggccgagc acgtcatgct ggtagatttg     1260
gccagaaatg atattaaccg tgtgtgtgag cccaccagta ccacggttga tcgtttattg     1320
actgtggaga gattttctca tgtgatgcat cttgtgtcag aagtcagtgg aacattgaga     1380
ccaaacaaga ctcgcttcga tgctttcaga tccatttttcc cagcaggaac cgtctccggt     1440
gctccgaagg taagagcaat gcaactcata ggagaattgg aaggagaaaa gagaggtgtt     1500
tatgcggggg ccgtaggaca ctggtcgtac gatggaaaat cgatggacac atgtattgcc     1560
ttaagaacaa tggtcgtcaa ggacggtgtc gcttaccttc aagccggagg tggaattgtc     1620
tacgattctg accccatga cgagtacatc gaaaccatga acaaaatgag atccaacaat     1680
aacaccatct tggaggctga gaaaatctgg accgataggt tggccagaga cgagaatcaa     1740
agtgaatccg aagaaaacga tcaatgaacg gaggacgtaa gtaggaattt atg           1793
```

<210> SEQ ID NO 38
<211> LENGTH: 957
<212> TYPE: DNA
<213> ORGANISM: artificial sequence
<220> FEATURE:
<223> OTHER INFORMATION: Sequence of the PpURA5 auxotrophic marker

<400> SEQUENCE: 38

```
tctagaggga cttatctggg tccagacgat gtgtatcaaa agacaaatta gagtatttat       60
aaagttatgt aagcaaatag gggctaatag ggaaagaaaa attttggttc tttatcagag      120
ctggctcgcg cgcagtgttt ttcgtgctcc tttgtaatag tcattttga ctactgttca      180 gattgaaatc acattgaaga tgtcactgga ggggtaccaa aaaaggtttt tggatgctgc      240
agtggcttcg caggccttga agtttggaac tttcaccttg aaaagtggaa gacagtctcc      300
atacttcttt aacatgggtc ttttcaacaa agctccatta gtgagtcagc tggctgaatc      360
ttatgctcag gccatcatta acagcaacct ggagatagac gttgtatttg gaccagctta      420
taaaggtatt cctttggctg ctattaccgt gttgaagttg tacgagctgg gcggcaaaaa      480
atacgaaaat gtcggatatg cgttcaatag aaaagaaaag aaagaccacg gagaaggtgg      540
aagcatcgtt ggagaaagtc taagaataa aagagtactg attatcgatg atgtgatgac      600
tgcaggtact gctatcaacg aagcatttgc tataattgga gctgaaggtg ggagagttga      660
aggttgtatt attgccctag atagaatgga gactacagga gatgactcaa ataccagtgc      720
tacccaggct gttagtcaga gatatggtac ccctgtcttg agtatagtga cattggacca      780
tattgtggcc catttgggcg aaactttcac agcagacgag aaatctcaaa tggaaacgta      840
```

```
tagaaaaaag tatttgccca ataagtatg aatctgcttc gaatgaatga attaatccaa        900
ttatcttctc accattattt tcttctgttt cggagctttg ggcacggcgg cggatcc         957
```

<210> SEQ ID NO 39
<211> LENGTH: 709
<212> TYPE: DNA
<213> ORGANISM: artificial sequence
<220> FEATURE:
<223> OTHER INFORMATION: Sequence of the part of the Ec lacZ gene that
      was used to construct the PpURA5 blaster (recyclable auxotrophic
      marker)

<400> SEQUENCE: 39

```
cctgcactgg atggtggcgc tggatggtaa gccgctggca agcggtgaag tgcctctgga        60
tgtcgctcca caaggtaaac agttgattga actgcctgaa ctaccgcagc cggagagcgc       120
cgggcaactc tggctcacag tacgcgtagt gcaaccgaac gcgaccgcat ggtcagaagc       180
cgggcacatc agcgcctggc agcagtggcg tctggcggaa aacctcagtg tgacgctccc       240
cgccgcgtcc cacgccatcc gcatctgac accagcgaa atggatttt gcatcgagct       300 gggtaataag cgttggcaat ttaaccgcca gtcaggcttt ctttcacaga tgtggattgg       360
cgataaaaaa caactgctga cgccgctgcg cgatcagttc acccgtgcac cgctggataa       420
cgacattggc gtaagtgaag cgaccccgcat tgaccctaac gcctgggtcg aacgctggaa       480
ggcggcgggc cattaccagg ccgaagcagc gttgttgcag tgcacggcag atacacttgc       540
tgatgcggtg ctgattacga ccgctcacgc gtggcagcat caggggaaaa ccttatttat       600
cagccggaaa acctaccgga ttgatggtag tggtcaaatg gcgattaccg ttgatgttga       660
agtggcgagc gatacaccgc atccggcgcg gattggcctg aactgccag                 709
```

<210> SEQ ID NO 40
<211> LENGTH: 542
<212> TYPE: PRT
<213> ORGANISM: Saccharomyces cerevisiae

<400> SEQUENCE: 40

```
Met Gln Ala Lys Ile Ile Tyr Ala Leu Ser Ala Ile Ser Ala Leu Ile
1               5                   10                  15

Pro Leu Gly Ser Ser Leu Leu Ala Pro Ile Glu Asp Pro Ile Val Ser
            20                  25                  30

Asn Lys Tyr Leu Ile Ser Tyr Ile Asp Glu Asp Trp Ser Asp Arg
        35                  40                  45

Ile Leu Gln Asn Gln Ser Val Met Asn Ser Gly Tyr Ile Val Asn Met
    50                  55                  60

Gly Asp Asp Leu Glu Cys Phe Ile Gln Asn Ala Ser Thr Gln Leu Asn
65                  70                  75                  80

Asp Val Leu Glu Asp Ser Asn Glu His Ser Asn Ser Glu Lys Thr Ala
                85                  90                  95

Leu Leu Thr Lys Thr Leu Asn Gln Gly Val Lys Thr Ile Phe Asp Lys
            100                 105                 110

Leu Asn Glu Arg Cys Ile Phe Tyr Gln Ala Gly Phe Trp Ile Tyr Glu
        115                 120                 125

Tyr Cys Pro Gly Ile Glu Phe Val Gln Phe His Gly Arg Val Asn Thr
    130                 135                 140

Lys Thr Gly Glu Ile Val Asn Arg Asp Glu Ser Leu Val Tyr Arg Leu
145                 150                 155                 160

Gly Lys Pro Lys Ala Asn Val Glu Glu Arg Glu Phe Glu Leu Leu Tyr
```

```
                165                 170                 175
Asp Asp Val Gly Tyr Tyr Ile Ser Glu Ile Ile Gly Ser Gly Asp Ile
            180                 185                 190
Cys Asp Val Thr Gly Ala Glu Arg Met Val Glu Ile Gln Tyr Val Cys
            195                 200                 205
Gly Gly Ser Asn Ser Gly Pro Ser Thr Ile Gln Trp Val Arg Glu Thr
    210                 215                 220
Lys Ile Cys Val Tyr Glu Ala Gln Val Thr Ile Pro Glu Leu Cys Asn
225                 230                 235                 240
Leu Glu Leu Leu Ala Lys Asn Glu Asp Gln Lys Asn Ala Ser Pro Ile
            245                 250                 255
Leu Cys Arg Met Pro Ala Lys Ser Lys Ile Gly Ser Asn Ser Ile Asp
            260                 265                 270
Leu Ile Thr Lys Tyr Glu Pro Ile Phe Leu Gly Ser Gly Ile Tyr Phe
            275                 280                 285
Leu Arg Pro Phe Asn Thr Asp Glu Arg Asp Lys Leu Met Val Thr Asp
            290                 295                 300
Asn Ala Met Ser Asn Trp Asp Glu Ile Thr Glu Thr Tyr Tyr Gln Lys
305                 310                 315                 320
Phe Gly Asn Ala Ile Asn Lys Met Leu Ser Leu Arg Leu Val Ser Leu
            325                 330                 335
Pro Asn Gly His Ile Leu Gln Pro Gly Asp Ser Cys Val Trp Leu Ala
            340                 345                 350
Glu Val Val Asp Met Lys Asp Arg Phe Gln Thr Thr Leu Ser Leu Asn
            355                 360                 365
Ile Leu Asn Ser Gln Arg Ala Glu Ile Phe Phe Asn Lys Thr Phe Thr
    370                 375                 380
Phe Asn Glu Asp Asn Gly Asn Phe Leu Ser Tyr Lys Ile Gly Asp His
385                 390                 395                 400
Gly Glu Ser Thr Glu Leu Gly Gln Ile Thr His Ser Asn Lys Ala Asp
            405                 410                 415
Ile Asn Thr Ala Glu Ile Arg Ser Asp Glu Tyr Leu Ile Asn Thr Asp
            420                 425                 430
Asn Glu Leu Phe Leu Arg Ile Ser Lys Glu Ile Ala Glu Val Lys Glu
            435                 440                 445
Leu Leu Asn Glu Ile Val Ser Pro His Glu Met Glu Val Ile Phe Glu
    450                 455                 460
Asn Met Arg Asn Gln Pro Asn Asn Asp Phe Glu Leu Ala Leu Met Asn
465                 470                 475                 480
Lys Leu Lys Ser Ser Leu Asn Asp Asn Lys Val Glu Gln Ile Asn
            485                 490                 495
Asn Ala Arg Met Asp Asp Asp Glu Ser Thr Ser His Thr Thr Arg Asp
            500                 505                 510
Ile Gly Glu Ala Gly Ser Gln Thr Thr Gly Asn Thr Glu Ser Glu Val
            515                 520                 525
Thr Asn Val Ala Ala Gly Val Phe Ile Glu His Asp Glu Leu
    530                 535                 540

<210> SEQ ID NO 41
<211> LENGTH: 1629
<212> TYPE: DNA
<213> ORGANISM: Saccharomyces cerevisiae

<400> SEQUENCE: 41
```

```
atgcaagcta aaattatata tgctctgagc gcaatttctg cgttgattcc gttaggatca    60
tcactattag cacctataga agaccccata gtatcgaata agtacctcat atcttacatc   120
gatgaggacg actggagtga taggatatta caaaatcagt ctgtcatgaa ctcgggatat   180
atagtgaata tgggcgacga ccttgaatgc tttattcaaa atgcaagcac tcaattgaat   240
gatgtattgg aagactcaaa tgagcatagc aatagtgaaa agacagcatt attaactaaa   300
accctgaatc aaggtgttaa gacaattttc gataaattaa atgaacggtg catcttctac   360
caagccggat tttggattta cgagtactgt cctggcatag aatttgttca gttccatggt   420
agagtaaata caaaaactgg tgaaatagta aatcgagatg aatctttggt ctaccgcctg   480
ggaaaaccaa agcaaatgt agaagagaga gaatttgaac tactttatga cgatgtagga   540
tattacatca gcgaaattat agggtcaggt gatatttgcg atgtgacggg ggctgaaaga   600
atggttgaaa tacaatatgt ctgtggcggc tcaaactctg gaccatcgac tattcaatgg   660
gtgagagaaa caaaaatttg tgtttatgaa gcccaagtta ccatacctga attgtgcaat   720
ttagaattac tagccaaaaa tgaagaccaa agaacgcct cacctatact ttgcaggatg   780
cccgcaaaat caaaaattgg tagtaactct attgatttaa tcaccaaata tgaaccgatt   840 ttttaggtt ctggaatata ctttctaagg cccttaaca ccgacgaaag agacaaatta   900
atggttactg acaatgccat gtcaaattgg gatgagatta cggaaacata ttaccagaaa   960 tttgaaatg ccataaacaa aatgcttagt ttgagattag tatcgttacc taatggacat  1020
attctccagc ctggtgactc atgtgtttgg ttggcggaag tggttgatat gaaagatcgg  1080
tttcaaacca ctttatcgtt gaacatactt aattcacaga gagcagagat atttttcaac  1140
aagacgttta catttaatga agataatgga aacttcctat catacaaaat tggggatcat  1200
ggcgagtcaa ctgaacttgg tcaaataacc cactcaaaca agcagatat aaataccgca  1260 gaaattcggt cagatgaata cttaattaac actgataatg agctattctt gaggatttct  1320
aaggagatag cagaagtgaa agaattatta acgaaatcg taagtccaca tgaaatggaa  1380
gtaatatttg aaaacatgag aaatcaaccg aataatgatt ttgaactggc gttgatgaac  1440
aagttgaaat cctcattaaa tgatgataac aaagttgagc agataaacaa cgcaaggatg  1500
gatgatgatg aaagcactag tcatacaacc agagacatcg gggaagctgg atcacaaacg  1560
acagggaata ctgaatcgga ggtaacaaac gtagcagctg tgtttttcat cgaacatgat  1620
gagctttaa                                                          1629
```

<210> SEQ ID NO 42
<211> LENGTH: 360
<212> TYPE: PRT
<213> ORGANISM: Pichia pastoris

<400> SEQUENCE: 42

Met Ile Lys Val Leu Leu Phe Leu Leu Ser Leu Ser Ser Leu Val Lys
1               5                   10                  15

Ala Leu Asp Asp Ser Ile Asp Lys Asn Ser Val Tyr Thr Ile Asn Tyr
                20                  25                  30

Leu Asn His Ala Ile Ser Pro Thr Ser Glu Lys Ile Val Thr Leu Arg
            35                  40                  45

Ser Thr Asp Asp Gln Tyr Phe Glu Cys Leu Phe Asn Asp Glu Ile Asp
        50                  55                  60

Thr Asp Gln Lys Leu His Gln Lys Gln Ile Leu Lys Thr Leu Pro Ala
65                  70                  75                  80

Gln Tyr Asn Leu Ser Glu Ile Pro Glu Leu Gln Thr Glu Ile Asn Ser
                85                  90                  95

Ala Phe Asn Ile Leu Glu Asn Tyr Asn Leu Asn Asp Ala Gln Pro Thr
            100                 105                 110

Lys Asp Arg Tyr Trp Thr Tyr Gln Ile Ile Asn Gly Lys Leu Tyr Gln
        115                 120                 125

Tyr Asn Gly Asn Leu Arg Ile Val Leu Ala Asn Ile Pro Lys Asn Leu
    130                 135                 140

Thr Arg Glu Asp Ile Val Leu Glu Lys Asn Met His Gln Ser Val Phe
145                 150                 155                 160

Leu Ser Leu Ser Leu Gln Asn Gly Ala Ile Cys Asp Leu Thr Phe Thr
                165                 170                 175

Pro Arg Lys Thr Asn Ile Arg Phe Gln Tyr Val Asn Lys Leu Asn Thr
            180                 185                 190

Leu Gly Ile Val Ser Ala Asp Glu Ile Gln Thr Cys Glu Tyr Glu Ile
        195                 200                 205

Leu Ile Asn Val Pro Lys Phe Lys Asp Thr Ile Phe Gln Tyr Gly Phe
    210                 215                 220

Leu Glu Pro Leu Lys Lys Ile Asp Cys Tyr Ser Ser Asp Ser Ser Met
225                 230                 235                 240

Ile Asn Leu Ala Asp Tyr Gln Ile Ser Val Leu Ser His Lys Trp Phe
                245                 250                 255

Leu Gly Ala Lys Asp Phe Arg Leu Ile Leu Ile Thr Asp Val Ser Asn
            260                 265                 270

Pro Pro Val Ile Ser Ile Glu Glu Leu Asn Leu Ile Phe Gln Thr Phe
        275                 280                 285

Pro Lys Tyr Gly Pro Pro Glu Leu Gly Ile Thr Gly Glu Ile Ser Pro
    290                 295                 300

His Asp Thr Phe Ile Phe Arg Ile Pro Val Tyr Ser Tyr Asn Arg Thr
305                 310                 315                 320

Lys Phe Gly Asp Val Leu Val Glu Gln Asn Ile Arg Gly Glu Lys Arg
                325                 330                 335

Phe Leu Phe Thr Glu Asp Arg Ile Pro His Asp Thr Pro Asn Phe Arg
            340                 345                 350

Val Tyr Asn Gly Val Asn Val Asn
        355                 360

<210> SEQ ID NO 43
<211> LENGTH: 1140
<212> TYPE: DNA
<213> ORGANISM: Pichia pastoris

<400> SEQUENCE: 43
atgataaagg tcctgctatt cctgctctcc ctatcaagtc ttgtgaaagc tttggatgat      60
tccattgata agaattctgt ggtaagtctt ttaattttg ttttcacaag atcatgccgt     120
gctaactggg tactatagta taccataaac tacttaaatc atgccatctc acccacctca     180
gaaaaaatag tgacattaag atcaacggac gatcaatatt ttgagtgttt gtttaatgat     240
gaaattgata ctgaccagaa actacatcaa aagcagattc tgaaaactct tccagctcaa     300
tacaacttga gtgaaatacc agaacttcaa actgaaataa actctgcatt caatatactt     360
gaaaactata acctcaacga tgctcagcca accaaggaca gatattggac atatcaaata     420
ataaatggaa aattgtacca atataacggg aacttgcgaa ttgtcctggc taatataccc     480
aagaatctga cgagggaaga catagttctg gagaagaata tgcaccaatc ggtgttttta     540

```
tcactcagct tacaaaacgg tgccatttgt gatttgactt tcactcctag aaagacaaat      600
atacggtttc aatacgttaa caagctcaac actctaggaa ttgtctccgc cgatgaaata      660
cagacctgcg aatatgaaat tcttatcaat gttcctaagt tcaaagatac cattttcag      720 tacggatttt tggagccttt gaagaagatt gattgctact cgagtgatag ctcaatgata      780
aatttggcag actaccaaat atctgtcctt tcccataaat ggttcttagg ggccaaagat      840
ttcaggttga ttttgatcac tgatgtgtct aaccctcccg tgatatcaat agaagaactg      900
aatctcatat ttcaaacatt tcctaaatac ggtcccccag agctcgggat cactggtgag      960
atttcacccc atgacacttt tatcttcaga attcctgtgt acagctacaa taggacaaaa     1020
ttcggtgacg tactggttga gcagaatatc aggggagaga aaaggttcct attcactgaa     1080
gacagaatac ctcatgacac tccaaacttt agagtgtata acggagttaa tgtgaattaa     1140
```

<210> SEQ ID NO 44
<211> LENGTH: 520
<212> TYPE: PRT
<213> ORGANISM: Aspergillus fumigates

<400> SEQUENCE: 44

```
Met Ile Arg Arg Ile Arg Thr Leu Thr Pro Leu Leu Val Leu Ala Cys
1               5                   10                  15

Ala Gly Ser Gly Ala Trp Ala Ser Lys Lys Ala Phe Asn Ile Gln Asp
            20                  25                  30

Asp Leu Leu Ala Tyr Pro Gln Phe Gln Val Phe Phe Pro Asp Glu Tyr
        35                  40                  45

Ile Leu Asp Ala Arg Ala Arg Glu Leu Leu Gln Asn Gln Gln Glu Ser
    50                  55                  60

Ser Ser Ala Ser Ala Asp Lys Thr Phe Ser Glu Gly Asn Asp Ala Gln
65                  70                  75                  80

Val Tyr Leu Gly Ser Arg Lys Asp Gln Ser Glu Asp Val Asn Lys Glu
                85                  90                  95

Thr Ile Glu Gly Ser Gly Phe Thr Tyr Glu Glu Met Leu Leu Glu Gly
            100                 105                 110

Gln Arg Tyr Leu Cys Ser Ile Pro Gln Val Asp Asn Gly Asn Arg Asp
        115                 120                 125

Gln Thr Asn Gly Ala Glu Ser Thr Ser Lys Glu Asp Glu Gln Arg Glu
    130                 135                 140

Ile Ala Arg Ala Thr Asp Arg Gly Leu Glu Leu Leu Arg Glu Met Glu
145                 150                 155                 160

Gly Lys Cys Met Tyr Tyr Ile Ser Gly Trp Trp Ser Tyr Ser Phe Cys
                165                 170                 175

Tyr Lys Lys Gln Ile Lys Gln Phe His Ala Leu Pro Ser Gly Pro Gly
            180                 185                 190

Val Pro Asn Tyr Pro Pro Ile Glu Asp Ser Thr Thr His Ser Phe Val
        195                 200                 205

Leu Gly Arg Phe Pro Asn Ser Gly Asp Asp Glu Asp Leu Glu Gly Asp
    210                 215                 220

Ala Glu His Lys Lys Thr Thr Thr Asp Val Ala Glu Leu Gln Thr Lys
225                 230                 235                 240

Gly Gly Ser Arg Tyr Leu Val Gln Arg Leu Gly Gly Thr Lys Cys
                245                 250                 255

Asp Leu Thr Gly Lys Asp Arg Lys Ile Glu Val Gln Phe His Cys His
            260                 265                 270
```

```
Pro Gln Ser Thr Asp Arg Ile Gly Trp Ile Lys Glu Leu Thr Thr Cys
        275                 280                 285

Ser Tyr Leu Met Val Ile Tyr Thr Pro Arg Leu Cys Asn Asp Val Ala
        290                 295                 300

Phe Leu Pro Pro Gln Gln Asp Glu Ala His Ala Ile Glu Cys Arg Glu
305                 310                 315                 320

Ile Leu Ser Glu Glu Val Ser Asp Trp Glu Ala Asn Arg Glu Tyr
                325                 330                 335

His Leu Ala Gln Gln Leu Val Glu Ser Ala Ile Thr Pro Glu Phe Pro
            340                 345                 350

Val Val Gly Asp Ile Glu Val Gly Ala His Lys Trp Val Gly Ser Glu
            355                 360                 365

Gly Lys Gln Ile Glu Lys Gly Arg Val Ala Ser Ile Gly Glu Lys
        370                 375                 380

Ile Glu Val Val Ala Lys Arg Gln Asn Gly Glu Ile Thr Arg Leu Ser
385                 390                 395                 400

Lys Glu Glu Leu Lys Lys Tyr Gly Leu Asp Pro Glu Lys Ile Glu Thr
                405                 410                 415

Leu Lys Ser Arg Leu Glu Glu Leu Ala Lys Gly Lys Asp Trp Thr Leu
            420                 425                 430

Glu Ile Val Glu Ser Asn Gly Glu Arg Gly Leu Val Gly Thr Val Asp
            435                 440                 445

Ser Asn Asp Asp Glu Lys Glu Asp His Ala Ala Gln Gly Ser Ile Ser
        450                 455                 460

Gln Pro Ala Gln Gly Thr Thr Ala Asp Lys Gly Glu Ser Asn Ala Glu
465                 470                 475                 480

Thr Gly Glu Glu Lys Lys Lys Ala Asp Glu Lys Ile Asp His Tyr Glu
                485                 490                 495

Pro Glu Lys Ser Gly Pro Thr Thr Asp Asp Ala Asp Asp Gly Ser Glu
            500                 505                 510

Glu Ile Phe Phe Lys Asp Glu Leu
            515                 520

<210> SEQ ID NO 45
<211> LENGTH: 1563
<212> TYPE: DNA
<213> ORGANISM: Aspergillus fumigates

<400> SEQUENCE: 45
atgattcgac gtatacggac tcttacccca ttgctggtgc tggcttgtgc tggttccggc      60
gcatgggcca gcaagaaggc gttcaacata caagatgatc tacttgcata tcctcaattt     120
caagtcttct tccctgatga atacattctt gatgcgcgag caagggagtt attacagaat     180
caacaagaga gctcttcggc ttccgctgat aagacattct ccgaaggcaa tgatgcgcaa     240
gtatatctgg gaagccgaaa agatcaatct gaagacgtca ataaagagac gatagaagga     300
tctgggttca catacgagga gatgctcctt gagggacaga gatatctctg ttccattccg     360
caagtcgaca acggaaacag ggaccagacg aacggagcgg aaagcaccag taaagaggat     420
gaacagcgag aaattgcacg cgcgacggac cgtggcctgg aacttctgcg cgagatggaa     480
ggcaaatgca tgtactacat atccggatgg tggtcatact cattctgcta caagaagcaa     540
atcaagcagt tcatgcact accgtccggt ccaggcgtgc ccaactaccc gccgatagaa     600
gactctacga cccattcttt cgtgctgggc aggtttccca acagcggcga cgacgaggat     660
```

```
ttggaggggg atgcggagca caaaaagaca actacagatg tcgccgagct ccagactaaa      720
ggcgggtcgc ggtacttagt gcagcggctg ggggcggaa ccaagtgcga cttgacaggc       780
aaagaccgga agatcgaagt gcagttccac tgccatccgc aatctacaga tcggatcggt     840
tggatcaagg aacttactac ttgctcatat ctcatggtga tctacactcc gcgcttgtgc     900
aatgatgtcg catttctgcc gcctcagcag gacgaggctc acgcgatcga atgccgcgag     960
attctctccg aggaagaggt ttccgactgg gaagcaaacc gggaatatca tttggctcag    1020
cagctcgtcg aatcagcgat tacacccgag tttcctgttg tcggggatat cgaggtcggg    1080
gcgcacaagt gggtgggatc ggaaggcaag cagatcgaga agggtcgagt ggcatccatt    1140
ggagaagaga agatcgaggt agttgccaag cgccaaaatg gagagatcac aaggttgtcc    1200
aaggaggagt tgaagaaata cggtcttgat cctgagaaga ttgagacgct gaaaagccgc    1260
ctcgaggagc ttgccaaggg taaggactgg acactggaga ttgtcgagtc taacggcgag    1320
cgtggcttag tcggaactgt cgactccaac gacgatgaga agaggatca cgccgcacag     1380 ggctctatat cgcagccggc acaggaact acagctgaca aggggaatc caatgcagag     1440 acaggagagg aaaagaagaa ggcagacgag aagatagacc attacgagcc agaaaaatca    1500
gggccgacca ctgatgatgc cgacgacggc agcgaggaaa tcttcttcaa ggatgagctc    1560
tag                                                                  1563

<210> SEQ ID NO 46
<211> LENGTH: 305
<212> TYPE: PRT
<213> ORGANISM: Saccharomyces cerevisiae

<400> SEQUENCE: 46

Met Phe Pro His Leu Ile Leu Pro Ala Ile Gly Ser Ser Lys Val Arg
1               5                   10                  15

Thr Met Val Leu Pro Phe Ala Phe Val Gly Phe Phe Ile Phe Pro Ile
                20                  25                  30

Cys Leu Ala Ser Leu Leu Asp Trp Asn Asp Ala Tyr Glu Tyr Pro Lys
            35                  40                  45

Tyr Ser Phe Glu Trp Ser Asn Val Ser Ile Leu Glu Gly Asp Ile Asp
        50                  55                  60

Ser Ile Lys Glu Lys Thr Glu Lys Thr Lys Leu Ser Ser Leu Phe Tyr
65                  70                  75                  80

Ala Gly Lys His Glu Tyr Phe Cys Val Tyr Pro Asn Ala Ser Leu Ile
                85                  90                  95

Lys Gln Asn Ser Thr Thr Glu Pro Ser Tyr Asp Leu Gln Glu Leu Arg
            100                 105                 110

Ile Gln Gly Thr Glu Lys Ile Asn Glu Leu Ala Asn Val Phe Leu Ile
        115                 120                 125

Glu Asn Arg Gly Tyr Trp Thr Tyr Asp Tyr Val Tyr Gly Gln His Val
130                 135                 140

Arg Gln Tyr His Leu Glu Pro Gln Gln Gly Ser Asp Lys Val Leu Ala
145                 150                 155                 160

Asn Pro Met Tyr Ile Leu Gly Thr Ala Pro Asn Thr Gln Thr Lys Lys
                165                 170                 175

Asn Leu Glu Glu Asn Trp Ala Ile Gly Phe Val Glu Gly Lys Ala Tyr
            180                 185                 190

Leu Gln Thr Thr Phe Arg Asn Gly Thr Met Cys Asp Ile Thr Lys Arg
        195                 200                 205
```

```
Pro Arg His Val Ile Leu Ser Tyr Glu Cys Ser Thr Asn Ser Asp Thr
    210                 215                 220

Pro Glu Ile Thr Gln Tyr Gln Glu Val Ser Ser Cys Ala Tyr Ser Met
225                 230                 235                 240

Thr Ile His Val Pro Gly Leu Cys Ser Leu Pro Ala Phe Lys Ile Gln
                245                 250                 255

Glu Asp Ile Pro Ser Glu Lys Ile Val Cys Tyr Asn Val Ile Lys Glu
                260                 265                 270

Lys Ser Asn Glu Val Asp His Lys Asp Ser Gln His Val Val Asp Glu
            275                 280                 285

Val Ala Gln Thr Ser Pro Pro Glu Val Lys Val Glu Thr Gln Ser
    290                 295                 300

Ser
305

<210> SEQ ID NO 47
<211> LENGTH: 918
<212> TYPE: DNA
<213> ORGANISM: Saccharomyces cerevisiae

<400> SEQUENCE: 47
atgtttccac atttgattct acctgcaatc ggctcatcta agttaggac tatggtgcta        60 ccatttgctt ttgtggggtt ttttatttt ccaatatgtt tagcttcttt gttagactgg      120
aatgatgcat atgaatatcc taaatattcg tttaatgga gtaatgtgtc aatattagag      180
ggcgacattg actcaattaa agaaaaaact gaaaaaacta attatcgtc attattctat       240 gctggaaagc atgaatattt ttgtgtatat cccaatgcgt ctcttataaa acaaaatagc      300
acaaccgaac caagctatga tttacaagaa ttgcggatac aagggactga aaaaatcaat     360
gagcttgcta atgtatttt aatcgagaat cgtggttatt ggacttatga ctatgtctac      420
ggtcaacacg tgcgtcaata tcatttggag ccgcagcaag gttctgacaa agtccttgct     480
aaccctatgt atatacttgg tacggcacct aacactcaaa ctaaaaagaa tttggaagaa     540
aattgggcta ttggatttgt tgaaggtaaa gcatatttgc aaacaacttt ccgaaatggg    600
actatgtgcg acattactaa agagaccaaga cacgtaattc taagttatga atgcagtaca   660
aattcggata ctcctgaaat tactcaatat caagaagttt caagctgtgc atattcaatg    720
actattcacg ttcccggttt atgctcatta cctgctttca aaattcaaga ggacatacccc  780 tctgaaaaaa ttgtgtgcta taatgtaatt aaagaaaaat caaacgaagt cgaccataag    840
gattcccagc acgttgttga tgaagttgct caaacatctc cgcctgaggt gaaggaggta    900
gagacgcaat caagttag                                                    918

<210> SEQ ID NO 48
<211> LENGTH: 2004
<212> TYPE: DNA
<213> ORGANISM: Artificial Sequence
<220> FEATURE:
<223> OTHER INFORMATION: Pichia pastoris ATT1 5' region in pGLY5933

<400> SEQUENCE: 48
ggccgggact acatgaggcc gattcttcaa gccagggaaa ttaattgctt gaaccggaaa       60
atcattaagg caggcaacga aaatccaac tccttggttg aattgactca aaagtttatc     120
ttacggagaa aagctaaaga catcaatacg aatttccttc cgccaaaaac tgaactgata    180
ctgatggttc caatgactga attacaacag gagctataca aggatataat tgaaactaac   240
```

```
caagccaagc ttggcttgat caacgacaga aacttttttc ttcaaaaaat tttgattctt    300
cgtaaaatat gcaattcacc ctccctgctg aaagacgaac ctgattttgc cagatacaat    360
ctcggcaata gattcaatag cggtaagatc aagctaacag tactgctttt acgaaagctg    420
tttgaaacca ccaatgagaa gtgtgtgatt gtttcaaact tcactaaaac tttggacgta    480
cttcagctaa tcatagagca caacaattgg aaataccacc gactagatgg ttcgagtaaa    540
ggacgggaca aaatcgtacg agattttaac gagtcgcctc aaaaagatcg attcatcatg    600
ttgctttctt ccaaggcagg gggagtgggg ctcaacttaa ttggagcctc acgcttaatt    660 cttttttgata cgactggaa tcccagtgtt gacattcaag caatggctag agtgcatcga    720
gacgggcaga aaaggcacac ctttatctat cgtttgtata cgaaaggcac aattgacgaa    780
aagatcctac aaaggcaatt gatgaaacaa aatctgagcg acaaattcct ggatgataat    840
gatagcagca aggatgatgt gtttaacgac tacgatctca aagatttgtt tactgtagat    900
cttgacacga attgtagtac acacgatttg atggaatgtt tatgtaatgg gcggctgaga    960
gatccgactc ccgtcttgga agcagaagaa tgcaagacaa aaccgttgga ggccgttgac   1020
gacacggatg atggtggat gtcagctctg gatttcaaac agttatcaca aaaagaggag   1080
acaggtgctg tgtcaacaat gcgtcaatgt ctgctcggat atcaacacat tgatccaaag   1140
attttggaac caacagaacc tgtagggac gatttggtat tggcaaacat cctcgcggag   1200
tcctcaggct tggctaaatc tgcattgtca tctgaaaaga aacccaagaa accagtggtg   1260
aactttatct ttgtgtcagg ccaagactaa gctggaagaa cggaacttta atcgaaggaa   1320
aaattaaatg tcaaagtggg tcgatcagga gataatccat gcttcacgtg attttttctta   1380 ataaacgccg gaaaaacttt cttttttgtg accaaaatta tccgatctga aaaaaaatta   1440
cgcatgcgtg aagtaggatg agagacttac tgttgaactt tgtgagacga ggggaaaagg   1500
aatatcctga tcgtaaacaa aaaagttttc cagcccaatc gggaacatct gcgaagtgtt   1560
ggaattcaac ccctctttcg aaaatgttcc attttaccca aaattattgt tattaaataa   1620
tacatgtgtt actagcaaag tctgcgcttt ccatgtctca gattcggcag ataacaaagt   1680
tgacacgttc ttgcgagata cgcatgaatc ttttggctgc ttttttgtgaa agagaaatgg   1740 tgccatatat tgcagacgcc cctgaaagat tagtgtgcgg ctgagtcttt ttttttttctc   1800 aaccagcttt ttctttttat tgggtaccat cgcgcacgca ggactcatgc tccattagac   1860
ttctgaacca cctgacttaa tattcatgga cggacgcttt tatccttaaa ttgttcatcc   1920
attcctcaat ttttccgttt gccctccctg tactattaaa ttacaaaagc tgatcttttt   1980
caagtgtttc tctttgaatc gctc                                         2004
```

<210> SEQ ID NO 49
<211> LENGTH: 1854
<212> TYPE: DNA
<213> ORGANISM: Artificial Sequence
<220> FEATURE:
<223> OTHER INFORMATION: Pichia pastoris ATT1 3' region in pGLY5933

<400> SEQUENCE: 49

```
ggaccctgaa gacgaagaca tgtctgcctt agagtttacc gcagttcgat tcccaacctt     60
ttcagctacg acaacagccc cgcctcctac tccagtcaat gcaacagtc ctgaaaacat    120 caagacctcc actgtggacg atttttttgaa agctactcaa gatccaaata caaagagat    180 actcaacgac atttacagtt tgattttttga tgactccatg gatcctatga gcttcggaag    240
tatggaacca agaaacgatt tggaagttcc ggacactata atggattaat ttgcagcggg    300
```

-continued

```
cctgtttgta tagtctttga ttgtgtataa tagaattact acgcgtatat cccgatctgg      360
aagtaacatg aagtttccc attttcgcgc agtctcctac tcgtatcctc cccacccctt       420
accgatgacg caaaaggtca ctagataagc atagcatagt ttcatcccct tgctctttcct    480 tgtaccaaca gatcatggct gggaatctca aggatattct atccttgtcg aggaagacag     540
caaggaatct gaagcaggct ctggatgagc ttgcggagca ggtgatcaac caccaacgga     600
gacgaccagc tctggtccga gttcctatca acaacaacct taggcgcaag agccagcagt    660 ccttttttgaa tcgcaggtca ttccatcttt ggaccagcaa gtacaaccca ctttttgga    720 ggggaggcag aagcaacgtt ctggaccagc ttaaccgtga agctttaagg tacagatcgt    780
cttttgcgaa acccggattt tatccaagtg ggctgtatca gtcaactttc cctcaaagag   840
gtagtaggat gttttccacc tgcgcctact catgtcagca ggaggcagtc aaaaacttga    900
cttccgctgt tcgtgctttg ttacaaagtg gtgctaattt cggcagtcaa atgaaacaaa    960
tgaaacactg ttcgcaaaag aagaagcact tctctaaatt ttctaagagg cttacttctt   1020
ccactgccgc tgggtctggc aagaatgctg aacaagctcc ttctggtttg gccgaaggat  1080
ccgctgttgt ttttagcctt gaacgtcaaa gtcacaatac tgagttggaa ggaatcttgg    1140
atcaagaaac ttcttccatt ctcgaggaag aaatggttca acatgagcgt cacctggcta   1200
ttattagaga agaaatccag agaattagtg agaatctagg atcattacca ttaatcatgt  1260
ctggtcacaa gattgaggta tttttcccca attgtgacac tgttaaatgt gagcaactga   1320
tgagagattt ggctattacg aaaggggttg tgaggcgtca tgattctact gctgagcatt   1380
caagctccag gtcatttgtt ccagaagatt gcttgtattc ctcagggtca agttcaccga   1440
atcctttatc ctcaacttct tcgaaatcat tgatagagt ctcattggac tacatttcct    1500
ctcggtctac atctgatcaa accactggtt ctgagtacac atctctgtct caacaatatc   1560
acctggttag caattacaac cctgtactat cctcagcccc gggttcttcg agggtcttgg    1620
agctgaatac tcccgagtcc actatggaag gcagtacaga tctggagtat ttaacgcgag   1680
acgatgtgtt gctgttaaat gtctaatcta gacctatcct tcattctata gcttagtt     1740 gagttttacg taagccctag tttttgttaa ttcttatcga tttatggtta gtgtaccact    1800
caactcacga tgatatatcc caggagctgt tgtgcatta taactaccaa tcct           1854
```

<210> SEQ ID NO 50
<211> LENGTH: 1392
<212> TYPE: DNA
<213> ORGANISM: Artificial Sequence
<220> FEATURE:
<223> OTHER INFORMATION: DNA encodes Homo sapiens endomannosidase
      (codon-optimized for expression in Pichia pastoris)

<400> SEQUENCE: 50

```
atggctaagt tcagaagaag aacctgtatt atccttgctt tgtttatttt gtttatcttt      60
tcccttatga tgggattgaa gatgttgaga cctaacaccg ccacttttgg tgcaccattc    120
ggacttgatt tgcttcctga attgcatcaa agaactatcc atttgggtaa aaacttcgat    180
ttccagaaat cagacagaat caatagtgaa acaaacacca gaatttgaa gtcagttgag    240 atcacaatga agcctagtaa agcttctgaa ttgaatcttg atgagcttcc accttttgaac   300 aactatttgc atgttttcta ctatagttgg tacggtaacc cacaattcga tggaaagtat   360
atccattgga atcacccagt cttggaacat tgggacccta gaattgctaa aaactaccca    420
cagggtagac acaatccacc tgatgacatt ggttcttcct tttatcctga attgggatct    480
```

```
tactcaagta gagatccatc cgttattgag actcacatga gacaaatgag atcagctagt      540
atcggtgttt tggcccttc ttggtatcca cctgatgtca acgacgaaaa tggagagcca       600
actgataacc ttgttcctac aattttggac aaggctcata atacaactt gaaggtcact       660 ttccacattg aaccttattc aatagagat gaccagaaca tgtacaagaa cgttaagtac       720
atcatcgata agtacggtaa ccatccagca ttctacagat acaagactaa gacaggaaat     780
gctttgccta tgttctacgt ctatgactct tacattacta gccagagaa atgggctaac      840 ttgcttacta catctggttc cagatcaatt agaaattctc cttacgatgg acttttatc      900 gccttgcttt tgaagagaa gcataagtac gatatcttgc aatccggttt cgacggaatc      960
tacacttatt ttgccacaaa cggtttcacc tacggatctt cccaccagaa ttgggcatct    1020
ttgaagttgt tttgtgataa gtacaatttg attttcatcc catcagtcgg tcctggatat    1080
attgacactt ctatcagacc atggaacacc caaaacacta gaaacagaat taatggtaaa    1140
tactacgaaa tcggactttc cgctgccttg caaaccagac cttccttgat ttcaatcact    1200
tcttttaacg aatggcatga gggtactcag attgaaaagg ctgttccaaa agaacatca     1260 aataccgtct acttggatta tagaccacac aagcctggat tgtaccttga gttgacaaga    1320
aaatggtctg aaaagtattc caagagaga gcaacctacg ctcttgacag acaattgcca    1380
gtttcttaat ga                                                         1392

<210> SEQ ID NO 51
<211> LENGTH: 1416
<212> TYPE: DNA
<213> ORGANISM: Artificial Sequence
<220> FEATURE:
<223> OTHER INFORMATION: Mouse mannosidase IB catalytic domain

<400> SEQUENCE: 51
gatccagaag acatggagat caagaagaaa agagacaaaa ttaaagagat gatgaaacat        60
gcctgggata attacagaac atacggatgg ggacataatg aactaaggcc tattgcaagg      120
aaaggccatt ccactaacat attcggaagc tcacagatgg gtgccaccat agtggatgct      180 ttggatacc tttatatcat ggggcttcat gatgaattca tggatgggca aagatggatt       240
gaagaaaacc ttgatttcag tgtgaattca gaagtgtctg tctttgaagt taacattcgc      300
tttattggag ggctcctcgc tgcatattac ctgtcaggag aggaaatatt caagactaaa     360
gcagtgcagt tggctgagaa actccttcct gcctttaaca cacctactgg gattccctgg    420
gcaatggtga acctgaaaag tggagtaggt cgaaactggg gctgggcgtc tgcaggcagc     480
agcatcctgg ctgagttcgg caccctgcac atggagtttg tgcacctcag ctacttgacc     540
ggtgacttga cttactataa taaggtcatg cacattcgga aactactgca gaaaatggaa     600
cgcccaaatg gtctttatcc aaattattta aacccaagaa cagggcgctg gggtcagtat    660
cacacatcag ttggtggtct gggagatagt ttttatgaat acttactgaa agcatggctg    720
atgtcagata aaacagacca cgaggcaaga aggatgtatg acgatgctgt tgaggctata    780
gaaaaacatc ttattaagaa gtcccgagga ggtctggttt ttattggaga atggaagaat    840
ggacacttgg aaaggaagat gggcacttg gcctgctttg ctggggaat gtttgcccctt     900 ggagcagatg gttccagaaa ggataaagct ggccactact agaactaggg gcagaaatt    960 gcacgaacat gtcatgagtc atatgacaga actgcattga aactaggtcc ggagtcattc   1020
aagtttgatg gtgcagtgga agccgtggct gtgcggcagg ctgaaaagta ttacatcctt   1080
```

```
cgtccagaag taattgaaac ctattggtat ctatggcgat ttacccacga cccaagatac    1140
aggcagtggg gctgggaagc agcactggct attgagaagt cgtgccgggt cagcggtggg    1200
ttttctggtg tcaaggatgt atacgccccg accctgtgc atgacgacgt gcagcagagc     1260 tttttcttg ctgaaacatt aaaatacttg tacctgctgt tctctggcga tgaccttcta     1320
cctttagacc actgggtgtt taacacagag gcgcaccctc tgccggtgtt gcgcttagcc    1380
aacagcactc tttcaggtaa tcctgctgtc cgatga                              1416

<210> SEQ ID NO 52
<211> LENGTH: 426
<212> TYPE: DNA
<213> ORGANISM: Artificial Sequence
<220> FEATURE:
<223> OTHER INFORMATION: SEC12 leader 9

<400> SEQUENCE: 52
atgaacacta tccacataat aaaattaccg cttaactacg ccaactacac ctcaatgaaa     60
caaaaaatct ctaaattttt caccaacttc atccttattg tgctgctttc ttacattta    120 cagttctcct ataagcacaa tttgcattca atgcttttca attacgcgaa ggacaatttt   180
ctaacgaaaa gagacaccat ctcttcgccc tacgtagttg atgaagactt acatcaaaca   240
actttgtttg gcaaccacgg tacaaaaaca tctgtaccta gcgtagattc cataaaagtg   300
catggcgtgc atgagacgag ttctgtgaat ggaactgaag tcttatgtac tgaaagtaac   360
attattaata ctggagggc agagtttgag atcaccaacg caacttttcg agaaatagat    420
gatgct                                                               426

<210> SEQ ID NO 53
<211> LENGTH: 502
<212> TYPE: DNA
<213> ORGANISM: Artificial Sequence
<220> FEATURE:
<223> OTHER INFORMATION: PpSTT3 promoter

<400> SEQUENCE: 53
accagtcttg aagattcaga cgtagacatg gataaatttg ttgacgctat ggatatttca     60
ccgttgccag atgccgcaga ttcgtcattt tctacggtta aagcttccag acagagttca   120
ctaaccacaa gaaaactaat tccgtccaaa caaagtaaga gccttctaag ctctttgaag   180
aacgctgaag ctcaaccaga tgaaacagaa atagttccac ccttaggtgc accctcacga   240
atgaatttgg tagaacctaa tatggtgctt gaagataata ataaatagat caatcaactc   300
accgaacaaa tgattatata attgggctct cctttcctgc tagcccttgc acttcccttc   360
cctagtaaat acatccgaga gcatccttcg cgaataccttc caacacata aacagtacac   420 tactccgccg aaaaagacac gttggagcga ctagcttaaa atactctcca ccgccaaatc   480
ctccctcaac ggatctccaa ca                                             502

<210> SEQ ID NO 54
<211> LENGTH: 32
<212> TYPE: PRT
<213> ORGANISM: Artificial Sequence
<220> FEATURE:
<223> OTHER INFORMATION: Insulin analogue B chain (des B30) :Asn at 1
      and 31 beta-1 linked to a paucimannose N-glycan

<400> SEQUENCE: 54

Asn Gly Thr Phe Val Asn Gln His Leu Cys Gly Ser His Leu Val Glu
1               5                   10                  15
```

```
Ala Leu Tyr Leu Val Cys Gly Glu Arg Gly Phe Phe Tyr Thr Asn Lys
            20                  25                  30
```

<210> SEQ ID NO 55
<211> LENGTH: 85
<212> TYPE: PRT
<213> ORGANISM: Artificial Sequence
<220> FEATURE:
<223> OTHER INFORMATION: Sc alpha mating factor signal sequence and
      pro-peptide

<400> SEQUENCE: 55

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg
                85
```

<210> SEQ ID NO 56
<211> LENGTH: 10
<212> TYPE: PRT
<213> ORGANISM: Artificial Sequence
<220> FEATURE:
<223> OTHER INFORMATION: N-terminal spacer

<400> SEQUENCE: 56

```
Glu Glu Ala Glu Ala Glu Ala Glu Ala Lys
1               5                   10
```

<210> SEQ ID NO 57
<211> LENGTH: 32
<212> TYPE: PRT
<213> ORGANISM: Artificial Sequence
<220> FEATURE:
<223> OTHER INFORMATION: B-chain

<400> SEQUENCE: 57

```
Asn Gly Thr Phe Val Asn Gln His Leu Cys Gly Ser His Leu Val Glu
1               5                   10                  15

Ala Leu Tyr Leu Val Cys Gly Glu Arg Gly Phe Phe Tyr Thr Asn Lys
            20                  25                  30
```

<210> SEQ ID NO 58
<211> LENGTH: 21
<212> TYPE: PRT
<213> ORGANISM: Artificial Sequence
<220> FEATURE:
<223> OTHER INFORMATION: A-chain

<400> SEQUENCE: 58

```
Gly Ile Val Glu Gln Cys Cys Thr Ser Ile Cys Ser Leu Tyr Gln Leu
1               5                   10                  15

Glu Asn Tyr Cys Asn
                20
```

<210> SEQ ID NO 59
<211> LENGTH: 1826
<212> TYPE: DNA
<213> ORGANISM: Artificial Sequence
<220> FEATURE:
<223> OTHER INFORMATION: PpADE4-5UTR+ORF

<400> SEQUENCE: 59

```
tacacgatca caagttgtgt atagtctttt ctttaaactg atcgtagacc agaccaccac      60
agcgtagcca atgttatttt attcattaat cgaaaaagtt ttggttcagg cgcgacaagg     120
tagtaagaaa aaaattctgc atgaattgat tcttcacttg gtacttgatt cattgaacaa     180
tataaacaca gataatgtgt gggattcttg gaattgtatt ggctgatcag tcagaagatg     240
ttgcagctga attgttagat ggagccatgt ttttgcaaca taggggacaa gatgccgcag     300
gtattgtgac ctgtgcagga ggacgttttt atcaatgcaa aggtaatgga atggccaagg     360
acgtacttac ggagcaacgt atgaaagggc tggtaggtaa tatgggaatt gcgcagctaa     420
gatatccgac tgctggttct agtgccatga gcgaagcgca gccgttttat gttaacagtc     480
catacggaat tgcactttct cataatggta atcttgtgaa tggacgtaat ctccgccaga     540
aattagatga tgttcttcat cgccatataa atacagatag tgatagcgag ttactgttga     600
acatttttgc tgctgagttg gctcagtacg acaagaaaag agttaactca gaagacattt     660
tcaaggccct cgttggtgtc tacagagaat gtcgtggagc ttatgcttgt gtcagtatgt     720
tggccggcta tggtattatt ggatttcgtg atcctcatgg tatcagacct ttagtcgtcg     780
gagaacgtgt gagagtgtcc caaactcccg gtgacactca cttgcaatgc gattatatgc     840
ttgcctctga gagtgtagtt ttaaaggctc atggatttca caactttagg gatattttac     900
caggtgaagc tgttattatc acaaagagag ggcctccgga gttttgtcaa attgttcctg     960
cgaaagccta cactccggat attttttgaat acgtttattt tgctagacct gattcgatta    1020
tggatggaat atctgtctac cgaagccgtt tggcaatggg cgcaaaacta gcccagaaaa    1080
tcacctctcg ttttaccagt cagtccttaa acgtagttag agaaattgat gtggtgatac    1140
ctgttccaga tacatctcga ccttcagctc tggaatgtgc cgtgacgctt ggcataccat    1200
tcagagaagg ttttgtcaaa atcgttatg tgggccgtac cttcattatg ccgaaccaga    1260
aggaaagaac ttcgtctgtg cgacgtaaat taaacgctat gtcttctgag tttgctggtc    1320
gtaacgtttt gttaattgac gactcgatcg taagaggaac cacgtccaag gaaatcgtta    1380
acatggcaag agaagctggc gctaacaaag tatactttgc atcatgctct ccagtcatac    1440
gatacaatca tatatatggc attgacctcg cagattcacg tgctttggtg ggatttggtc    1500
gatcagaaag ggaggtatct gacttgatag gtgctgacga tgtaatttac cagtcacttg    1560
atgatttgaa atcctgttgt gttcaggagc ccgaactccc atccgagtta ccctcaacta    1620
ggattgcatt cacccaacca cctccgaaga ttaatggatt tgaggtgggt gtattcaccg    1680
gagtttatgt aactggagag gaagatcatt atctcaagga gttagaacag gtaagagcta    1740
aaaatgagcg atcacgtatt aatggctgtg gtatagacgt taaagcggag actgatatttt    1800
ctttgtttaa tagaggggag agttga                                        1826
```

<210> SEQ ID NO 60
<211> LENGTH: 1220
<212> TYPE: DNA
<213> ORGANISM: Artificial Sequence
<220> FEATURE:
<223> OTHER INFORMATION: PpADE4-3UTR

<400> SEQUENCE: 60

```
tagtaaagag catatcagtt gcaaatctca tacttacatc tgtccaattc gtcaatcatg    60
caactagtgt gtctaaccgc taatgtgcaa ccaaatccaa ttaatggaag aataaagtct   120
tccgtaaatt ggtttgcttc gcaaatctct cgatatatga ggtattaaag aaagtaagaa   180
tatgaaatcg taactggtaa tagatggatg tatctagaat caaccaacta ataagacaaa   240
cattgtttgc agcgctatca tgtcttttac agtaagtctt ttctgtcaag tggataaacg   300
ggtcaaaaat tataatgatg tacgtacgtt cgccttcgca ccataaacga cgaggcctaa   360
ttttttactat ataataacaa aagttaagac agtaatacccc tgtcgcttta catcagacaa   420
aatcatgttg ttgagtagtc agtcattgat tcatgagttc atttctaaat acttgaaatc   480
caatatgaac tacctcacaa tttaaaaagg aagataatca atcctattat tcgctggcca   540
ccgtaatgcc atattcggat cagatgaaaa cgaagcatag gttgaatata agcaatctaa   600
cttcgttcag catttgctct gaaaaataca ccaaaaaaac atgcgattta gattgtgatg   660
ctgctcttga ccctgcccta tgtttcaaac tacggatcac tttcttaaaa aagcgggct   720
gcatatttcc agataatcat gacgcatcca cctcgttaca atgtacctaa actaaaagac   780
aacgacagcc cccttggttg tgcagatcat catctcctat caaacagcac acaaaaaact   840
gggtaataag tttagaacga gttacaaaat gtcttcctcc ttttgcaatt ctaatctacg   900
cggaatctgt caccctctta ggtttattct cttacagtac ttcccctaga atcccgacaa   960
gagctaaaca aaaacttagg ccagaaagca aagttcccctt agcatataat ttacctagct  1020
ttgttaggct atttcgaact tgattccgtt caatcgccca ctccacttca tcttcgacat  1080
tatcttccat caattctcct tctacagaaa cataggctga cccatctaaa gaagatcttt  1140
cagtaatgtc ttgtttcttt tgttgcagtg gtgagccatt ttgacttcgt gaaagtttct  1200
ttagaatagt tgtttccaga                                              1220
```

<210> SEQ ID NO 61
<211> LENGTH: 1025
<212> TYPE: DNA
<213> ORGANISM: Artificial Sequence
<220> FEATURE:
<223> OTHER INFORMATION: PpADE8-5UTR+ORF

<400> SEQUENCE: 61

```
aacccaactg ctctgctgtt atcctcatgc atgatgttga gacacatgtc tttgaacagc    60
tatgccgaca agatcgaaaa ctctgtcttg aagaccattg cttctggacc agagcacaga   120
actaaggact tgaaaggaac ctcctcgact tcaaacttca ccgaacaagt tatcaagaac   180
ttgtaatagt gaacggttat gaaaatgaat gcttcatgac ttgaggctcc tttcgttaga   240
aatatagata gatgtagcag tcttttgaaa cggttgaaaa atgtattaac gatctttact   300
agtaattatg gtttgcagtt cgcacttttt tttttcagcc tttatcatcg atcacactag   360
gaaaaaaaaa tcaagctagt ctagtaacga tgacgcctaa gatattagta ctcatttctg   420
gtaatggaag caacctccag gctctcatta atgccaagga gcaaggccag ctgaaagcag   480
aaatatcttt ggtcatatcc tcaagtagta aggcatttgg catcgaaaga gccaggaaac   540
acaacattcc agtccgagtg catgagctga agtcatacta ccagggaatt cccaaagagg   600
agaaagccaa acgagccgaa aagagaaacg attttgatca agacctggtc aagatcatat   660
tgagcgagaa gcctgatctt gttgtttgtg ccggctggat gcttatacta ggtgaaaaat   720
```

```
tcttacaacc tttacaagag aagaacatct ccatcataaa cttgcatcca tccttgcctg      780
gagcctttga gggaattaat gcaatcgaaa gatcttataa tgccggtcag aatggcgaaa      840
ttactaaggg tggtatcatg atccatcggg ttattctgga ggttgataga ggacaacctc      900
tcatagtgag agaaatagat gttatcaaag gagagacgct agagtcgtgg gaggcaagaa      960
tccattcttt agaacaccaa gcaatagtgg atggaactaa caaggcattg gacgagttga     1020
aataa                                                                 1025

<210> SEQ ID NO 62
<211> LENGTH: 1077
<212> TYPE: DNA
<213> ORGANISM: Artificial Sequence
<220> FEATURE:
<223> OTHER INFORMATION: PpADE8-3UTR

<400> SEQUENCE: 62
gggtcacata taagccaatt aatttcttca atttcttta tccgttaaca gtatgttgta       60
tatctttatg cttcagtatc tacctccatt ggaaccacag tttcctcaat atcgacaaga     120
ttgtagatac tctctttcaa caccgcagta gtgcctctag caaacttgta tgacttaacc     180
ttggcttcac ggacgttagg cttcagatag tttctgtaca attgggcatc ttttccaact     240
tccatgacac aaaggtccac gttagaaccg gatcccaaat cattccagat acctgcctca     300
atagcttctg tgcacagctt cattgcctct tccttagtca agccttcttt ccagttgctc     360
tccaagacag ccatggccgc cagcgaacct gatcccaaag attgatagaa tccaatatcg     420
gtggatccat gcgcatggat agaaaacaag tgggctcctg taggatcaac accaccgacg     480
attagatagg ctccaatgtg accttggtac ttgaacagat gttgtttcag catcgtcaat     540
gctgtgacca ctcgaggttt cctttctgta gacatggcat gcaattctag atttgatcca     600
atcagttgtg taaccatctc tgtatcagca gcggtacctg ctcctgcaca ccatatagta     660
ggtgacaacc tgtgtagctt ttcacaattc ttgtcagcca cgataggacc tgacgtagct     720
ctggtatcgg cagcgatcac aacacctcct tcaaatttaa ctcccacaat ggtggttcct     780
gtggaagttg ccttcggaga gccaaatccc ttagctgaaa ggaattgatt tctttggtgg     840
ttatcgaaac tgaggcctgc catattcgtg tgatggtatg gtgaacgagt ttgtcaagtg     900
ggttgaattt gccttcagga tattacgatt cgagaagtac attctatcga tgtcggatgt     960
gagatacata cattaaaact catacgtcaa aggtatgcaa ctacggctct caagaacctt    1020
ttatatacag gacgttagtt gaccaccttg tcacatctat ggcacagttc gtgatct       1077
```